US011094887B2

(12) United States Patent
Kang et al.

(10) Patent No.: US 11,094,887 B2
(45) Date of Patent: Aug. 17, 2021

(54) FLUORENE-BASED COMPOUND, ORGANIC LIGHT-EMITTING DEVICE USING SAME AND METHOD FOR PREPARING SAME

(71) Applicant: LG Chem, Ltd., Seoul (KR)

(72) Inventors: Sungkyoung Kang, Daejeon (KR); Jaesoon Bae, Daejeon (KR); Jaechol Lee, Daejeon (KR); Seokhee Yoon, Daejeon (KR); Donggu Lee, Daejeon (KR); Yongwook Kim, Daejeon (KR); Ho Gyu Lee, Daejeon (KR)

(73) Assignee: LG Chem, Ltd.

( * ) Notice: Subject to any disclaimer, the term of this patent is extended or adjusted under 35 U.S.C. 154(b) by 343 days.

(21) Appl. No.: 16/338,100

(22) PCT Filed: Dec. 11, 2017

(86) PCT No.: PCT/KR2017/014484
§ 371 (c)(1),
(2) Date: Mar. 29, 2019

(87) PCT Pub. No.: WO2018/159933
PCT Pub. Date: Sep. 7, 2018

(65) Prior Publication Data
US 2020/0028083 A1 Jan. 23, 2020

(30) Foreign Application Priority Data
Feb. 28, 2017 (KR) .................. 10-2017-0026712

(51) Int. Cl.
*H01L 51/00* (2006.01)
*H01L 51/50* (2006.01)
(Continued)

(52) U.S. Cl.
CPC .......... *H01L 51/006* (2013.01); *C07C 211/61* (2013.01); *C07C 217/76* (2013.01);
(Continued)

(58) Field of Classification Search
CPC .......... C09D 7/63; C09D 4/00; C07C 211/61; C07C 217/76; H01L 51/006; H01L 51/56; H01L 51/5056
See application file for complete search history.

(56) References Cited

U.S. PATENT DOCUMENTS

2004/0062949 A1    4/2004   Pfeiffer et al.
2005/0240011 A1   10/2005   Wallace et al.
(Continued)

FOREIGN PATENT DOCUMENTS

CN   105733562 A   7/2016
EP   2610240 A1   7/2013
(Continued)

OTHER PUBLICATIONS

International Search Report for PCT/KR2017/014484, dated Mar. 26, 2018.
(Continued)

*Primary Examiner* — Vu A Nguyen
(74) *Attorney, Agent, or Firm* — Lerner, David, Littenberg, Krumholz & Mentlik, LLP

(57) ABSTRACT

The present specification relates to a fluorene-based compound of Formula 1, a coating composition comprising the fluorene-based compound of Formula 1, an organic light emitting device using the same, and a manufacturing method thereof.

19 Claims, 2 Drawing Sheets

(51) Int. Cl.

| | |
|---|---|
| H01L 51/56 | (2006.01) |
| C07C 211/61 | (2006.01) |
| C07C 217/76 | (2006.01) |
| C09K 11/06 | (2006.01) |
| C09D 7/63 | (2018.01) |
| C09D 4/00 | (2006.01) |
| C09D 7/40 | (2018.01) |

(52) U.S. Cl.
CPC ............... *C09D 4/00* (2013.01); *C09D 7/40* (2018.01); *C09D 7/63* (2018.01); *C09K 11/06* (2013.01); *C09K 2211/1007* (2013.01); *C09K 2211/1011* (2013.01); *H01L 51/0035* (2013.01); *H01L 51/0039* (2013.01); *H01L 51/0058* (2013.01); *H01L 51/5056* (2013.01); *H01L 51/5088* (2013.01); *H01L 51/56* (2013.01)

(56) References Cited

U.S. PATENT DOCUMENTS

| | | |
|---|---|---|
| 2012/0326137 A1 | 12/2012 | Song et al. |
| 2015/0094437 A1 | 4/2015 | Caille et al. |
| 2015/0115239 A1 | 4/2015 | Pflumm et al. |
| 2019/0225581 A1 | 7/2019 | Scheible |
| 2019/0237669 A1 | 8/2019 | Kang et al. |

FOREIGN PATENT DOCUMENTS

| | | |
|---|---|---|
| JP | 2004514257 A | 5/2004 |
| JP | 2006504764 A | 2/2006 |
| JP | 2015511215 A | 4/2015 |
| JP | 2016160420 A | 9/2016 |
| JP | 2016194021 A | 11/2016 |
| JP | 2019531311 A | 10/2019 |
| JP | 2019532958 A | 11/2019 |
| KR | 20030072355 A | 9/2003 |
| KR | 20090114716 A | 11/2009 |
| KR | 20090117078 A | 11/2009 |
| KR | 20120112277 A | 10/2012 |
| KR | 20130028813 A | 3/2013 |
| KR | 20140107594 A | 9/2014 |
| KR | 20140132562 A | 11/2014 |
| KR | 20140146103 A | 12/2014 |
| KR | 20150034379 A | 4/2015 |
| KR | 20150093995 A | 8/2015 |
| KR | 20150093995 A * | 8/2015 |
| KR | 20160041124 A | 4/2016 |
| KR | 20160067728 A | 6/2016 |
| WO | 0241414 A1 | 5/2002 |

OTHER PUBLICATIONS

International Search Report for PCT/KR2018/000347 dated Apr. 13, 2018.
Extended European Search Report including the Search Opinion for Application No. 17899165.9 dated Oct. 9, 2019, 9 pages.
Extended European Search Report including the Search Opinion for Application No. 18760593.6 dated Oct. 9, 2019, 9 pages.

* cited by examiner

[Figure 1]
| 701 |
|---|
| 601 |
| 501 |
| 401 |
| 301 |
| 201 |
| 101 |
[Figure 2]
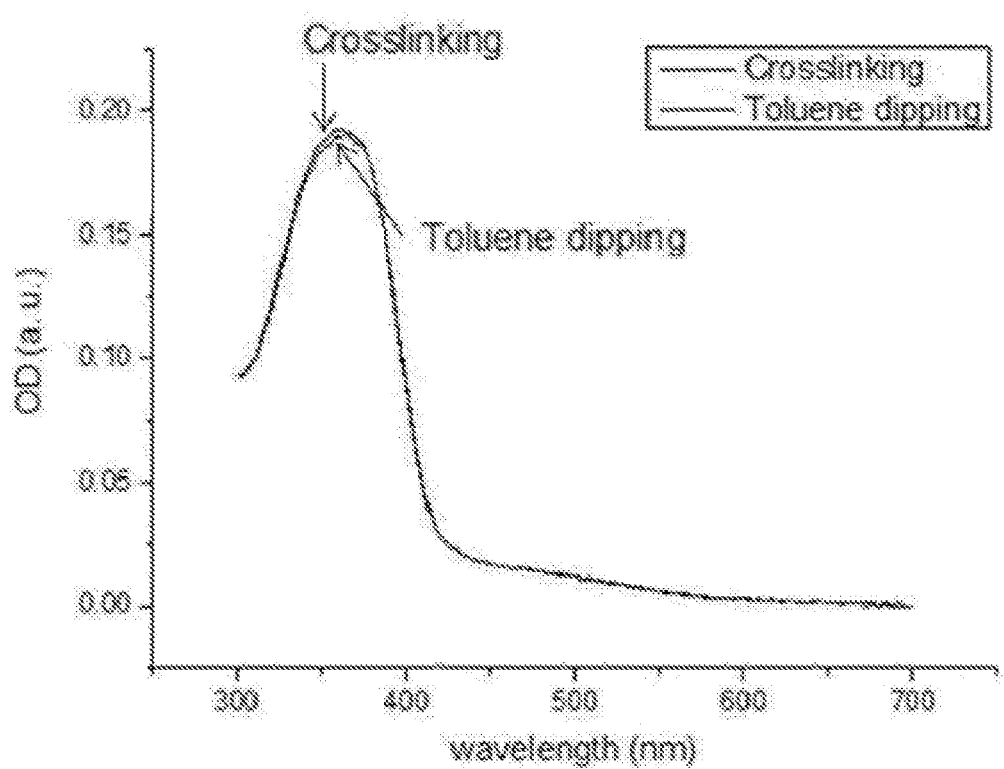

[Figure 3]
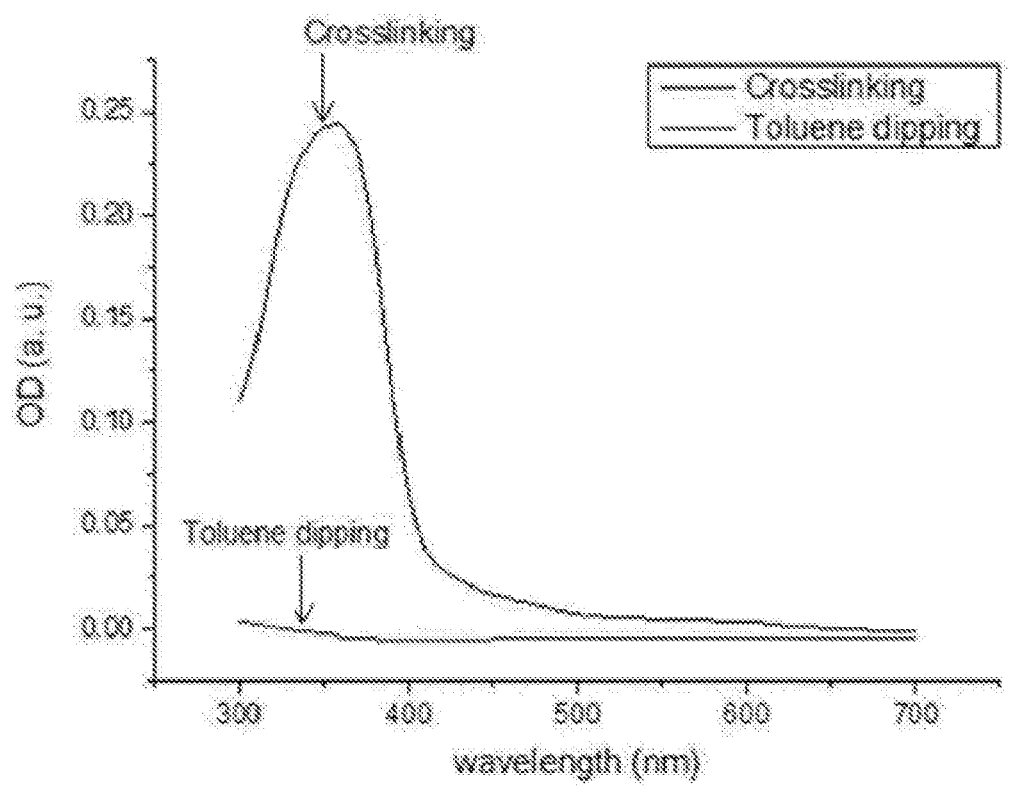

FLUORENE-BASED COMPOUND, ORGANIC LIGHT-EMITTING DEVICE USING SAME AND METHOD FOR PREPARING SAME

CROSS-REFERENCE TO RELATED APPLICATIONS

The present application is a national phase entry under 35 U.S.C. § 371 of International Application No. PCT/KR2017/014484 filed Dec. 11, 2017, which claims priority from Korean Patent Application No. 10-2017-0026712 filed Feb. 28, 2017, all of which are incorporated herein by reference.

TECHNICAL FIELD

The present specification relates to a fluorene-based compound, a coating composition comprising the fluorene-based compound, an organic light emitting device formed by using the coating composition, and a manufacturing method thereof.

BACKGROUND ART

An organic light emission phenomenon is one of the examples of converting an electric current into visible rays through an internal process of a specific organic molecule. The principle of the organic light emission phenomenon is as follows. When an organic material layer is disposed between an anode and a cathode, if an electric current is applied between the two electrodes, electrons and holes are injected into the organic material layer from the cathode and the anode, respectively. The electrons and the holes which are injected into the organic material layer are recombined to form an exciton, and the exciton falls down again to the ground state to emit light. An organic light emitting device using this principle may be generally composed of a cathode, an anode, and an organic material layer disposed therebetween, for example, an organic material layer comprising a hole injection layer, a hole transport layer, a light emitting layer, and an electron transport layer.

The materials used in the organic light emitting device are mostly pure organic materials or complex compounds in which organic materials and metals form a complex, and may be classified into a hole injection material, a hole transport material, a light emitting material, an electron transport material, an electron injection material, and the like according to the use thereof. Here, an organic material having a p-type property, that is, an organic material, which is easily oxidized and electrochemically stable when the material is oxidized, is usually used as the hole injection material or the hole transport material. Meanwhile, an organic material having an n-type property, that is, an organic material, which is easily reduced and electrochemically stable when the material is reduced, is usually used as the electron injection material or the electron transport material. As the light emitting layer material, a material having both p-type and n-type properties, that is, a material, which is stable in both the oxidation and reduction states, is preferred, and when an exciton is formed, a material having high light emitting efficiency for converting the exciton into light is preferred.

In order to obtain a high efficiency organic light emitting device which is capable of being driven at low voltage, holes or electrons injected into the organic light emitting device need to be smoothly transferred to a light emitting layer, and simultaneously, the injected holes and electrons need not go out of the light emitting layer. For this purpose, the materials used in the organic light emitting device need to have an appropriate band gap and HOMO or LUMO energy levels.

In addition, the materials used in the organic light emitting device need to have excellent chemical stability, excellent charge mobility, excellent interface characteristics with electrodes or adjacent layers, and the like. That is, the materials used in the organic light emitting device need to be minimally deformed by moisture or oxygen. Further, by having appropriate hole or electron mobility to make a balance between densities of holes and electrons in a light emitting layer of the organic light emitting device, the materials used in the organic light emitting device need to enable excitons to be maximally formed. Moreover, the materials used in the organic light emitting device need to enable the interface with an electrode comprising a metal or a metal oxide to be improved for the stability of the device.

In addition to those mentioned above, materials used in an organic light emitting device for a solution process need to additionally have the following properties.

First, the materials used in the organic light emitting device need to form a storable homogenous solution. Since a commercialized material for a deposition process has good crystallinity so that the material is not dissolved well in a solution or the crystals thereof are easily formed even though the material forms a solution, it is highly likely that according to the storage period, the concentration gradient of the solution varies or a defective device is formed.

Second, layers in which a solution process is carried out need to have resistance to a solvent and a material, which are used during a process of forming other layers, and are required to have excellent current efficiency and excellent service life characteristics when an organic light emitting device is manufactured.

Therefore, there is a need for developing a new organic material in the art.

DETAILED DESCRIPTION OF THE INVENTION

Technical Problem

An object of the present specification is to provide a fluorene-based compound, which can be used in an organic light emitting device for a solution process, and an organic light emitting device comprising the same.

Technical Solution

Provided is a fluorene-based compound represented by the following Formula 1.

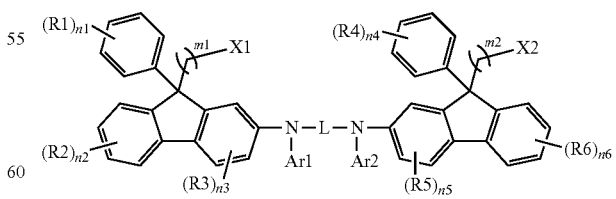

[Formula 1]

In Formula 1,

L is a substituted or unsubstituted arylene group; or a substituted or unsubstituted heteroarylene group, R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, Ar1 and Ar2 are the same as or different from each other, and are each independently a substituted or unsubstituted aryl group; or a substituted or unsubstituted heteroaryl group, X1 and X2 are the same as or different from each other, and are each independently a photocurable group or a thermosetting group, n1 and n4 are each independently an integer of 0 to 5,
n2 and n6 are each independently an integer of 0 to 4,
n3 and n5 are each independently an integer of 0 to 3,
when n1 to n6 are each 2 or more, R1s to R6s are each independently the same as or different from each other, and
m1 and m2 are each 0 or 1.

The present specification provides a coating composition comprising the fluorene-based compound.

The present specification also provides an organic light emitting device comprising: a first electrode; a second electrode; and an organic material layer having one or more layers provided between the first electrode and the second electrode, in which one or more layers of the organic material layer comprise the coating composition or a cured product thereof, and the cured product of the coating composition is in a state where the coating composition is cured by a heat treatment or a light treatment.

Finally, the present specification provides a method for manufacturing an organic light emitting device, the method comprising: preparing a substrate; forming a first electrode on the substrate; forming an organic material layer having one or more layers on the first electrode; and forming a second electrode on the organic material layer, in which the forming of the organic material layer comprises forming the organic material layer having one or more layers by using the coating composition.

Advantageous Effects

A fluorene-based compound according to an exemplary embodiment of the present specification forms a stable thin film, which is not damaged in the next solution process, by a heat treatment at 250° C. or less or a UV treatment. A thin film on which a coating composition comprising a compound according to an exemplary embodiment of the present specification, a curing initiator, and a P-doping material is applied is formed as a stable thin film, which is not damaged in the next solution process, by a heat treatment at 250° C. or less or a UV treatment. The fluorene-based compound according to an exemplary embodiment of the present specification may be used as a material for an organic material layer of an organic light emitting device for a solution process, and may provide low driving voltage, high light emitting efficiency, and high service life characteristics. Further, as the fluorene-based compound is used, the solubility is increased, so that there are advantages in that when an ink of a solution process is prepared, the selection of the solvent is widened, and the melting point and the curing temperature can be lowered.

BRIEF DESCRIPTION OF DRAWINGS

FIG. 1 illustrates an example of an organic light emitting device according to an exemplary embodiment of the present specification.

FIG. 2 is a view illustrating a result of a film retention rate experiment of a coating composition comprising Compound A and a p-doping material.

FIG. 3 is a view illustrating a result of a film retention rate experiment of a coating composition comprising Comparative Compound 1 and a p-doping material.

101: Substrate
201: Anode
301: Hole injection layer
401: Hole transport layer
501: Light emitting layer
601: Layer which simultaneously injects and transports electrons
701: Cathode

BEST MODE

In general, since an arylamine-based single molecule used in an organic light emitting device for a solution process does not have resistance to a solvent in the next process, a curing group needs to be introduced into the arylamine-based single molecule which can be used in an organic light emitting device for a solution process. A thin film manufactured by subjecting a coating composition comprising a fluorene compound, to which an amine group is bonded, according to the present invention, a curing initiator, and a p-doping material to a heat or light treatment provides an organic light emitting device having excellent resistance to a solvent and excellent current efficiency and device characteristics.

Further, when a styrene group or an ethenyl group as a curing group is bonded to a fluorene-based compound according to an exemplary embodiment of the present specification, the curing group is introduced into the number 9 carbon position of fluorene, at which a conjugation with the core structure of the fluorene is broken, thereby reducing interference on a thin film at a moiety at which the fluorene to which a cured body is bonded is connected to an arylamine-based single molecule core backbone and minimizing undesirable effects on a molecular orbital function of the core backbone, and as a result, it is possible to manufacture an organic light emitting device having a longer service life.

Hereinafter, the present specification will be described in detail.

When one member is disposed "on" another member in the present specification, this comprises not only a case where the one member is brought into contact with another member, but also a case where still another member is present between the two members.

When one part "comprises" one constituent element in the present specification, unless otherwise specifically described, this does not mean that another constituent element is excluded, but means that another constituent element may be further included.

In the present specification, the term "combination thereof" included in the Markush type expression means a mixed or combined state of two or more selected from the group consisting of constituent elements described in the Markush type expression, and means comprising one or more selected from the group consisting of the above-described constituent elements.

An exemplary embodiment of the present specification provides a fluorene-based compound represented by the following Formula 1.

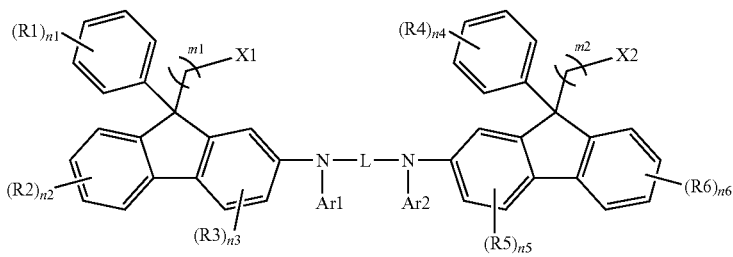

[Formula 1]

In Formula 1,

L is a substituted or unsubstituted arylene group; or a substituted or unsubstituted heteroarylene group, R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, Ar1 and Ar2 are the same as or different from each other, and are each independently a substituted or unsubstituted aryl group; or a substituted or unsubstituted heteroaryl group, X1 and X2 are the same as or different from each other, and are each independently a photocurable group or a thermosetting group, n1 and n4 are each independently an integer of 0 to 5, n2 and n6 are each independently an integer of 0 to 4, n3 and n5 are each independently an integer of 0 to 3, when n1 to n6 are each 2 or more, R1s to R6s are each independently the same as or different from each other, and m1 and m2 are each 0 or 1.

In an exemplary embodiment of the present specification, the fluorene-based compound of Formula 1 is preferably compounds having solubility to a suitable organic solvent.

In the present specification, the "a thermosetting group or a photocurable group" may mean a reactive substituent which cross-links compounds by being exposed to heat and/or light. The cross-linkage may be produced while radicals produced by decomposing carbon-carbon multiple bonds and cyclic structures by means of a heat treatment or light irradiation are linked to each other.

In an exemplary embodiment of the present specification, the thermosetting group or the photocurable group is any one of the following structures.

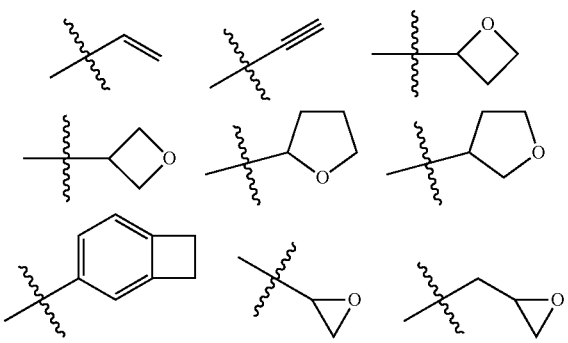

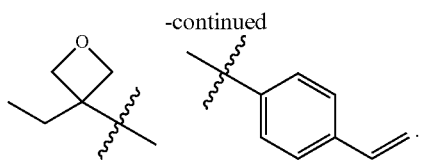

-continued

In an exemplary embodiment of the present specification, a fluorene-based compound comprising a thermosetting group or a photocurable group has an economic effect in terms of time and cost because an organic light emitting device can be manufactured by a solution application method.

Further, when a coating layer is formed by using a coating composition comprising a fluorene-based compound comprising a thermosetting group or a photocurable group, the thermosetting group or the photocurable group forms a cross-linkage by heat or light, and as a result, when an additional layer is stacked on an upper portion of the coating layer, the fluorene-based compound included in the coating composition is prevented from being washed away by a solvent, thereby retaining the coating layer and simultaneously stacking the additional layer on the upper portion.

Additionally, when the thermosetting group or the photocurable group forms a cross-linkage, so that a coating layer is formed, there is an effect in that chemical resistance of the coating layer to the solvent is enhanced, and the film retention rate is high.

Further, in the case of a fluorene-based compound according to an exemplary embodiment of the present specification, an organic light emitting device may be manufactured by a solution application method, thereby enabling a large area of the device to be implemented.

A fluorene-based compound in which a cross-linkage is formed by a heat treatment or light irradiation according to an exemplary embodiment of the present specification has an effect in that the thermal stability is excellent because a plurality of fluorene-based compounds is cross-linked, and thus the cross-linkage is provided in the form of a thin film in the organic light emitting device.

In addition, the fluorene-based compound according to an exemplary embodiment of the present specification comprises an amine structure in the core structure and thus may have appropriate energy level and bandgap as hole injection, a hole transport material or a light emitting material in the organic light emitting device. Furthermore, it is possible to finely adjust appropriate energy level and bandgap by adjusting a substituent of a fluorene-based compound of Formula 1 according to an exemplary embodiment of the present specification, and to provide an organic light emitting device having low driving voltage and high light emitting efficiency by improving interfacial characteristics between the organic materials.

Hereinafter, the substituent of the present specification will be described in detail.

A position where a substituent is not bonded to the compound described in the present specification may be hydrogen, or deuterium may be bonded to the position.

In the present specification,

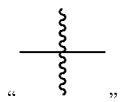

and "------" mean a moiety bonded to another substituent or a bonding portion.

In the present specification, the term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being unsubstituted or substituted with one or more substituents selected from the group consisting of hydrogen; deuterium; a halogen group; a nitrile group; a nitro group; a hydroxyl group; an alkyl group; an alkoxy group; an alkenyl group; an aryl group; and a heteroaryl group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, the halogen group is fluorine; chlorine; bromine; or iodine.

In the present specification, the alkyl group may be straight-chained, branched or cyclic, and the number of carbon atoms thereof is not particularly limited, but is preferably 1 to 40. According to an exemplary embodiment, the number of carbon atoms of the alkyl group is 1 to 20. Specific examples thereof comprise a methyl group, an ethyl group, a propyl group, an n-propyl group, an isopropyl group, a butyl group, an n-butyl group, an isobutyl group, a tert-butyl group, a sec-butyl group, a pentyl group, an n-pentyl group, an isopentyl group, a tert-pentyl group, a hexyl group, an n-hexyl group, heptyl, an n-heptyl group, a hexyl group, an n-hexyl group, and the like, but are not limited thereto.

In the present specification, the alkoxy group may be straight-chained, branched, or cyclic.

The number of carbon atoms of the alkoxy group is not particularly limited, but is preferably 1 to 20. Specific examples thereof comprise a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, an neopentyloxy group, an isopentyloxy group, an n-hexyloxy group, a 3,3-dimethylbutyloxy group, a 2-ethylbutyloxy group, an n-octyloxy group, an n-nonyloxy group, an n-decyloxy group, a benzyloxy group, a p-methylbenzyloxy group, and the like, but are not limited thereto.

In the present specification, the alkenyl group may be straight-chained or branched, and the number of carbon atoms thereof is not particularly limited, but is preferably 2 to 40. Specific examples thereof comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, and the like, but are not limited thereto.

In the present specification, a silyl group may be represented by a formula of —SiRR'R", and R, R', and R" may be each hydrogen; a substituted or unsubstituted alkyl group; or a substituted or unsubstituted aryl group. Specific examples thereof comprise a trimethylsilyl group, a triethylsilyl group, a tert-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 40. According to another exemplary embodiment, the number of carbon atoms of the cycloalkyl group is 3 to 20. Specific examples thereof comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 40. According to an exemplary embodiment, the number of carbon atoms of the aryl group is 6 to 20. Examples of the monocyclic aryl group comprise a phenyl group, a biphenyl group, a terphenyl group, and the like, but are not limited thereto. Examples of the polycyclic aryl group comprise a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the fluorenyl group may be

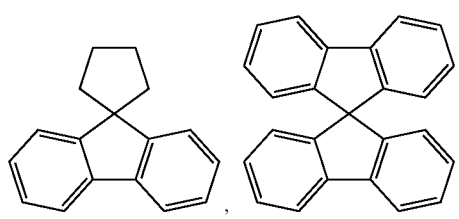

(spirobifluorene),

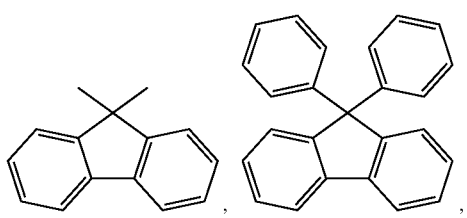

and the like. However, the fluorenyl group is not limited thereto.

In the present specification, a heteroaryl group comprises one or more atoms other than carbon, that is, one or more heteroatoms, and specifically, the heteroatom may comprise one or more atoms selected from the group consisting of O, N, Se, S, and the like. The number of carbon atoms thereof is not particularly limited, but is preferably 2 to 60. According to an exemplary embodiment, the number of carbon atoms of the heteroaryl group is 2 to 40. According to an exemplary embodiment, the number of carbon atoms of the heteroaryl group is 2 to 20. The heteroaryl group may be monocyclic or polycyclic. Examples of a heterocyclic group comprise a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the arylene group may be selected from the above-described examples of the aryl group, except for being a divalent group.

In the present specification, the alkylene group may be selected from the above-described examples of the alkyl group, except for being a divalent group.

In the present specification, the heteroarylene group may be selected from the above-described examples of the heteroaryl group, except for being a divalent group.

According to an exemplary embodiment of the present specification, R1 to R6 are the same as or different from each other, and are each independently hydrogen; deuterium; a halogen group; a substituted or unsubstituted alkyl group; a substituted or unsubstituted aryl group; or a substituted or unsubstituted heteroaryl group.

According to another exemplary embodiment, R1 to R6 are the same as or different from each other, and are each independently hydrogen; deuterium; a halogen group; a substituted or unsubstituted alkyl group having 1 to 40 carbon atoms; a substituted or unsubstituted aryl group having 6 to 60 carbon atoms; or a substituted or unsubstituted heteroaryl group having 2 to 60 carbon atoms.

In still another exemplary embodiment, R1 to R6 are the same as or different from each other, and are each independently hydrogen; deuterium; a halogen group; or a substituted or unsubstituted alkyl group having 1 to 20 carbon atoms.

According to yet another exemplary embodiment, R1 to R6 are the same as or different from each other, and are each independently hydrogen; deuterium; a halogen group; a substituted or unsubstituted methyl group; a substituted or unsubstituted ethyl group; a substituted or unsubstituted propyl group; a substituted or unsubstituted butyl group; a substituted or unsubstituted isobutyl group; a substituted or unsubstituted tert-butyl group; a substituted or unsubstituted pentyl group; or a substituted or unsubstituted hexyl group.

In still yet another exemplary embodiment, R1 to R6 are the same as or different from each other, and are each independently hydrogen; deuterium; a halogen group; a methyl group unsubstituted or substituted with a halogen group; an ethyl group unsubstituted or substituted with a halogen group; a propyl group unsubstituted or substituted with a halogen group; a substituted or unsubstituted butyl group; an isobutyl group unsubstituted or substituted with a halogen group; a tert-butyl group unsubstituted or substituted with a halogen group; a pentyl group unsubstituted or substituted with a halogen group; or a hexyl group unsubstituted or substituted with a halogen group.

According to a further exemplary embodiment, R1 to R6 are the same as or different from each other, and are each independently hydrogen; deuterium; fluorine; a methyl group unsubstituted or substituted with fluorine; an ethyl group; a propyl group; a butyl group; an isobutyl group; a tert-butyl group; a pentyl group; or a hexyl group.

According to another further exemplary embodiment, R1 and R4 are the same as or different from each other, and are each independently hydrogen; deuterium; fluorine; a methyl group unsubstituted or substituted with fluorine; an ethyl group; a propyl group; a butyl group; an isobutyl group; a tert-butyl group; a pentyl group; or a hexyl group.

According to still another further exemplary embodiment, R2, R3, R5, and R6 are hydrogen.

According to an exemplary embodiment of the present specification, n2, n3, n5, and n6 are each an integer of 0 to 2.

According to another exemplary embodiment, n2, n3, n5, and n6 are each 0 or 1.

According to still another exemplary embodiment, n1 and n4 are each an integer of 0 to 5.

According to yet another exemplary embodiment, n1 and n4 are each 0, 1, 2, or 5.

In an exemplary embodiment of the present specification, L is a substituted or unsubstituted arylene group; or a substituted or unsubstituted heteroarylene group.

In an exemplary embodiment of the present specification, L is a substituted or unsubstituted arylene group having 6 to 30 carbon atoms; or a substituted or unsubstituted heteroarylene group having 2 to 30 carbon atoms.

According to another exemplary embodiment, L may be a substituted or unsubstituted phenylene group; a substituted or unsubstituted biphenylene group; a substituted or unsubstituted terphenylene group; a substituted or unsubstituted fluorenylene group; a substituted or unsubstituted phenanthrenylene group; a substituted or unsubstituted binaphthylene group; or a substituted or unsubstituted naphthylene group, or a group to which two or more among the substituents are linked.

In an exemplary embodiment of the present specification, L may be any one of the following structures, but is not limited thereto, and the following structures may be additionally substituted.

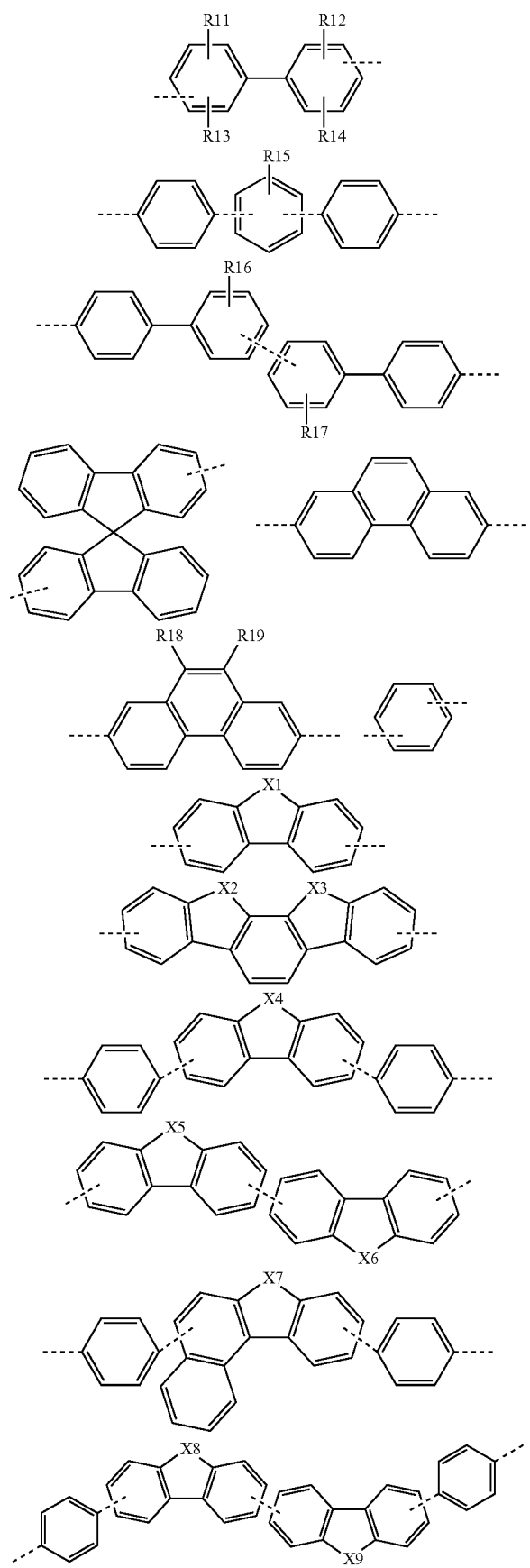
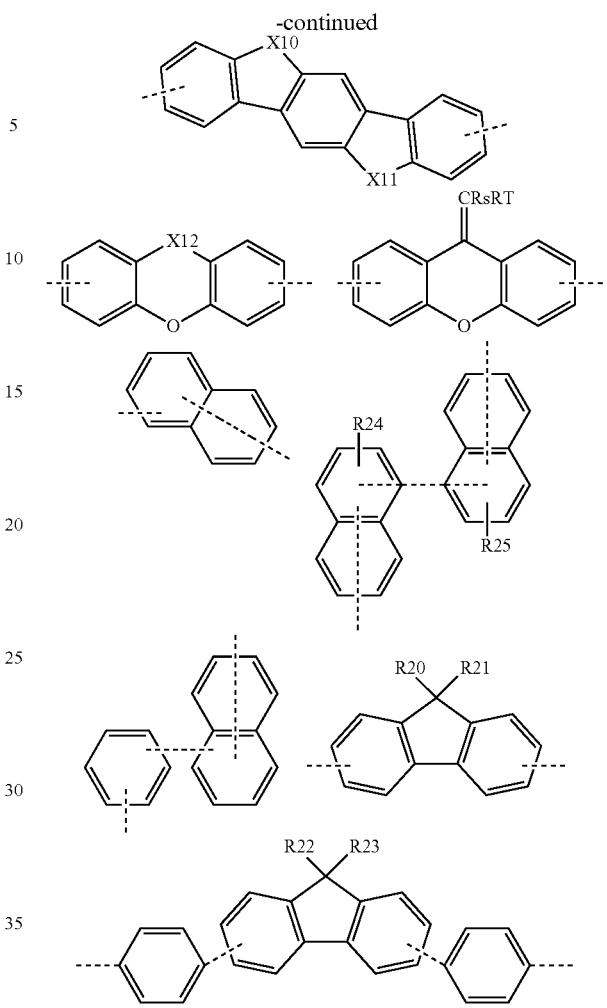

In the structures,

X12 is S, SO, CRuRv, SiRwRx or NRy,

X1 to X11 are the same as or different from each other, and are each independently O, S, SiR'R" or NR, and R11 to R25, Rs, Rt, Ru, Rv, Rw, Rx, Ry, R, R', and R" are the same as or different from each other, and are each independently hydrogen; deuterium; a halogen group; a substituted or unsubstituted alkyl group; or a substituted or unsubstituted aryl group.

In an exemplary embodiment of the present specification, R11 to R25, Rs, Rt, Ru, Rv, Rw, Rx, and Ry are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In another exemplary embodiment, R11 to R25, Rs, Rt, Ru, Rv, Rw, Rx, and Ry are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

According to still another exemplary embodiment, R11 to R25, Rs, Rt, Ru, Rv, Rw, Rx, and Ry are the same as or different from each other, and are each independently hydrogen; deuterium; a halogen group; a substituted or unsubstituted alkyl group having 1 to 20 carbon atoms; or an aryl group having 6 to 20 carbon atoms, which is unsubstituted or substituted with an alkyl group having 1 to 20 carbon atoms.

According to yet another exemplary embodiment, R11 to R25, Rs, Rt, Ru, Rv, Rw, Rx, and Ry are the same as or different from each other, and are each independently hydrogen; deuterium; a halogen group; a substituted or unsubstituted alkyl group having 1 to 8 carbon atoms; or an aryl group having 6 to 12 carbon atoms, which is unsubstituted or substituted with an alkyl group having 1 to 10 carbon atoms.

According to still yet another exemplary embodiment, R11 to R25, Rs, Rt, Ru, Rv, Rw, Rx, and Ry are the same as or different from each other, and are each independently hydrogen; deuterium; a substituted or unsubstituted methyl group; a substituted or unsubstituted ethyl group; a substituted or unsubstituted propyl group; a substituted or unsubstituted butyl group; a substituted or unsubstituted t-butyl group; a substituted or unsubstituted pentyl group; a substituted or unsubstituted hexyl group; or a phenyl group unsubstituted or substituted with a methyl group, a butyl group or a hexyl group.

According to a further exemplary embodiment, R11 to R23, Rs, Rt, Ru, Rv, Rw, Rx, and Ry are the same as or different from each other, and are each independently hydrogen; deuterium; a methyl group; an ethyl group; a propyl group; a butyl group; a t-butyl group; a pentyl group; a hexyl group; or a phenyl group unsubstituted or substituted with a methyl group, a butyl group or a hexyl group.

In an exemplary embodiment of the present specification, R, R', and R" are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In another exemplary embodiment, R, R', and R" are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

According to still another exemplary embodiment, R, R', and R" are the same as or different from each other, and are each independently hydrogen; deuterium; a halogen group; a substituted or unsubstituted alkyl group having 1 to 20 carbon atoms; or an aryl group having 6 to 20 carbon atoms, which is unsubstituted or substituted with an alkyl group having 1 to 20.

In yet another exemplary embodiment, R11 to R25, Rs, Rt, Ru, Rv, Rw, Rx, and Ry are the same as or different from each other, and are each independently hydrogen; deuterium; a halogen group; a substituted or unsubstituted alkyl group having 1 to 8 carbon atoms; or an aryl group having 6 to 12 carbon atoms, which is unsubstituted or substituted with an alkyl group having 1 to 10 carbon atoms.

According to still yet another exemplary embodiment, R, R', and R" are the same as or different from each other, and are each independently hydrogen; deuterium; a substituted or unsubstituted methyl group; a substituted or unsubstituted ethyl group; a substituted or unsubstituted propyl group; a substituted or unsubstituted butyl group; a substituted or unsubstituted t-butyl group; a substituted or unsubstituted pentyl group; a substituted or unsubstituted hexyl group; or a phenyl group unsubstituted or substituted with a methyl group, a butyl group, a t-butyl group or a hexyl group.

According to a further exemplary embodiment, R, R', and R" are the same as or different from each other, and are each independently hydrogen; deuterium; a methyl group; an ethyl group; a propyl group; a butyl group; a t-butyl group; a pentyl group; a hexyl group; or a phenyl group unsubstituted or substituted with a methyl group, a butyl group, a t-butyl group or a hexyl group.

In an exemplary embodiment of the present specification, X12 is S or SO.

In an exemplary embodiment of the present specification, X12 is CRuRv, SiRwRx or NRy.

In an exemplary embodiment of the present specification, L may be any one of the following structures.

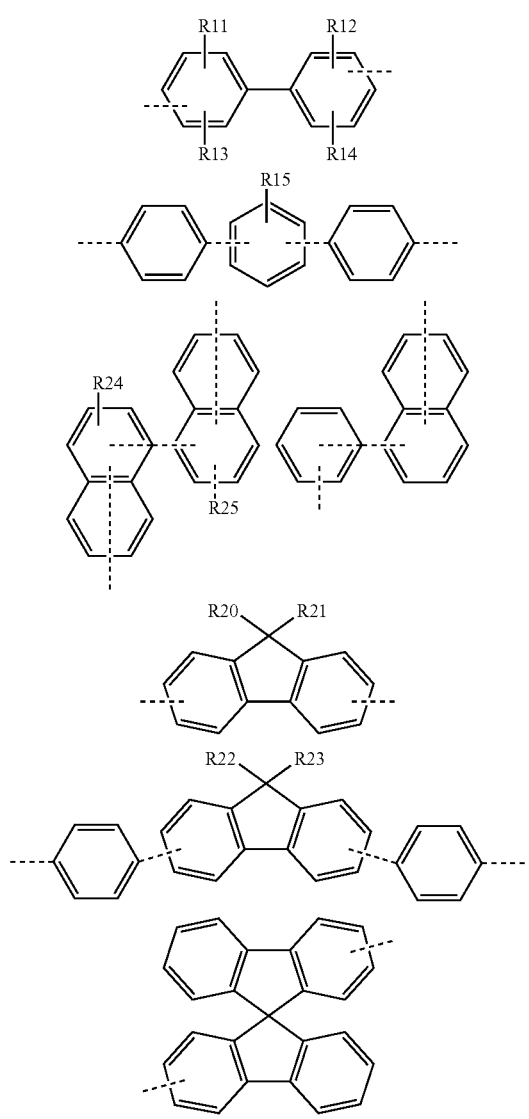

The structures may be further substituted with a substituted or unsubstituted alkyl group; or a substituted or unsubstituted aryl group.

According to an exemplary embodiment of the present specification, Formula 1 may be any one of the following Formulae 2 to 8.

[Formula 2]
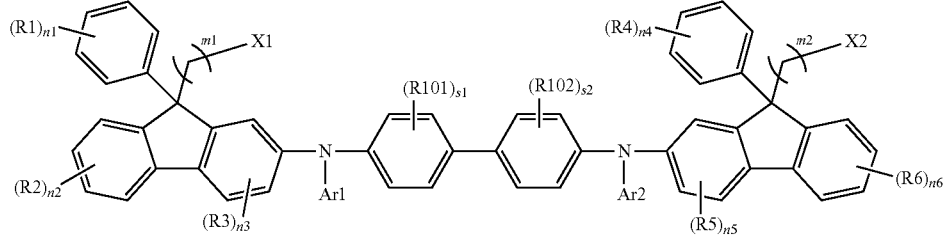
[Formula 3]
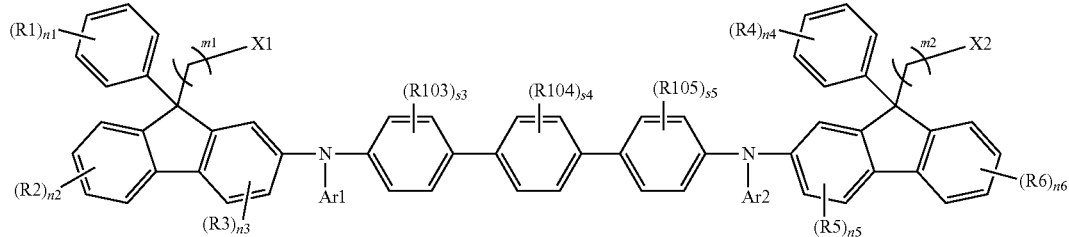
[Formula 4]
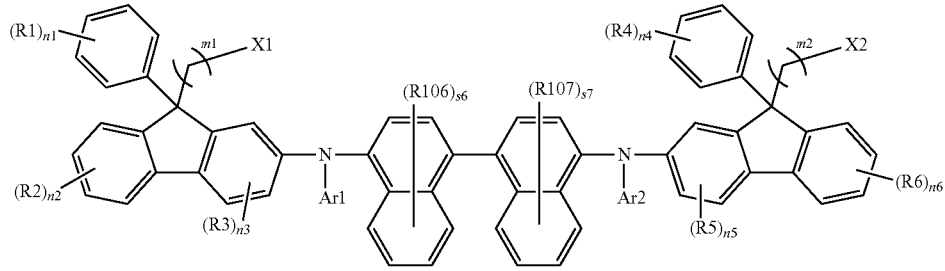
[Formula 5]
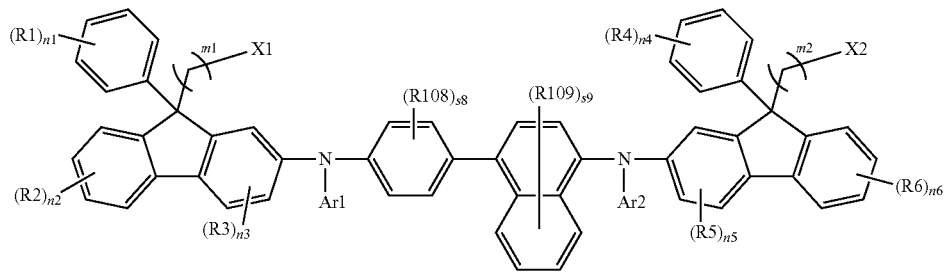
[Formula 6]
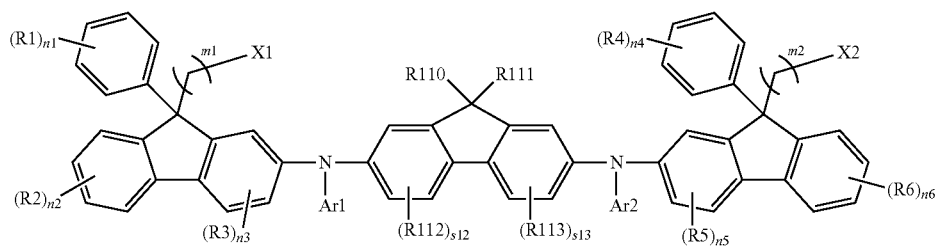
[Formula 7]
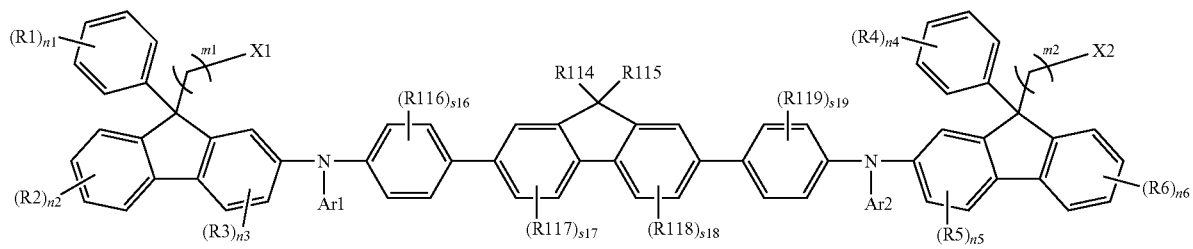

-continued

[Formula 8]

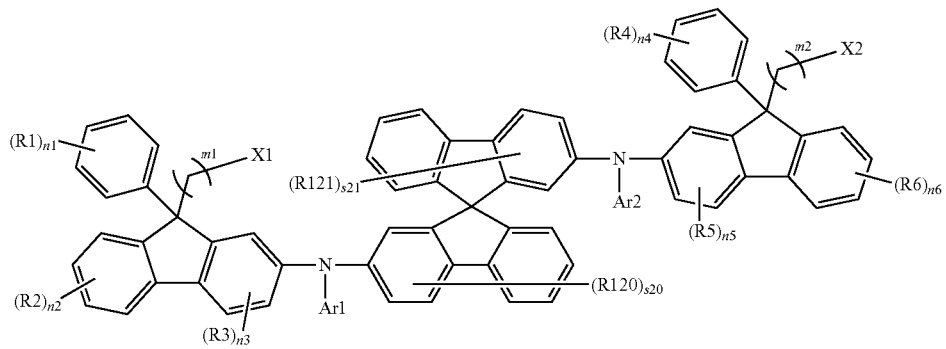

In Formulae 2 to 8, the definitions of R1 to R6, n1 to n6, m1, m2, Ar1, Ar2, X1, and X2 are the same as those in Formula 1, R101 to R121 are the same as or different from each other, and are each independently hydrogen; deuterium; a halogen group; a substituted or unsubstituted alkyl group; or a substituted or unsubstituted aryl group, s1 to s5, s8, s16, and s19 are each an integer of 0 to 4, s6, s7, and s9 are each integer of 0 to 6, s12, s13, s17, and s18 are each an integer of 0 to 3, s20 and s21 are each an integer of 0 to 7, and when s1 to s9, s12, s13, and s16 to s21 are each 2 or more, the substituents in the parenthesis are the same as or different from each other.

According to an exemplary embodiment of the present specification, R101 to R121 are the same as or different from each other, and are each independently hydrogen; deuterium; a halogen group; a substituted or unsubstituted alkyl group having 1 to 20 carbon atoms; or a substituted or unsubstituted aryl group having 6 to 30 carbon atoms.

In another exemplary embodiment, R101 to R121 are the same as or different from each other, and are each independently hydrogen; deuterium; a halogen group; an alkyl group having 1 to 20 carbon atoms; or an aryl group having 6 to 30 carbon atoms, which is unsubstituted or substituted with an alkyl group having 1 to 20 carbon atoms.

According to still another exemplary embodiment, R101 to R121 are the same as or different from each other, and are each independently hydrogen; deuterium; a substituted or unsubstituted methyl group; a substituted or unsubstituted ethyl group; a substituted or unsubstituted propyl group; a substituted or unsubstituted butyl group; a substituted or unsubstituted t-butyl group; a substituted or unsubstituted pentyl group; a substituted or unsubstituted hexyl group; a substituted or unsubstituted phenyl group; a substituted or unsubstituted biphenyl group; or a substituted or unsubstituted naphthyl group.

In yet another exemplary embodiment, R101 to R121 are the same as or different from each other, and are each independently hydrogen; deuterium; a substituted or unsubstituted methyl group; a substituted or unsubstituted ethyl group; a substituted or unsubstituted propyl group; a substituted or unsubstituted butyl group; a substituted or unsubstituted t-butyl group; a substituted or unsubstituted pentyl group; a substituted or unsubstituted hexyl group; a phenyl group unsubstituted or substituted with one or more selected from the group consisting of a methyl group, an ethyl group, a propyl group, a butyl group, a t-butyl group, a pentyl group, and a hexyl group; a biphenyl group unsubstituted or substituted with one or more selected from the group consisting of a methyl group, an ethyl group, a propyl group, a butyl group, a t-butyl group, a pentyl group, and a hexyl group; or a naphthyl group unsubstituted or substituted with one or more selected from the group consisting of a methyl group, an ethyl group, a propyl group, a butyl group, a t-butyl group, a pentyl group, and a hexyl group.

According to a still yet exemplary embodiment, R101 to R121 are the same as or different from each other, and are each independently hydrogen; deuterium; a methyl group; an ethyl group; a propyl group; a butyl group; a t-butyl group; a pentyl group; a hexyl group; or a phenyl group unsubstituted or substituted with a methyl group, a butyl group, a t-butyl group or a hexyl group.

In an exemplary embodiment of the present specification, s1 to s9, s12, s13, and s16 to s21 are each 0 to 2.

In an exemplary embodiment of the present specification, Ar1 and Ar2 are the same as or different from each other, and are each independently a substituted or unsubstituted aryl group having 6 to 60 carbon atoms; or a substituted or unsubstituted heteroaryl group having 2 to 60 carbon atoms.

In another exemplary embodiment, Ar1 and Ar2 are the same as or different from each other, and are each independently a substituted or unsubstituted aryl group having 6 to 40 carbon atoms; or a substituted or unsubstituted heteroaryl group having 2 to 40 carbon atoms.

In an exemplary embodiment of the present specification, Ar1 and Ar2 may be any one of the following structures, but are not limited thereto, and the following structures may be additionally substituted.

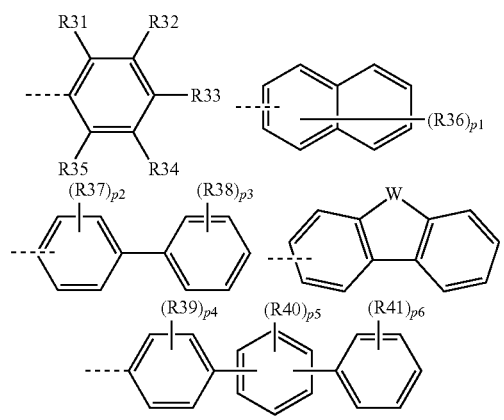

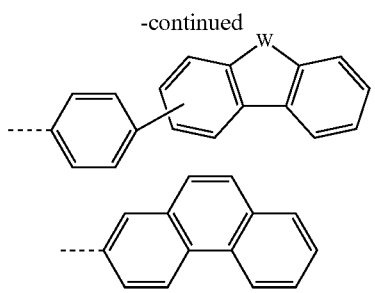

In the structures,

W is O, S, NRa, CRbRc or SiRdRe,

R31 to R41, Ra, Rb, Rc, Rd, and Re are the same as or different from each other, and are each independently hydrogen; deuterium; a halogen group; a substituted or unsubstituted alkyl group; or a substituted or unsubstituted aryl group, p1 is an integer of 0 to 7, p2, p4, and p5 are each an integer of 0 to 4, p3 and p6 are each an integer of 0 to 5, and when p1 to p6 are each 2 or more, the substituents in the parenthesis are the same as or different from each other.

In an exemplary embodiment of the present specification, R39 to R41 are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In an exemplary embodiment of the present specification, R39 to R41 are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In another exemplary embodiment, R39 to R41 are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

In still another exemplary embodiment, R39 to R41 are the same as or different from each other, and are each independently hydrogen.

In an exemplary embodiment of the present specification, R31 to R38 are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In another exemplary embodiment, R31 to R38 are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

In an exemplary embodiment of the present specification, R31 to R38 are the same as or different from each other, and are each independently hydrogen; deuterium; fluorine; a substituted or unsubstituted methyl group; a substituted or unsubstituted ethyl group; a substituted or unsubstituted propyl group; a substituted or unsubstituted phenyl group; a substituted or unsubstituted naphthyl group; or a substituted or unsubstituted biphenyl group.

In another exemplary embodiment, R31 to R38 are the same as or different from each other, and are each independently hydrogen; deuterium; fluorine; a methyl group; an ethyl group; a propyl group; a phenyl group; a naphthyl group; or a biphenyl group.

In an exemplary embodiment of the present specification, W is O.

In an exemplary embodiment of the present specification, W is S.

In an exemplary embodiment of the present specification, W is CRbRc.

In an exemplary embodiment of the present specification, W is SiRdRe.

In an exemplary embodiment of the present specification, Rb, Rc, Rd, and Re are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In an exemplary embodiment of the present specification, Rb, Rc, Rd, and Re are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In another exemplary embodiment, Rb, Rc, Rd, and Re are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

According to another exemplary embodiment, Rb, Rc, Rd, and Re are the same as or different from each other, and are each independently hydrogen; deuterium; a substituted or unsubstituted methyl group; a substituted or unsubstituted ethyl group; or a substituted or unsubstituted phenyl group.

According to still another exemplary embodiment, Rb, Rc, Rd, and Re are the same as or different from each other, and are each independently hydrogen; deuterium; a methyl group; an ethyl group; or a phenyl group.

According to an exemplary embodiment of the present specification, Ar1 and Ar2 are the same as or different from each other, and are each independently a substituted or unsubstituted phenyl group; a substituted or unsubstituted biphenyl group; a substituted or unsubstituted naphthyl group; a substituted or unsubstituted phenanthrenyl group; or a substituted or unsubstituted fluorenyl group.

In an exemplary embodiment of the present specification, Ar1 and Ar2 are the same as or different from each other, and are each independently a phenyl group unsubstituted or substituted with deuterium or an alkyl group; a biphenyl group unsubstituted or substituted with deuterium or an alkyl group; a naphthyl group unsubstituted or substituted with deuterium or an alkyl group; a phenanthrenyl group unsubstituted or substituted with deuterium or an alkyl group; or a fluorenyl group unsubstituted or substituted with deuterium or an alkyl group.

In another exemplary embodiment, Ar1 and Ar2 are the same as or different from each other, and are each independently a phenyl group unsubstituted or substituted with deuterium; a biphenyl group unsubstituted or substituted with deuterium; a naphthyl group; a phenanthrenyl group; or a fluorenyl group substituted with a methyl group.

According to an exemplary embodiment of the present specification, m1 and m2 are 0 or 1.

When m1 is 0, the number 9 carbon of fluorene is directly bonded to X1, and a specific structure thereof is as follows.

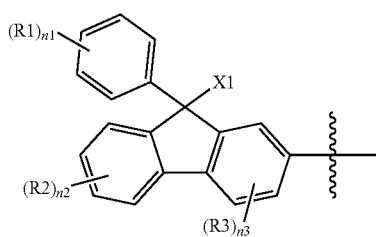

When m2 is 0, the number 9 carbon of fluorene is directly bonded to X2, and a specific structure thereof is as follows.

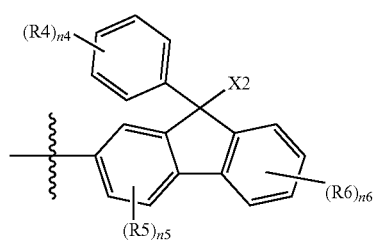

In an exemplary embodiment of the present specification, X1 and X2 are the same as or different from each other, and are each independently a photocurable group or a thermosetting group, and may be the following structure.

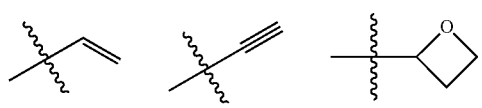

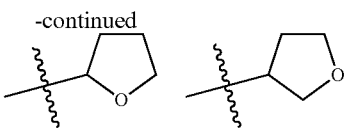

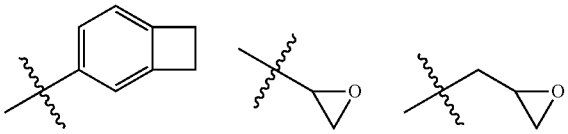

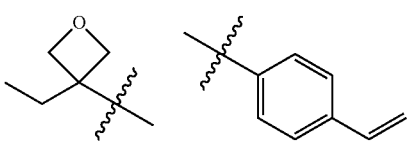

According to another exemplary embodiment, X1 and X2 may be

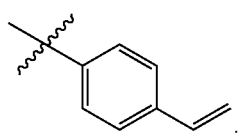 [SMILES: *c1ccc(C=C)cc1]

According to an exemplary embodiment of the present invention, the fluorene-based compound of Formula 1 may be represented by any one of the following compounds.

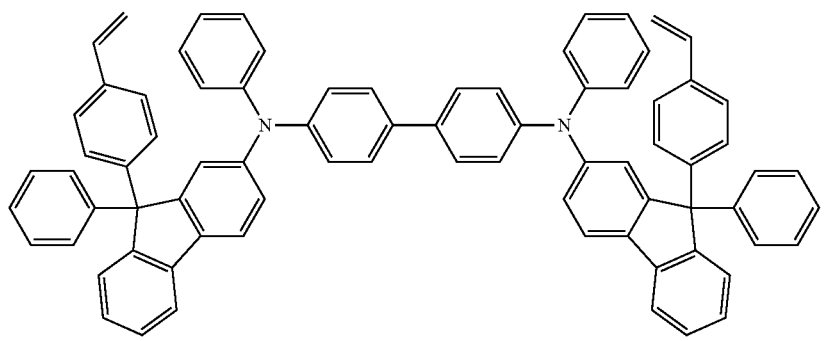

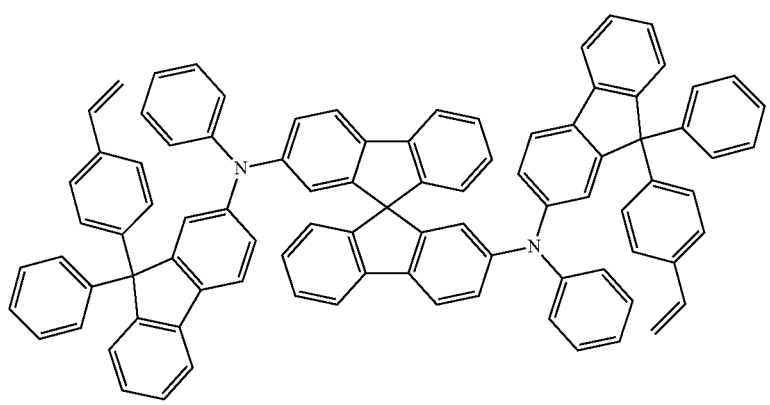

-continued
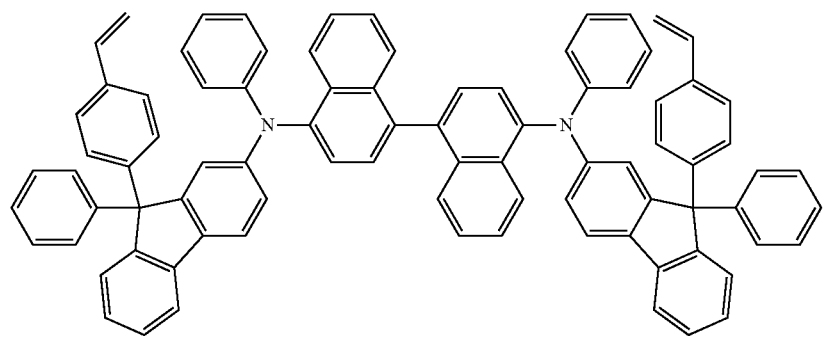
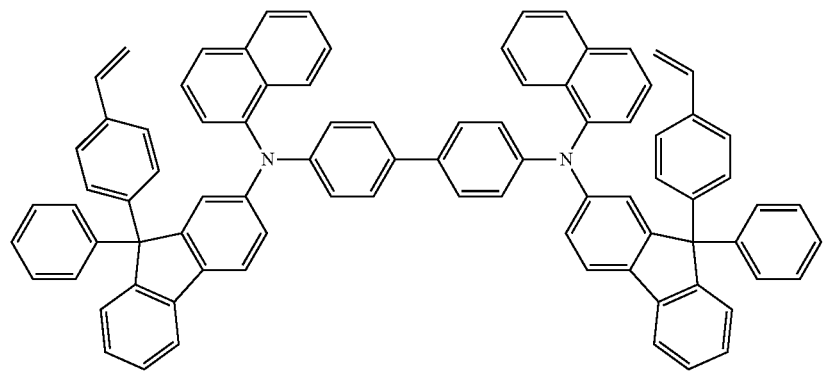
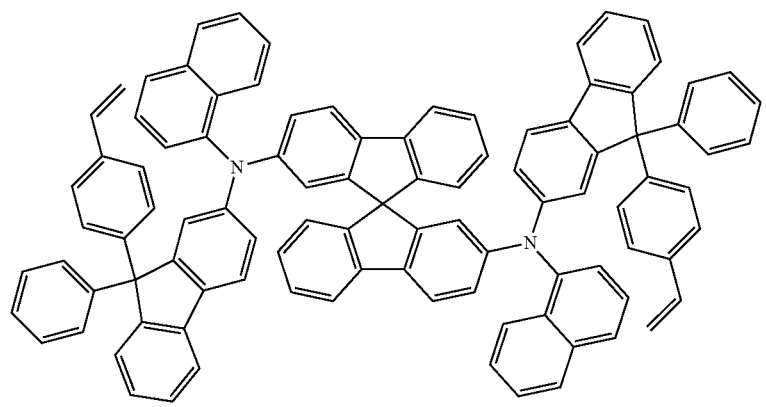
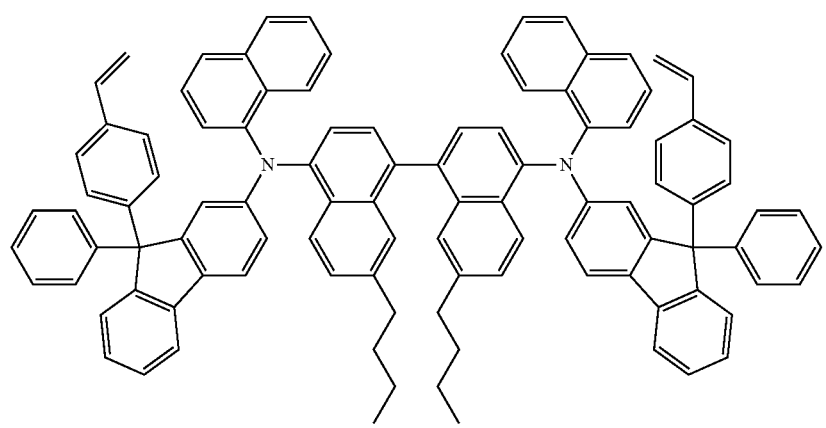

-continued
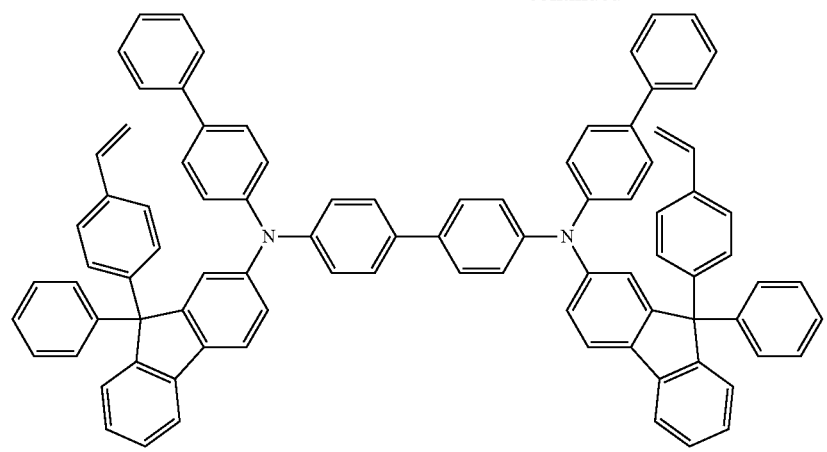
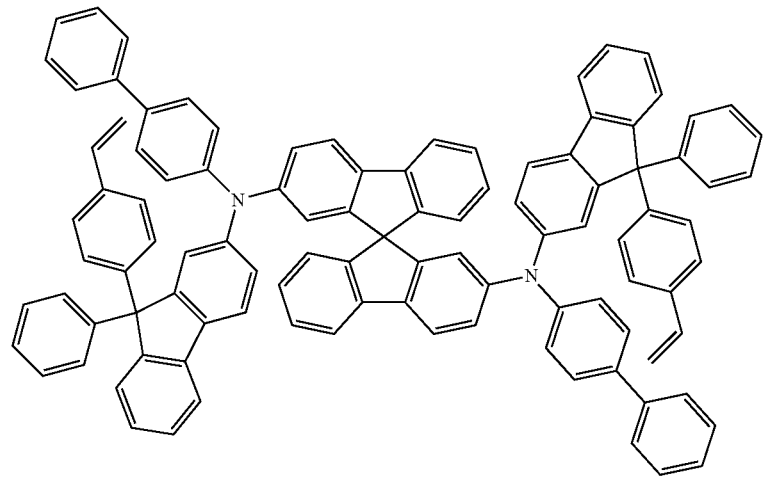
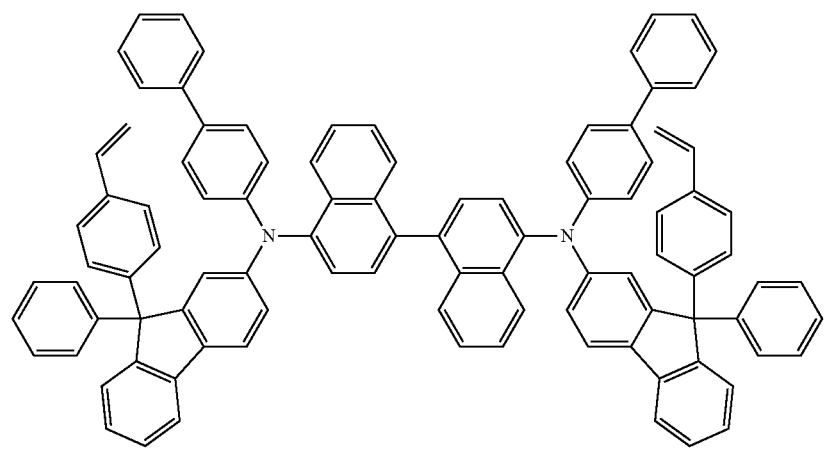
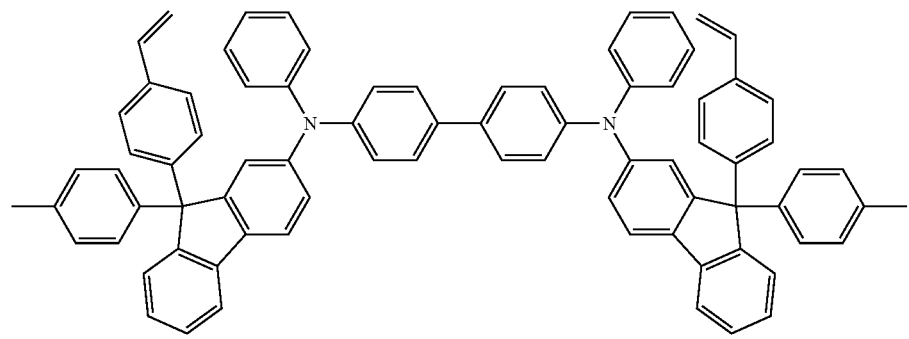

-continued
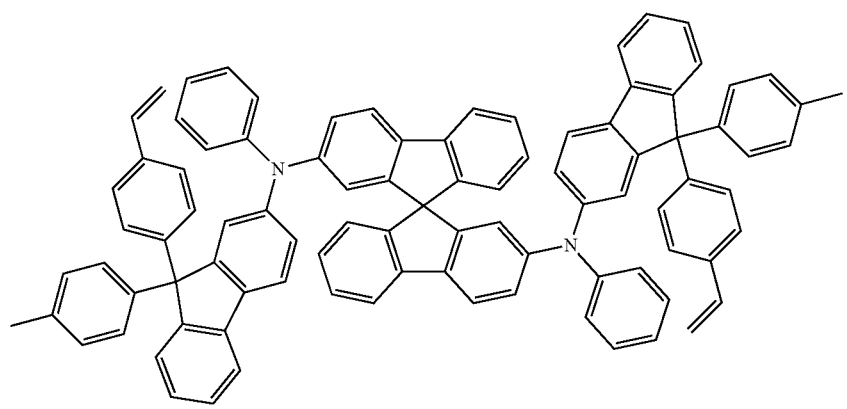
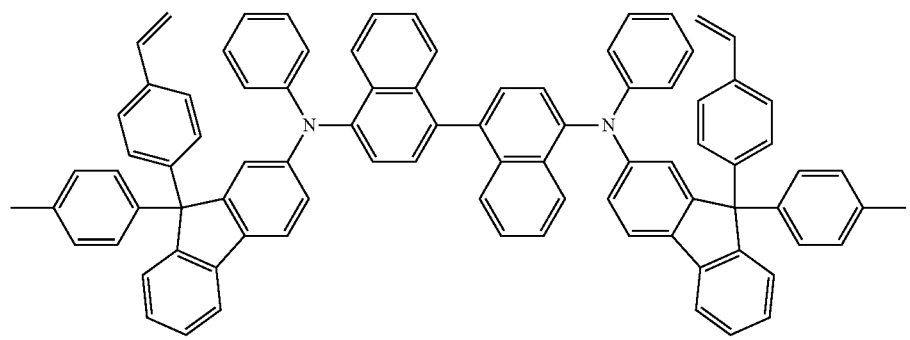
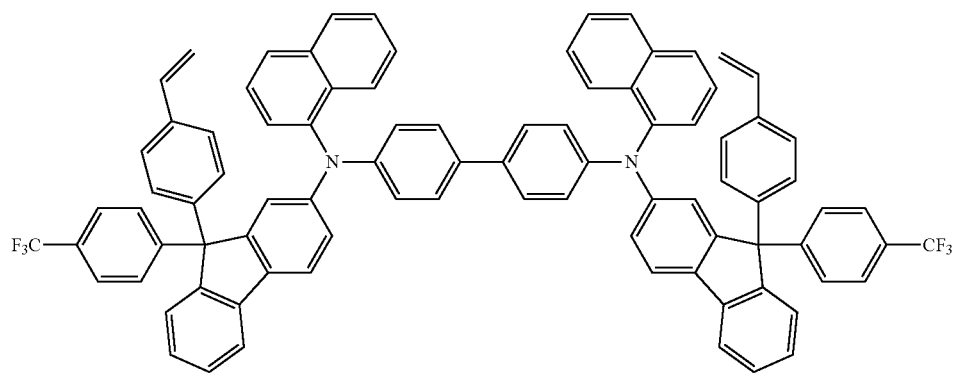
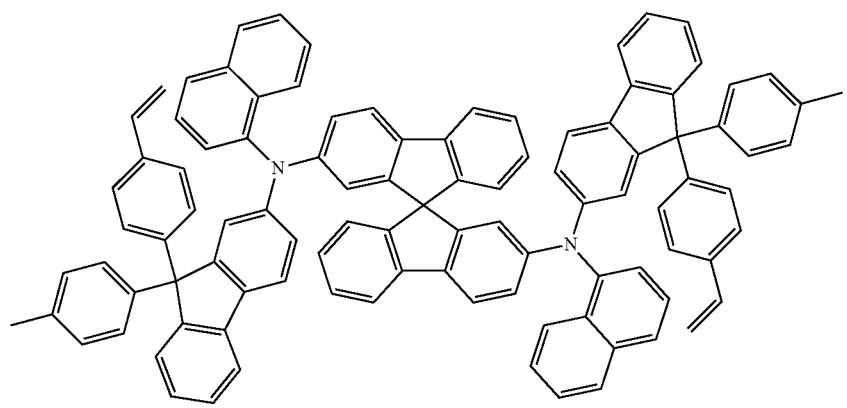

-continued
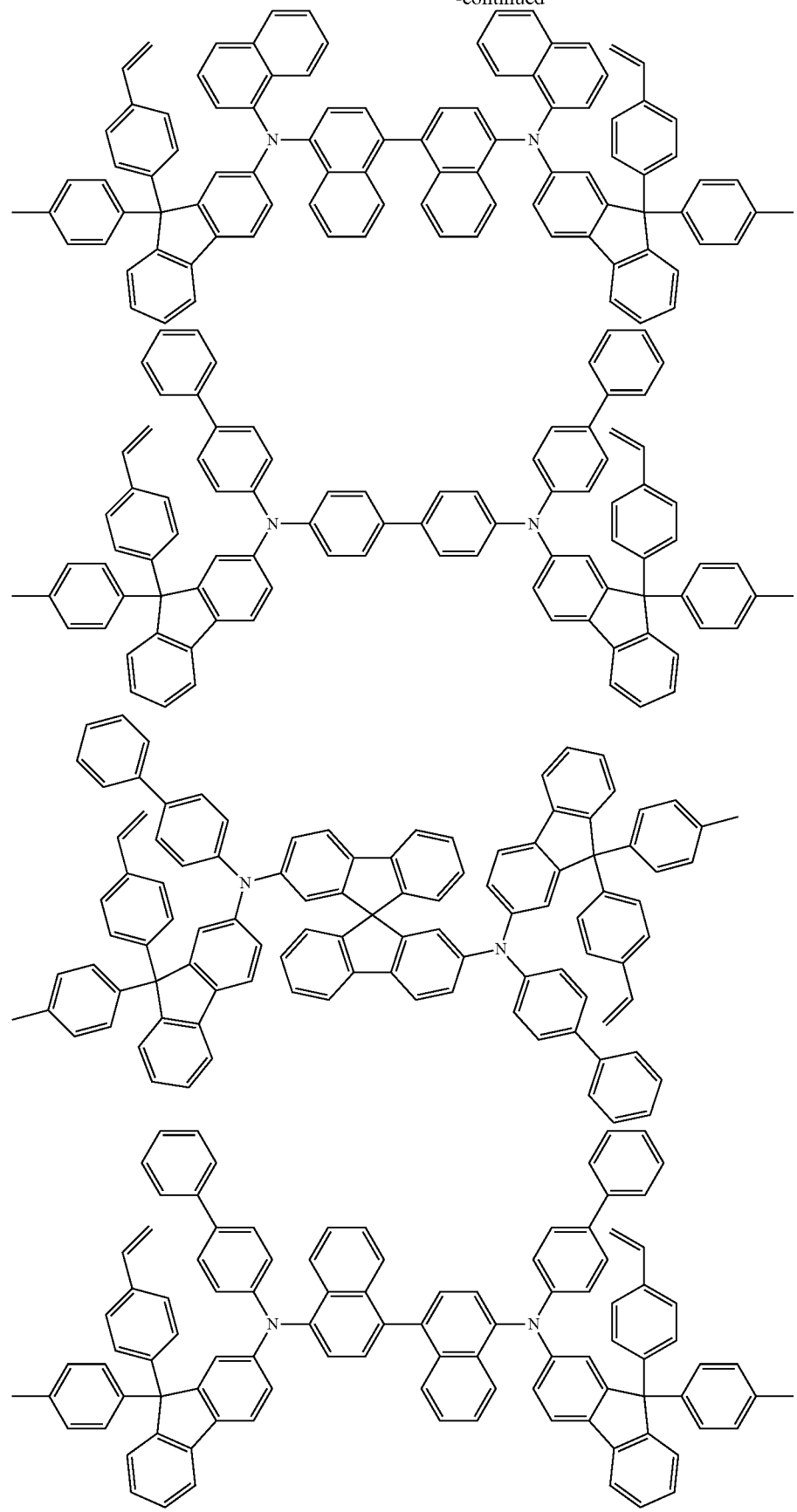

-continued
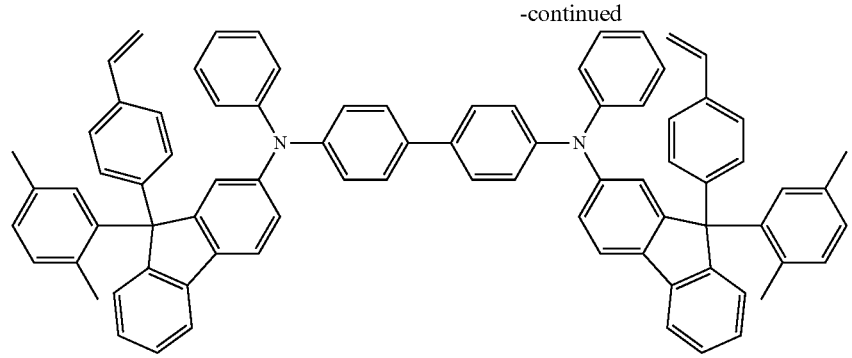
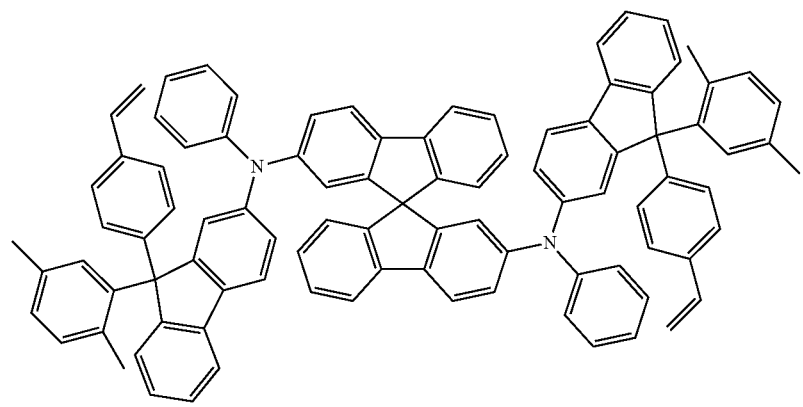
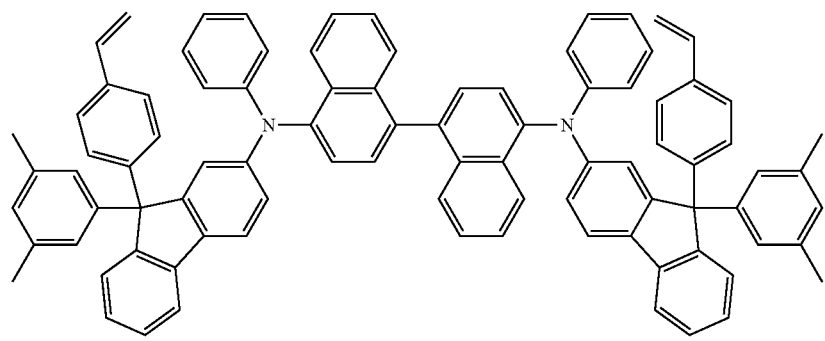
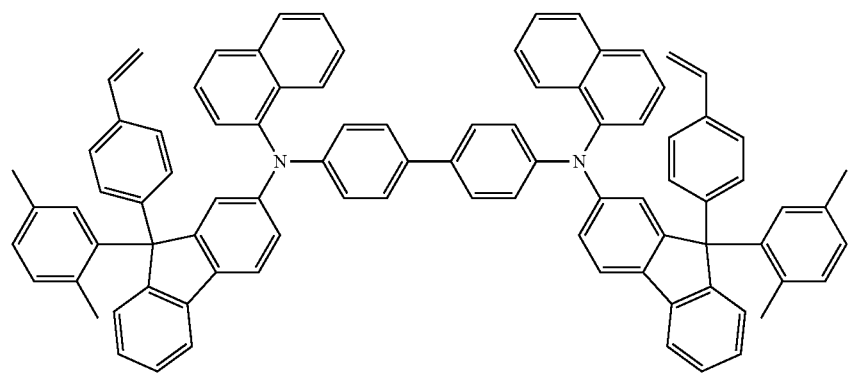

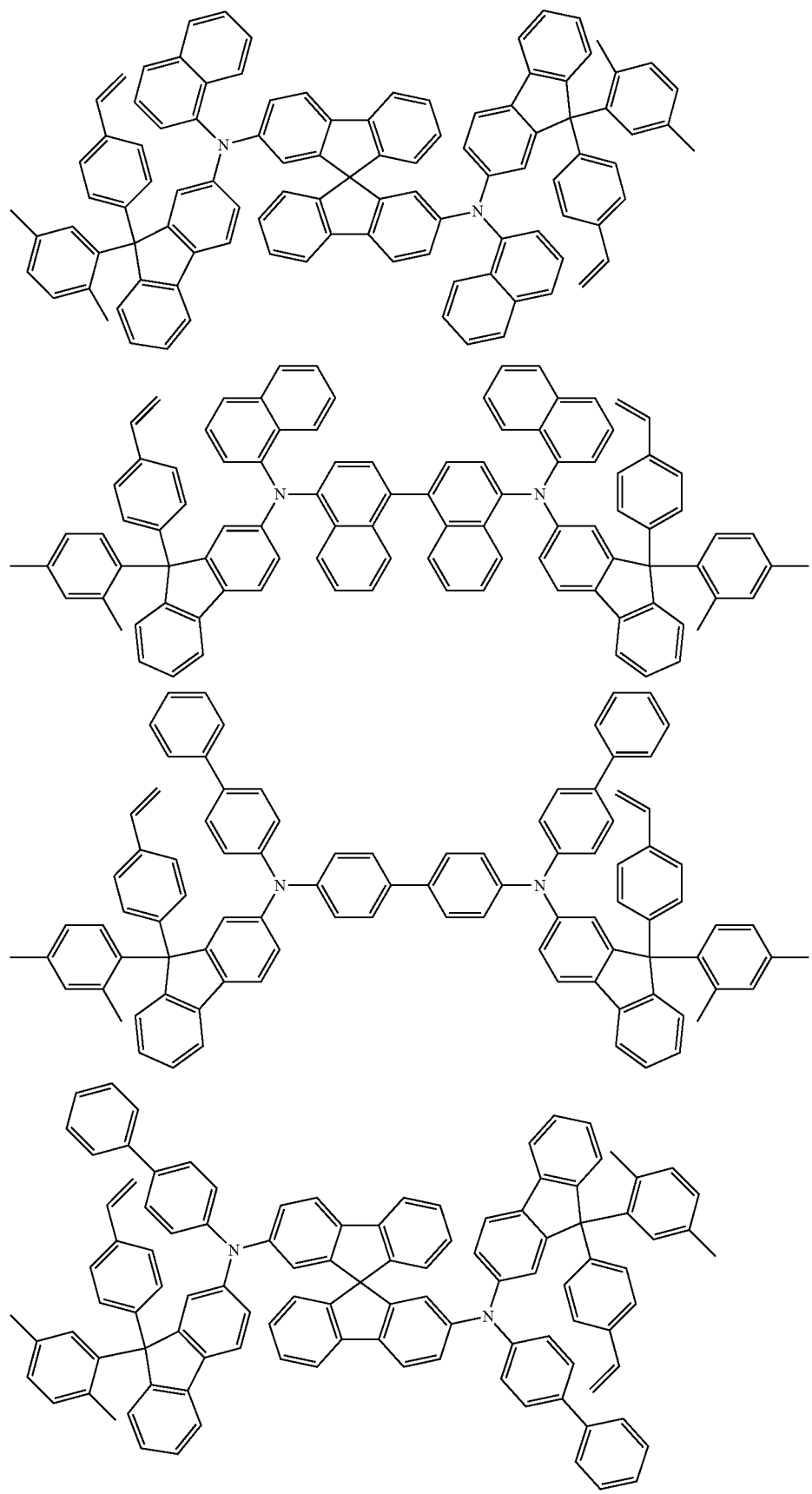

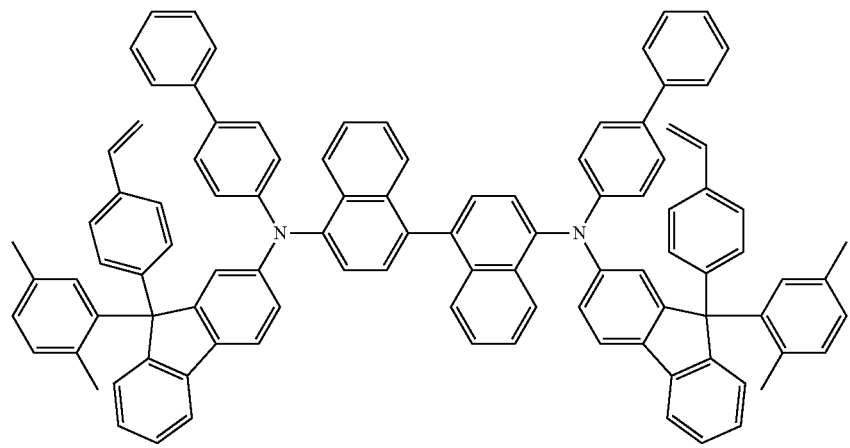
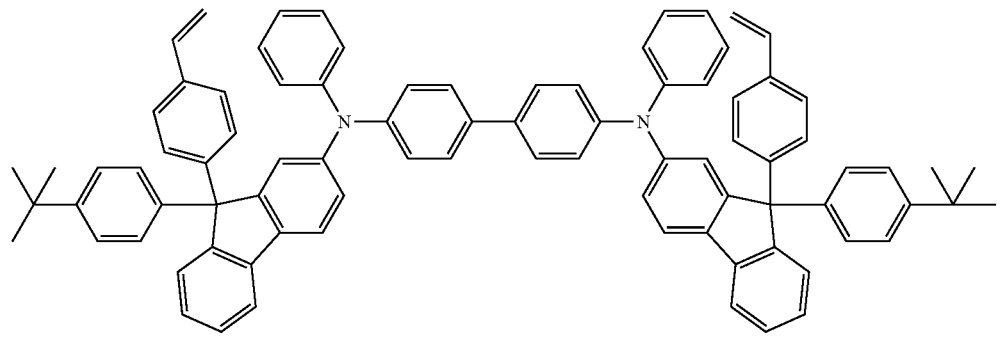
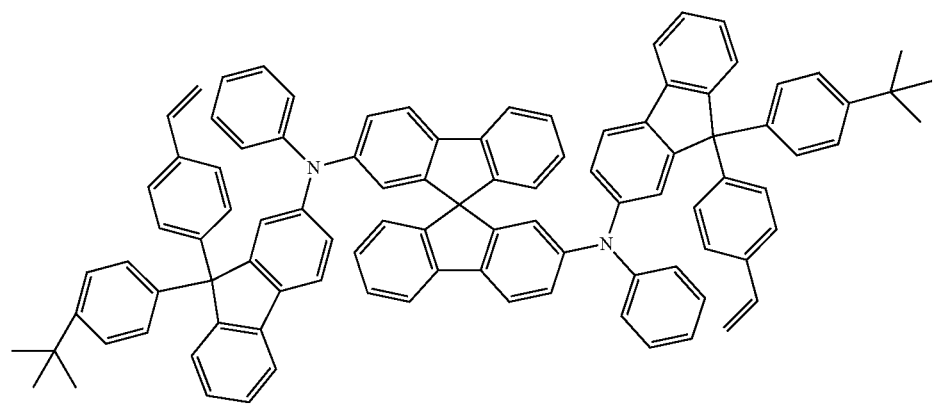
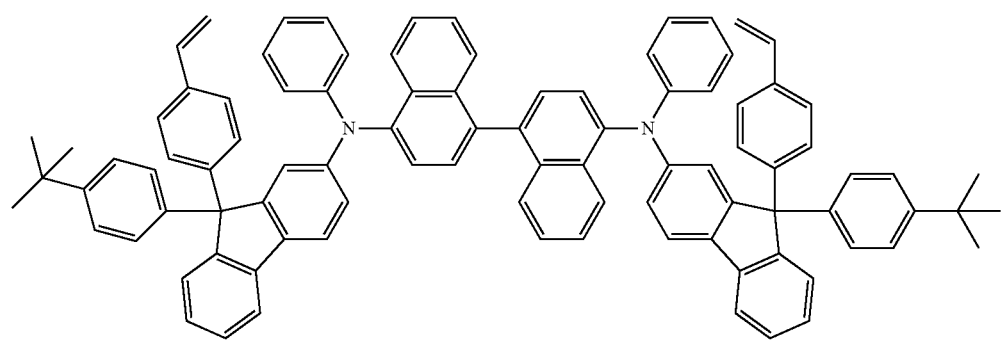

-continued
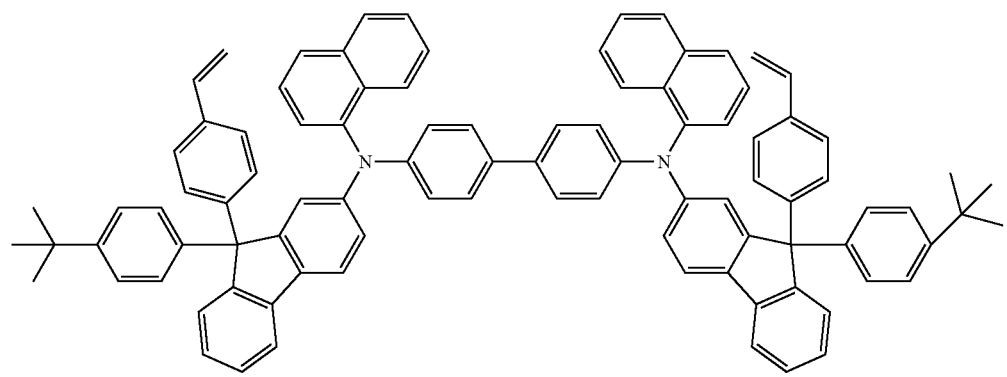
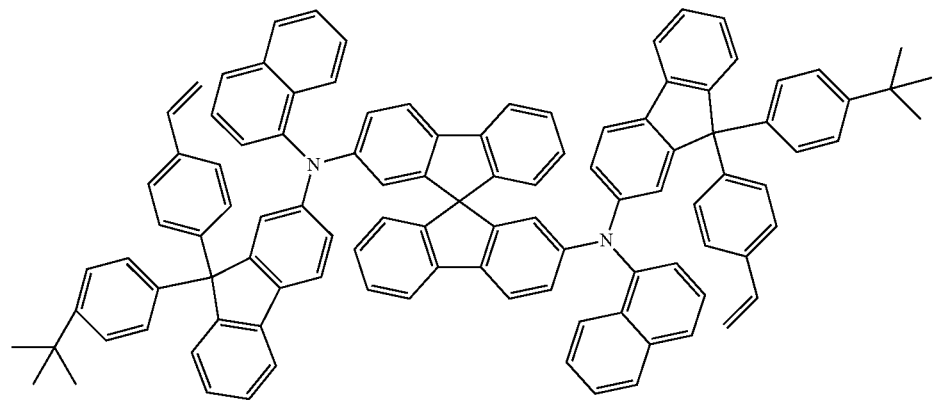
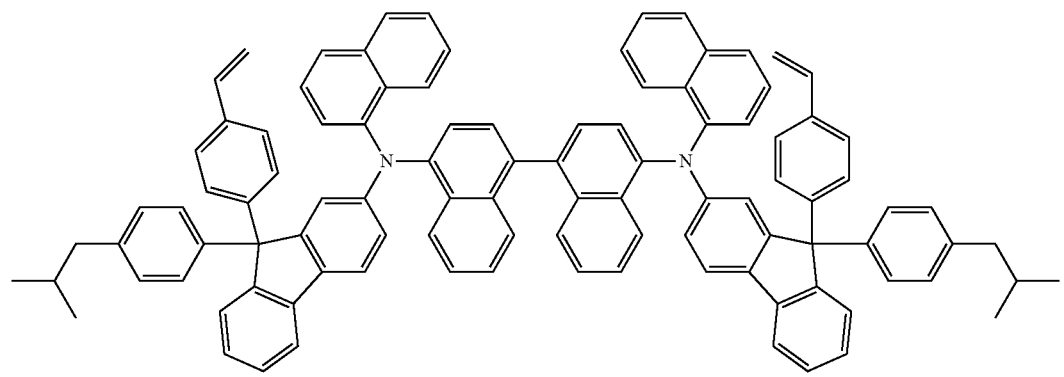
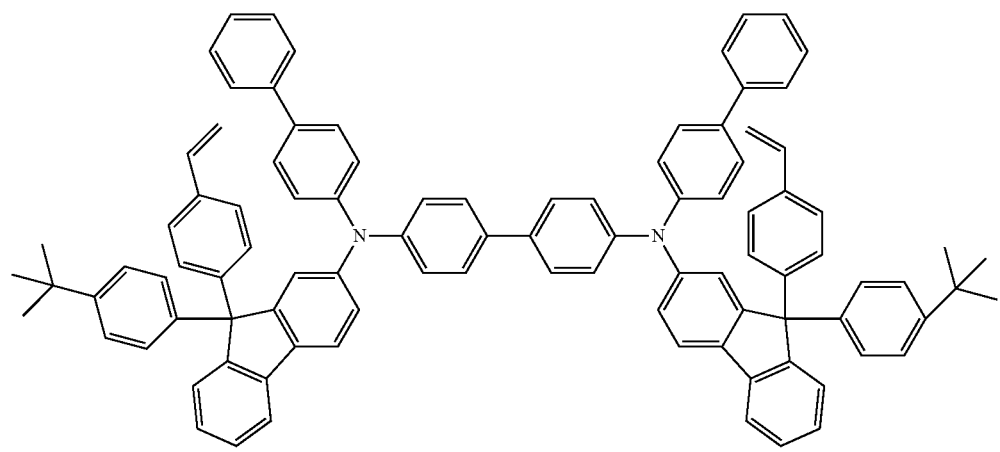

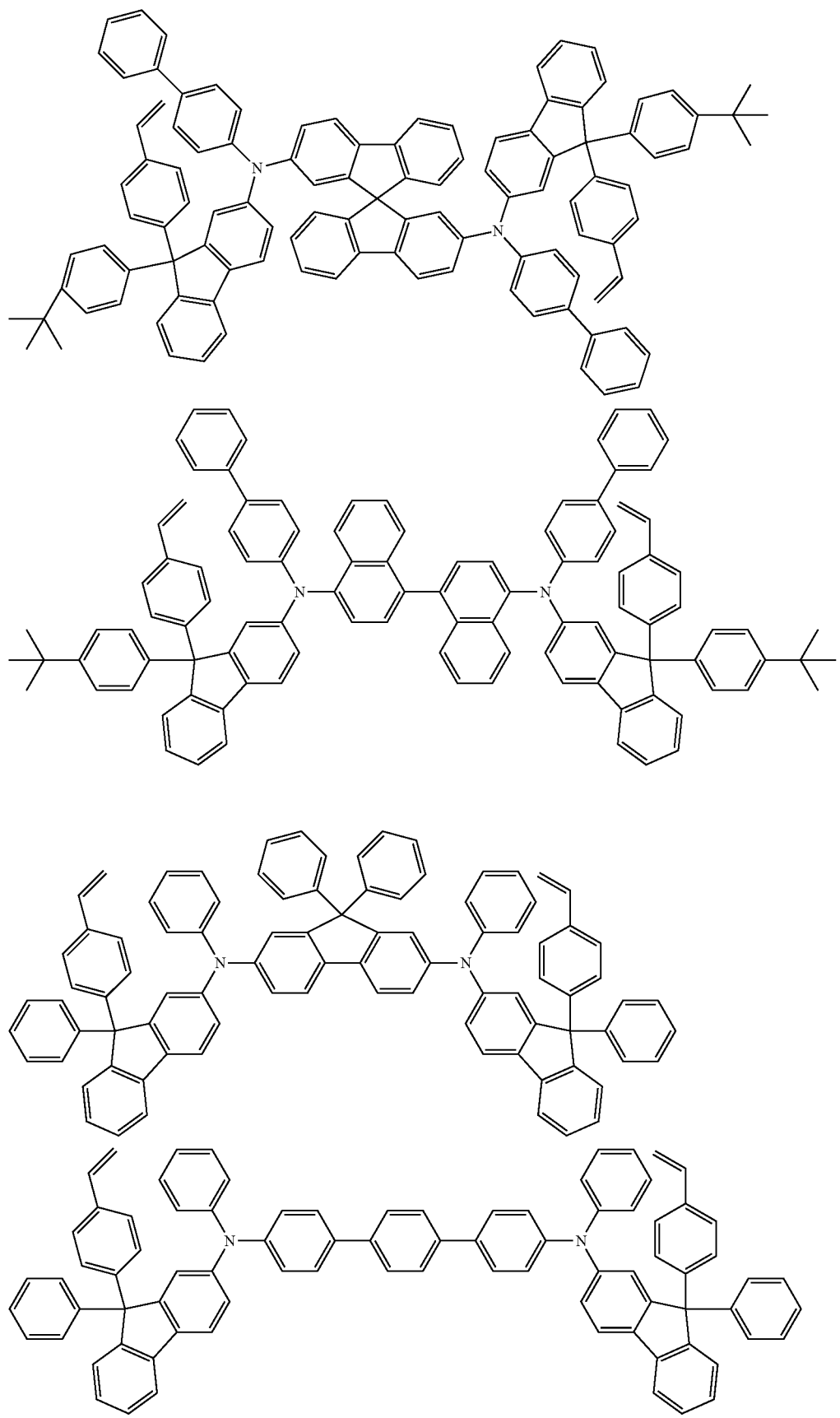

-continued
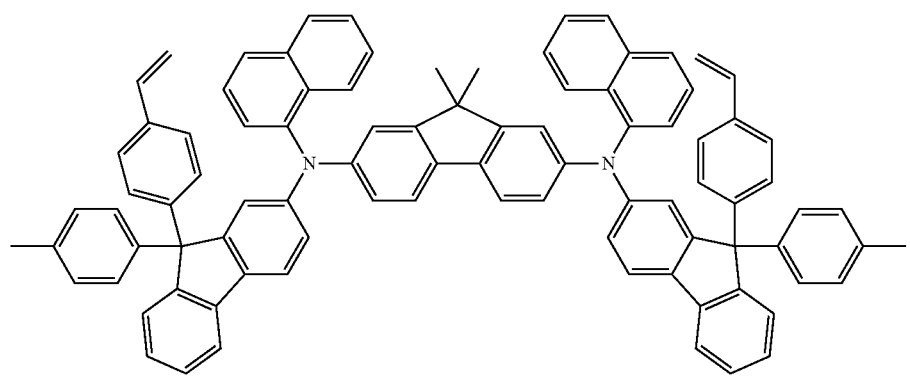
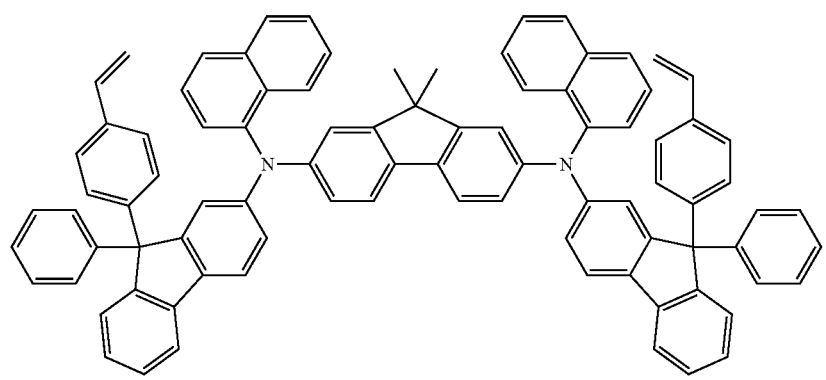
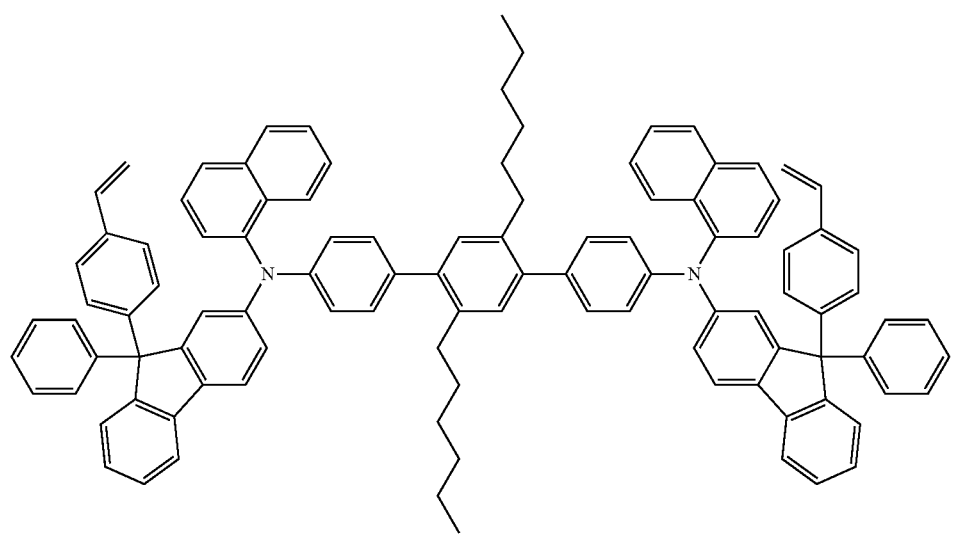

-continued
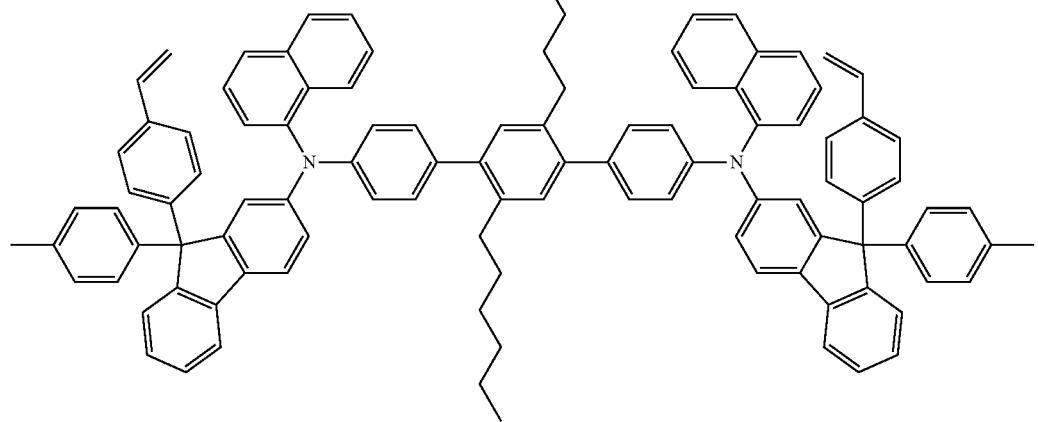
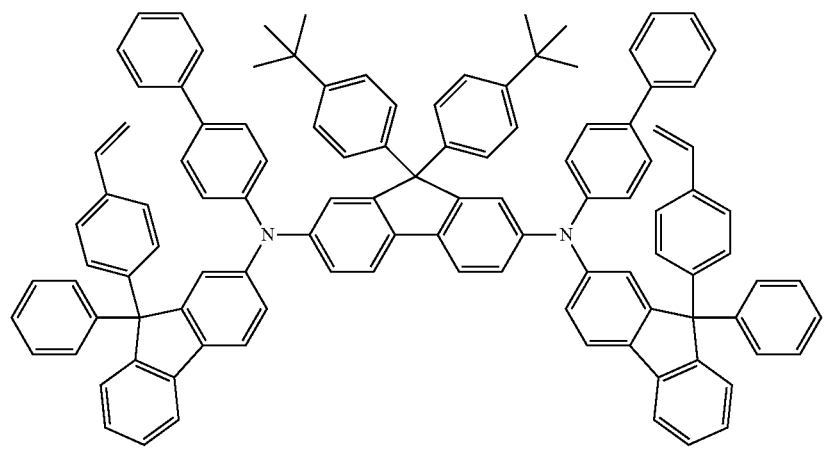
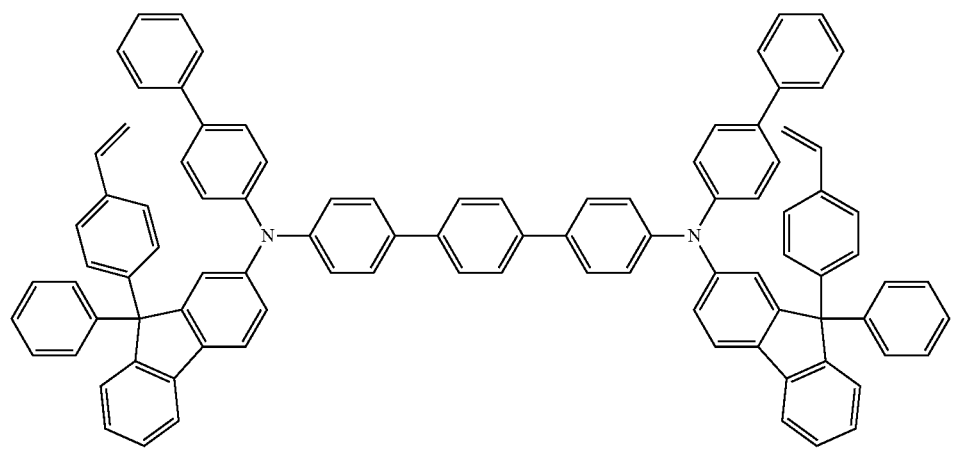

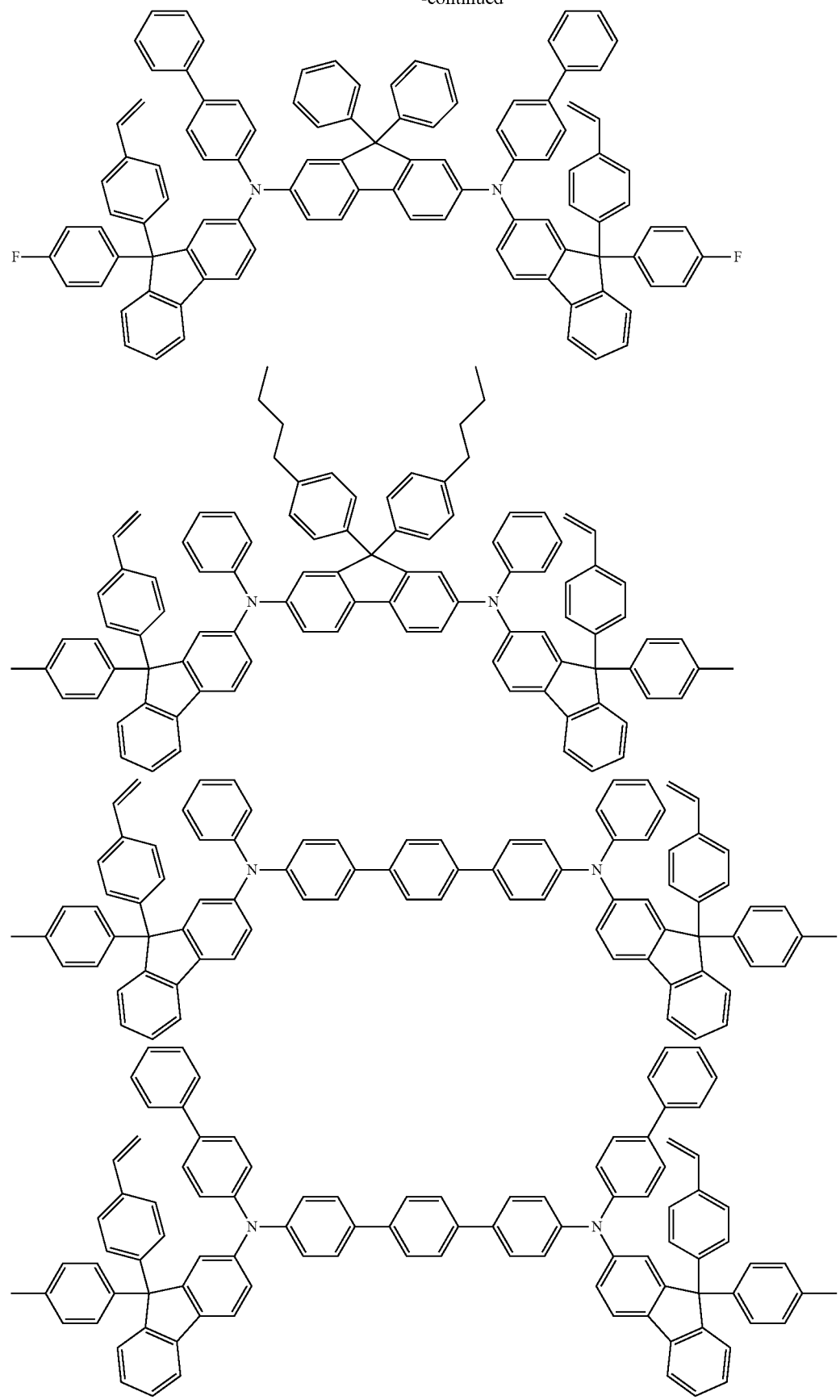

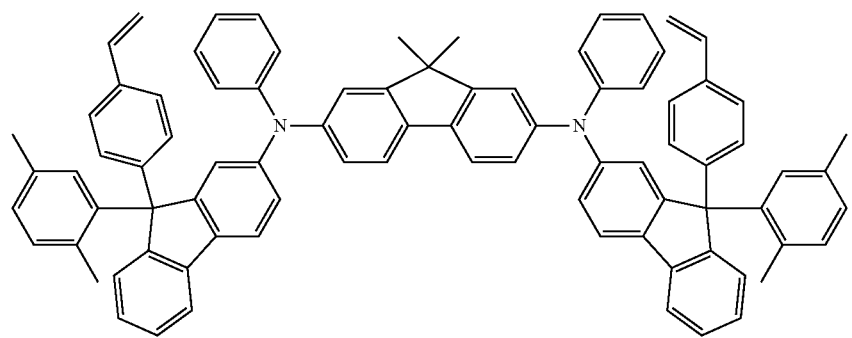
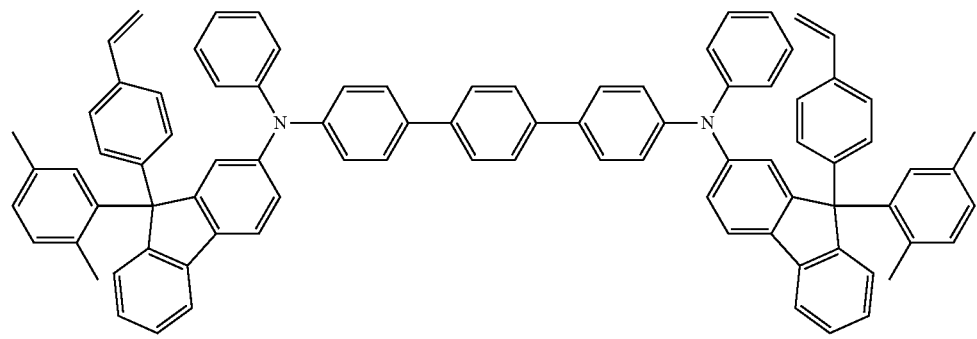
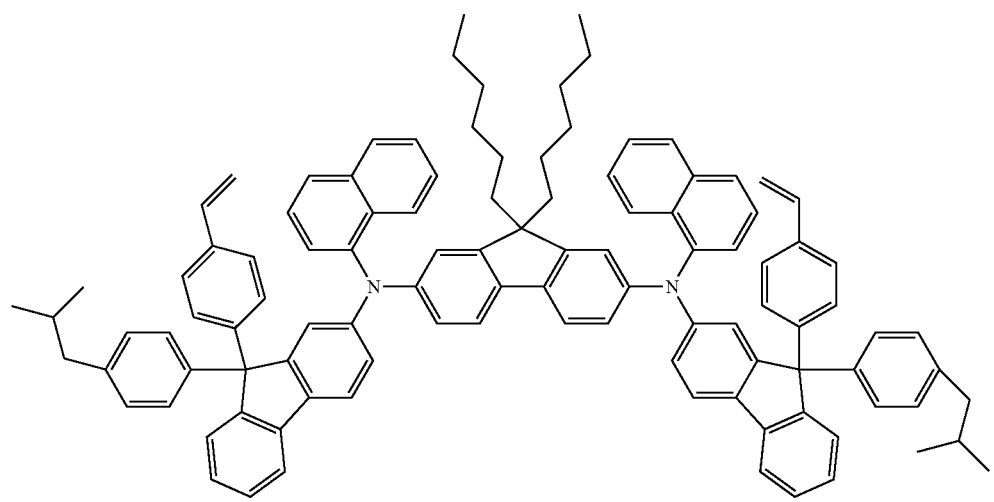
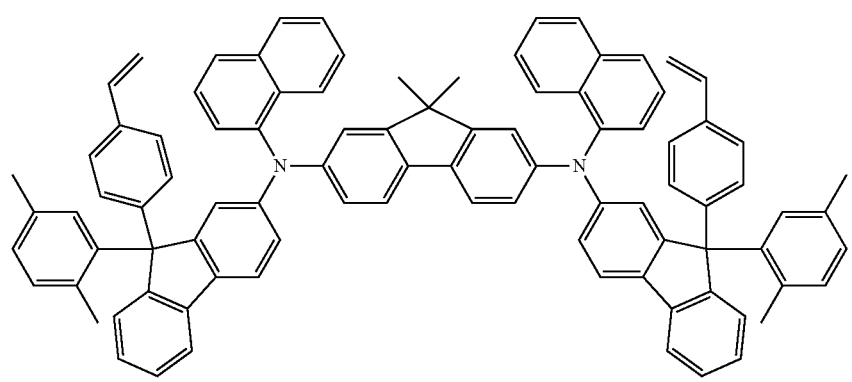

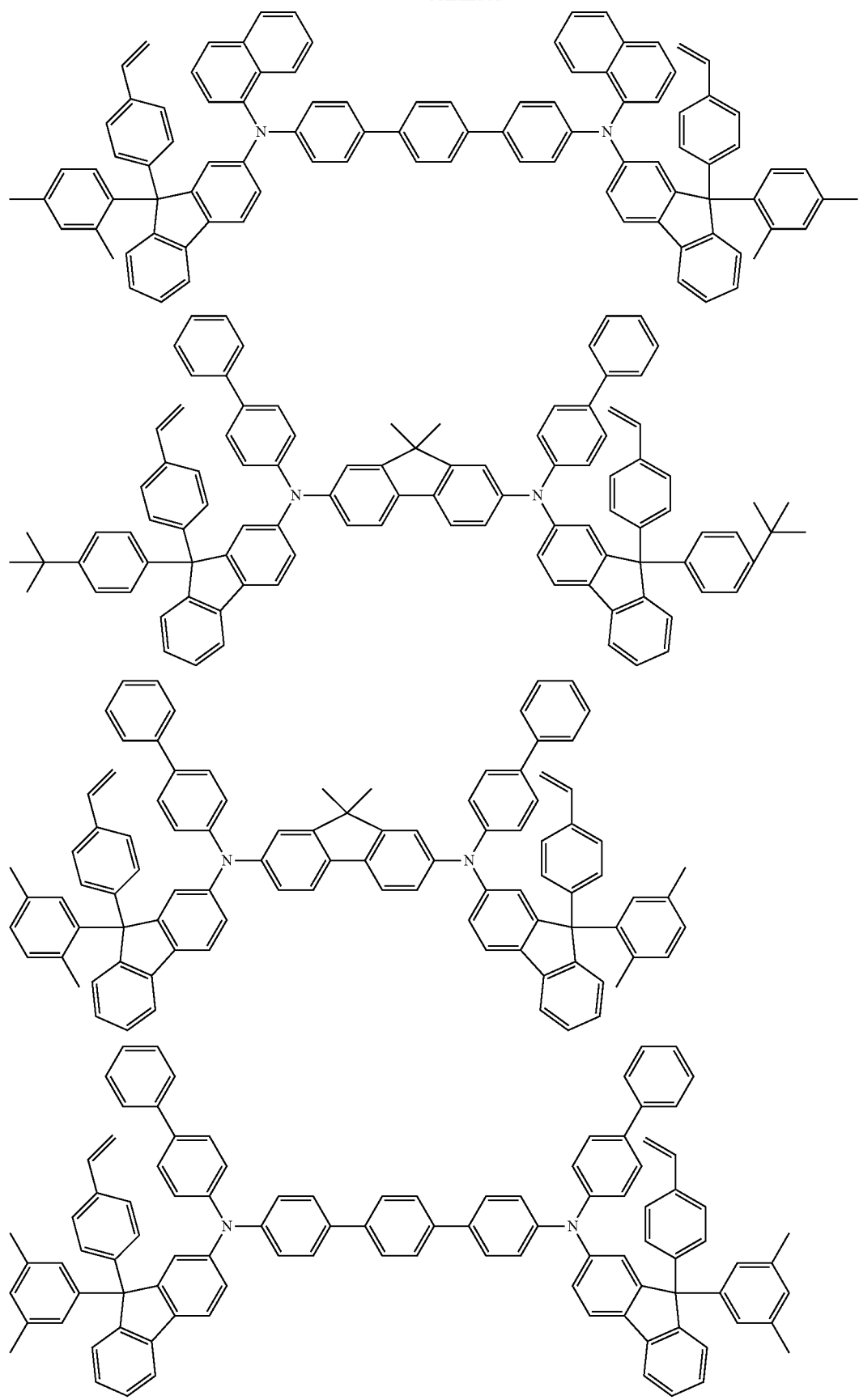

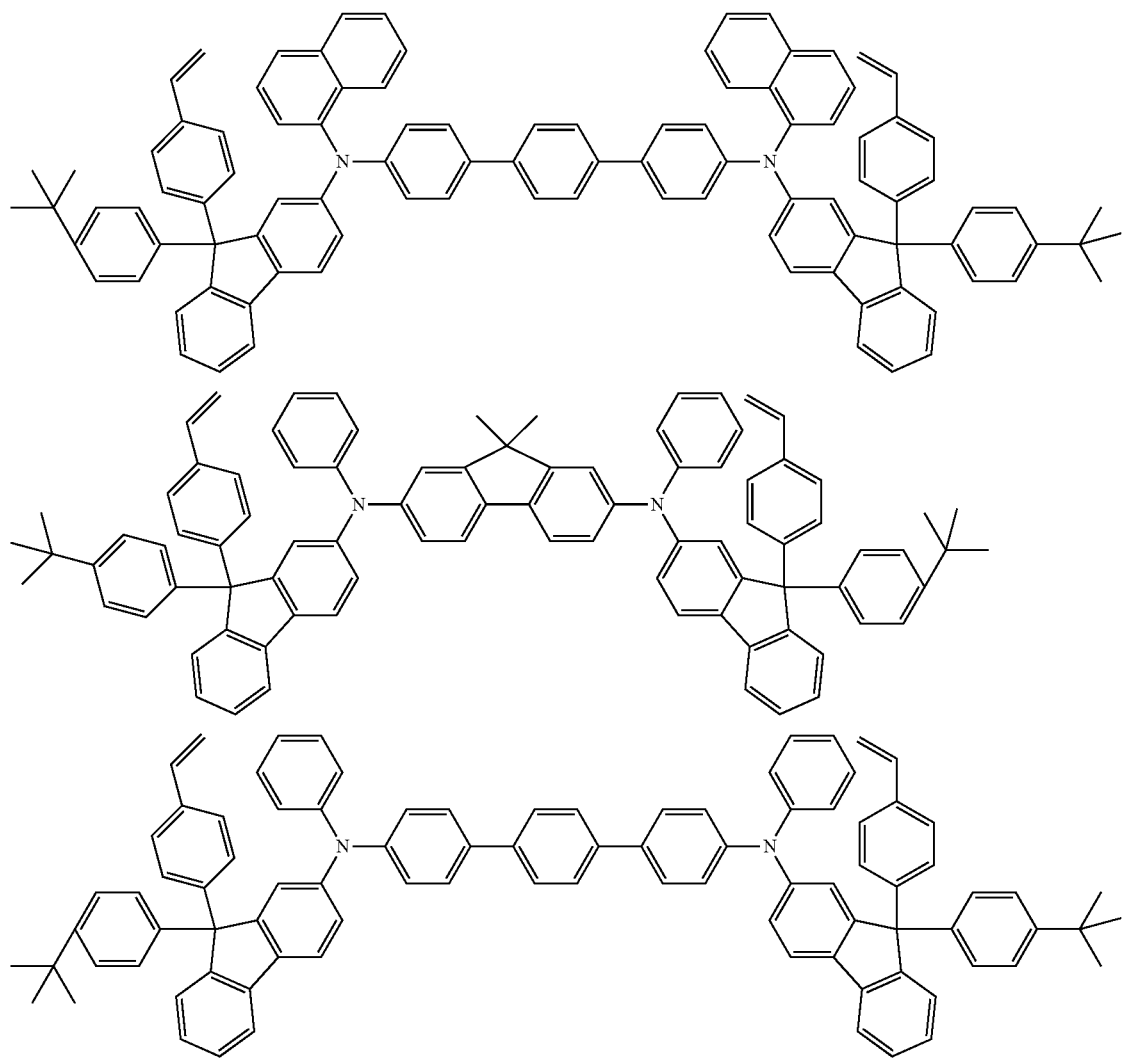
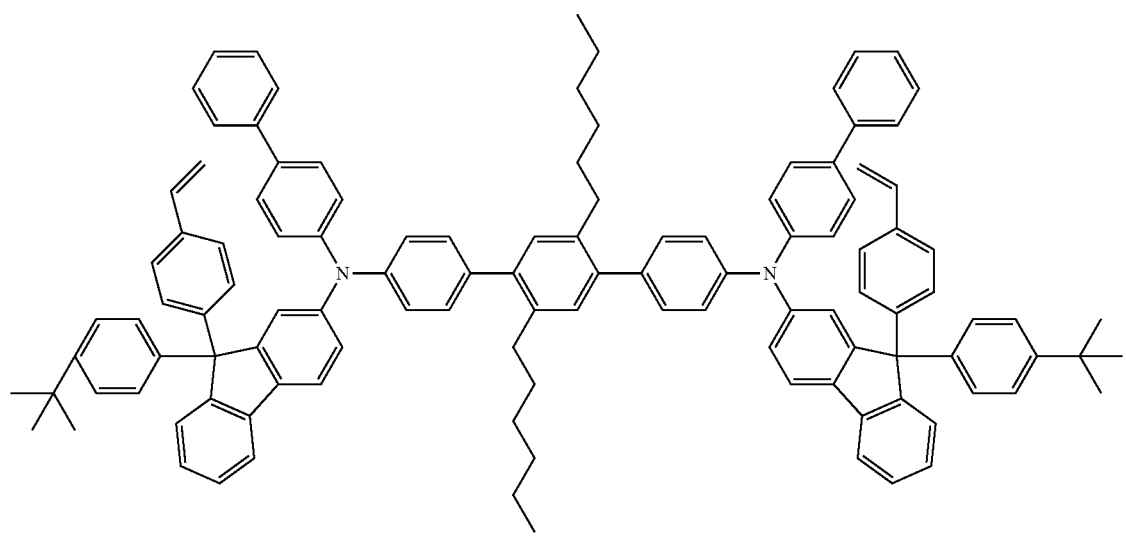

-continued
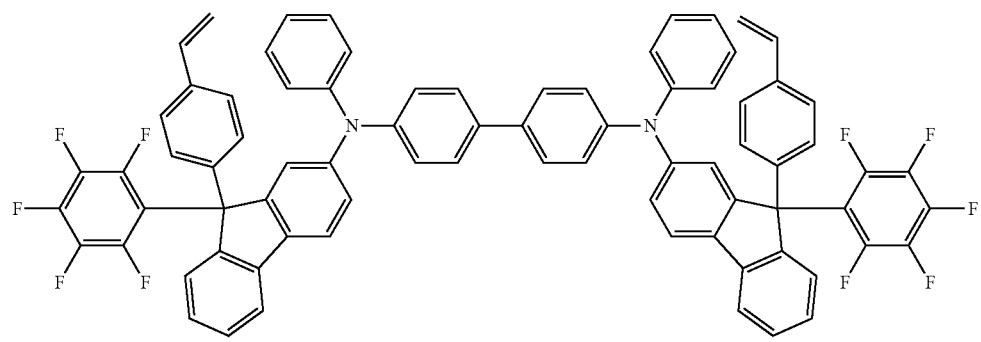
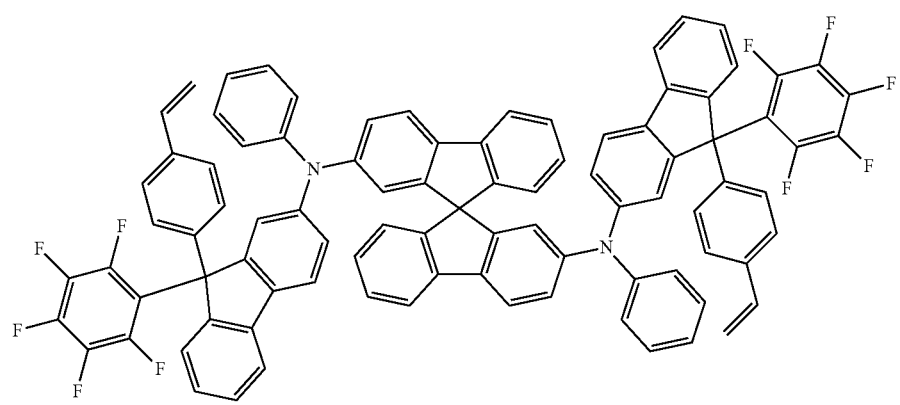
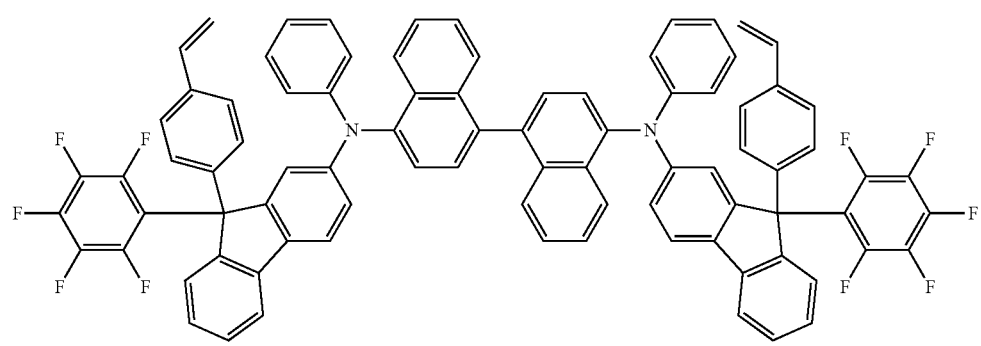
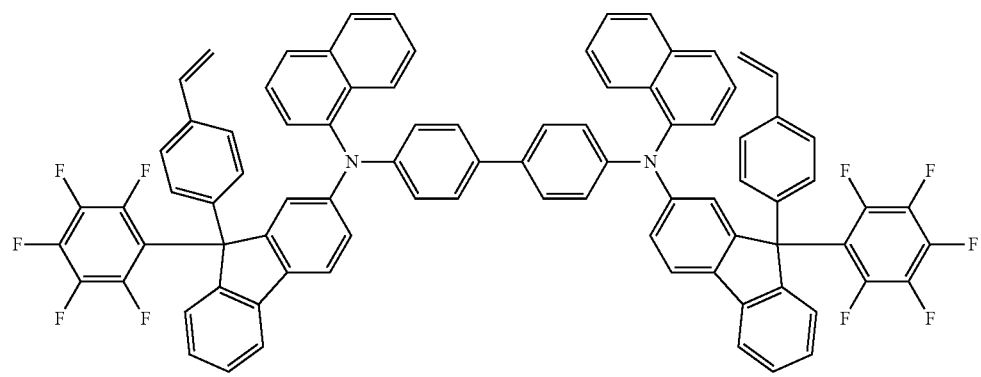

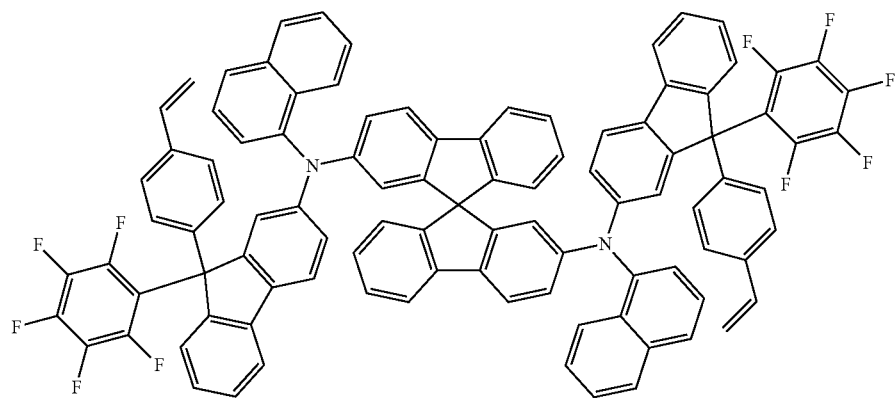
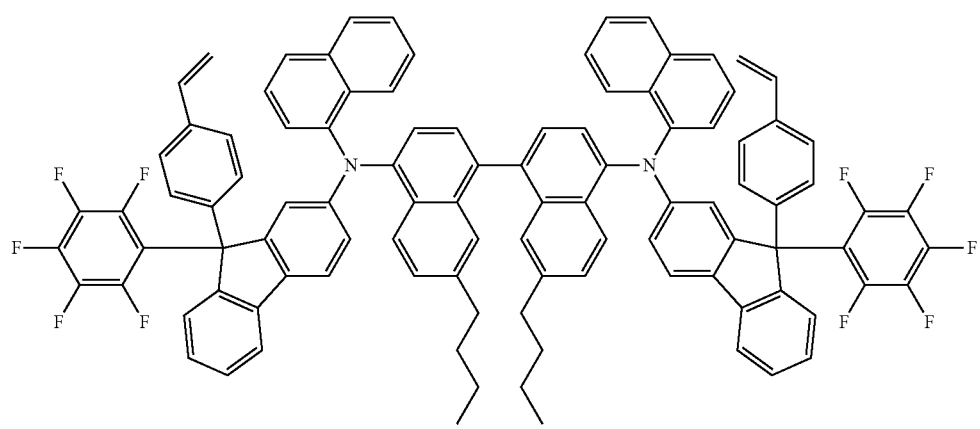
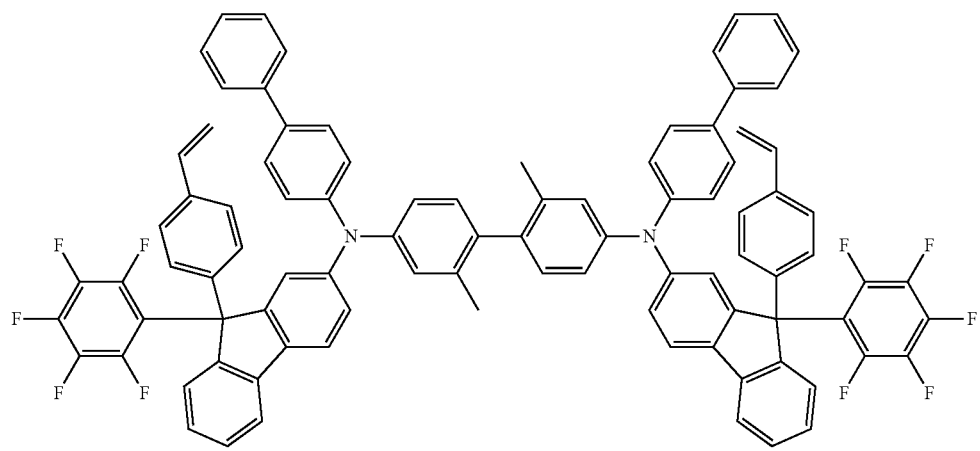

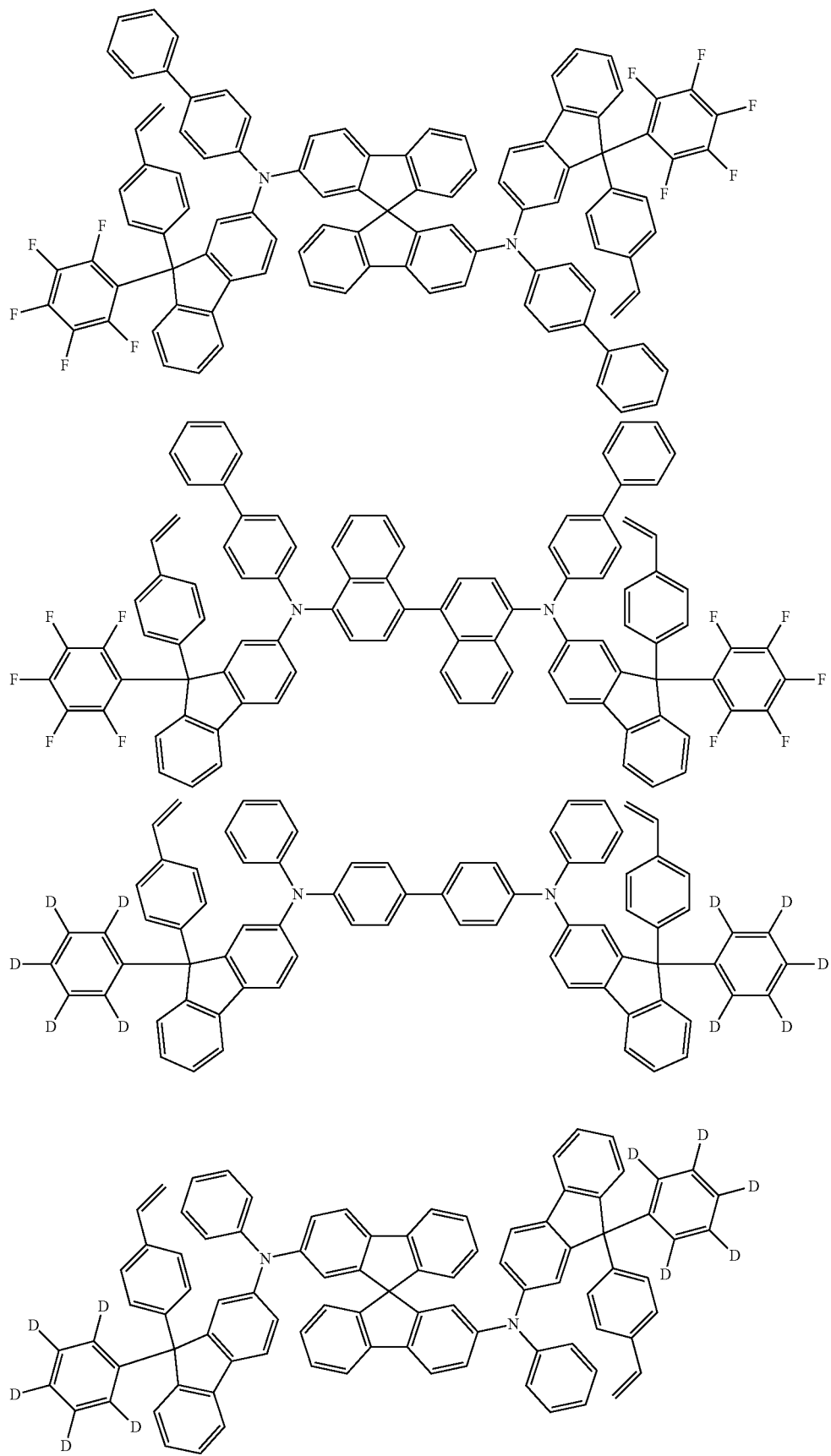

-continued
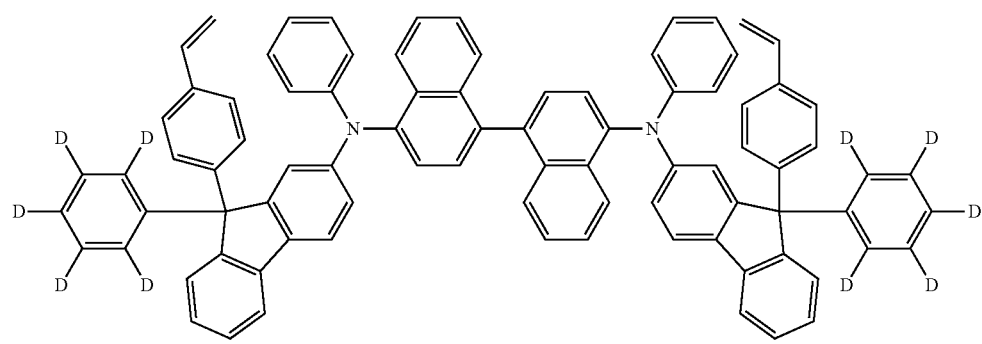
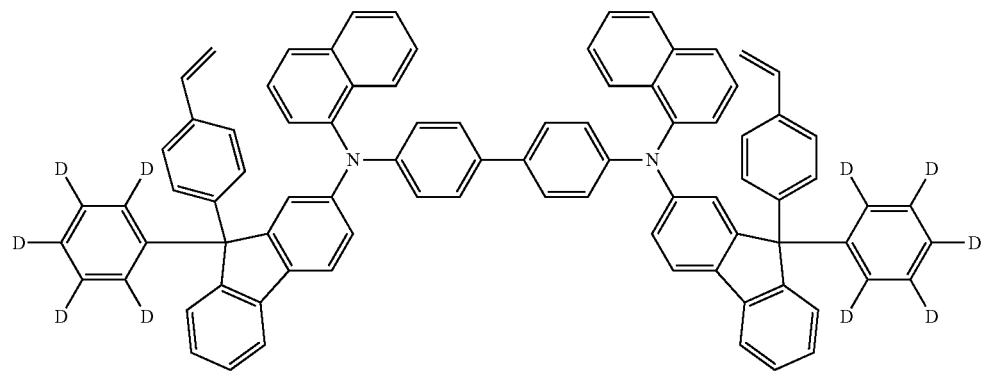
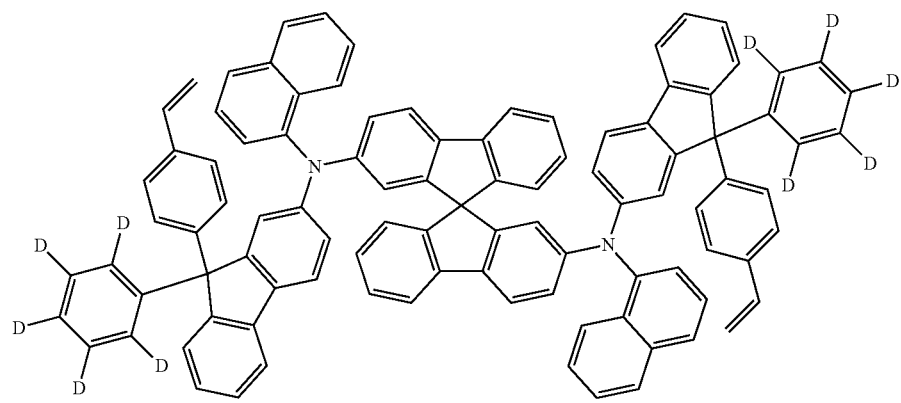
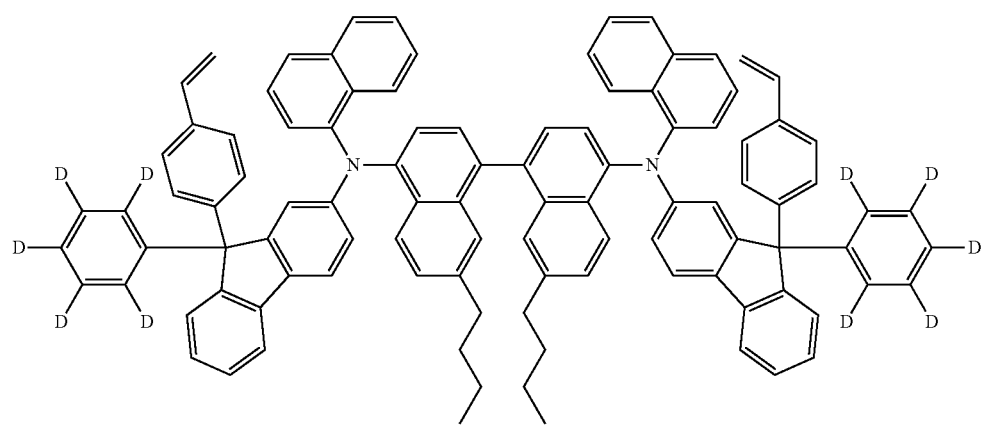

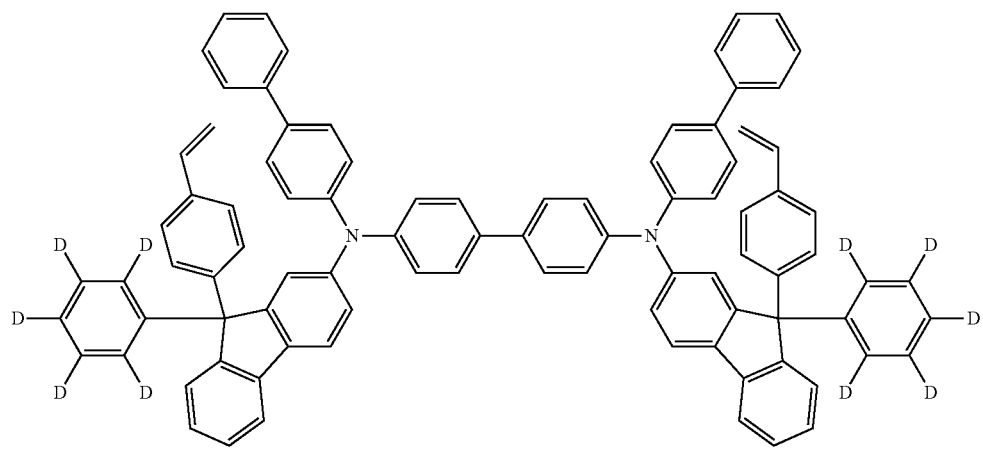
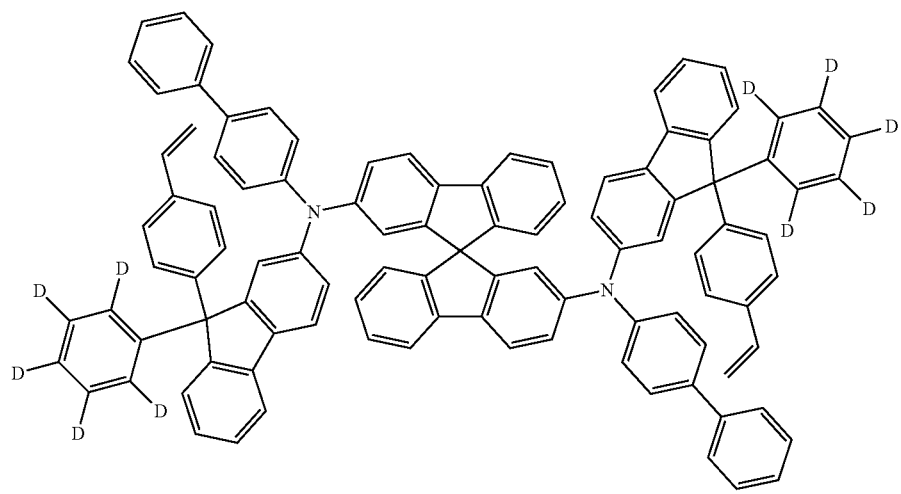
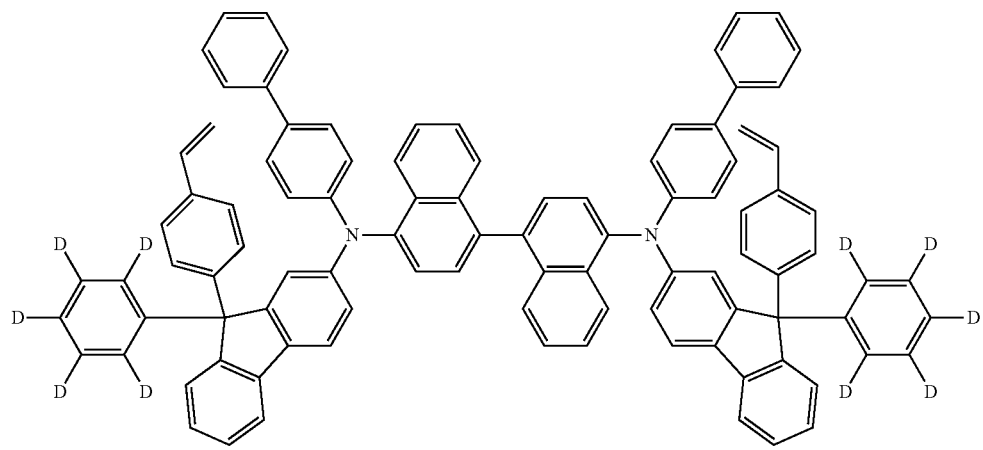

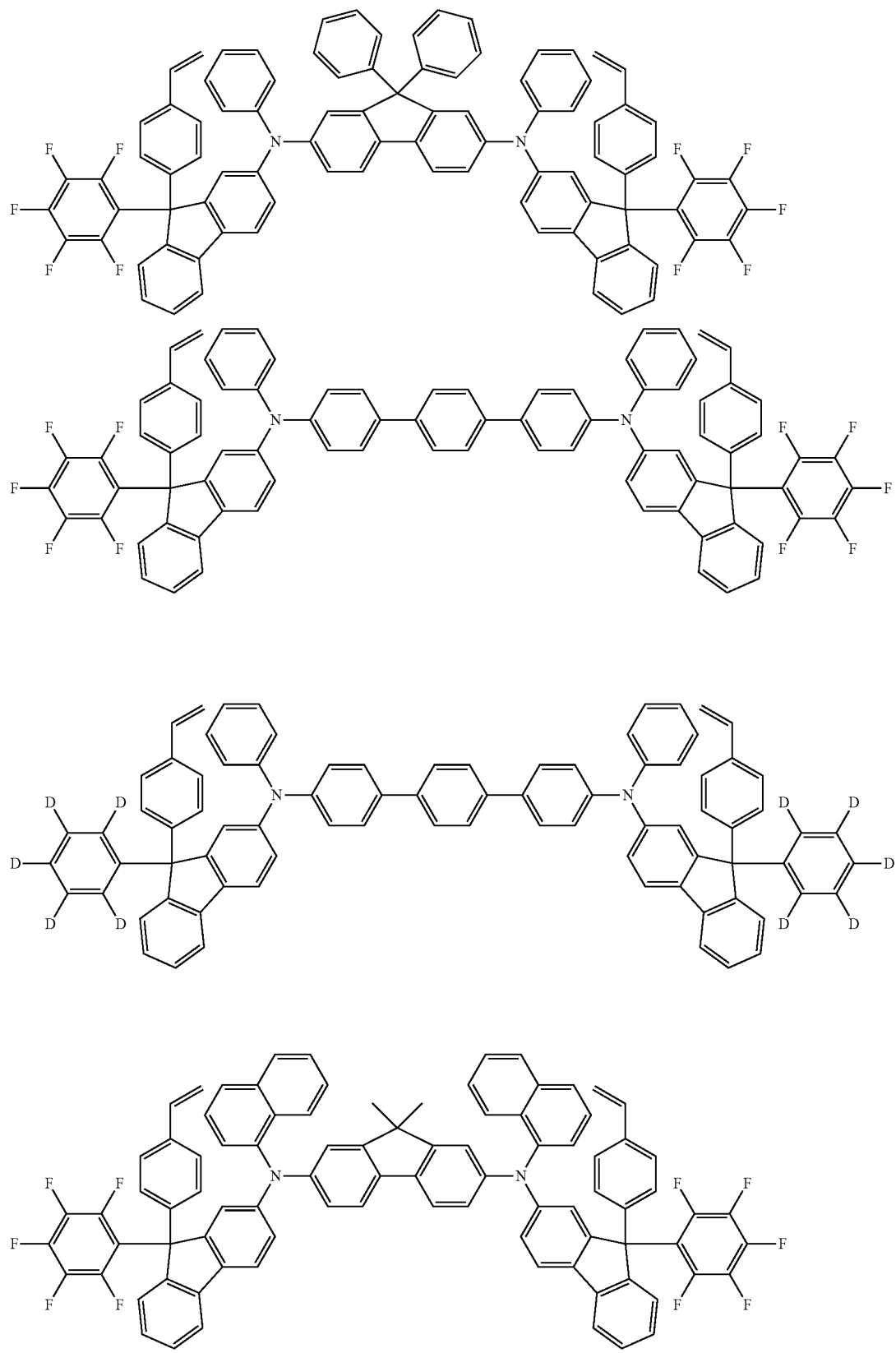

-continued
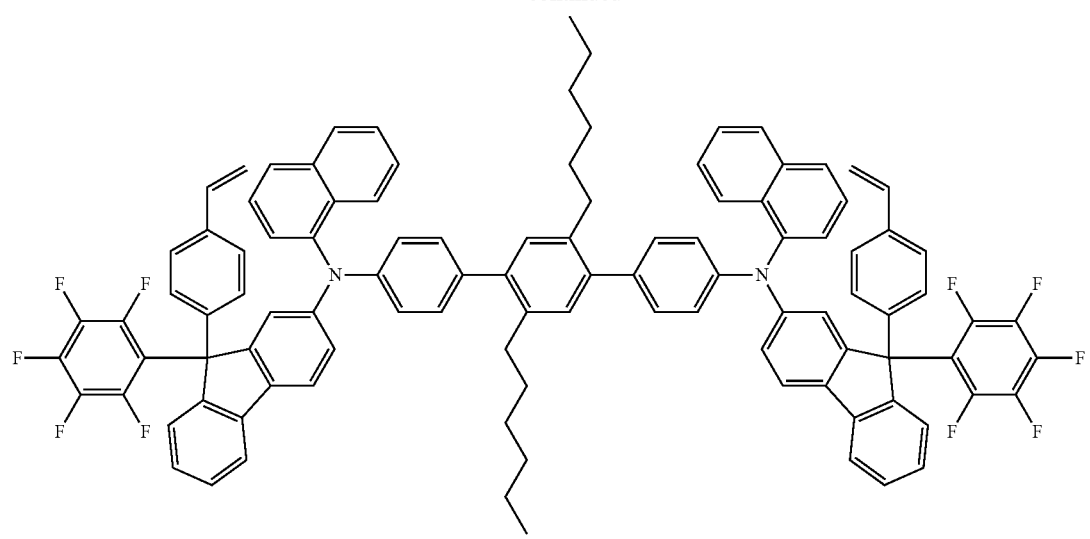
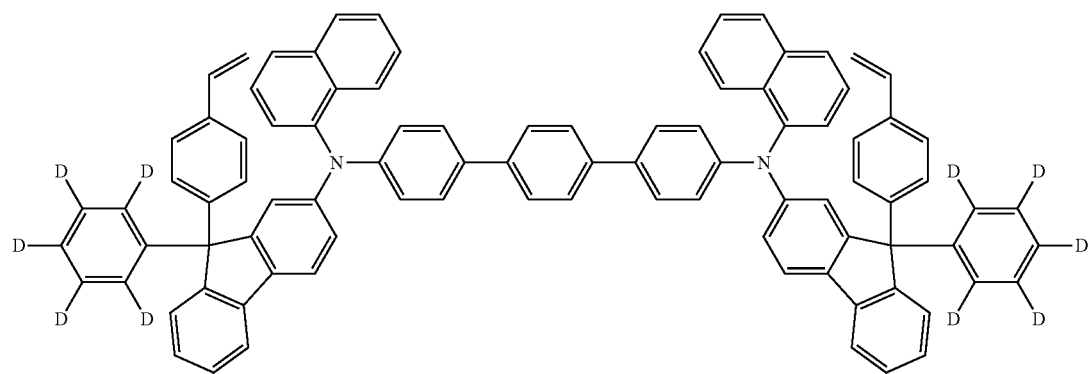
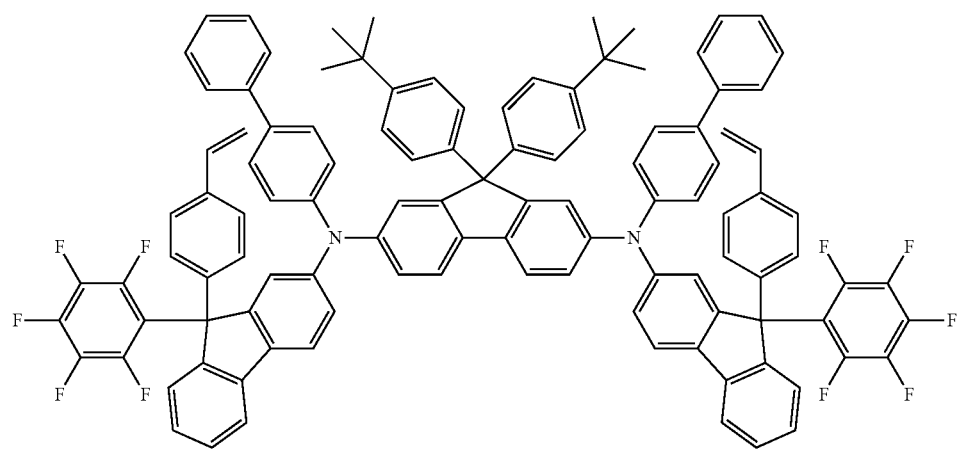

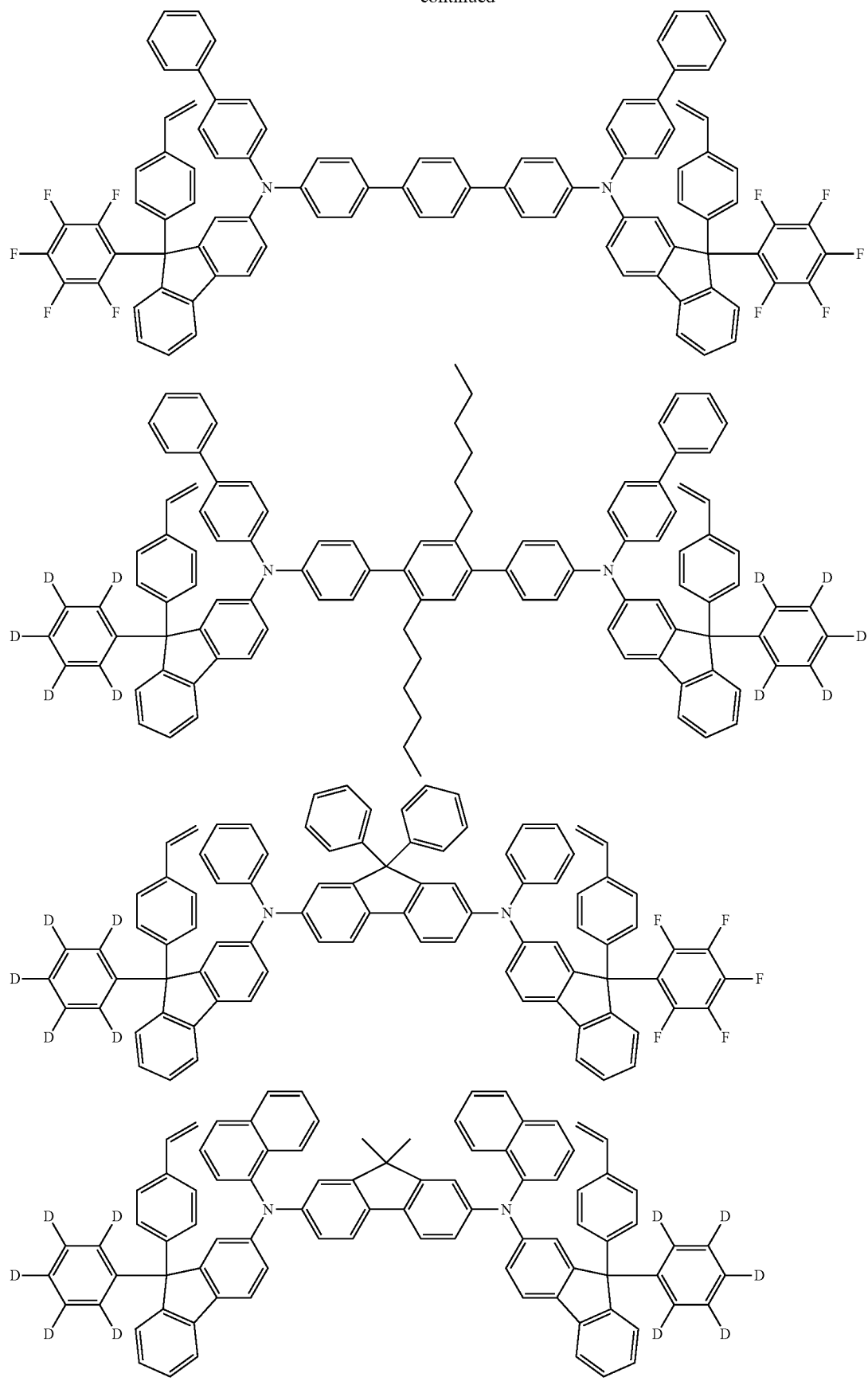

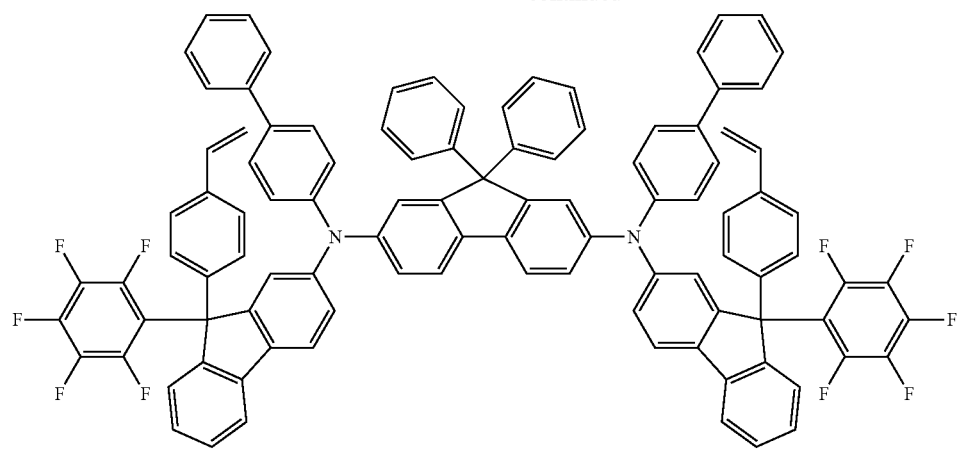
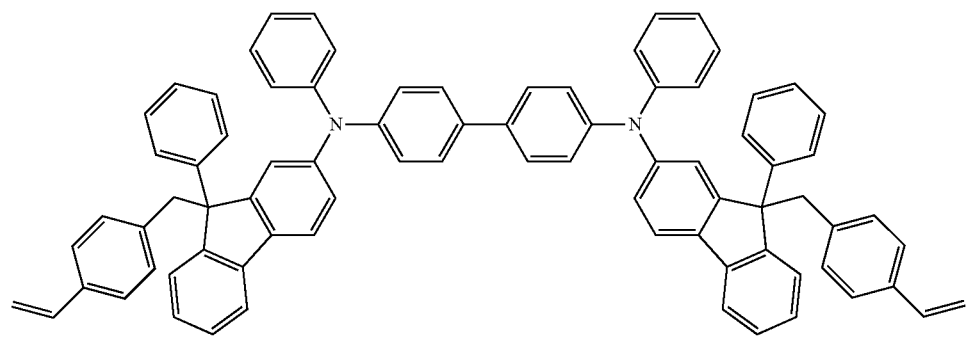
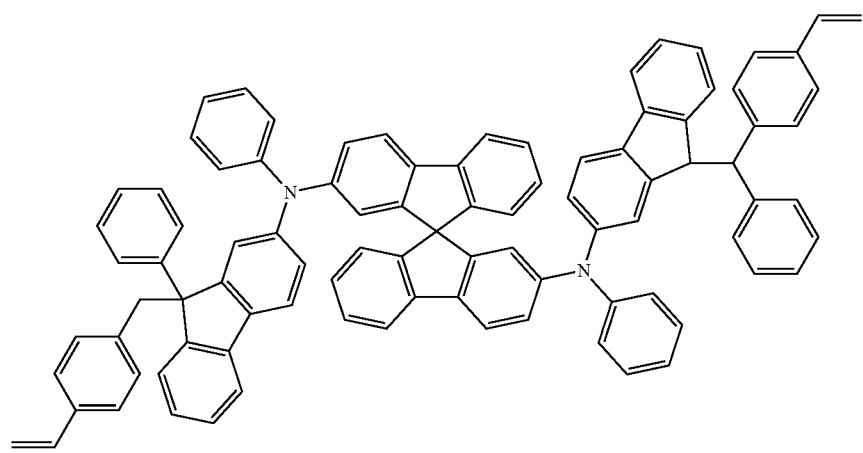
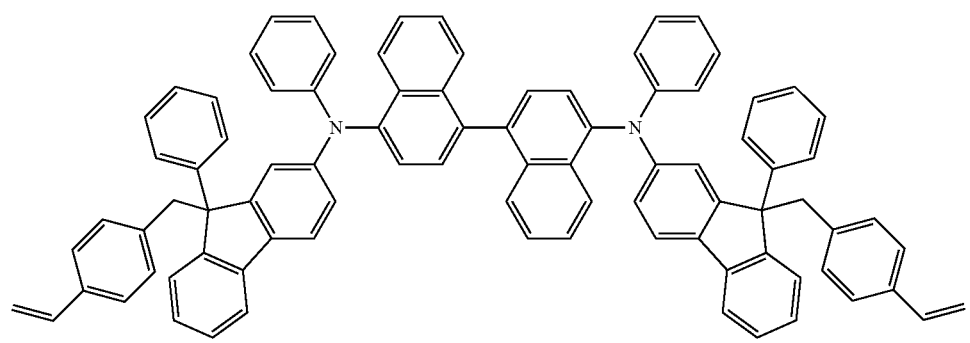

-continued
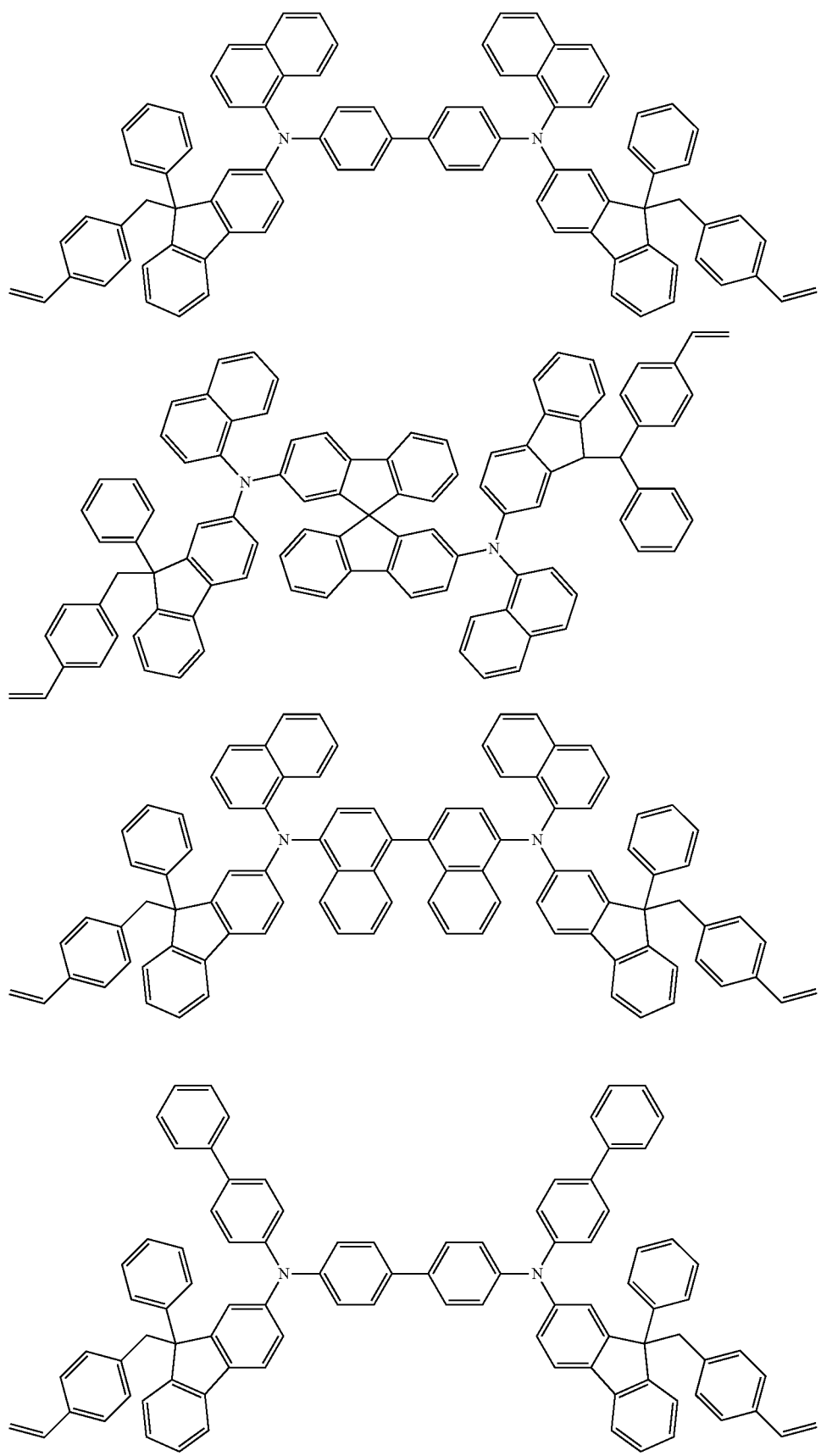

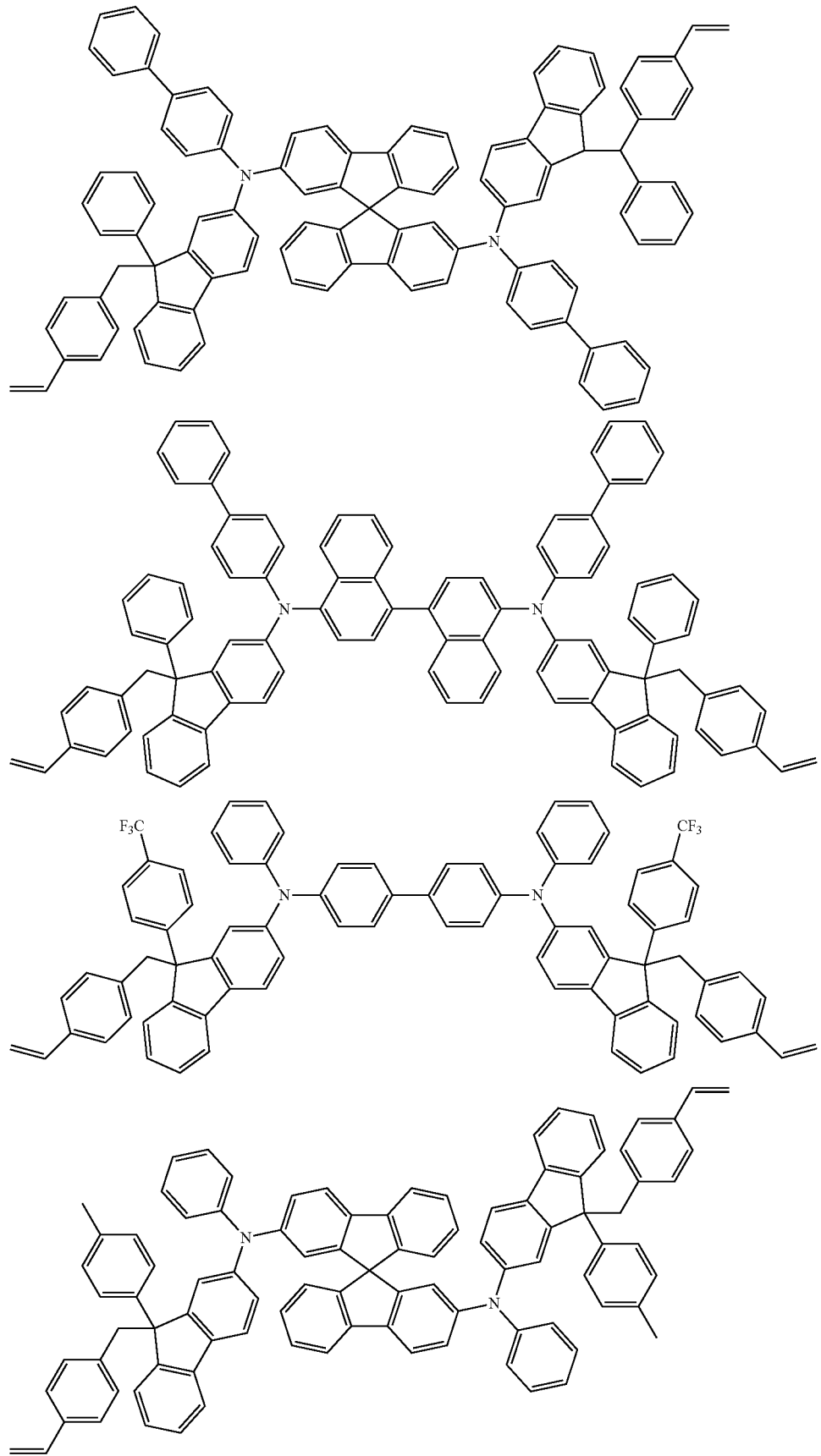

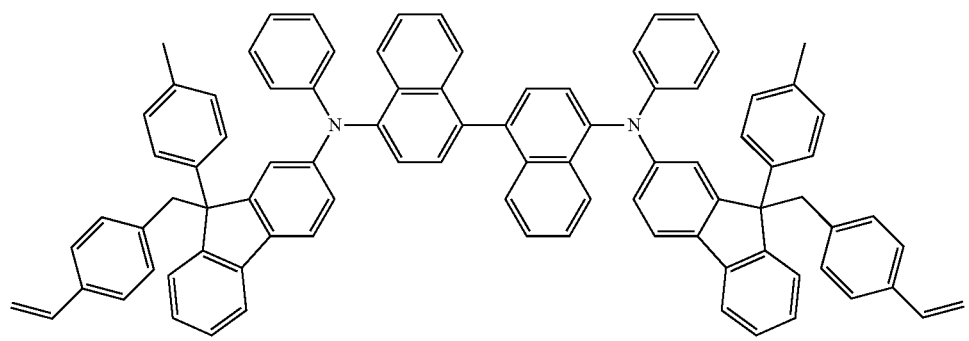
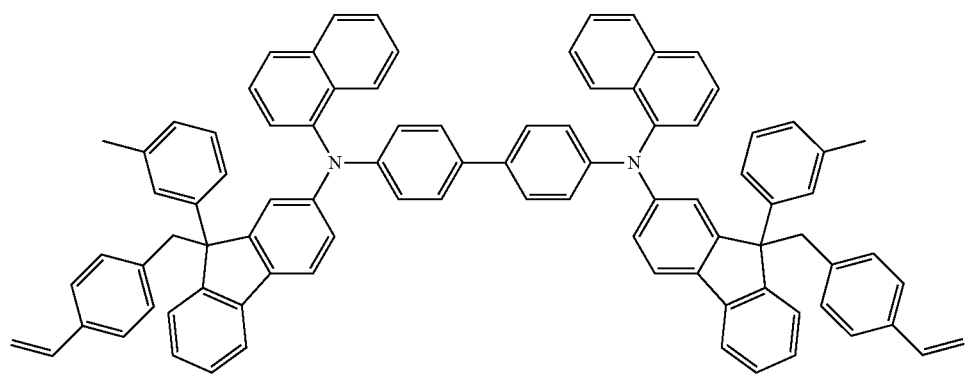
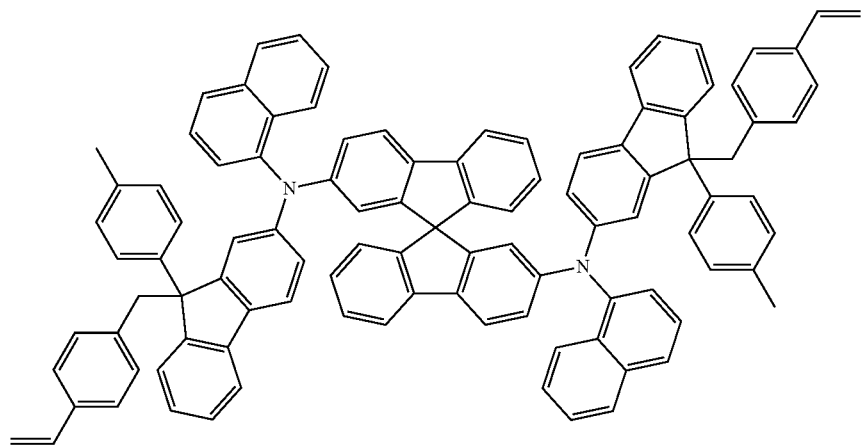
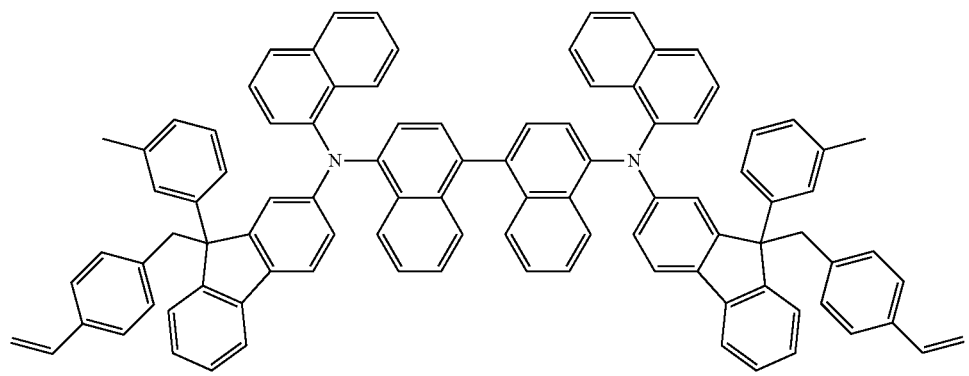

-continued
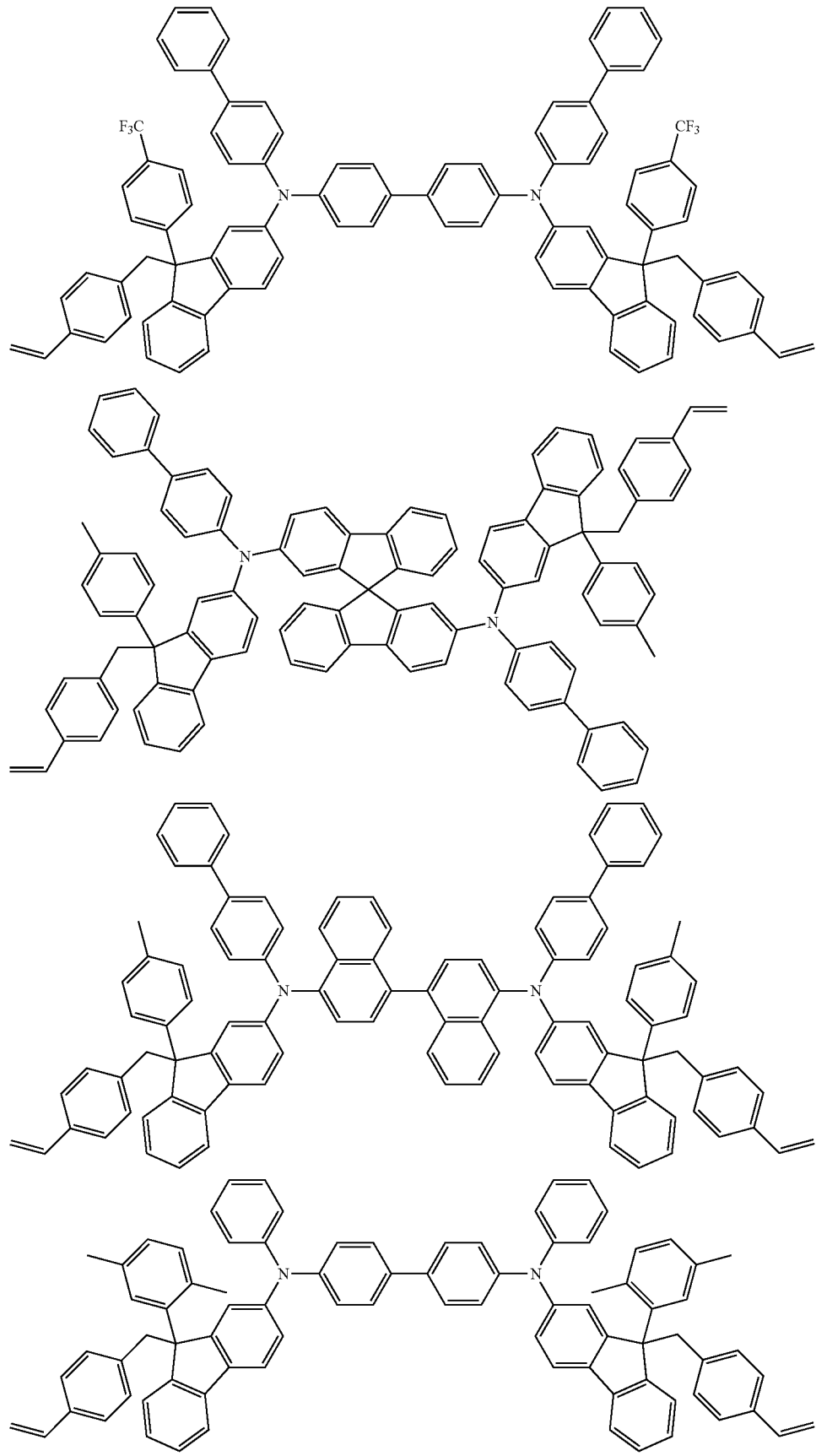

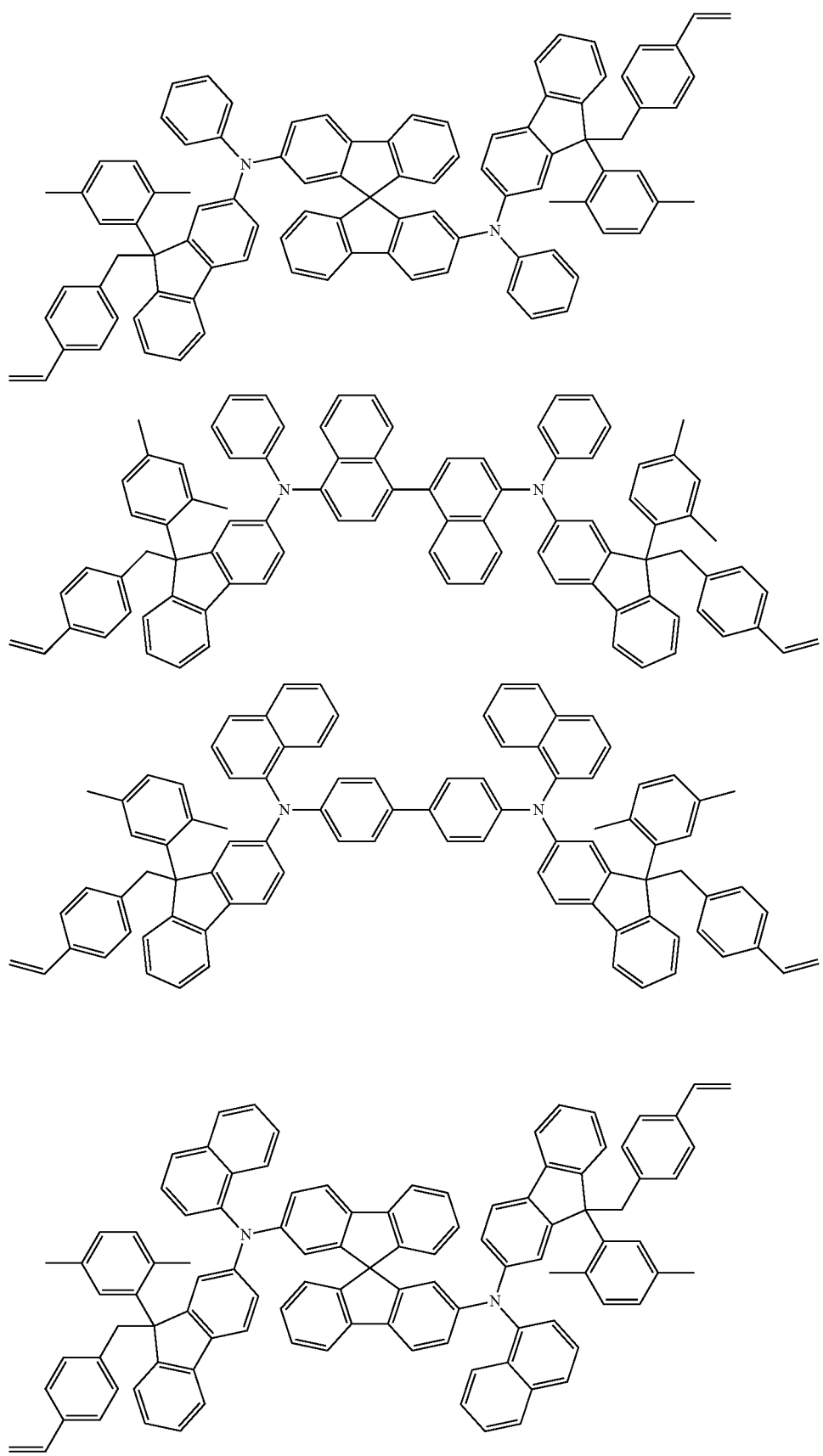

-continued
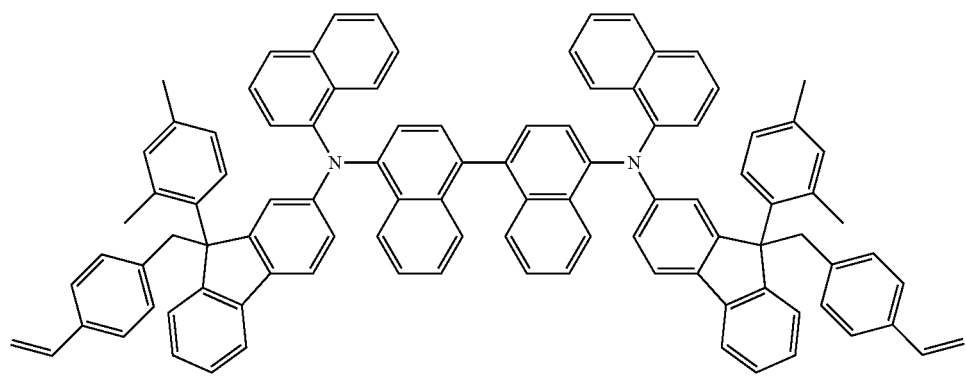
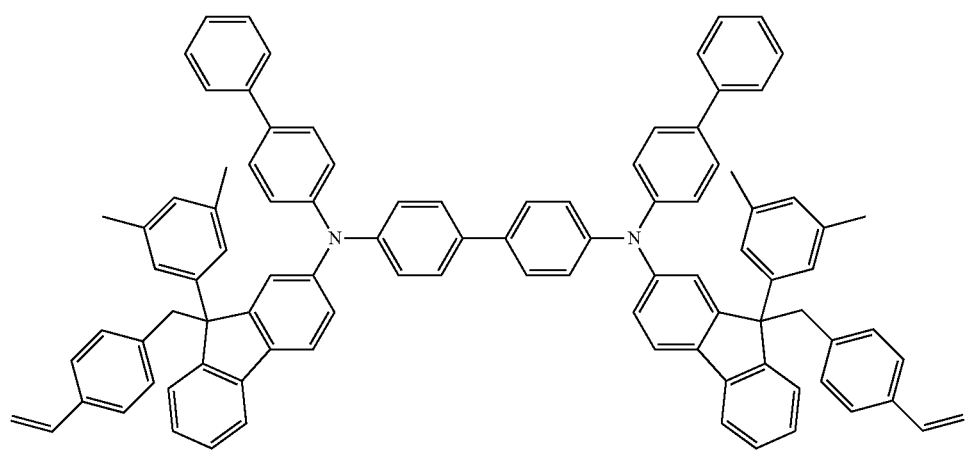
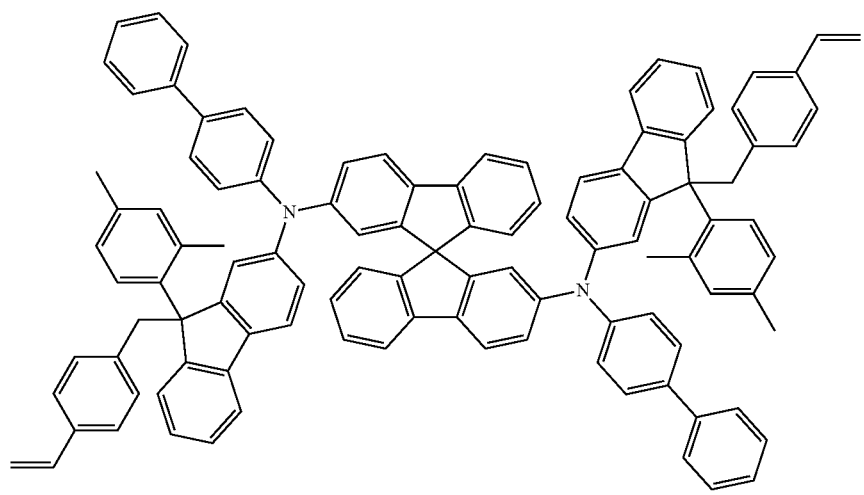

-continued
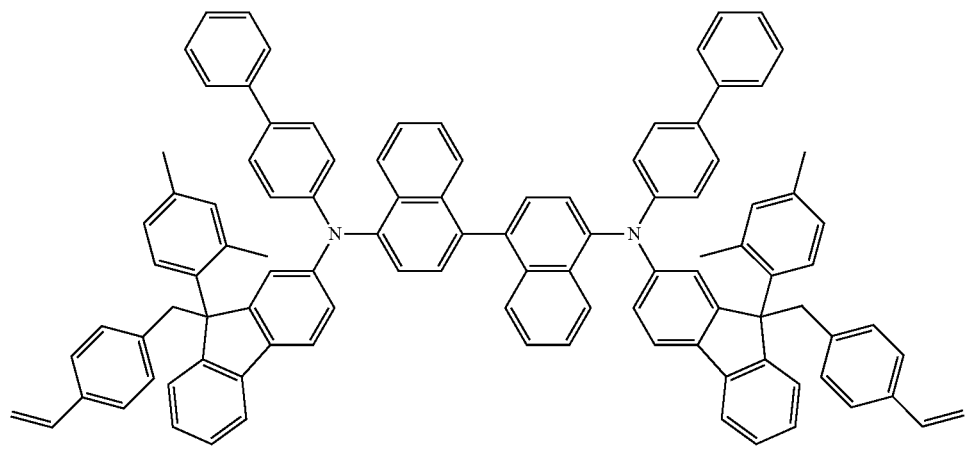
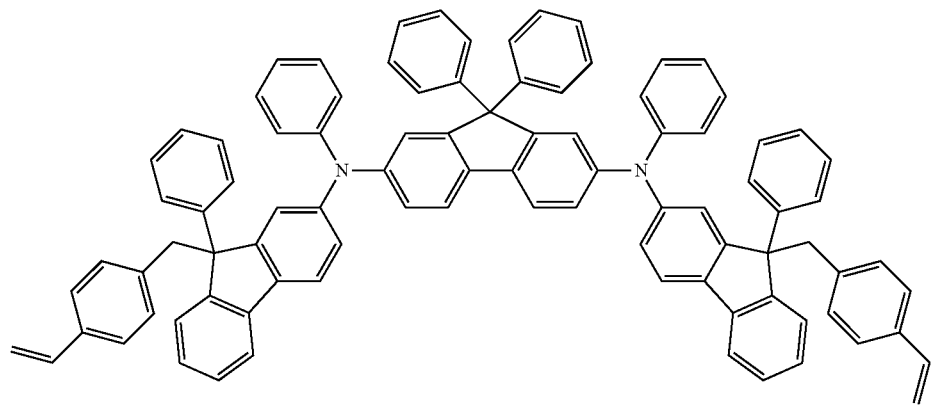
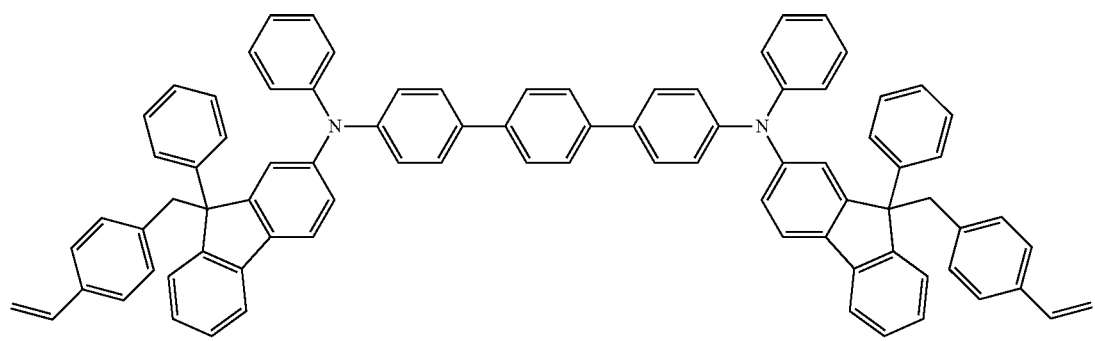
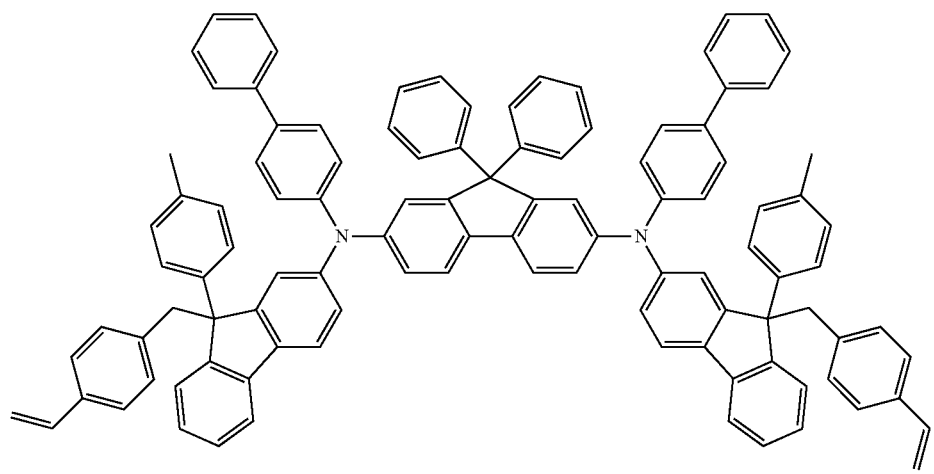

-continued
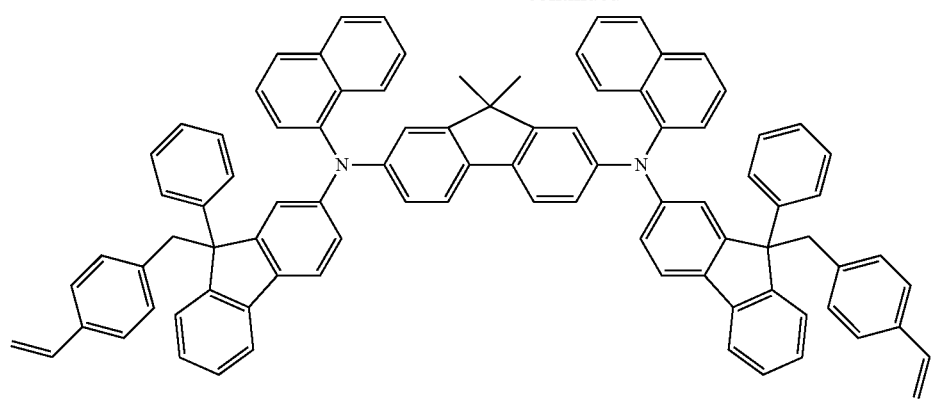
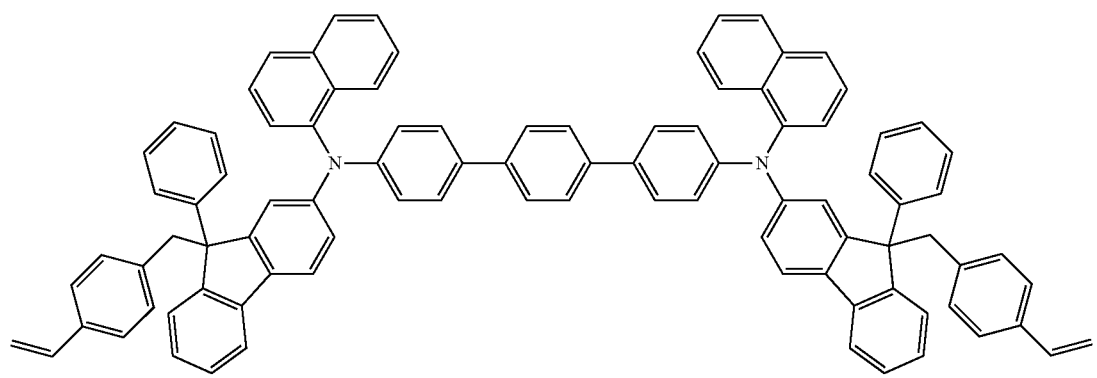
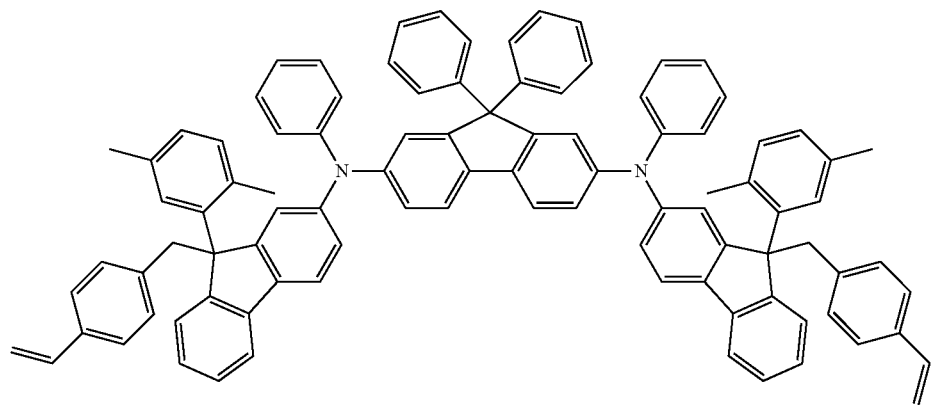
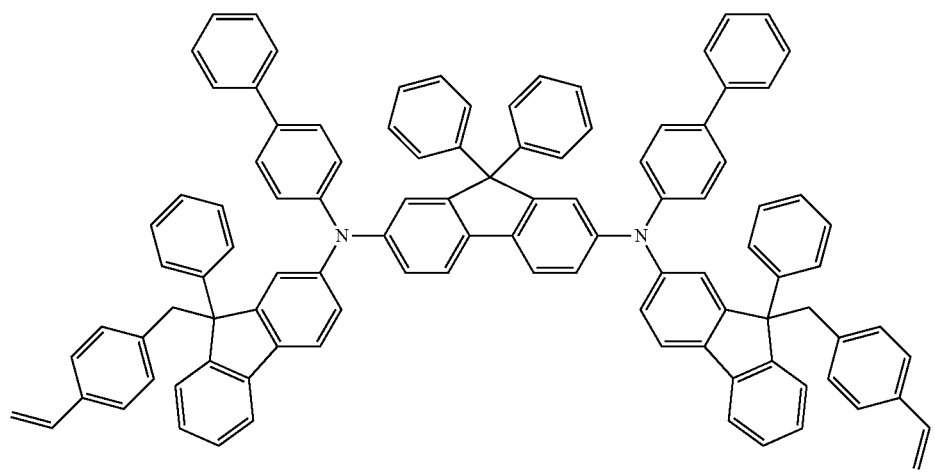

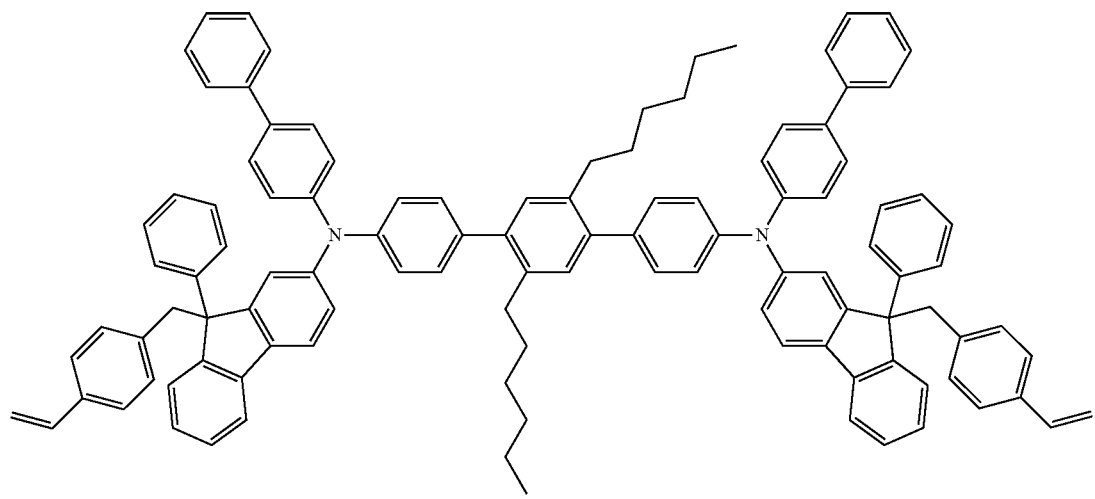
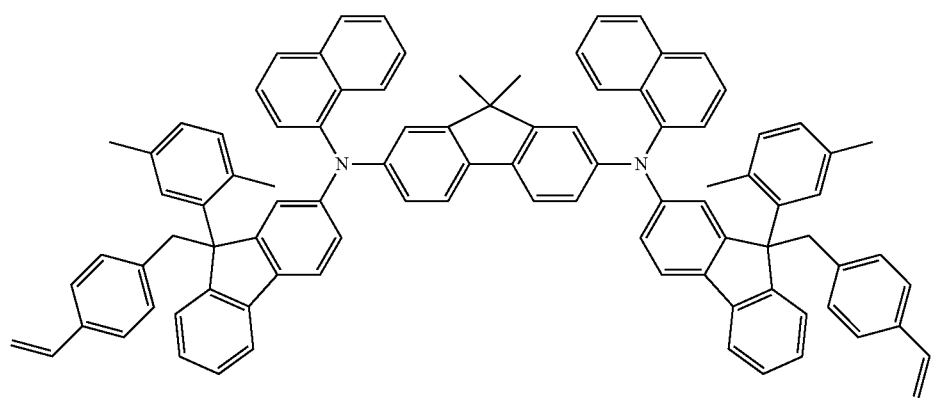
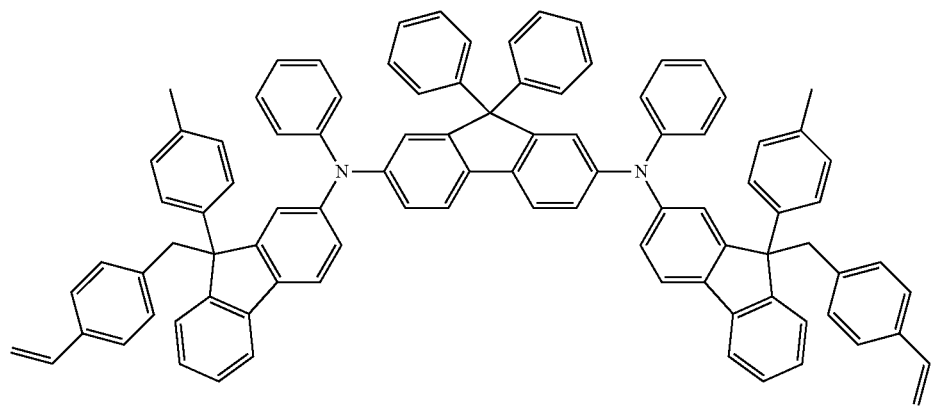
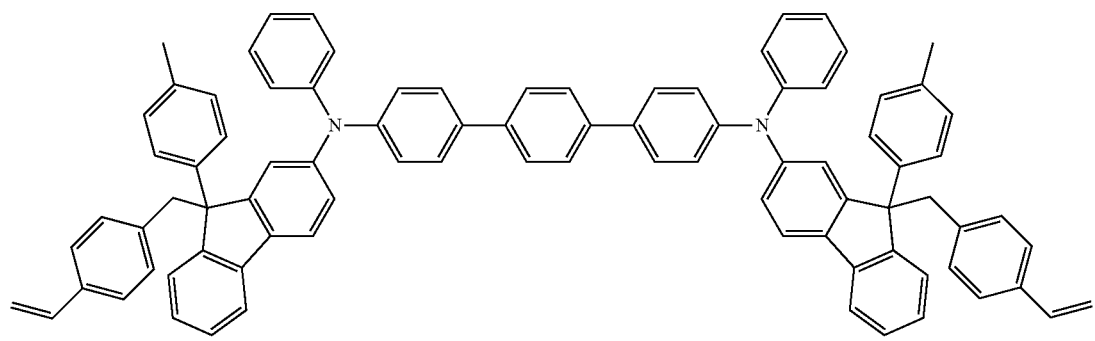

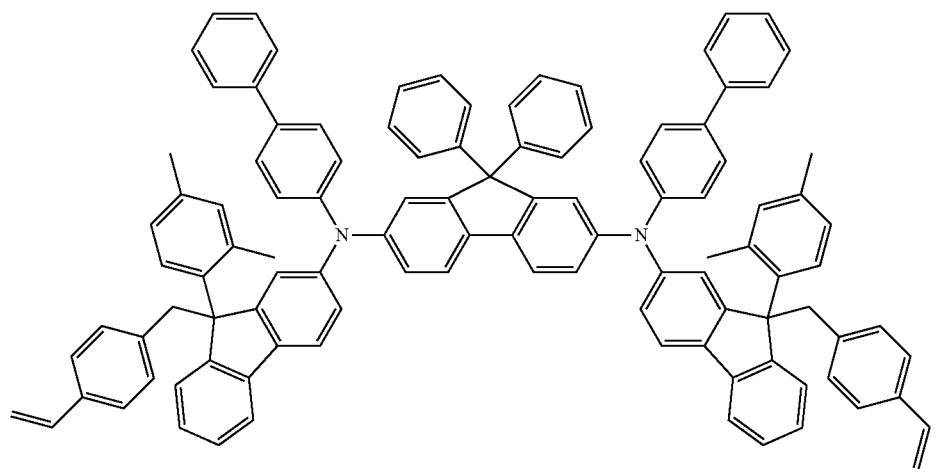
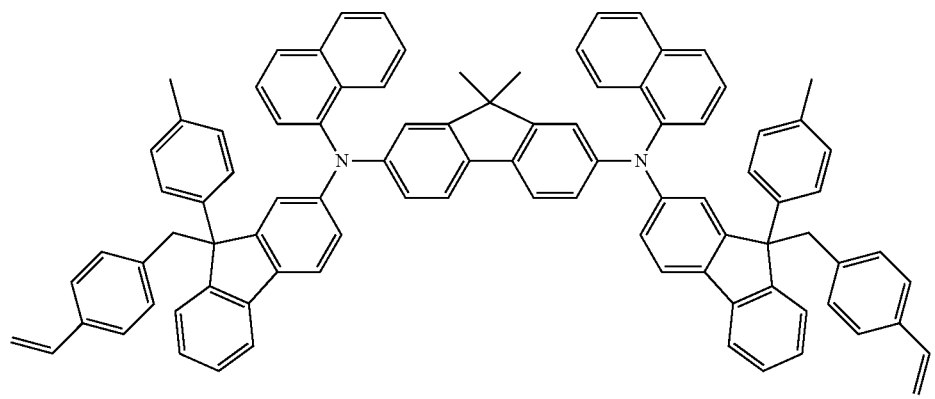
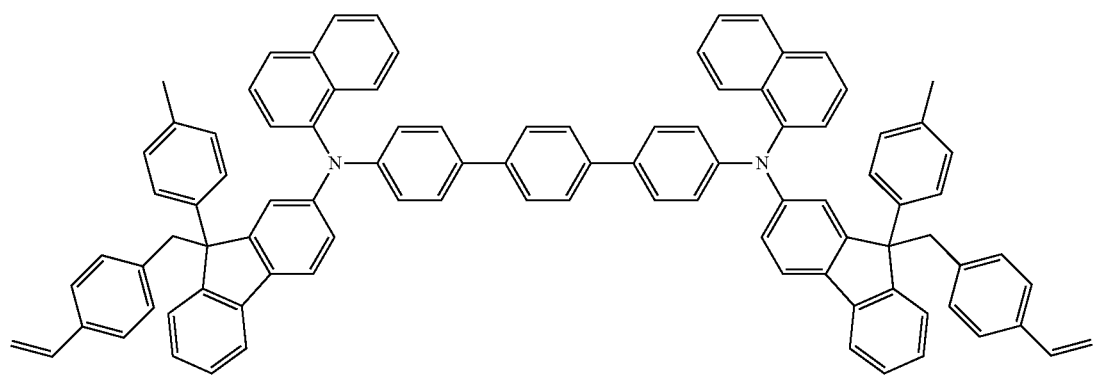
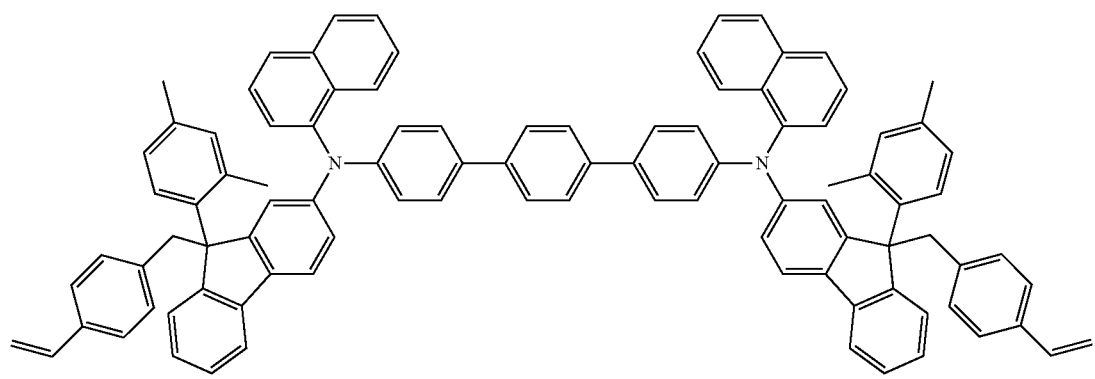

-continued
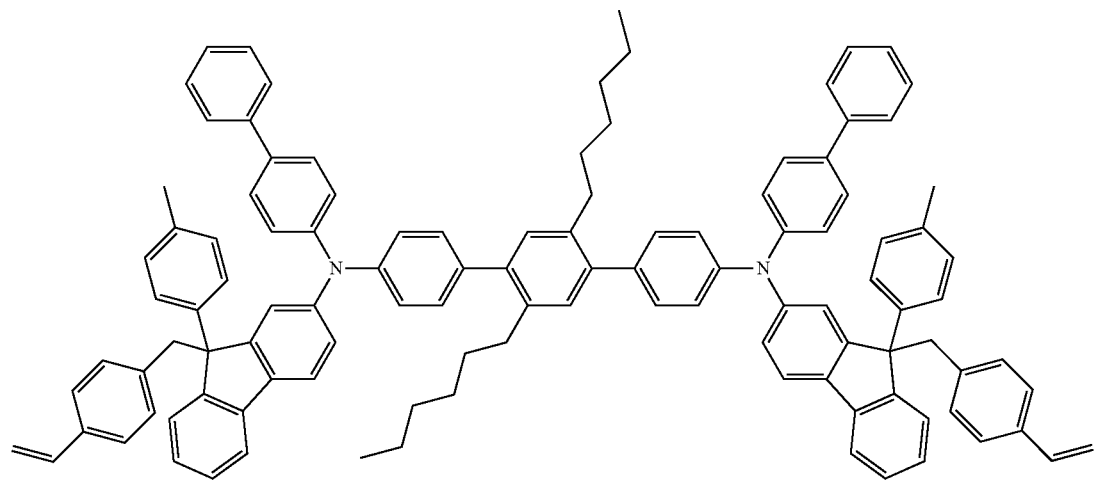
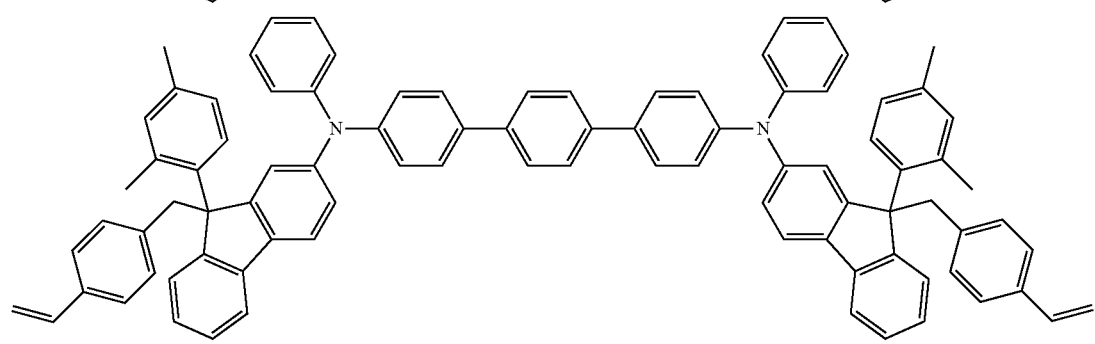
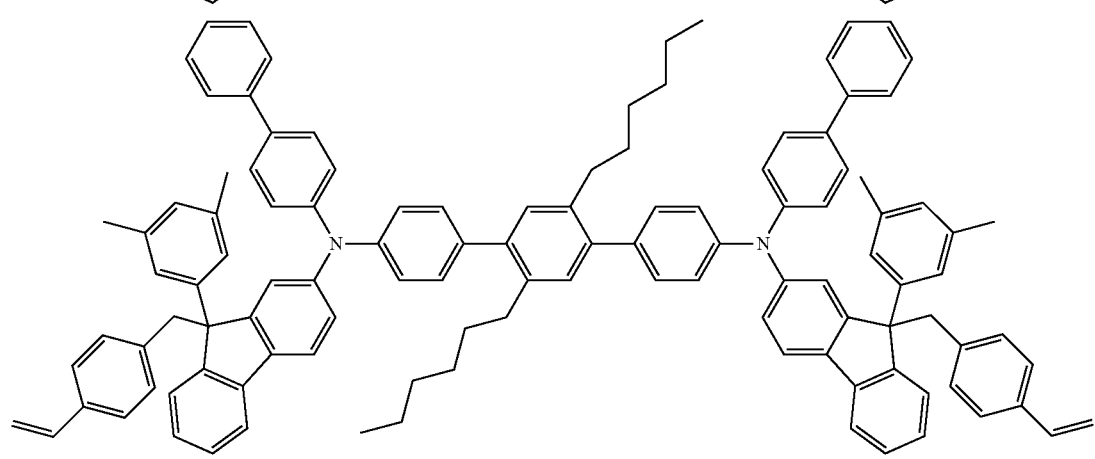
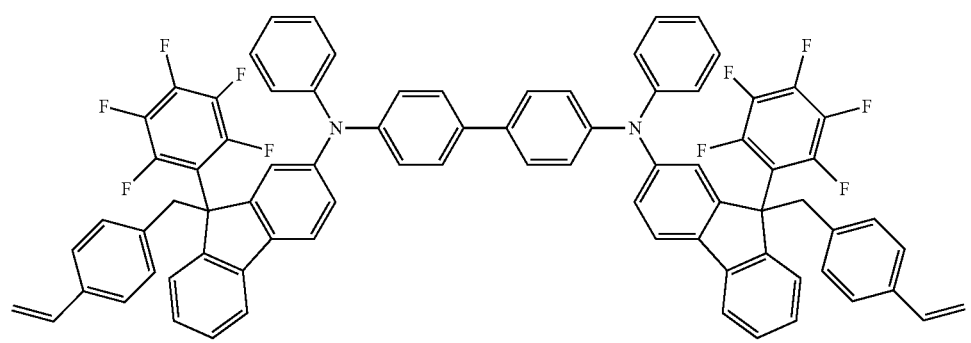

-continued
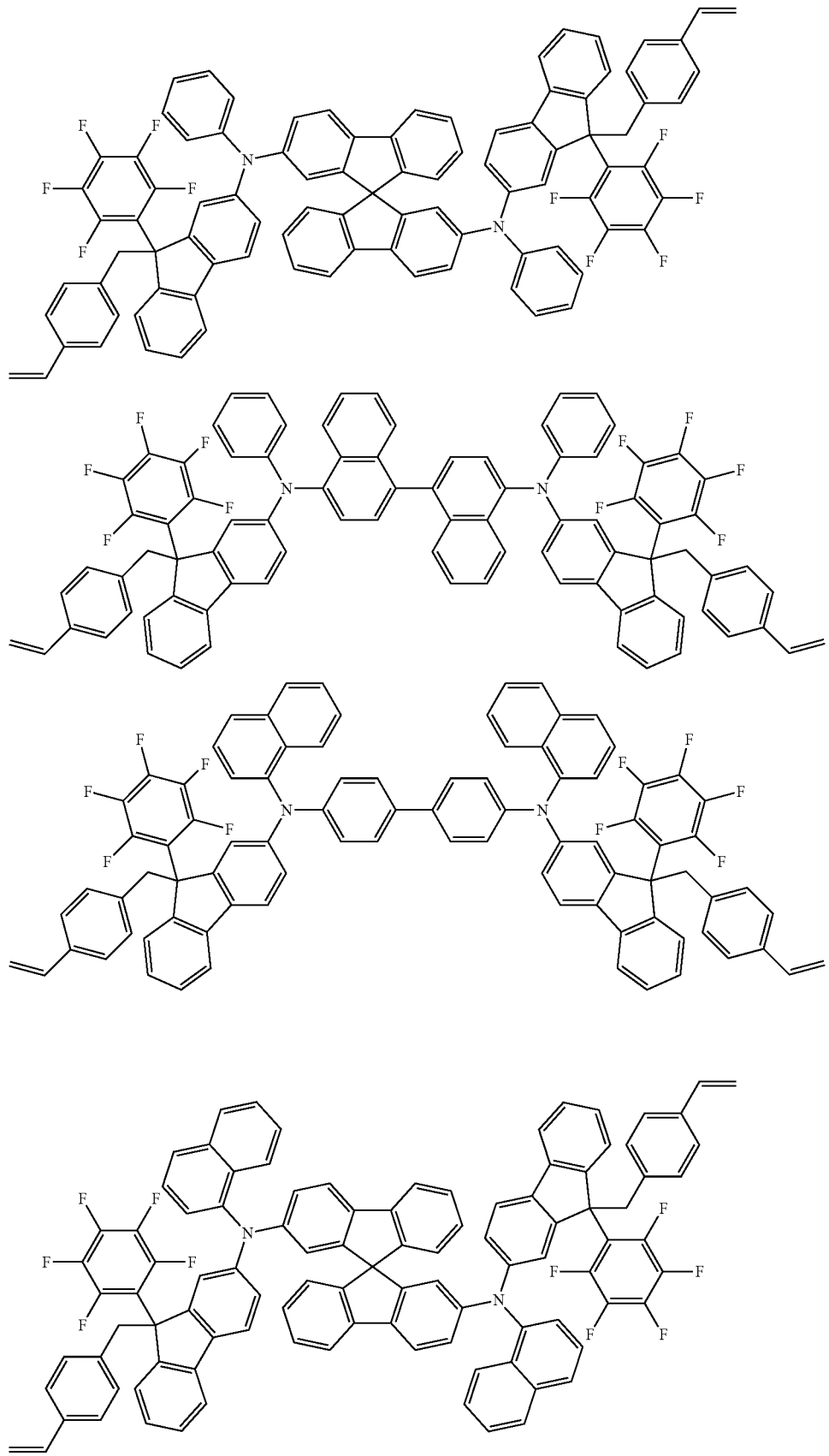

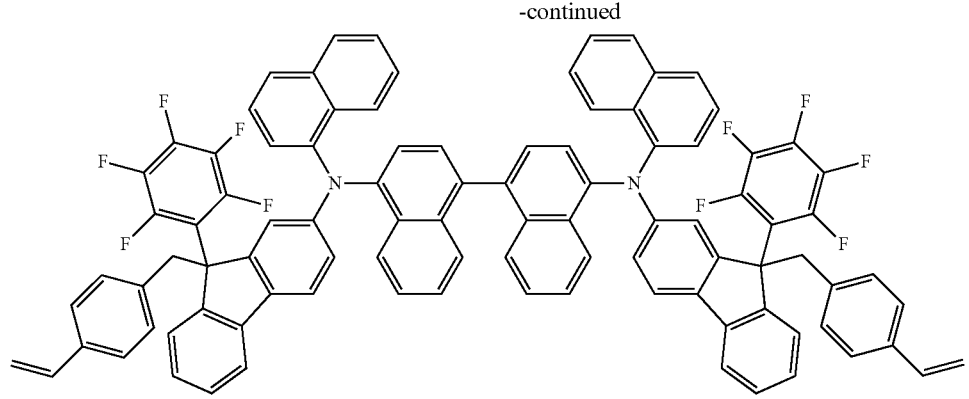
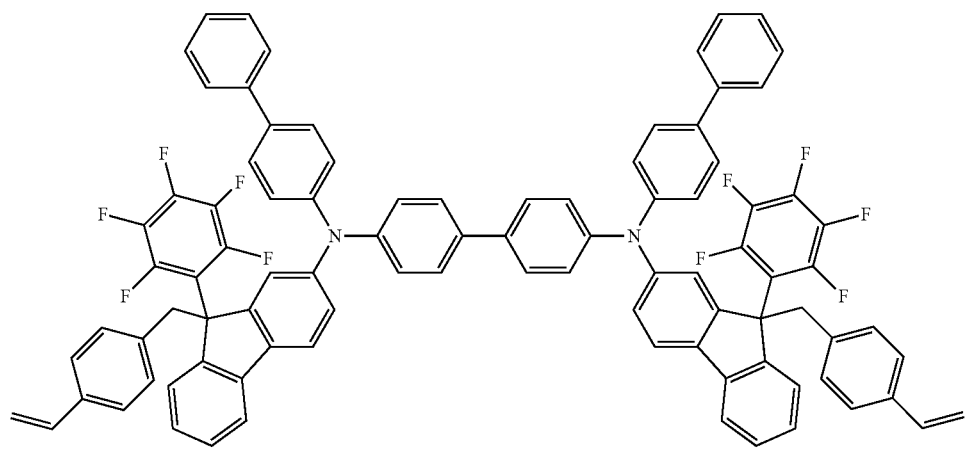
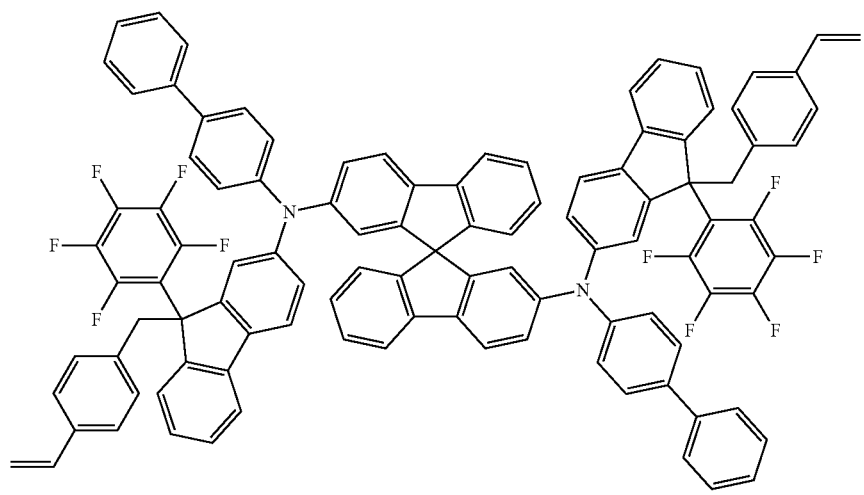

-continued
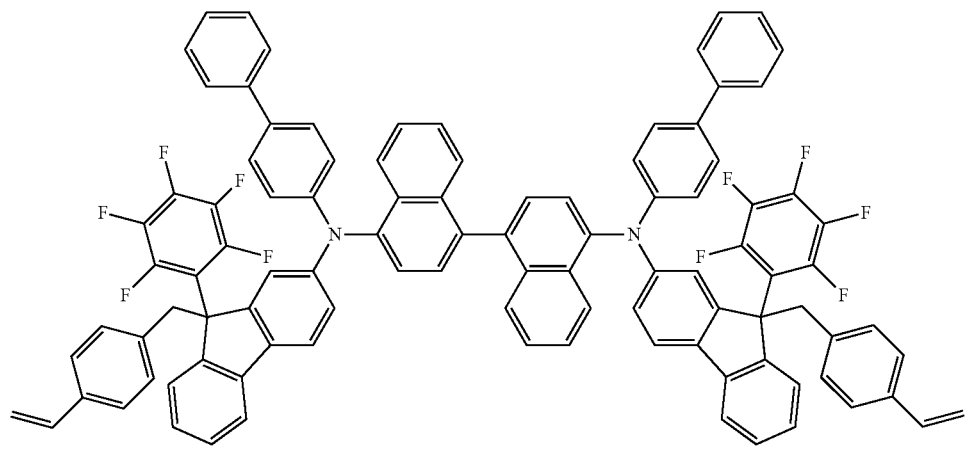
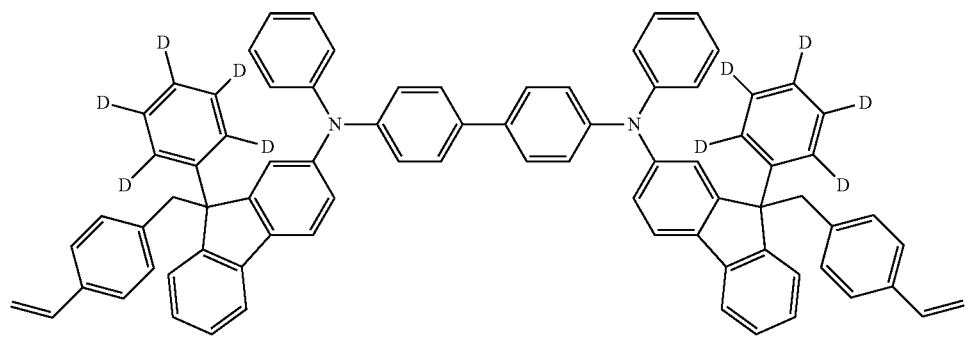
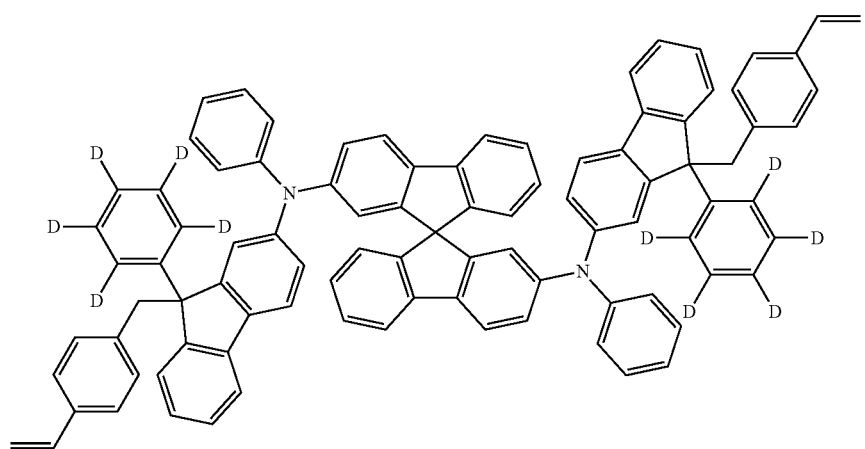
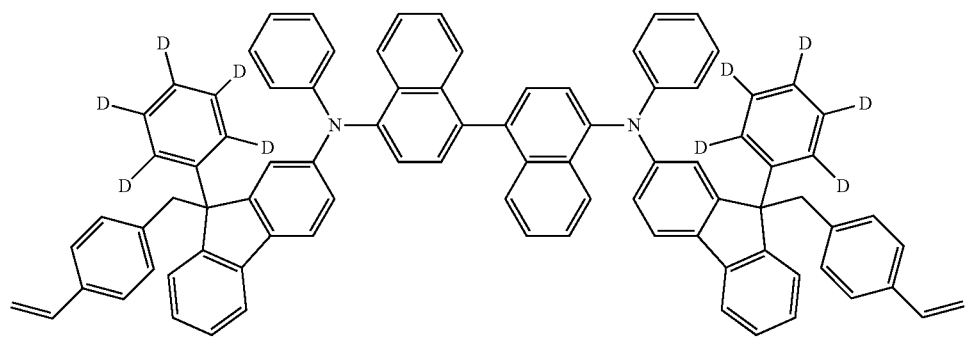

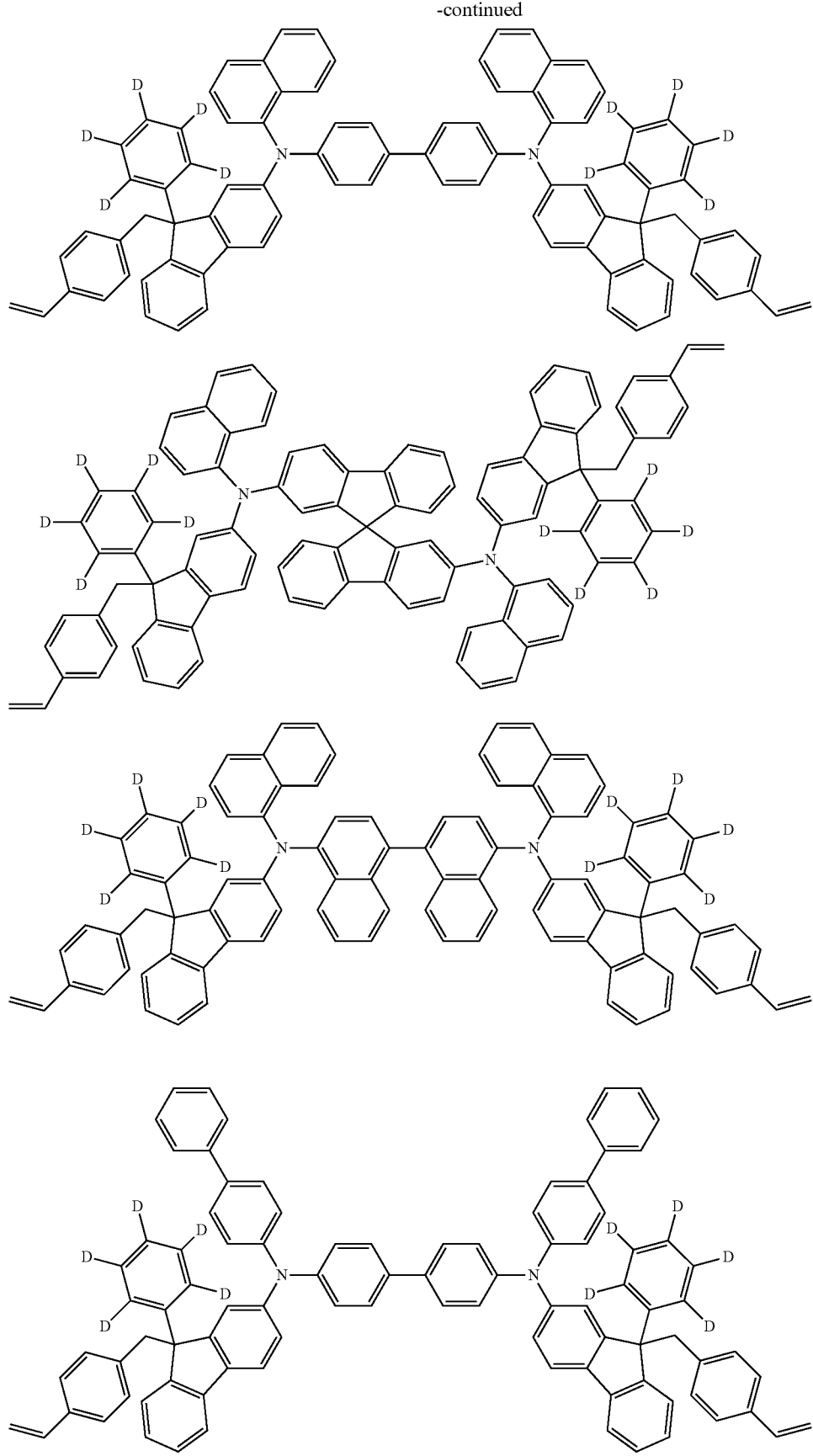

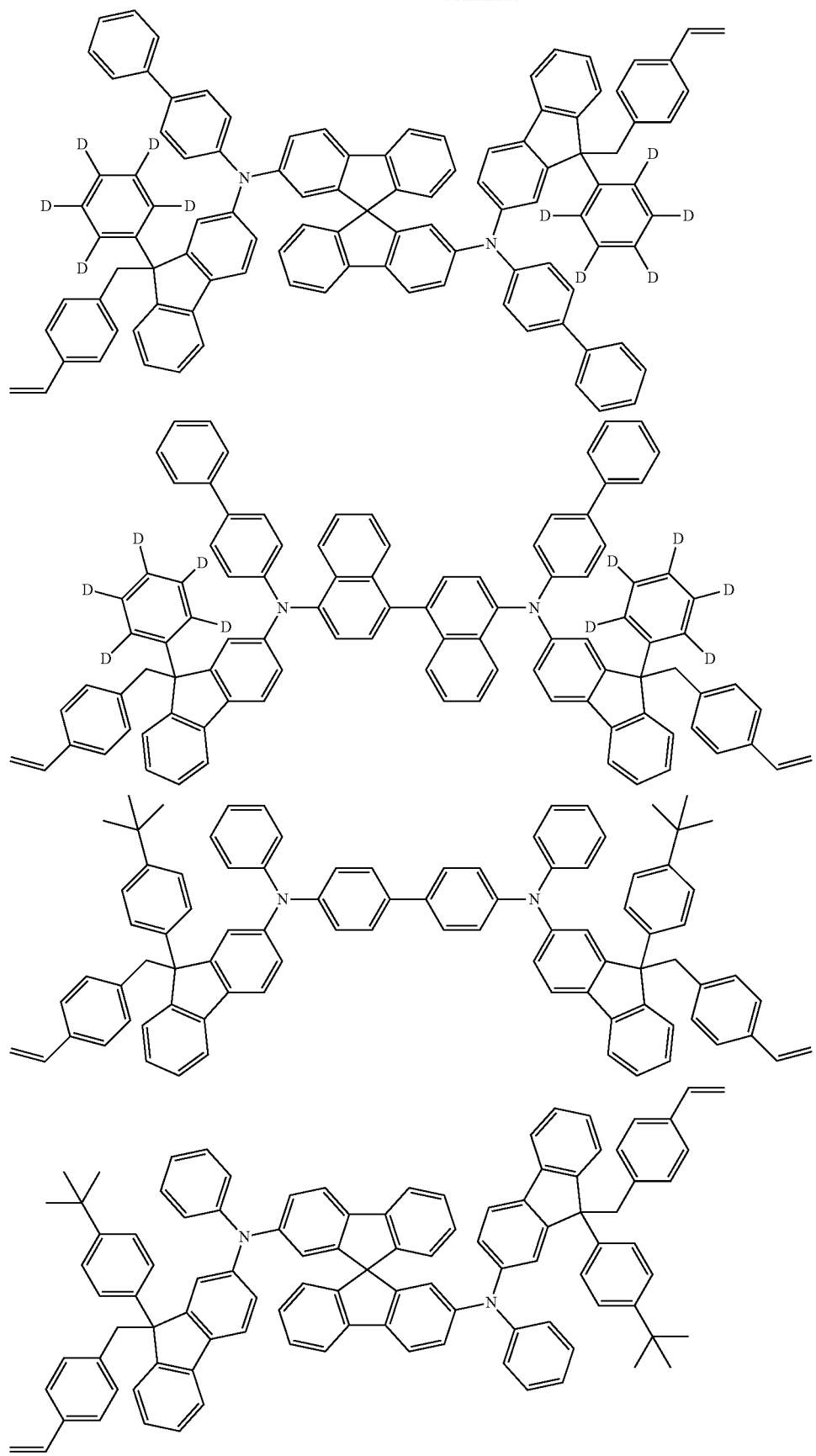

-continued
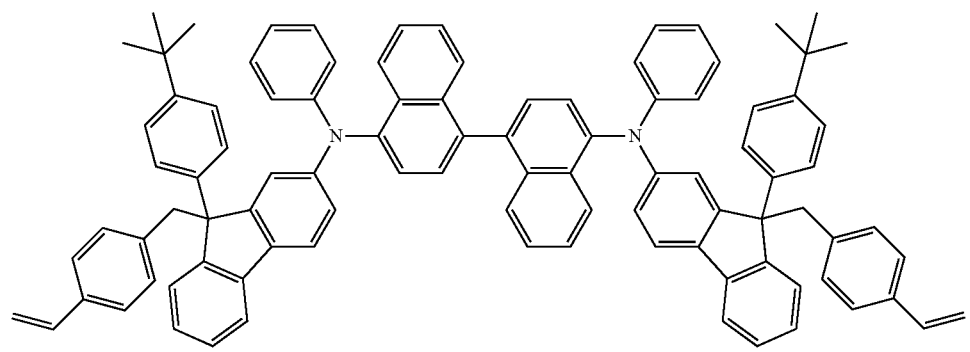
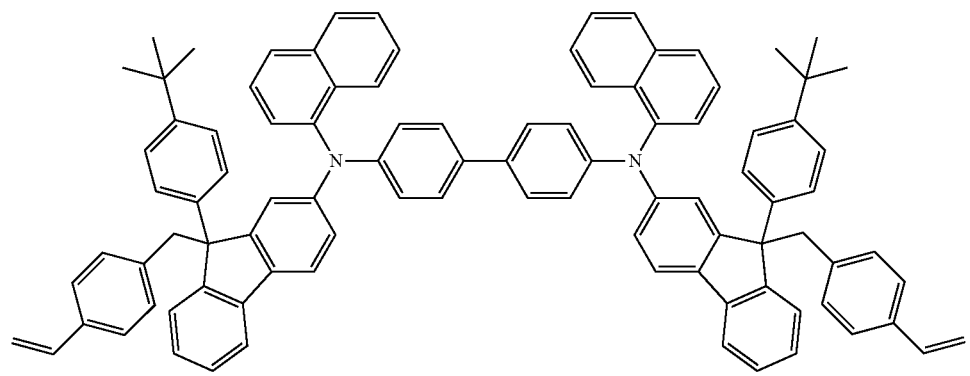
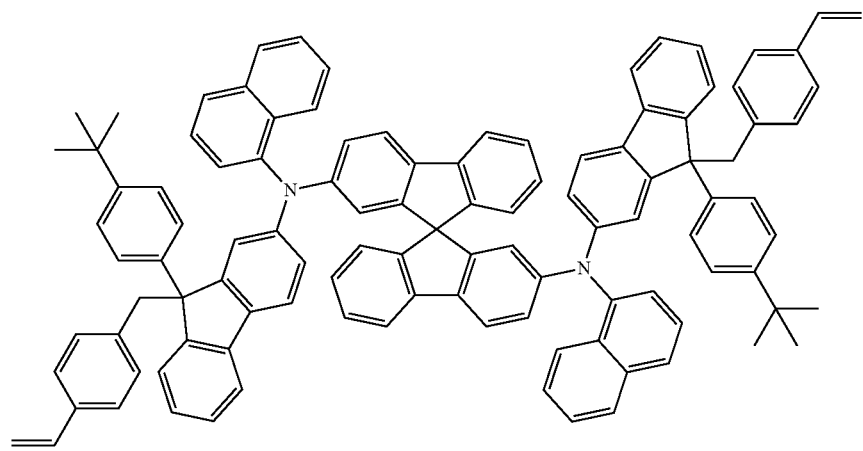
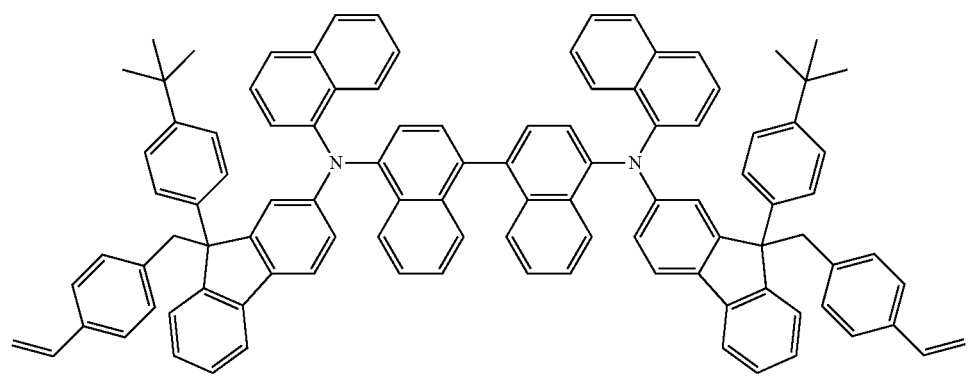

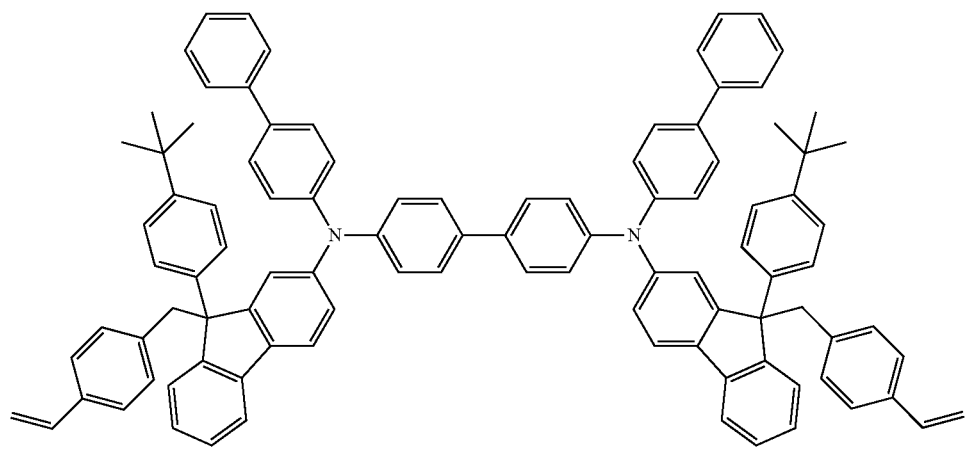
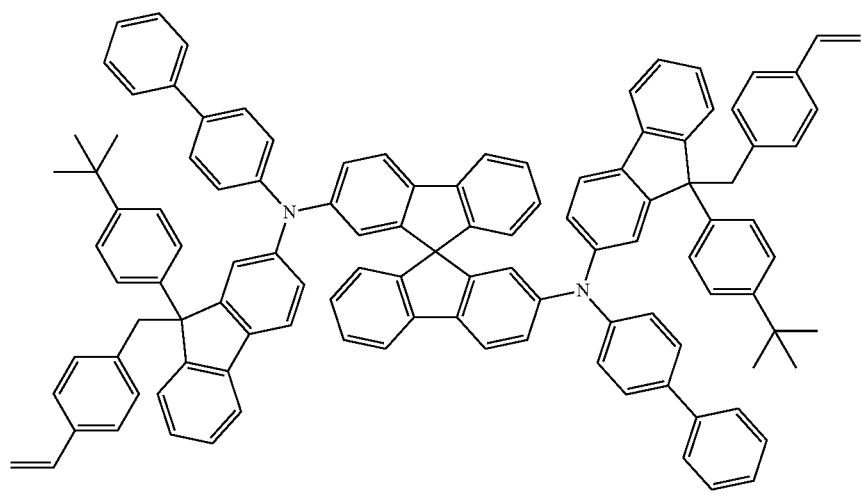
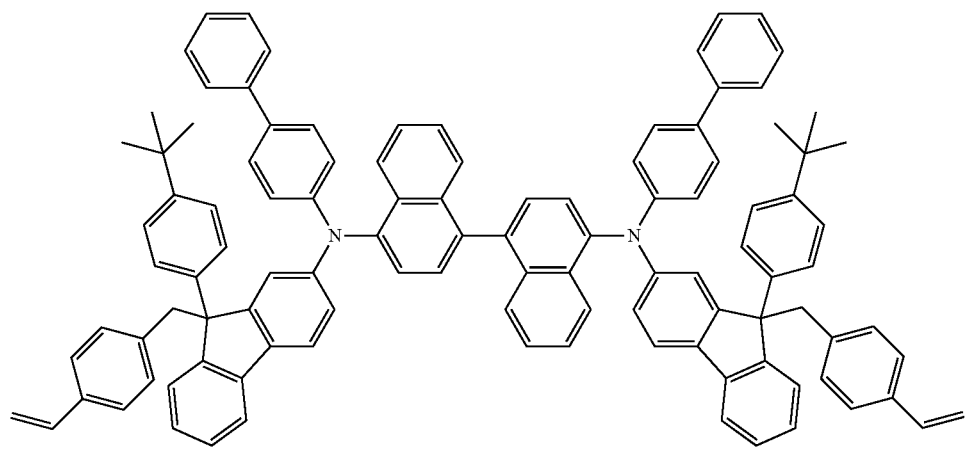

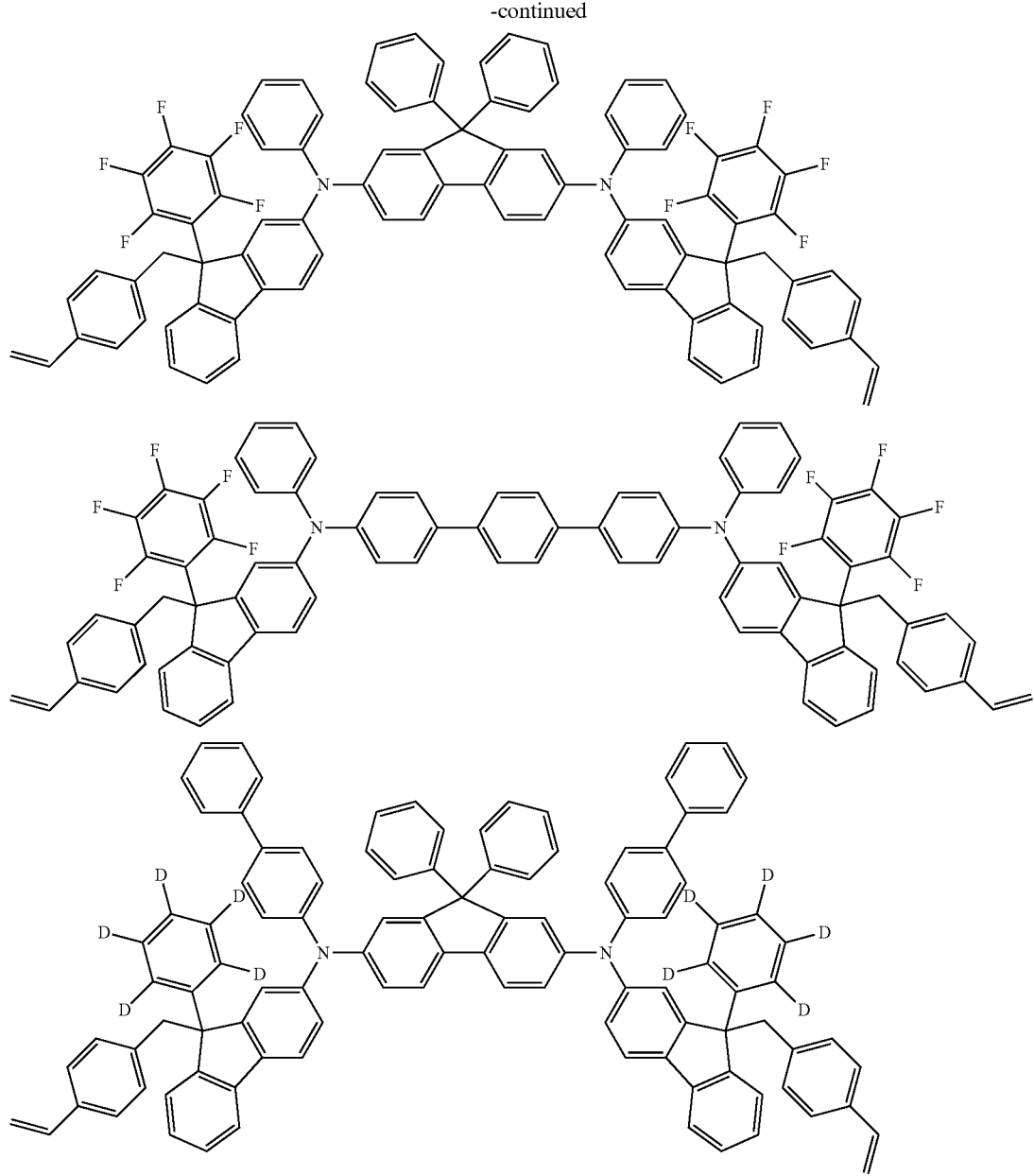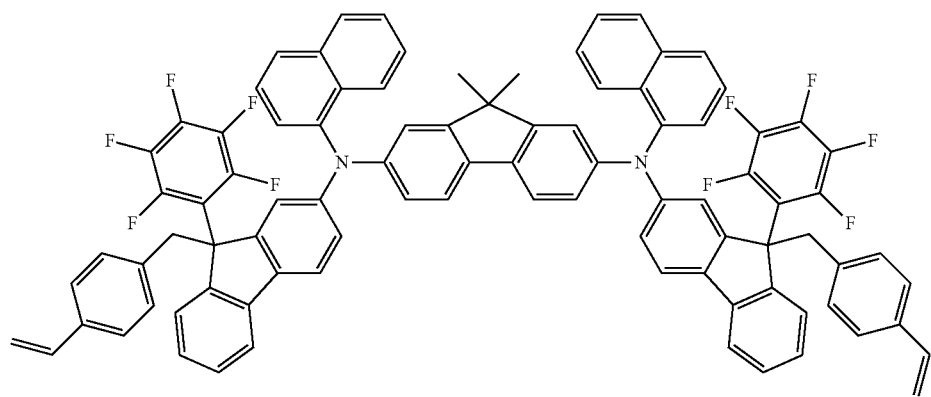

-continued
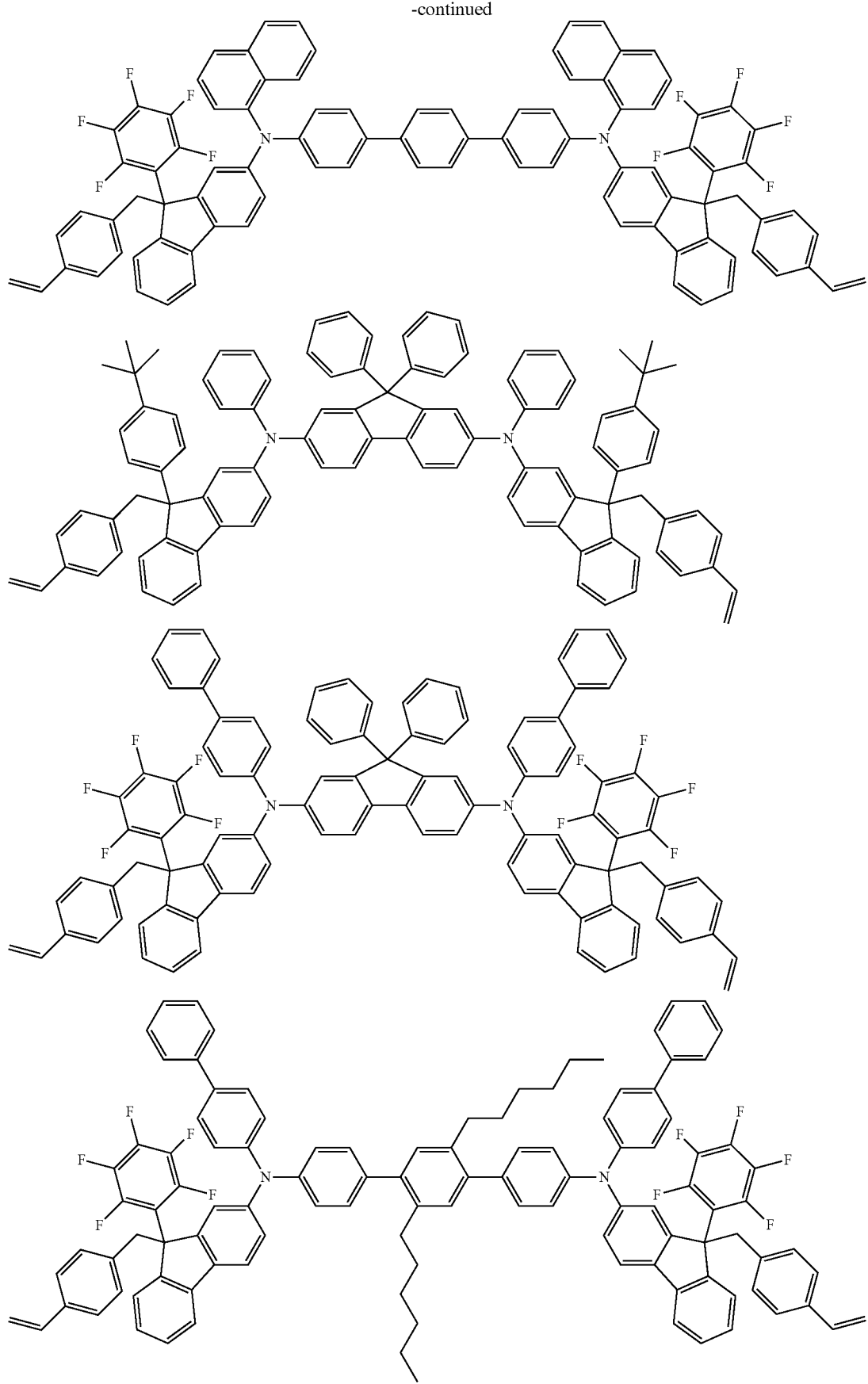

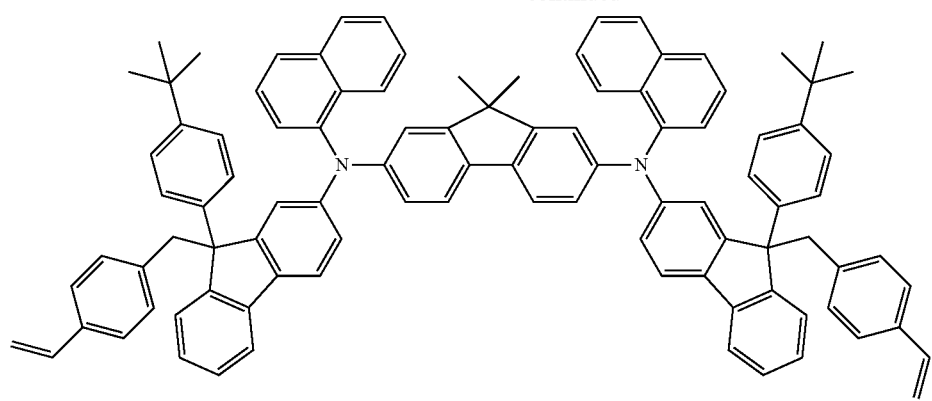
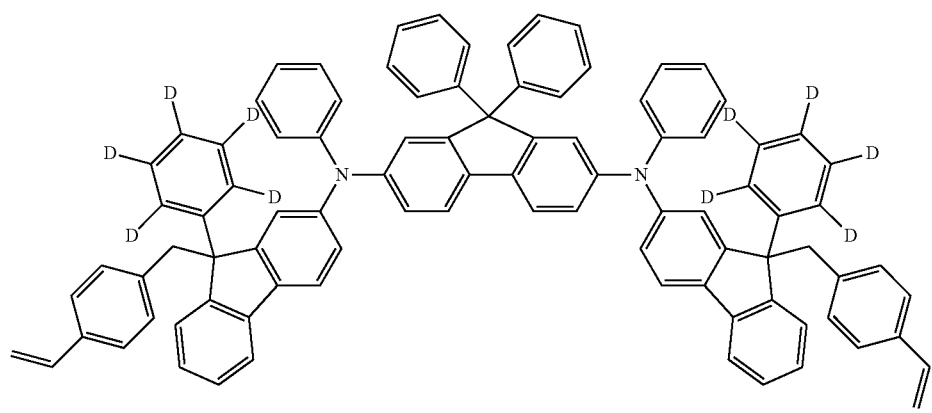
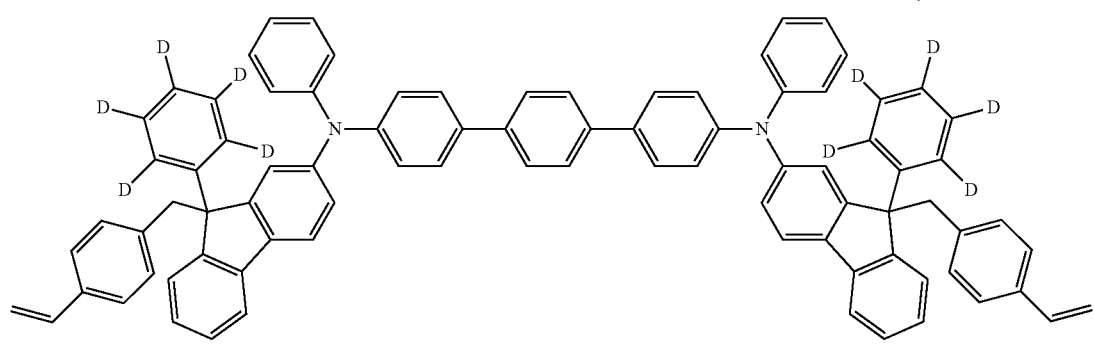
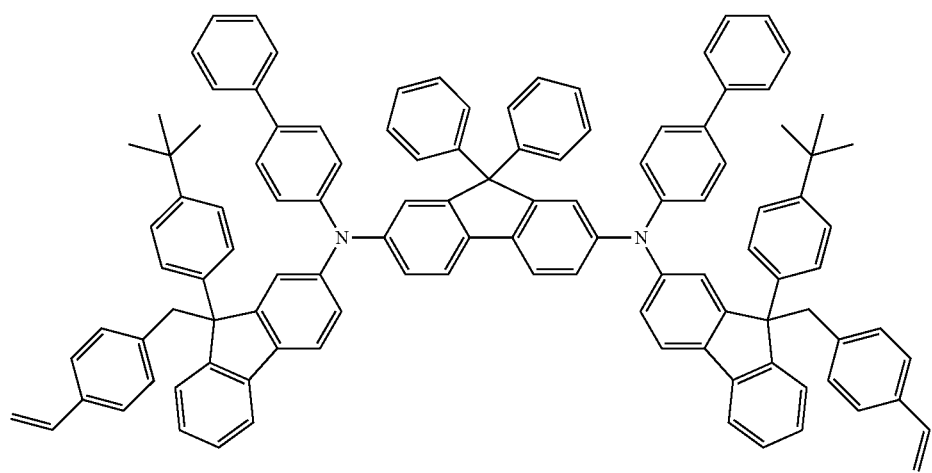

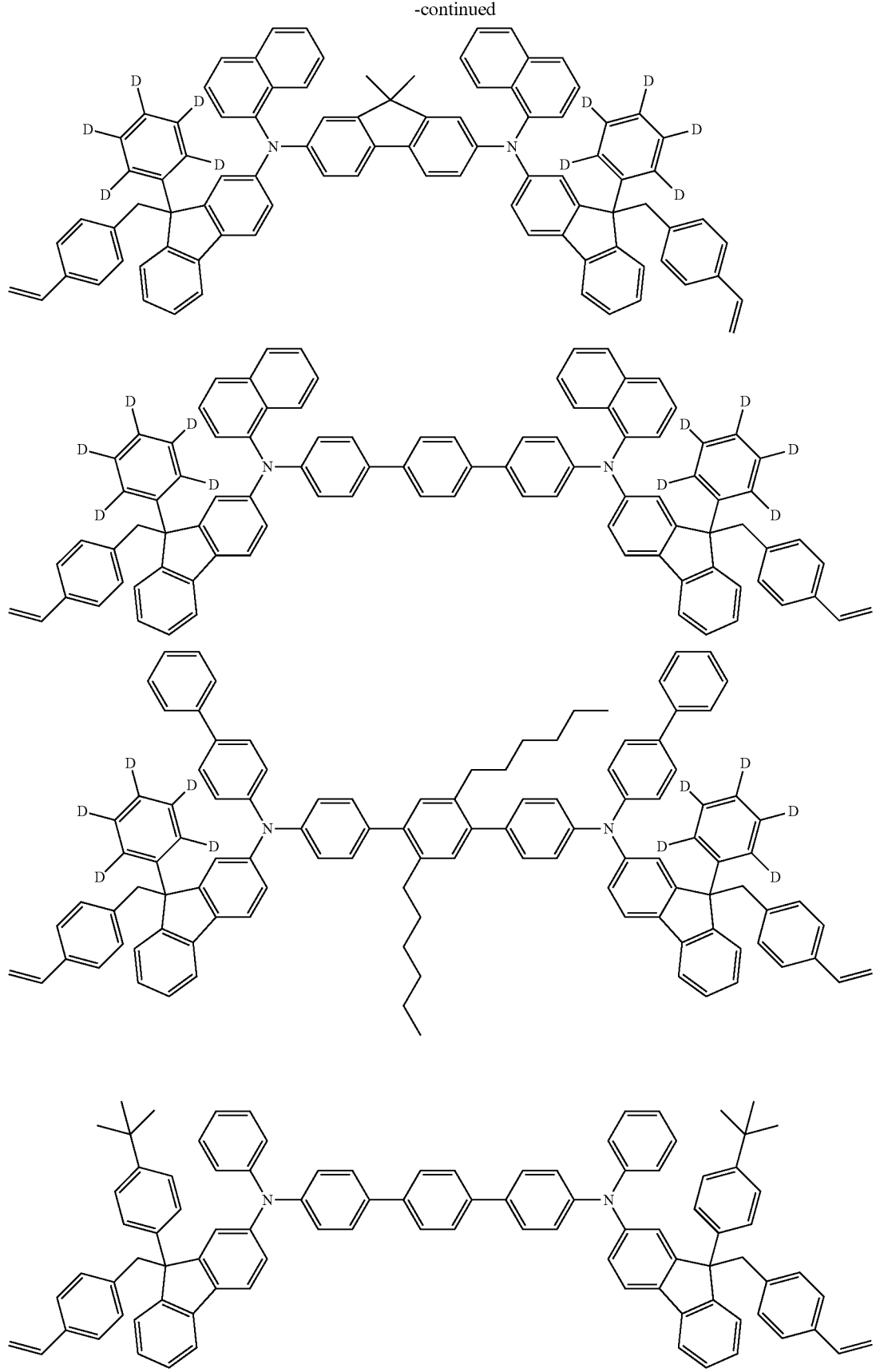

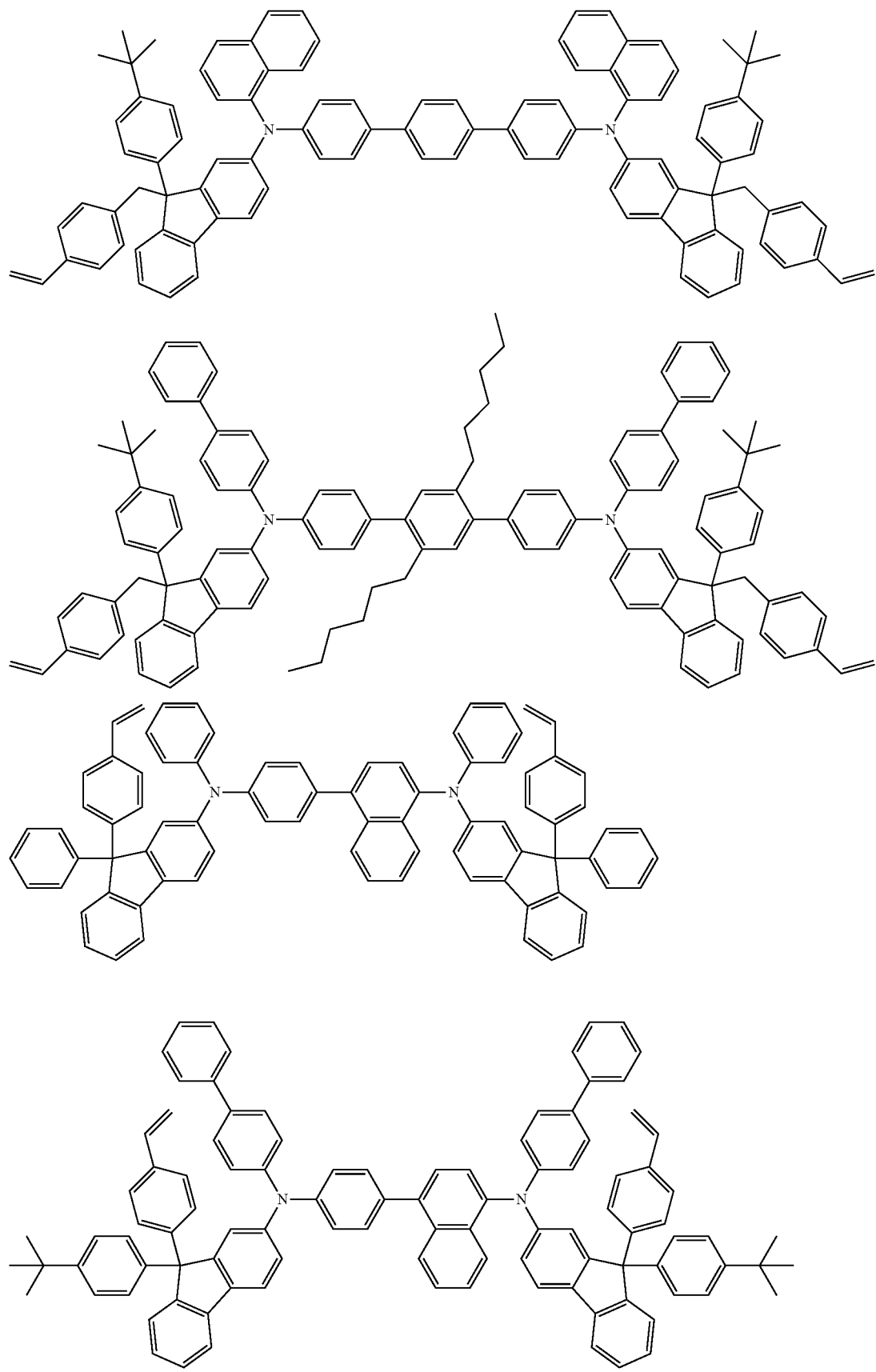

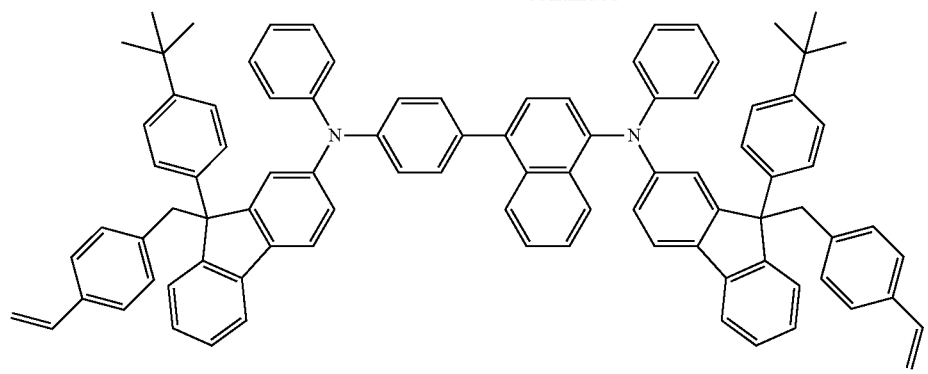
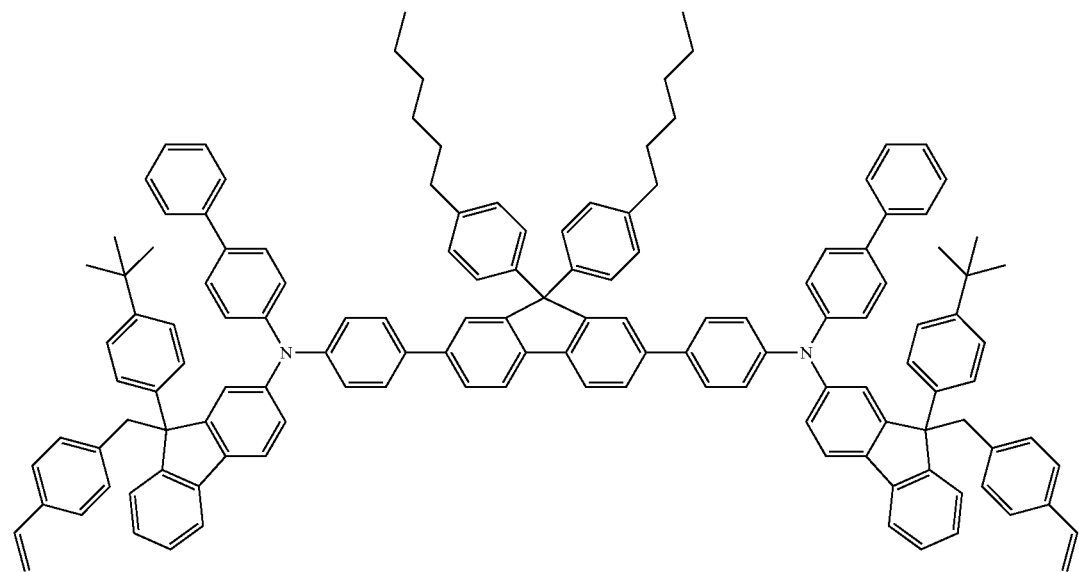
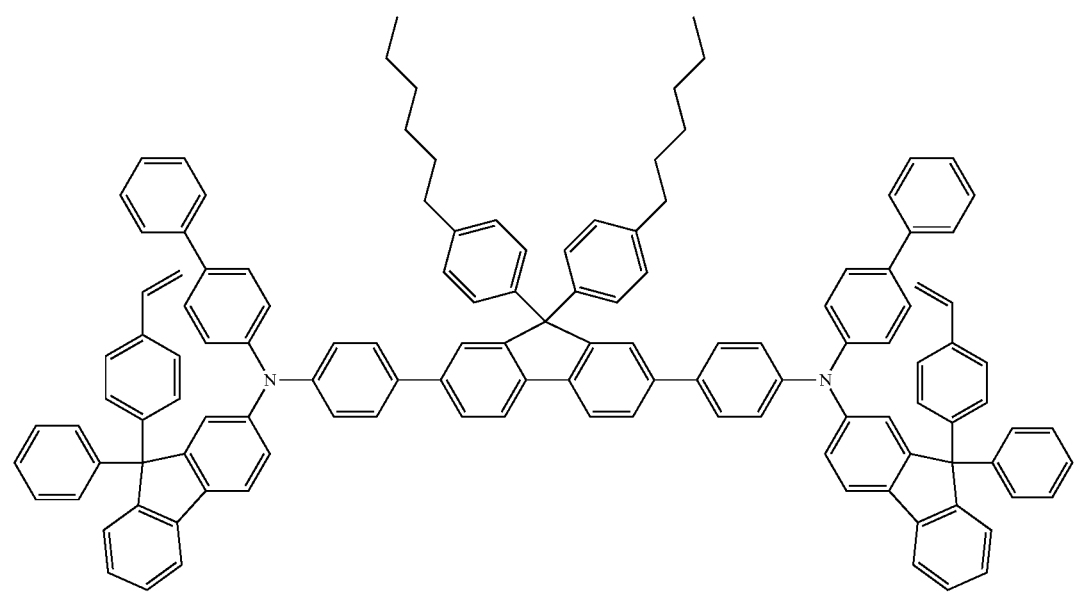

-continued
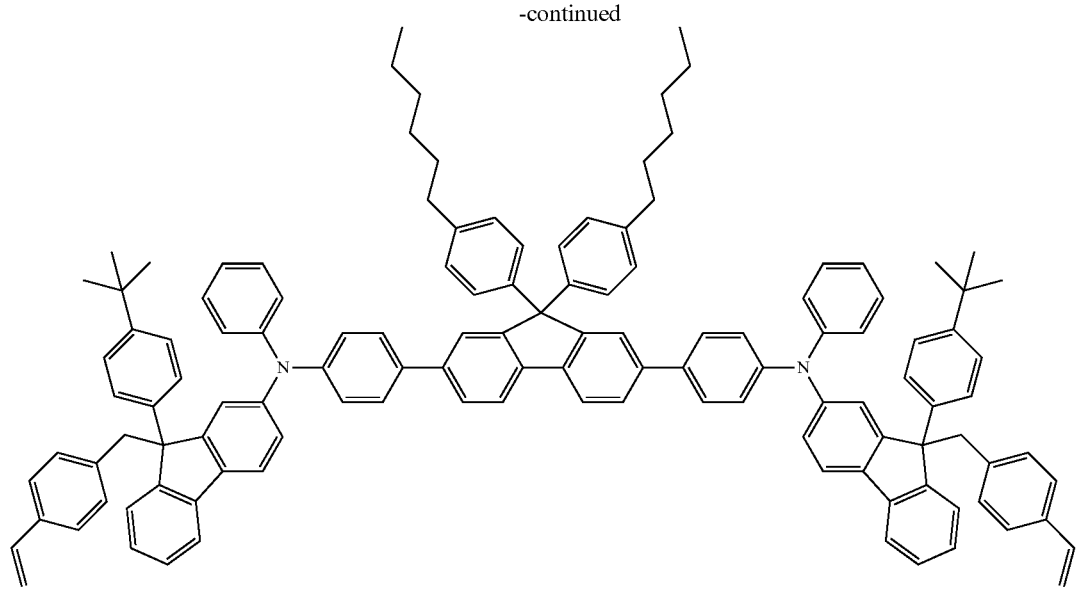
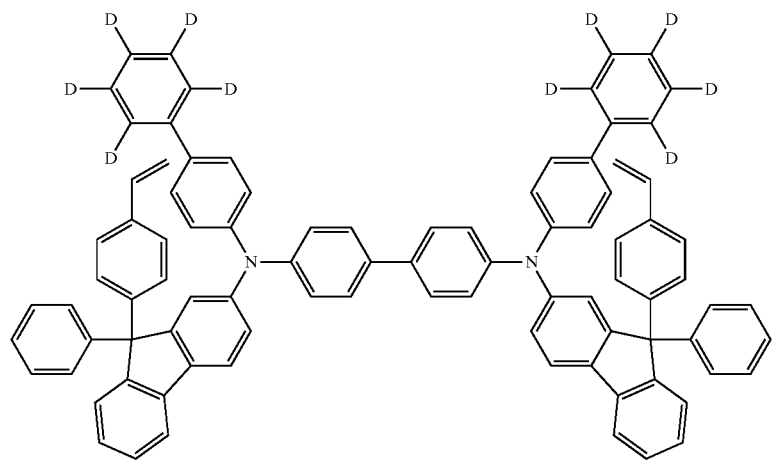
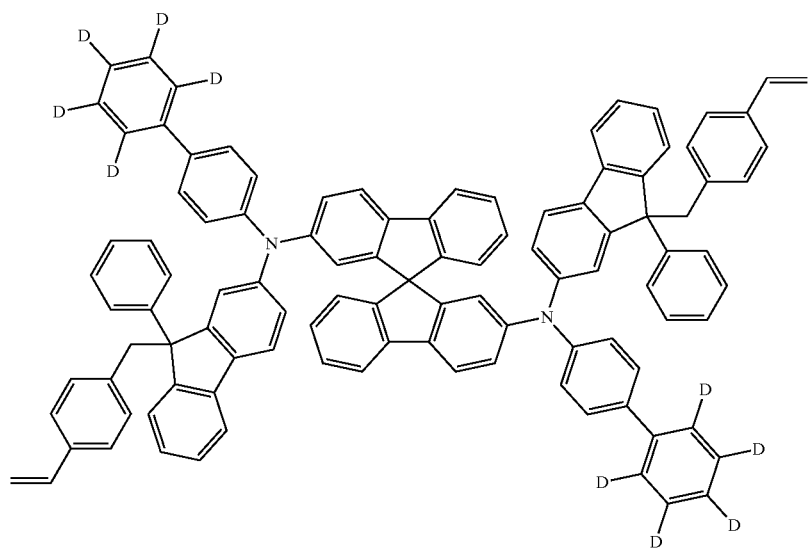

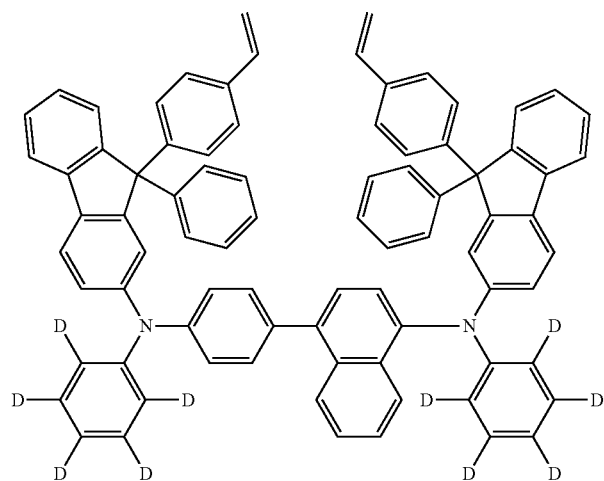
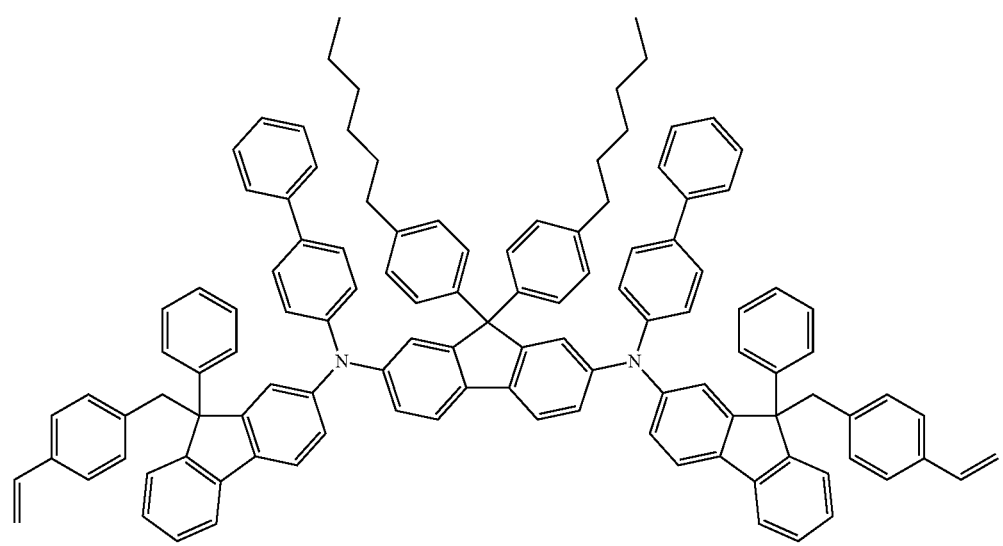
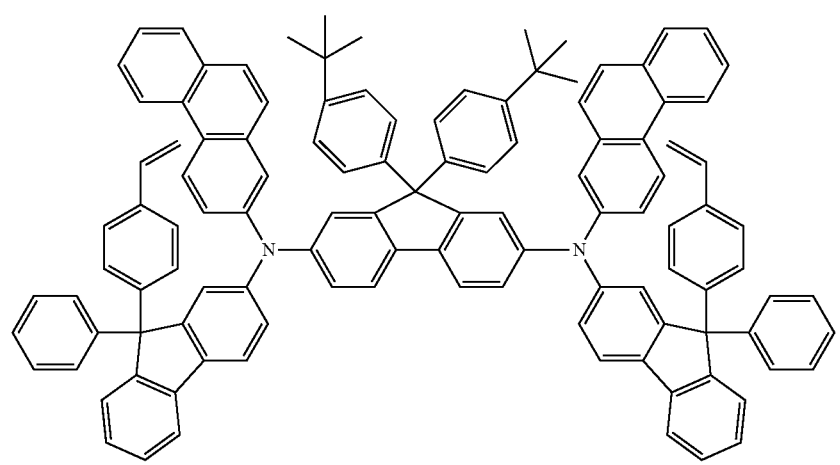

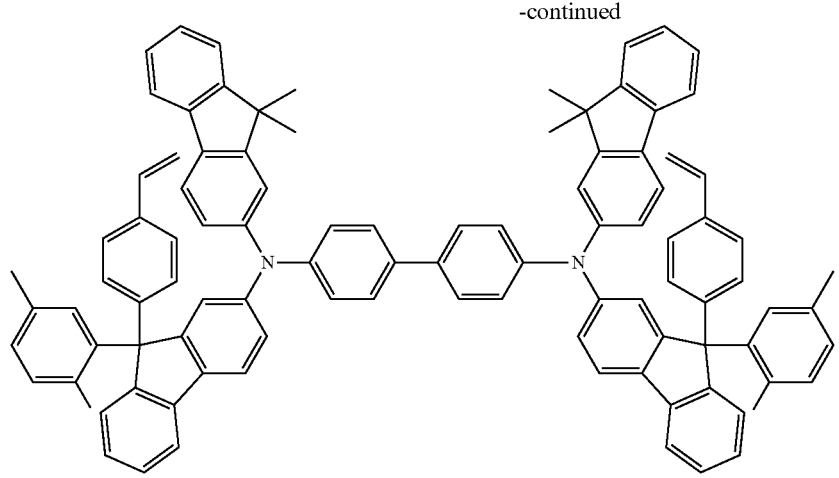

The fluorene-based compound according to an exemplary embodiment of the present specification may be prepared by a preparation method to be described below.

For example, for the fluorene-based compound of Formula 1, a core structure may be prepared by the following preparation method. The substituent may be bonded by a method known in the art, and the kind and position of the substituent or the number of substituents may be changed according to the technology known in the art.

<General Preparation Method of Formula 1>

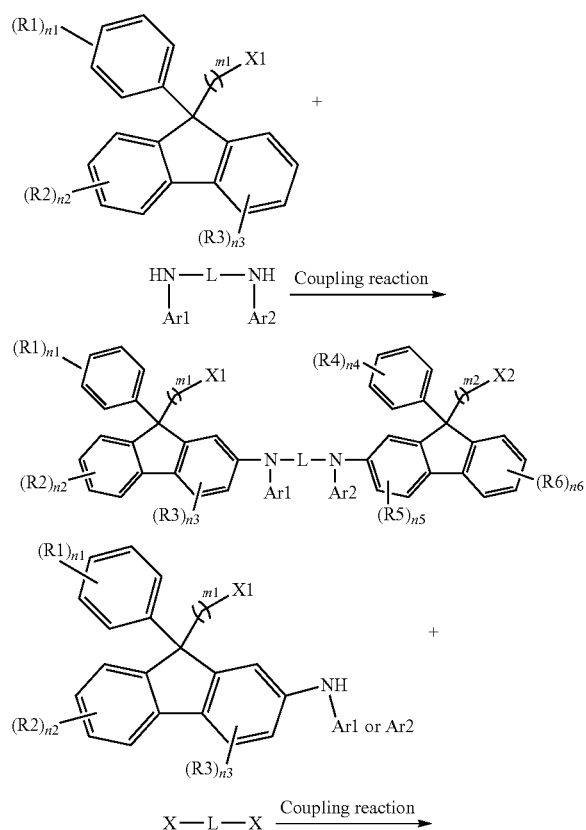

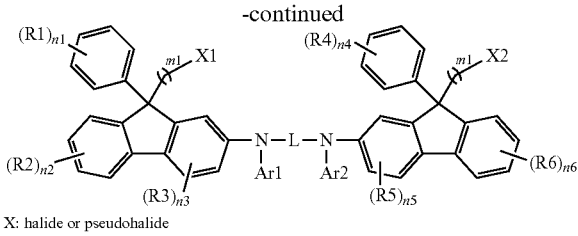

X: halide or pseudohalide

The substituents of the preparation method are the same as the definition of the substituents of Formula 1.

An exemplary embodiment of the present specification provides a coating composition comprising the above-described fluorene-based compound.

In an exemplary embodiment of the present specification, the coating composition comprises the fluorene-based compound and a solvent.

In an exemplary embodiment of the present specification, the coating composition may further comprise one or two compounds selected from the group consisting of a compound, in which a thermosetting group or a photocurable group is introduced into the molecule, and a polymer compound.

In an exemplary embodiment of the present specification, the coating composition may further comprise a compound in which a thermosetting group or a photocurable group is introduced into the molecule. When the coating composition further comprises a compound in which a thermosetting group or a photocurable group is introduced into the molecule, a cure degree of the coating composition may be further increased.

In an exemplary embodiment of the present specification, the compound in which a thermosetting group or a photocurable group is introduced into the molecule has a molecular weight of 1,000 g/mol to 3,000 g/mol.

In an exemplary embodiment of the present specification, the coating composition may further comprise a polymer compound. When the coating composition further comprises a polymer compound, ink characteristics of the coating composition may be enhanced. That is, a coating composition further comprising the polymer compound may provide a viscosity suitable for coating or inkjet printing.

In an exemplary embodiment of the present specification, the coating composition may be in a liquid phase. The "liquid phase" means that the coating composition is in a liquid state at room temperature under atmospheric pressure.

In an exemplary embodiment of the present specification, the solvent is exemplified as, for example, a chlorine-based solvent such as chloroform, methylene chloride, 1,2-dichloroethane, 1,1,2-trichloroethane, chlorobenzene, and o-dichlorobenzene; an ether-based solvent such as tetrahydrofuran and dioxane; an aromatic hydrocarbon-based solvent such as toluene, xylene, trimethylbenzene, and mesitylene; an aliphatic hydrocarbon-based solvent such as cyclohexane, methylcyclohexane, n-pentane, n-hexane, n-heptane, n-octane, n-nonane, and n-decane; a ketone-based solvent such as acetone, methyl ethyl ketone, cyclohexanone, isophorone, tetralone, decalone, and acetylacetone; an ester-based solvent such as ethyl acetate, butyl acetate, and ethyl cellosolve acetate; a polyhydric alcohol such as ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerin, and 1,2-hexanediol, and derivatives thereof; an alcohol-based solvent such as methanol, ethanol, propanol, isopropanol, and cyclohexanol; a sulfoxide-based solvent such as dimethyl sulfoxide; an amide-based solvent such as N-methyl-2-pyrrolidone and N,N-dimethylformamide; and a solvent such as tetralin, but the solvent is sufficient as long as the solvent may dissolve or disperse the fluorene derivative according to an exemplary embodiment of the present invention, and is not limited thereto.

In another exemplary embodiment, the solvents may be used either alone or in a mixture of two or more solvents.

In an exemplary embodiment of the present specification, the coating composition may further comprise one or two or more additives selected from the group consisting of a thermal polymerization initiator and a photopolymerization initiator.

In an exemplary embodiment of the present specification, as a result of measuring the fluorene-based compound of Formula 1 by a differential scanning calorimeter (DSC), a difference in temperature between an exothermic peak and an endothermic peak before the exothermic peak is 20° C. or more.

The difference in temperature between the exothermic peak and the endothermic peak before the exothermic peak may be 20° C. to 200° C.

The differential scanning calorimeter (DSC) means a device which can quantitatively measure variables such as a change in enthalpy of a sample to heat based on a quantitative analysis of the sample and a change in area of a peak during the denaturalization of the sample from positions, shapes, and the number of the peaks obtained by showing a flow of heat as a function of temperature from the measurement of an amount of energy (enthalpy) required to maintain the difference in temperature between the sample and a reference material as zero while changing the temperatures of the sample and the reference material at a predetermined rate by a program.

In an exemplary embodiment of the present specification, the coating composition does not further comprise a p-doping material.

In an exemplary embodiment of the present specification, the coating composition further comprises a p-doping material.

In the present specification, the p-doping material means a material which allows a host material to have p-semiconductor characteristics. The p-semiconductor characteristics mean characteristics that electrons are injected or transported at the highest occupied molecular orbit (HOMO) energy level, that is, characteristics of a material having large hole conductivity.

In an exemplary embodiment of the present specification, the p-doping material may be F4TCNQ or an Farylborate-based compound, such as the following Formulae 9-1 to 9-3, but is not limited.

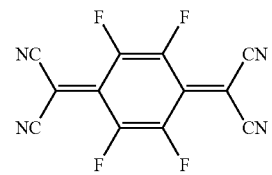

[Formula 9-1]

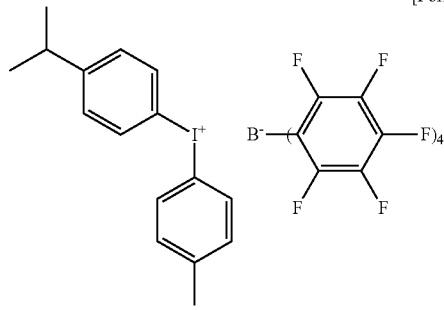

[Formula 9-2]

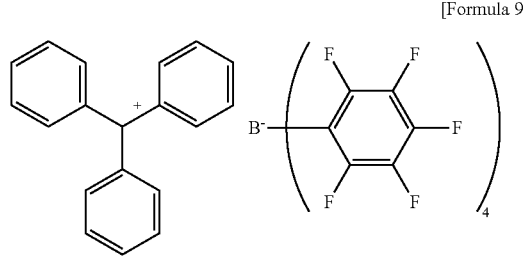

[Formula 9-3]

In the present specification, the p-doping material is sufficient as long as the material is a material which allows the host material to have p-semiconductor characteristics, one or two or more thereof may be used, and the kind thereof is not limited.

In an exemplary embodiment of the present specification, the content of the p-doping material is 0 wt % to 50 wt % based on the fluorene-based compound of Formula 1.

In an exemplary embodiment of the present specification, the content of the p-doping material is 0 to 30 wt % based on the total solid content of the coating composition. In an exemplary embodiment of the present specification, it is preferred that the content of the p-doping material is 1 to 30 wt % based on the total solid content of the coating composition, and in another exemplary embodiment, it is more preferred that the content of the p-doping material is 10 to 30 wt % based on the total solid content of the coating composition.

In another exemplary embodiment, the coating composition may further comprise: a single molecule comprising a thermosetting group or a photocurable group; or a single molecule comprising an end group capable of forming a polymer by heat. As described above, the single molecule comprising a thermosetting group or a photocurable group; or the single molecule comprising an end group capable of forming a polymer by heat may be a compound having a molecular weight of 2,000 g/mol or less.

In an exemplary embodiment of the present specification, the coating composition further comprises: a single molecule having a molecular weight of 2,000 g/mol or less and comprising a thermosetting group or a photocurable group; and a single molecule having a molecular weight of 2,000 g/mol or less and comprising an end group capable of forming a polymer by heat.

The single molecule comprising a thermosetting group or a photocurable group; and the single molecule comprising an end group capable of forming a polymer by heat may mean aryl of phenyl, biphenyl, fluorene, and naphthalene; arylamine; or a single molecule in which a thermosetting group or a photocurable group or an end group capable of forming a polymer by heat is substituted with fluorene.

In another exemplary embodiment, the coating composition has a viscosity of 2 cP to 15 cP.

In an exemplary embodiment of the present specification, the coating composition has a thin film retention rate of 95% or more in a thin film retention test, after a heat treatment at 250° C. or less. The coating composition of the present invention has excellent resistance to a solvent such as toluene and cyclohexanone because the thin film retention rate in the thin film retention test is 95% or more after the heat treatment at 250° C. or less.

In the thin film retention test, a thin film is first formed by spin-coating the coating composition onto a substrate (for example, glass, and the like), a heat treatment is performed in a nitrogen atmosphere, and then UV absorbance of the thin film is measured. Thereafter, the thin film retention rate is measured by dipping the thin film into a solvent such as toluene and cyclohexanone for about 10 minutes, drying the thin film, and then measuring UV absorbance of the thin film to compare the sizes of UV absorbance maximum peaks before and after dipping the thin film into the solvent (the size of the UV absorbance maximum peak after dipping the thin film into the solvent/the size of the UV absorbance maximum peak before dipping the thin film into the solvent× 100).

The present specification also provides an organic light emitting device formed by using the coating composition.

An exemplary embodiment of the present specification comprises: a first electrode; a second electrode; and an organic material layer having one or more layers provided between the first electrode and the second electrode, and one or more layers of the organic material layer are formed by using the coating composition or a cured product thereof. The cured product of the coating composition means a state where the coating composition is cured by a heat treatment or a light treatment.

In an exemplary embodiment of the present specification, the organic material layer comprising the coating composition or the cured product thereof is a hole transport layer, a hole injection layer, or a layer which simultaneously transports and injects holes.

In another exemplary embodiment, the organic material layer comprising the coating composition or the cured product thereof is a light emitting layer.

In still another exemplary embodiment, the organic material layer comprising the coating composition or the cured product thereof is a light emitting layer, and the light emitting layer comprises the fluorene-based compound as a host of the light emitting layer.

In an exemplary embodiment of the present specification, the organic light emitting device further comprises one or two or more layers selected from the group consisting of a hole injection layer, a hole transport layer, an electron transport layer, an electron injection layer, an electron blocking layer, and a hole blocking layer.

In an exemplary embodiment of the present specification, the first electrode is an anode, and the second electrode is a cathode.

According to another exemplary embodiment, the first electrode is a cathode, and the second electrode is an anode.

In still another exemplary embodiment, the organic light emitting device may be an organic light emitting device having a structure (normal type) in which an anode, an organic material layer having one or more layers, and a cathode are sequentially stacked on a substrate.

In yet another exemplary embodiment, the organic light emitting device may be an organic light emitting device having a reverse-direction structure (inverted type) in which a cathode, an organic material layer having one or more layer, and an anode are sequentially stacked on a substrate.

The organic material layer of the organic light emitting device of the present specification may also be composed of a single-layered structure, but may be composed of a multi-layered structure in which an organic material layer having two or more layers is stacked. For example, the organic light emitting device of the present invention may have a structure comprising a hole injection layer, a hole transport layer, a layer which simultaneously injects and transports holes, a light emitting layer, an electron transport layer, an electron injection layer, a layer which simultaneously injects and transport electrons, and the like as an organic material layer. However, the structure of the organic light emitting device is not limited thereto, and may comprise a fewer number of organic layers.

In the organic light emitting device of the present specification, [a substrate/a positive electrode/a hole injection layer/a hole transport layer/a light emitting layer/an electron injection layer/an electron transport layer/a negative electrode] may be stacked in this order.

In the organic light emitting device of the present specification according to another exemplary embodiment, [a substrate/a positive electrode/a hole injection layer/a hole transport layer/a light emitting layer/a layer which simultaneously injects and transport electrons/a negative electrode] may be stacked in this order.

For example, the structure of the organic light emitting device according to an exemplary embodiment of the present specification is exemplified in FIG. 1.

FIG. 1 exemplifies a structure of an organic light emitting device in which an anode 201, a hole injection layer 301, a hole transport layer 401, a light emitting layer 501, a layer which simultaneously injects and transport electrons 601, and a cathode 701 are sequentially stacked on a substrate 101.

FIG. 1 exemplifies an organic light emitting device, and the organic light emitting device is not limited thereto.

When the organic light emitting device comprises a plurality of organic material layers, the organic material layers may be formed of the same material or different materials.

The organic light emitting device of the present specification may be manufactured by the materials and methods known in the art, except that one or more layers of the organic material layer are formed by using a coating composition comprising the fluorene-based compound.

For example, the organic light emitting device of the present specification may be manufactured by sequentially stacking an anode, an organic material layer, and a cathode on a substrate. In this case, the organic light emitting device may be manufactured by depositing a metal or a metal oxide having conductivity, or an alloy thereof on a substrate to form an anode, forming an organic material layer comprising a hole injection layer, a hole transport layer, a light emitting layer, and a layer which simultaneously injects and transports electrons thereon through a deposition or solution process, and then depositing a material, which may be used as a cathode, thereon, by using a physical vapor deposition (PVD) method such as sputtering or e-beam evaporation. In addition to the method described above, an organic light emitting device may be made by sequentially depositing a cathode material, an organic material layer, and an anode material on a substrate.

The present specification also provides a method for manufacturing an organic light emitting device formed by using the coating composition.

Specifically, in an exemplary embodiment of the present specification, the method comprises: preparing a substrate; forming a first electrode on the substrate; forming an organic material layer having one or more layers on the first electrode; and forming a second electrode on the organic material layer, and one or more layers of the organic material layer are formed by using the coating composition.

According to an exemplary embodiment of the present specification, the organic material layer formed by using the coating composition is formed by using a solution process.

In an exemplary embodiment of the present specification, the organic material layer formed by using the coating composition is formed by using spin coating.

In another exemplary embodiment, the organic material layer formed by using the coating composition is formed by a printing method.

In still another exemplary embodiment of the present specification, examples of the printing method comprise inkjet printing, nozzle printing, offset printing, transfer printing or screen printing, and the like, but are not limited thereto.

For the coating composition according to an exemplary embodiment of the present specification, a solution process is suitable due to the structural characteristics, so that the organic material layer may be formed by a printing method, and as a result, there is an economic effect in terms of time and costs when a device is manufactured.

In an exemplary embodiment of the present specification, the forming of the organic material layer formed by using the coating composition comprises: coating the coating composition onto the cathode or the anode; and subjecting the coated coating composition to a heat treatment or a light treatment.

In an exemplary embodiment of the present specification, a heat treatment temperature in the subjecting of the coated coating composition to the heat treatment is 85° C. to 250° C.

In another exemplary embodiment, a heat treatment time in the subjecting of the coated coating composition to the heat treatment may be 1 minute to 1 hour.

In an exemplary embodiment of the present specification, when the coating composition does not comprise an additive, it is preferred that a cross-linkage proceeds by performing a heat treatment at a temperature of 100° C. to 250° C., and it is more preferred that a cross-linkage proceeds at a temperature of 120° C. to 200° C.

When the forming of the organic material layer formed by using the coating composition comprises the subjecting of the coated coating composition to the heat treatment or the light treatment, a plurality of fluorene-based compounds included in the coating composition may form a cross-linkage, thereby providing an organic material layer comprising a thin-filmed structure. In this case, it is possible to prevent the organic material layer from being dissolved or morphologically affected or decomposed by a solvent when another layer is stacked on the surface of the organic material layer formed by using the coating composition.

Therefore, when the organic material layer formed by using the coating composition is formed by a method comprising the subjecting of the coated coating composition to the heat treatment or the light treatment, resistance to a solvent is increased, so that a plurality of layers may be formed by repeatedly carrying out solution deposition and cross-linking methods, and stability is increased, so that service life characteristics of the device may be increased.

In an exemplary embodiment of the present specification, the coating composition comprising the fluorene-based compound may use a coating composition which is dispersed by being mixed with a polymeric binder.

In an exemplary embodiment of the present specification, as the polymeric binder, those which do not extremely suppress charge transport are preferred, and those which are not strong in absorbance to visible light are preferably used. As the polymeric binder, poly(N-vinylcarbazole), polyaniline, and derivatives thereof, polythiophene and derivatives thereof, poly(p-phenylene vinylene) and derivatives thereof, poly(2,5-thienylene vinylene) and derivatives thereof, polycarbonate, polyacrylate, polymethyl acrylate, polymethyl methacrylate, polystyrene, polyvinyl chloride, polysiloxane, and the like are exemplified.

Further, the fluorene-based compound according to an exemplary embodiment of the present specification may comprise fluorene and an amine group to comprise a fluorene-based compound alone in an organic material layer, may make a film prepared from a coating composition comprising a fluorene-based compound thinned through a heat treatment or a light treatment, and may comprise a material, which is obtained by using a coating composition mixed with another monomer, as a copolymer. In addition, the fluorene-based compound may comprise a material obtained by using a coating composition mixed with another polymer, as a copolymer or a mixture.

As the anode material, materials having a high work function are usually preferred so as to facilitate the injection of holes into an organic material layer. Specific examples of the anode material which may be used in the present invention comprise: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as $ZnO:Al$ or $SnO_2:Sb$; an electrically conductive polymer, such as poly(3-methylthiophene), poly[3,4-(ethylene-1,2-dioxy)thiophene] (PEDOT), polypyrrole, and polyaniline; and the like, but are not limited thereto.

As the cathode material, materials having a low work function are usually preferred so as to facilitate the injection of electrons into an organic material layer. Specific examples of the cathode material comprise: a metal such as barium, magnesium, calcium, sodium, potassium, titanium, indium, yttrium, lithium, gadolinium, aluminum, silver, tin, and lead, or alloys thereof; a multi-layer structured material such as LiF/Al or $LiO_2/Al$; and the like, but are not limited thereto.

The hole injection layer is a layer which injects holes from an electrode, and a hole injection material is preferably a compound which has a capability of transporting holes, and thus has an effect of injecting holes at an anode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the anode material and the HOMO of the neighboring organic material layer. Specific examples of the hole injection material comprise metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based electrically conductive polymers, and the like, but are not limited thereto.

The hole transport layer is a layer which accepts holes from a hole injection layer and transports the holes to a light emitting layer, and a hole transport material is suitably a material having high hole mobility which may accept holes from an anode or a hole injection layer and transfer the holes to a light emitting layer. Specific examples thereof comprise arylamine-based organic materials, electrically conductive polymers, block copolymers having both conjugated portions and non-conjugated portions, and the like, but are not limited thereto.

The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof comprise: an 8-hydroxy-quinoline aluminum complex ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, lubrene, and the like, but are not limited thereto.

The light emitting layer may comprise a host material and a dopant material. Examples of the host material comprise fused aromatic ring derivatives, or hetero ring-containing compounds, and the like. Specifically, examples of the fused aromatic ring derivatives comprise anthracene derivatives, pyrene derivatives, naphthalene derivatives, pentacene derivatives, phenanthrene compounds, fluoranthene compounds, and the like, and examples of the hetero ring-containing compounds comprise carbazole derivatives, dibenzofuran derivatives, ladder-type furan compounds, pyrimidine derivatives, and the like, but the examples thereof are not limited thereto.

Examples of the dopant material comprise an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof comprise a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof comprise styrylamine, styryldiamine, styryltriamine, styryltetramine, and the like, but are not limited thereto. Further, examples of the metal complex comprise an iridium complex, a platinum complex, and the like, but are not limited thereto.

The electron transport layer is a layer which accepts electrons from an electron injection layer and transports the electrons to a light emitting layer, and an electron transport material is suitably a material having high electron mobility which may proficiently accept electrons from a cathode and transfer the electrons to a light emitting layer. Specific examples thereof comprise: an Al complex of 8-hydroxyquinoline; a complex comprising $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof comprise cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof comprise fluorenone, anthraquinodimethane, diphenoquinone, thiopyran dioxide, oxazole, oxadiazole, triazole, imidazole, perylenetetracarboxylic acid, fluorenylidene methane, anthrone, and the like, and a derivative thereof, a metal complex compound, a nitrogen-containing 5-membered ring derivative, and the like, but are not limited thereto.

Examples of the metal complex compound comprise 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a cathode, and may be generally formed under the same conditions as those of the hole injection layer. Specific examples thereof comprise an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

In an exemplary embodiment of the present specification, the fluorene-based compound may be included in an organic solar cell or an organic transistor in addition to the organic light emitting device.

MODE FOR INVENTION

Hereinafter, the present specification will be described in detail with reference to Examples for specifically describing the present specification. However, the Examples according to the present specification may be modified in various forms, and it is not interpreted that the scope of the present specification is limited to the Examples described below.

The Examples of the present specification are provided to more completely explain the present specification to a person with ordinary skill in the art.

PREPARATION EXAMPLES

A fluorene-based compound to which a curable group is bonded may be synthesized by the following method.

1. Synthesis Method 1 of Fluorene to which Curable Group is Bonded (FS1-Preparation Examples 1 and 2)

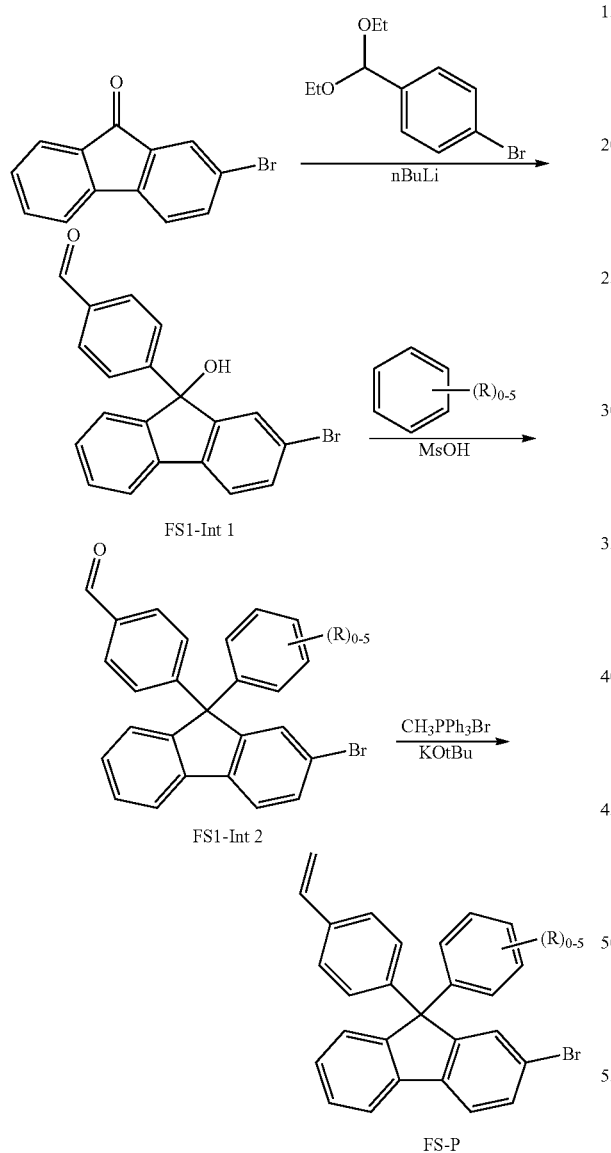

A method capable of bonding a curable group to fluorene is illustrated above. 1-bromo-4-(diethyoxymethyl)benzene is lithiated and added to fluorenone, and a fluorene cured body can be synthesized via a dehydration condensation reaction and a Wittig reaction of tertiary carbinol and arylene in the presence of acid. Fluorene cured bodies F1P and F2P were synthesized by the aforementioned method, and specific preparation methods of fluorene cured bodies F1P and F2P are shown in the following Preparation Examples 1 and 2. The fluorene cured body which may be synthesized as described above is not limited to F1P and F2P.

Preparation Example 1. Preparation of F1P

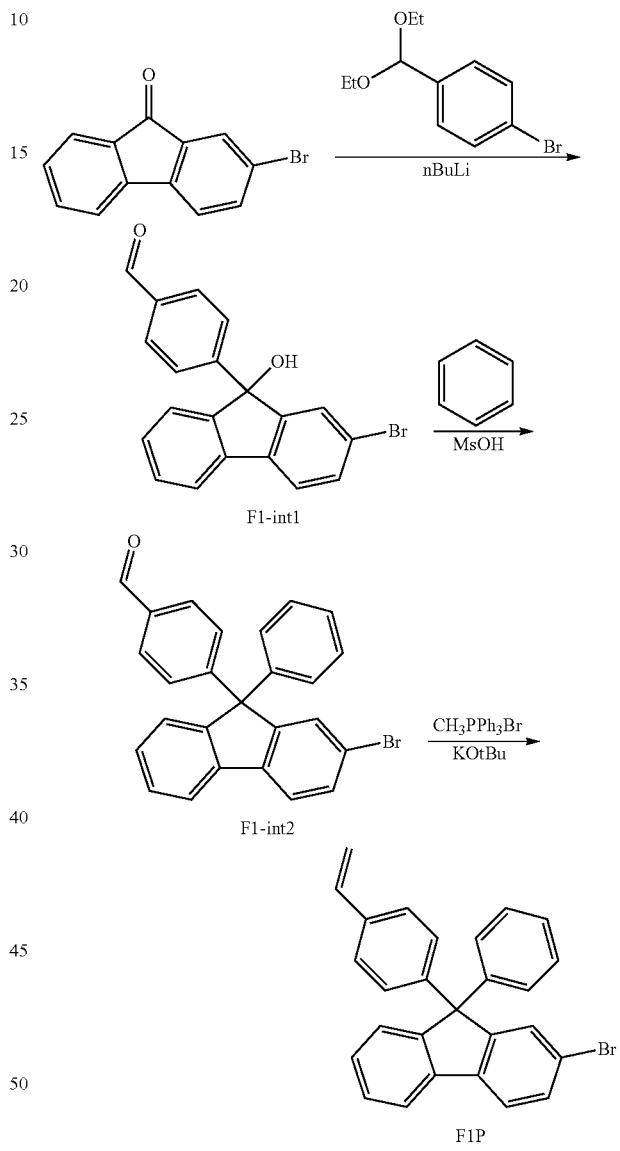

Synthesis of 4-(2-bromo-9-hydroxy-9H-fluoren-9-yl)benzaldehyde (F1-int1): 1-bromo-4-(diethyoxymethyl)benzene (30 g, 115 mmol) was dissolved in 250 ml of tetrahydrofuran and the temperature was lowered to −78° C. nBuLi (2.5 M in hexane, 42 ml, 105 mol) was added thereto, and the resulting mixture was stirred at −78° C. for 30 minutes. 2-bromo-9H-fluoren-9-one (18.9 g, 73 mmol) was added thereto at once and the resulting mixture was stirred overnight. The reaction was terminated with 1 N HCl (aq), followed by extraction with ethyl acetate. After the collected organic solution was dried using magnesium sulfate ($MgSO_4$) and filtered, the organic solvent was removed by a vacuum rotary evaporator. After the residue was column purified, the purified product was recrystallized (toluene/hexane) to obtain 23 g (yield 87%) g of F1-int1.

Synthesis of [4-(2-bromo-9-phenyl-9H-fluoren-9-yl)benzaldehyde](F1-int2): 400 ml of benzene was put into F1-int1 (11.5 g, 31.4 mmol), methane sulfonic acid (2.1 ml, 31.4 mmol) was added thereto, and then the resulting mixture was refluxed using a Dean-Stark apparatus. The acid was neutralized with saturated $NaHCO_3$ (aq), followed by column purification to obtain 6.5 g (yield 49%) of F1-int2.

Synthesis of 2-bromo-9-phenyl-9-(4-vinylphenyl)-9H-fluorene (F1P): F1-int2 (5.3 g, 12.3 mmol) and $CH_3BrPPh_3$ (8.8 g, 24.7 mmol) were added to tetrahydrofuran (THF), potassium tert-butoxide (2.77 g, 24.7 mmol) was added thereto at 0° C., and the resulting mixture was stirred for 1 hour. The reaction was stopped with water, and the product was extracted with ethyl acetate (EA). After magnesium sulfate ($MgSO_4$) was added to the collected organic solution and the resulting mixture was dried and filtered, the organic solvent was removed by a vacuum rotary evaporator. The residue was column purified to obtain 4.67 g (yield 89%) of F1P.

Preparation Example 2. Synthesis of F2P

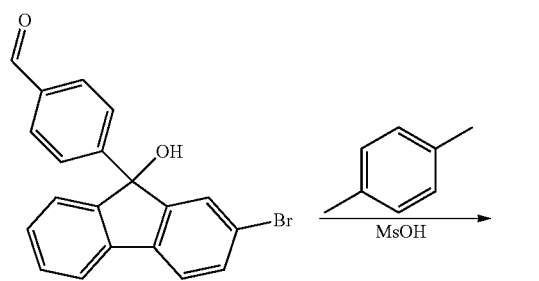

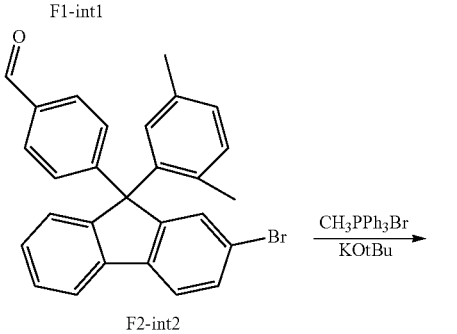

In the synthesis of F1-int2 in Preparation Example 1, xylene was used instead of benzene, and the mixture was stirred at 70° C. overnight instead of refluxing using a Dean-Stark apparatus. 6.6 g (73% second step yield) of F2P was obtained using F1-int2 (7.3 g, 20 mmol).

2. Synthesis Method 2 of Fluorene to which Curable Group is Bonded (FS2-Preparation Examples 3, 4, 5, and 6)

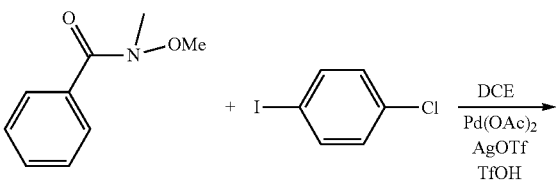

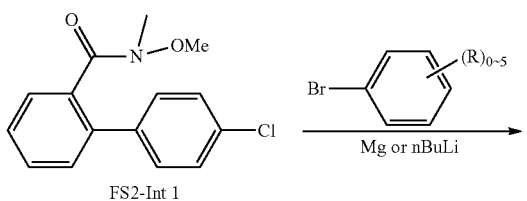

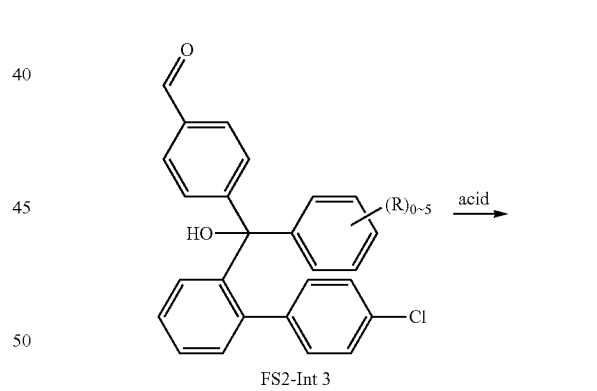

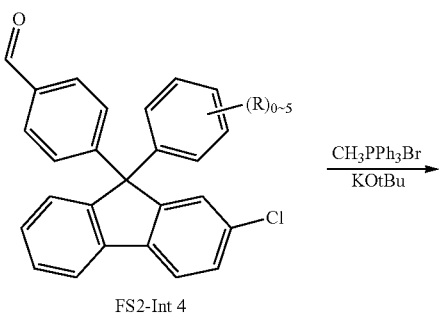

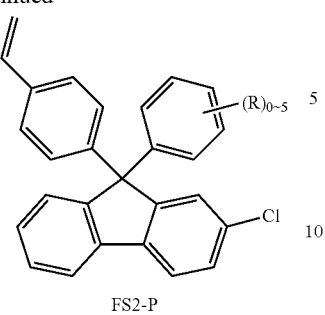

FS2-P

A method capable of synthesizing a fluorene cured body is illustrated above. FS2-int1 Weinreb amide is formed via a coupling reaction of N-methoxy-N-methylbenzamide and 1-chloro-4-iodobenzene. FS2-in3 is synthesized via two nucleophilic addition reactions, and a fluorene cured body can be synthesized via a dehydration condensation cyclization reaction and a Wittig reaction of tertiary carbinol and adjacent arylene in the presence of acid. Various fluorene cured body derivatives can be synthesized by varying the type of aryl halide used during the process of making FS2-in2. Fluorene cured bodies F3P, F4P, F5P, and F6P were synthesized by the aforementioned method, and specific preparation methods of fluorene cured bodies F3P to F6P are shown in the following Preparation Examples 3 and 6. The fluorene cured body which can be synthesized as described above is not limited to F3P, F4P, F5P, and F6P.

Preparation Example 3. Synthesis of F3P

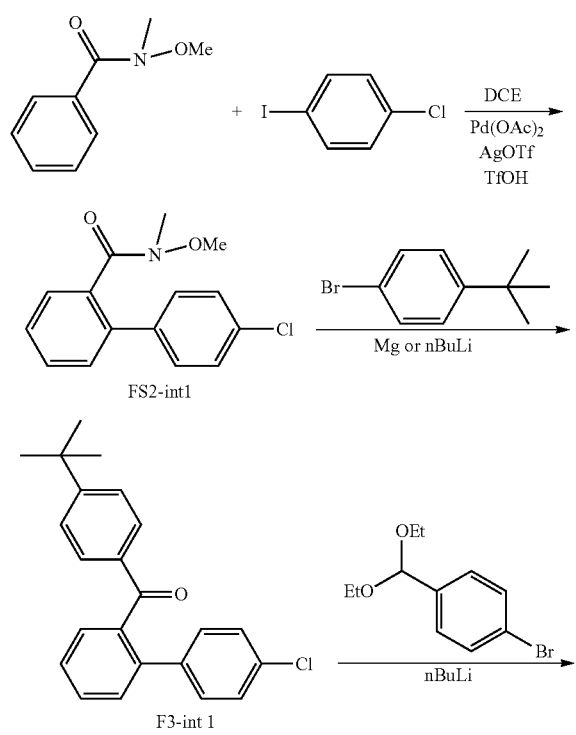

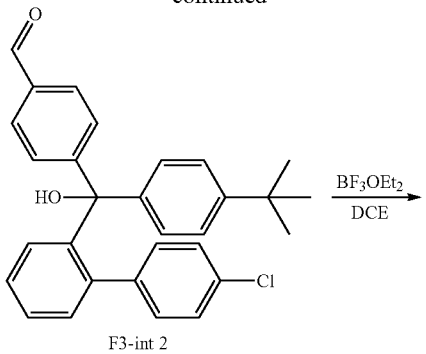

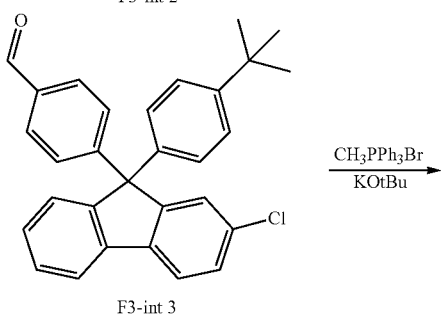

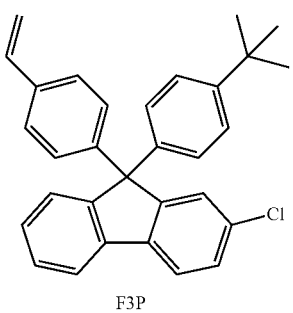

F3P

Synthesis of 4'-chloro-N-methoxy-N-methyl-[1,1'-biphenyl]-2-carboxamide (FS2-int1): 285 ml of 1,2-dichloroethane (DCE) and triflic acid (2.5 ml, 28.5 mmol) were put into a flask containing N-methoxy-N-methylbenzamide (9.4 g, 57 mmol), 1-chloro-4-iodobenzene (27.1 g, 114 mmol), palladium acetate (Pd(OAc)$_2$) (640 mg, 2.85 mmol), and silver triflate (AgOTf)(29.3 g, 114 mmol). The reaction flask was dipped into an oil bath at 80° C. and stirred overnight. The reaction solution was diluted with ethyl acetate, and the diluted product was allowed to pass through short silica column. The filtrate was concentrated by a vacuum rotary evaporator, and then the residue was column purified to obtain 14.2 g (90% yield) of FS2-int1.

Synthesis of (4-(tert-butyl)phenyl)(4'-chloro-[1,1'-biphenyl]-2-yl)methanone (F3-int1): 50 ml of tetrahydrofuran (THF) was put into a flask containing 1-bromo-tert-butylbenzene (8.0 g, 29.0 mmol), and the reaction flask was dipped into a dry ice-acetone bath. nBuLi (2.5 M in hexane, 10.5 mL, 26.2 mmol) was slowly added thereto, and then the resulting mixture was stirred for 1 hour. Next, FS2-int1 (5 g, 18.1 mmol) was dissolved in 15 ml of anhydrous tetrahydrofuran, the resulting solution was slowly put into the reaction flask and stirred for 1 hour, the dry ice-acetone bath was removed, and the solution was stirred for 12 hours. The reaction was stopped with water, and the aqueous layer was separated, followed by extraction with ethyl acetate (EA). After the organic layer was dried using MgSO$_4$ and filtered, the organic solvent was removed using a vacuum rotary evaporator. The residue was column purified to obtain 5.65 g (89.5% yield) of F3-int1.

Synthesis of 4-(9-(4-(tert-butyl)phenyl)-2-chloro-9H-fluoren-9-yl)benzaldehyde (F3-int3): 40 ml of tetrahydrofuran was put into a flask containing 1-bromo-4-(diethyoxymethyl)benzene (5.9 g, 22.9 mmol), and the reaction flask was dipped into a dry ice-acetone bath. nBuLi (2.5 M in hexane, 8.3 ml, 20.8 mmol) was added thereto, and the resulting mixture was stirred at −78° C. for 30 minutes. F3-int1 (5 g, 14.3 mmol) was dissolved in 20 ml of tetrahydrofuran, and the resulting solution was slowly added to the reaction flask. The mixture was stirred overnight while being warmed to room temperature. The reaction was terminated with 1 N HCl (aq), followed by extraction with ethyl acetate. The collected organic solution was dried using magnesium sulfate ($MgSO_4$). After the residue (crude F3-int2) was dissolved in dichloromethane, the reaction flask was dipped into an ice bath. 5.3 ml of a boron trifluoride-diethyl ether complex ($BF_3OEt_2$) was added to the solution, and the resulting mixture was stirred for 2 hours. The reaction was stopped with water, and the product was extracted with dichloromethane. The organic layer was dried using $MgSO_4$ and filtered. After the organic solvent was removed by a vacuum rotary evaporator, the residue was column purified to obtain 4.75 g (76% second step yield) of F3-int3.

Synthesis of 9-(4-(tert-butyl)phenyl)-2-chloro-9-(4-vinylphenyl)-9H-fluorene (F3P): F3-int3 (4.6 g, 10.5 mmol) and $CH_3BrPPh_3$ (7.5 g, 21 mmol) were put into tetrahydrofuran (THF), potassium tert-butoxide (2.36 g, 21 mmol) was added thereto at 0° C., and the resulting mixture was stirred for 1 hour. The reaction was stopped with water, and the product was extracted with ethyl acetate (EA). After magnesium sulfate ($MgSO_4$) was added to the collected organic solution and the resulting mixture was dried and filtered, the organic solvent was removed by a vacuum rotary evaporator. The residue was column purified to obtain 4.24 g (yield 93%) of F3P.

Preparation Examples 4 to 6

F4P, F5P, and F6P were synthesized using the compounds described in the following Table 1.

TABLE 1

| | Aryl-X used in the synthesis step of FS2-int 2 | Structure of FS2-int 2 | Structure of FS2-P | Total yield (from FS2-int1) |
|---|---|---|---|---|
| Preparation Example 4: Synthesis of F4P | (4-bromotoluene structure) | (F4 int 1) | F4P | 61% |
| Preparation Example 5: Synthesis of F5P | (deuterated bromobenzene, D-substituted) | (F5 int 1) | F5P | 66% |
| Preparation Example 6: Synthesis of F6P | (pentafluorobromobenzene) | (F6 int 1) | F6P | 44% |

3. Synthesis Method 3 of Fluorene to which Curable Group is Bonded (FS3-Preparation Examples 7 and 8)

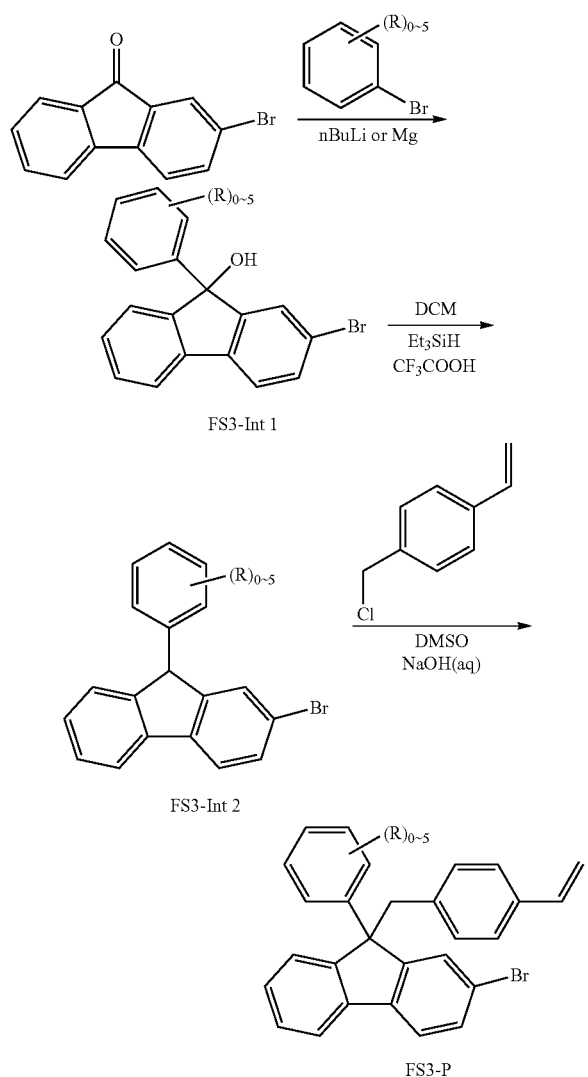

FS3-Int 1

FS3-Int 2

FS3-P

A method capable of synthesizing a fluorene cured body is illustrated above. FS3-int1 can be made by producing aryl lithium or aryl magnesium halide from aryl halide and adding aryl lithium or aryl magnesium halide to 2-bromofluorenone. Thereafter, an FS3-P form can be synthesized via a dehydroxylation reaction and the following reaction. Various fluorene cured body derivatives can be synthesized by varying the type of aryl halide used during the process of making FS3-int1. Fluorene cured bodies F7P and F8P were synthesized by the aforementioned method, and specific preparation methods of fluorene cured bodies F7P and F8P are shown in the following Preparation Examples 7 and 8. The fluorene cured body which can be synthesized as described above is not limited to F7P and F8P.

Preparation Example 7. Synthesis of F7P

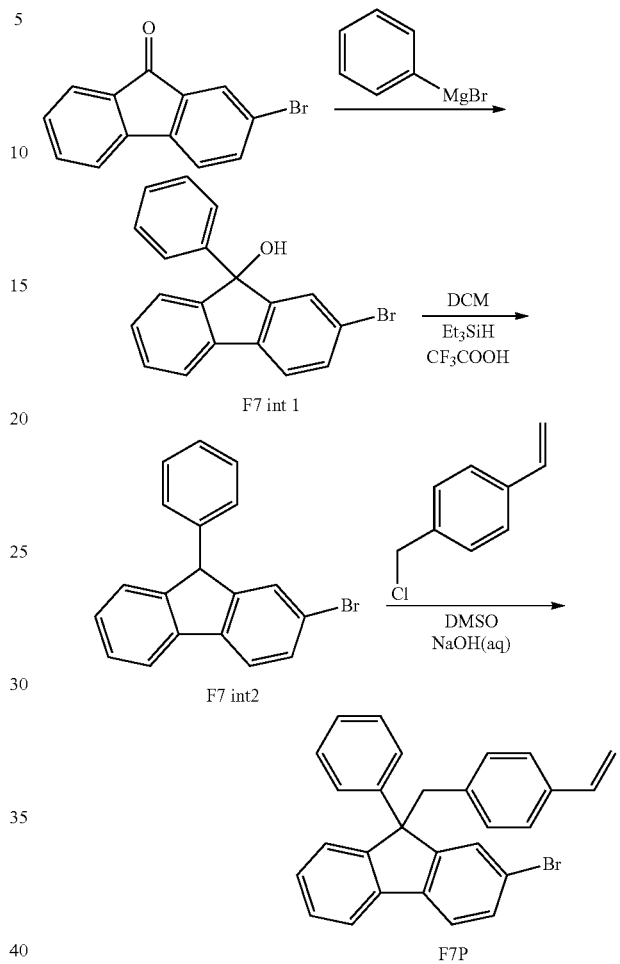

F7 int 1

F7 int2

F7P

Synthesis of 2-bromo-9-phenyl-9H-fluorene (F7 int 2): 2-bromo-9H-fluoren-9-one (18.1 g, 70 mmol) was dissolved in anhydrous tetrahydrofuran (THF). Phenylmagnesiumbromide (3 M in THF, 35 ml, 105 mmol) was added thereto, and the resulting mixture was stirred for 20 minutes. The reaction was stopped with $NH_4Cl$(aq), and the aqueous layer was separated, followed by extraction with ethyl acetate (EA). The organic layer was dried using $MgSO_4$, and the organic solvent was removed using a vacuum rotary evaporator. After the residue (F7 int2) was dissolved in dichloromethane [DCM], triethylsilane (16.8 ml, 104 mmol) and 8.4 ml of trifluoroacetic acid were added thereto, and the resulting mixture was stirred at room temperature overnight. The organic solvent was removed by a vacuum rotary evaporator, and silica filtering was performed. Again, the organic solvent was removed by a vacuum rotary evaporator, and the residue was recrystallized using dichloromethane and hexane to obtain 13.4 g (yield 60%) of F7 int 2.

Synthesis of 2-bromo-9-phenyl-9-(4-vinylbenzyl)-9H-fluorene (F7P): A flask containing F7 int 2 (13.4 g, 41.7 mmol), 4-vinylbenzyl chloride (8.4 g, 50 mmol), and 80 ml of dimethylsulfoxide (DMSO) was dipped into an oil bath at 50° C. 4 ml of a 50 wt % NaOH (aq) aqueous solution was added thereto, and the resulting mixture was stirred overnight. A solid obtained by dropping the reaction mixture to 400 ml of water and precipitating the product was obtained, and was stirred again in ethanol. The resulting product was dried in a vacuum oven to obtain 12.6 g (yield 70%) of F7P.

Preparation Example 8. Synthesis of F8P

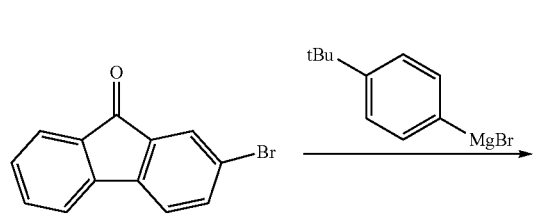

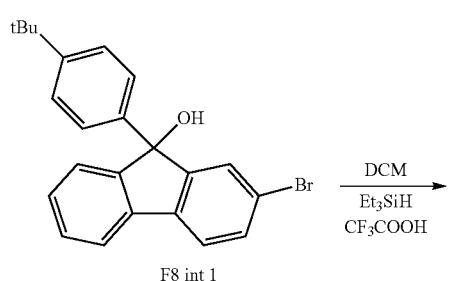

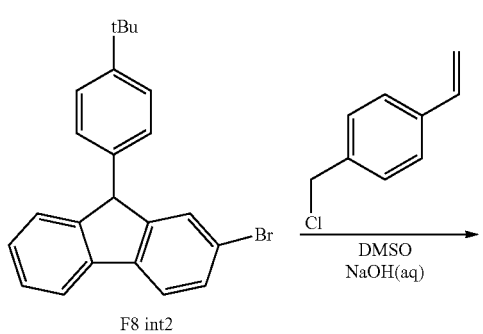

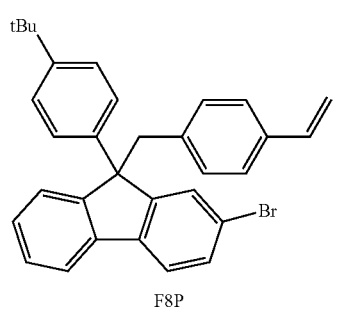

In the synthesis of F7-int1 in Preparation Example 7, 7.3 g (49% third step yield) of F8P was obtained using 4-tert-butylphenylmagnesium bromide instead of phenylmagnesium bromide.

4. Synthesis of Fluorene-Amine Derivative (Preparation Examples 9, 10, and 11)

Preparation Example 9

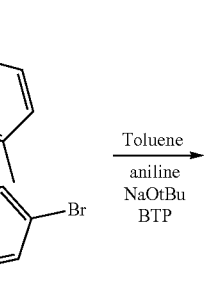

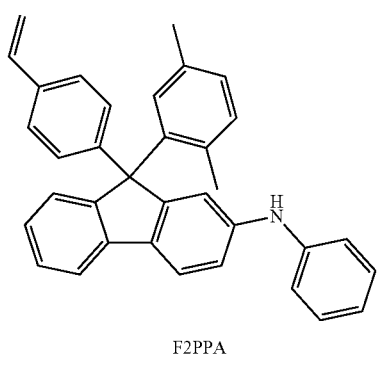

Synthesis of 9-(2,5-dimethylphenyl)-N-phenyl-9-(4-vinylphenyl)-9H-fluoren-2-amine (F2PPA): Toluene was put into a flask containing F2P (5.55 g, 12.3 mmol), aniline (3.44 g, 36.9 mmol), and sodium tert-butoxide (2.95 g, 30.75 mmol). The flask containing the reactants was dipped into an oil bath at 90° C., and then $Pd(PtBu_3)_2$ (314 mg, 0.62 mmol) was added thereto, and the flask was rotated for 1 hour. The reaction was stopped by adding water thereto, the product was extracted with dichloromethane (DCM), and then the organic layer was dried over $MgSO_4$. After the organic solvent was removed using a vacuum rotary evaporator, the residue was column purified to obtain 5.1 g (yield 90%) of F2PPA.

Preparation Examples 10 and 11

F1PBPA and F8PBPA were synthesized using the compounds described in the following Table 2.

TABLE 2

| | Starting material | Amine | Product | Yield |
|---|---|---|---|---|
| Preparation Example 10: Synthesis of F1PBPA | F1P | | F1PBPA | 87% |
| Preparation Example 11: Synthesis of F8PBPA | F8P | | F8PBPA | 82% |

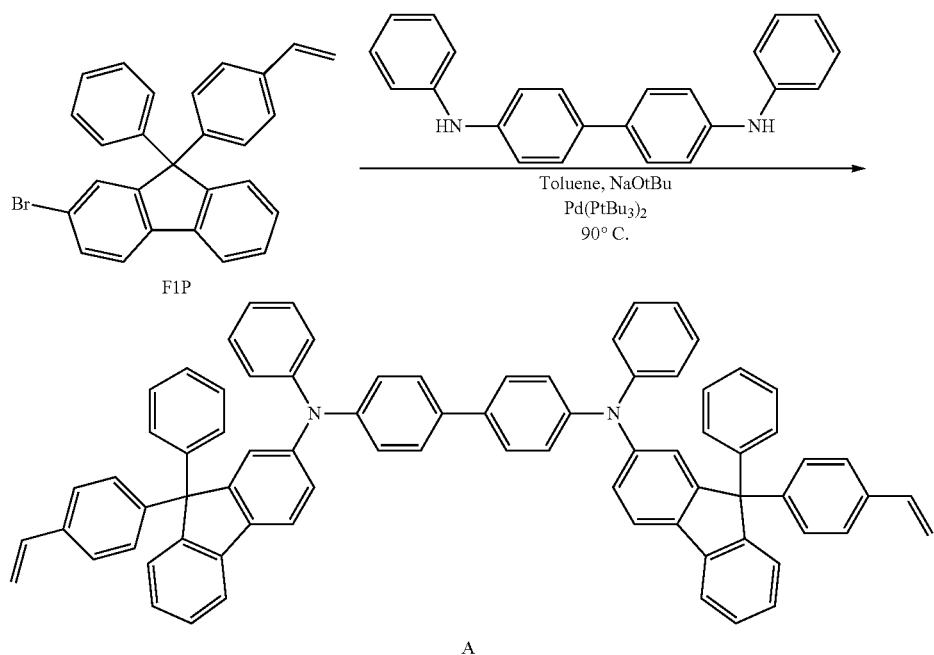

5. Synthesis Examples of Compounds A to L

Preparation Example 12. Synthesis of Compound A

Synthesis of Compound A: Toluene was put into a flask containing F1P (1.58 g, 3.74 mmol), N4,N4'-diphenyl-[1,1'-biphenyl]-4,4'-diamine (572 mg, 1.7 mmol), and sodium tert-butoxide (980 mg, 10.2 mmol). The flask containing the reactants was dipped into an oil bath at 90° C., and then Pd(PtBu₃)₂ (43 mg, 0.085 mmol) was added thereto, and the flask was rotated for 1 hour. The reaction was stopped by adding water thereto, the product was extracted with dichloromethane (DCM), and then the organic layer was dried over MgSO₄. After the organic solvent was removed using a vacuum rotary evaporator, the residue was column purified to obtain 950 mg (yield 55%, HPLC purity 99.5%) of Compound A. The NMR measurement value of Compound A is shown as follows.

$^1$H NMR: δ 7.71 (d, 2H), 7.65 (d, 2H), 7.42 (d, 4H), 7.35 (d, 4H), 7.27-7.20 (m, 18H), 7.17-7.13 (m, 4H), 7.11-7.06 (m, 14H), 7.03 (t, 2H), 6.70-6.64 (dd, 2H), 5.69 (d, 2H), 5.19 (d, 2H).

Preparation Example 13. Synthesis of Compound B

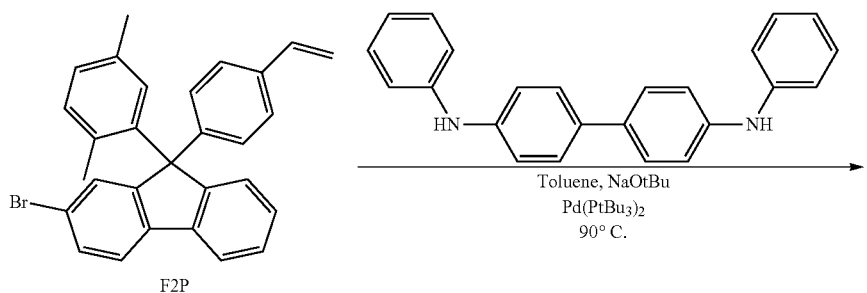

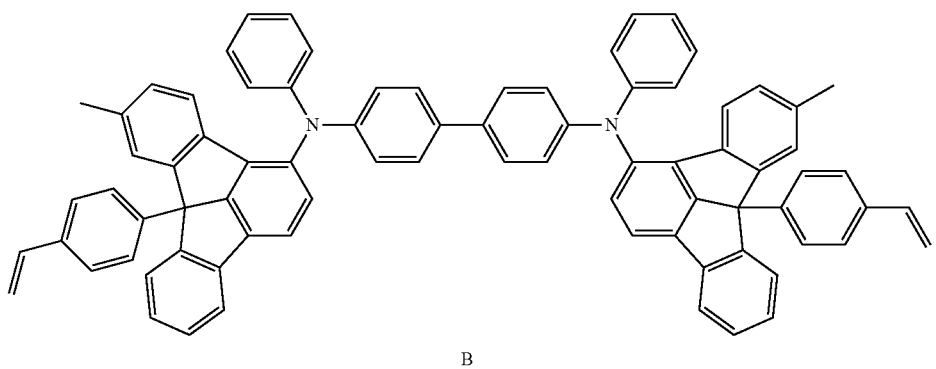

B

Synthesis of Compound B: Toluene was put into a flask containing F2P (1.37 g, 3.03 mmol), N4,N4'-diphenyl-[1,1'-biphenyl]-4,4'-diamine (464 mg, 1.38 mmol), and sodium tert-butoxide (769 mg, 8.3 mmol). The flask containing the reactants was dipped into an oil bath at 90° C., and then Pd(PtBu$_3$)$_2$ (36 mg, 0.085 mmol) was added thereto, and the flask was rotated for 1 hour. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 500 mg (yield 34%, HPLC purity 99.8%) of Compound B. The NMR measurement value of Compound B is shown as follows.

$^1$H NMR: δ 7.70 (d, 2H), 7.63 (d, 2H), 7.43 (d, 4H), 7.37 (t, 2H), 7.30-7.20 (m, 14H), 7.15-7.05 (m, 14H), 7.02 (t, 2H), 6.93 (s, 4H), 6.86 (s, 2H), 6.71-6.65 (dd, 2H), 5.70 (d, 2H), 5.20 (d, 2H), 2.15 (s, 6H), 1.57 (s, 6H).

Preparation Example 14. Synthesis of Compound C

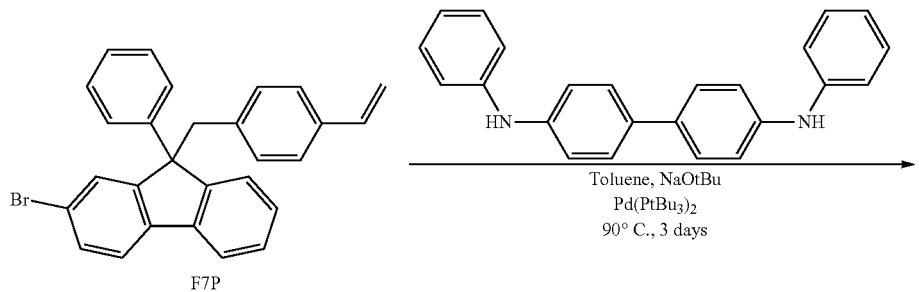

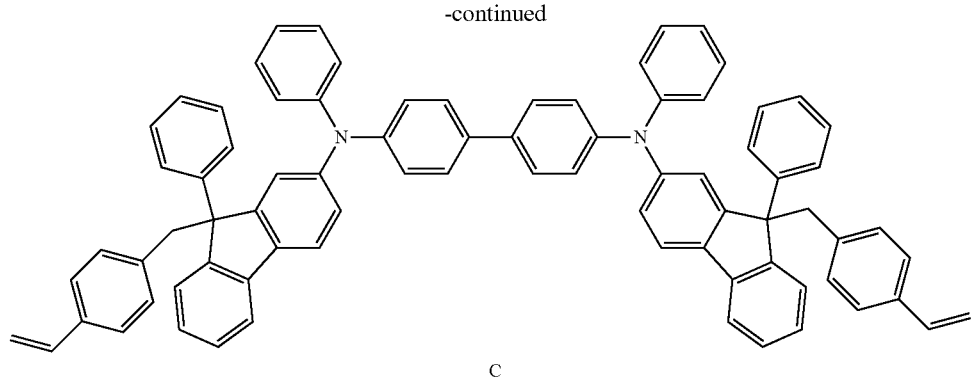

C

Synthesis of Compound C: Toluene was put into a flask containing F7P (1.84 g, 4.2 mmol), N4,N4'-diphenyl-[1,1'-biphenyl]-4,4'-diamine (673 mg, 2.0 mmol), and sodium tert-butoxide (769 mg, 8.0 mmol). The flask containing the reactants was dipped into an oil bath at 90° C., and then Pd(PtBu$_3$)$_2$ (82 mg, 0.16 mmol) was added thereto, and the flask was rotated for 1 hour. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 1.1 g (yield 52%, HPLC purity 99.2%) of Compound C. The NMR measurement value of Compound C is shown as follows.

$^1$H NMR: δ 7.51-7.46 (m, 6H), 7.44 (d, 2H), 7.40-7.36 (m, 2H), 7.31-7.23 (m, 16H), 7.23-7.17 (m, 2H), 7.14 (d, 2H), 7.13-7.09 (m, 8H), 7.05-7.01 (m, 4H), 6.97-6.92 (m, 4H), 6.57-6.49 (m, 2H), 6.49 (d, 4H), 5.58 (dd, 2H), 5.10 (dt, 2H), 3.85 (d, 2H), 3.63 (d, 2H).

Preparation Example 15. Synthesis of Compound D

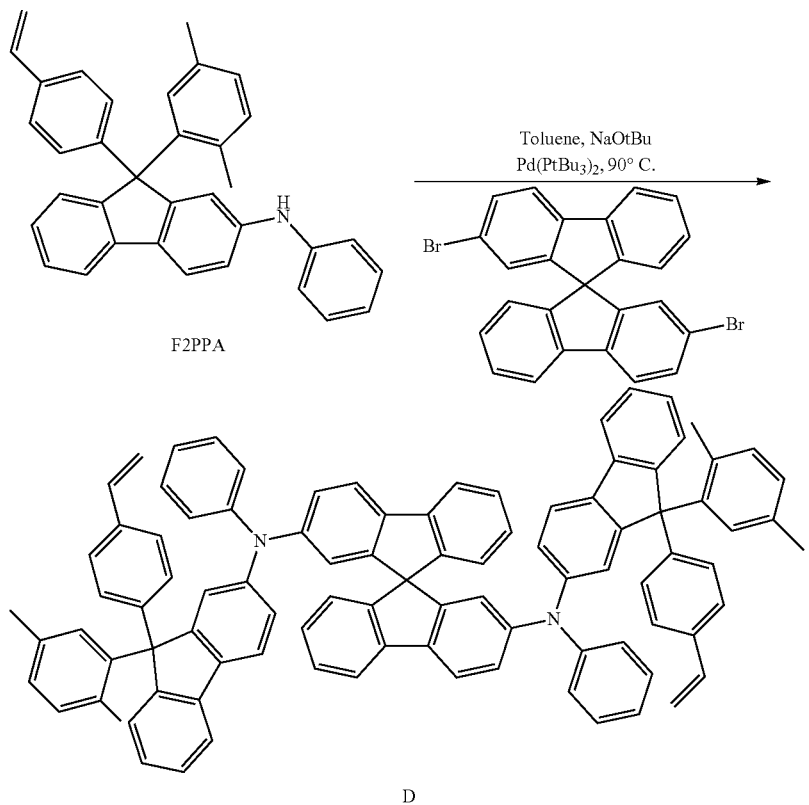

D

Synthesis of Compound D: Toluene was put into a flask containing F2PPA (2.32 g, 5.0 mmol), 2,2'-dibromo-9,9'-spirobi[fluorene] (948 mg, 2.0 mmol), and sodium tert-butoxide (960 mg, 10.0 mmol). The flask containing the reactants was dipped into an oil bath at 90° C., and then Pd(PtBu$_3$)$_2$ (72 mg, 0.14 mmol) was added thereto, and the flask was rotated for 1 hour. The reaction was stopped by adding water thereto, the product was extracted with dichloromethane (DCM), and then the organic layer was dried over MgSO₄. After the organic solvent was removed using a vacuum rotary evaporator, the residue was column purified to obtain 1.46 g (yield 59%, HPLC purity 99.2%) of Compound D. The NMR measurement value of Compound D is shown as follows.

¹H NMR: δ 7.74-7.69 (m, 4H), 7.68-7.63 (m, 2H), 7.62-7.56 (m, 2H), 7.39 (td, 2H), 7.33 (ddddd, 4H), 7.26 (tdd, 6H), 7.19-7.04 (m, 12H), 7.04-6.90 (m, 14H), 6.85 (d, 2H), 6.76-6.68 (m, 4H), 6.65-6.55 (m, 2H), 5.78-5.70 (m, 2H), 5.25 (dq, 2H), 2.16 (s, 6H), 1.57 (s, 6H).

Preparation Example 16. Synthesis of Compound E

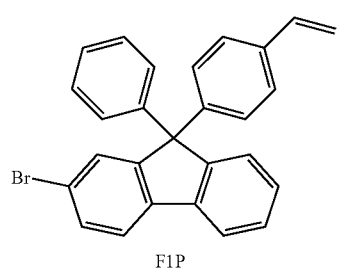

F1P

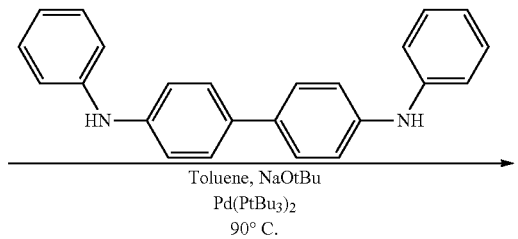

Toluene, NaOtBu
Pd(PtBu₃)₂
90° C.

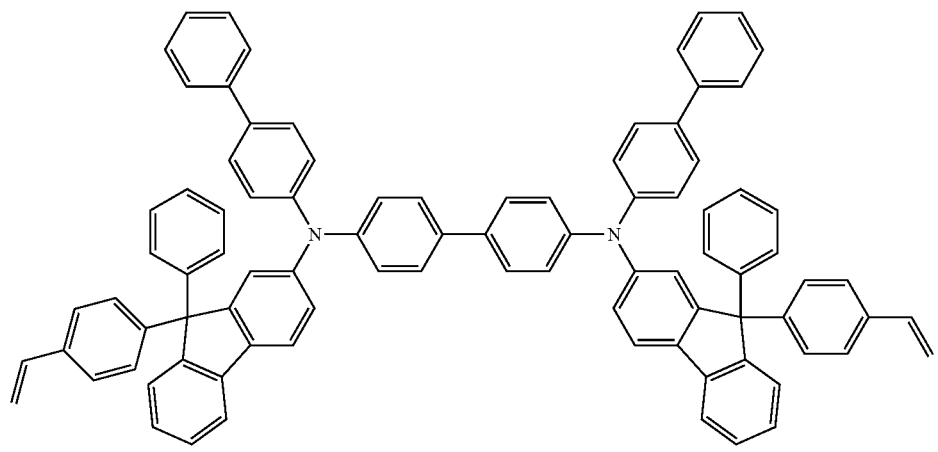

E

Synthesis of Compound E: Toluene was put into a flask containing F1P (1.53 g, 3.61 mmol), N4,N4'-diphenyl-[1,1'-biphenyl]-4,4'-diamine (801 mg, 1.64 mmol), and sodium tert-butoxide (946 mg, 9.84 mmol). The flask containing the reactants was dipped into an oil bath at 90° C., and then Pd(PtBu₃)₂ (42 mg, 0.08 mmol) was added thereto, and the flask was rotated for 1 hour. The reaction was stopped by adding water thereto, the product was extracted with dichloromethane (DCM), and then the organic layer was dried over MgSO₄. After the organic solvent was removed using a vacuum rotary evaporator, the residue was column purified to obtain 1.06 g (yield 55%, HPLC purity 99.4%) of Compound E. The NMR measurement value of Compound E is shown as follows.

¹H NMR: δ 7.73 (d, 2H), 7.69 (d, 2H), 7.59 (d, 4H), 7.48 (t, 8H), 7.43 (t, 4H), 7.38-7.30 (m, 8H), 7.28-7.11 (m, 30H), 6.71-6.65 (dd, 2H), 5.69 (d, 2H), 5.20 (d, 2H).

Preparation Example 17. Synthesis of Compound F

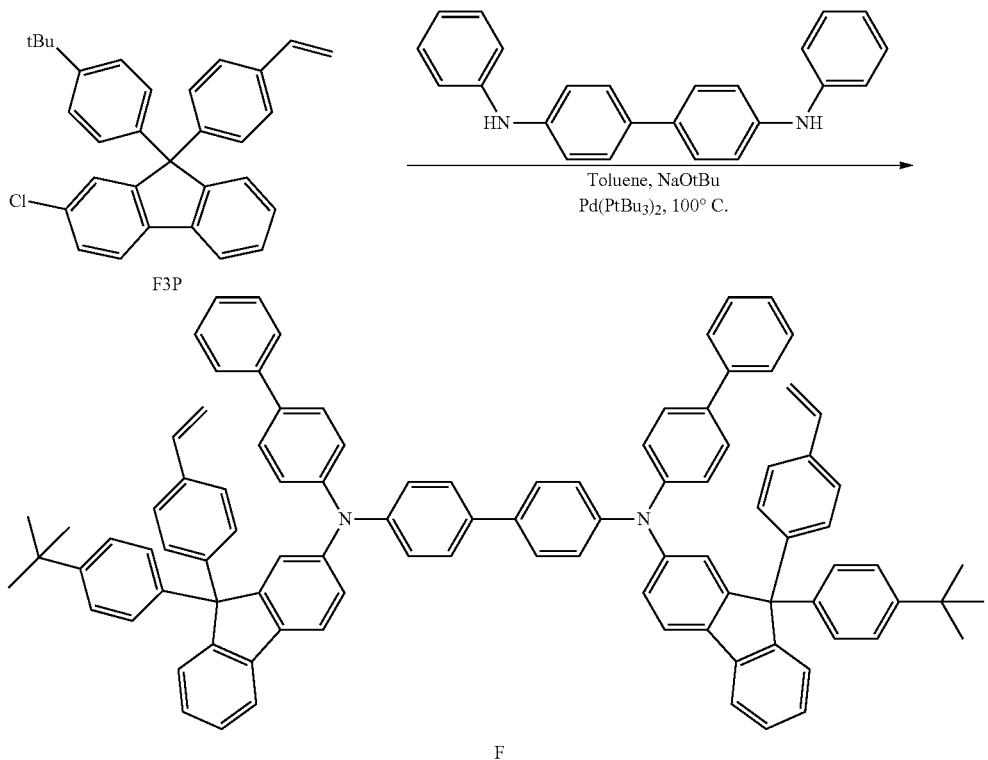

Synthesis of Compound F: Toluene was put into a flask containing F3P (1.83 g, 4.2 mmol), N4,N4'-diphenyl-[1,1'-biphenyl]-4,4'-diamine (673 mg, 2.0 mmol), and sodium tert-butoxide (769 mg, 8 mmol). The flask containing the reactants was dipped into an oil bath at 100° C., and then Pd(PtBu$_3$)$_2$ (42 mg, 0.08 mmol) was added thereto, and the flask was rotated for 12 hours. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 1.2 g (yield 47%, HPLC purity 99.3%) of Compound F. The NMR measurement value of Compound F is shown as follows.

$^1$H NMR: δ 7.73 (d, 2H), 7.68 (d, 2H), 7.58 (d, 4H), 7.47 (t, 8H), 7.43 (t, 4H), 7.38-7.21 (m, 18H), 7.17-7.05 (m, 18H), 6.71-6.65 (dd, 2H), 5.69 (d, 2H), 5.20 (d, 2H), 1.35 (S, 18H).

Preparation Example 18. Synthesis of Compound G

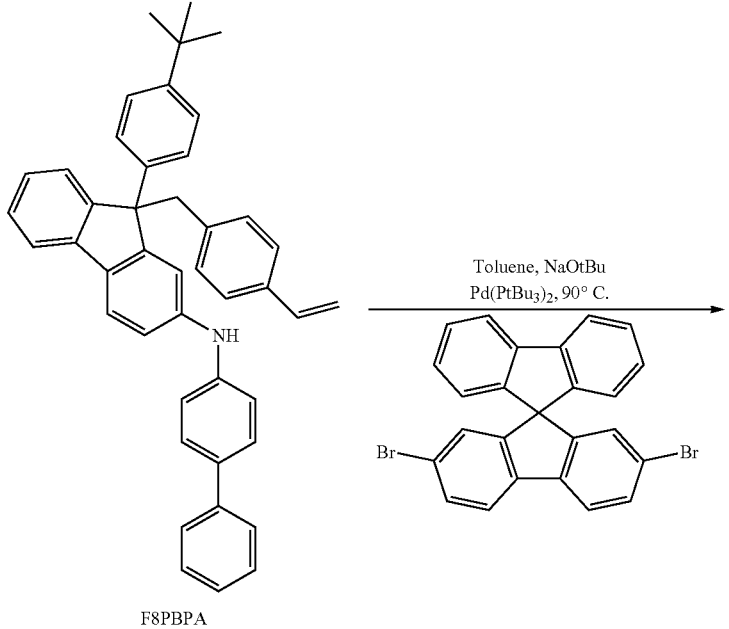

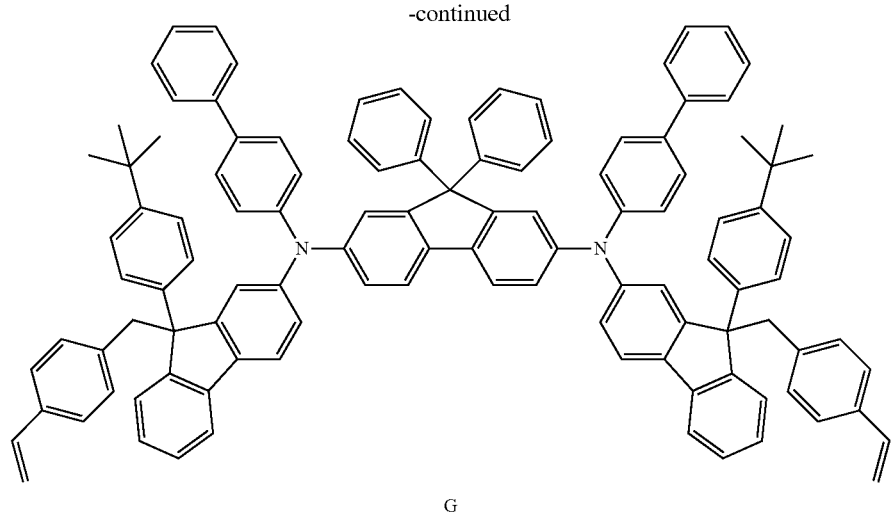

G

Synthesis of Compound G: Toluene was put into a flask containing F8PBPA (2.9 g, 5.0 mmol), 2,7-dibromo-9,9-diphenyl-9H-fluorene (952 mg, 2.0 mmol), and sodium tert-butoxide (960 mg, 10.0 mmol). The flask containing the reactants was dipped into an oil bath at 90° C., and then Pd(PtBu$_3$)$_2$ (72 mg, 0.14 mmol) was added thereto, and the flask was rotated for 1 hour. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 1.7 g (yield 58%, HPLC purity 99.3%) of Compound G. The NMR measurement value of Compound G is shown as follows.

$^1$H NMR: δ 7.82-7.73 (m, 6H), 7.68-7.62 (m, 18H), 7.55-7.34 (m, 10H), 7.34-7.05 (m, 30H), 6.58-6.50 (m, 2H), 6.49 (d, 4H), 5.57 (dd, 2H), 5.11 (dt, 2H), 3.84 (d, 2H), 3.63 (d, 2H), 1.35 (s, 18).

Preparation Example 19. Synthesis of Compound H

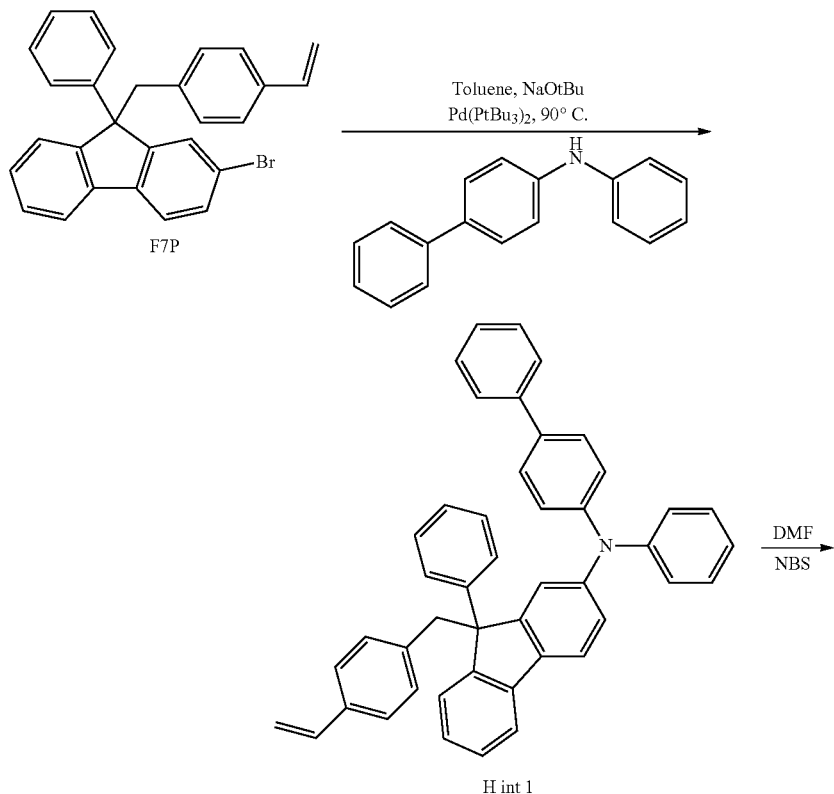

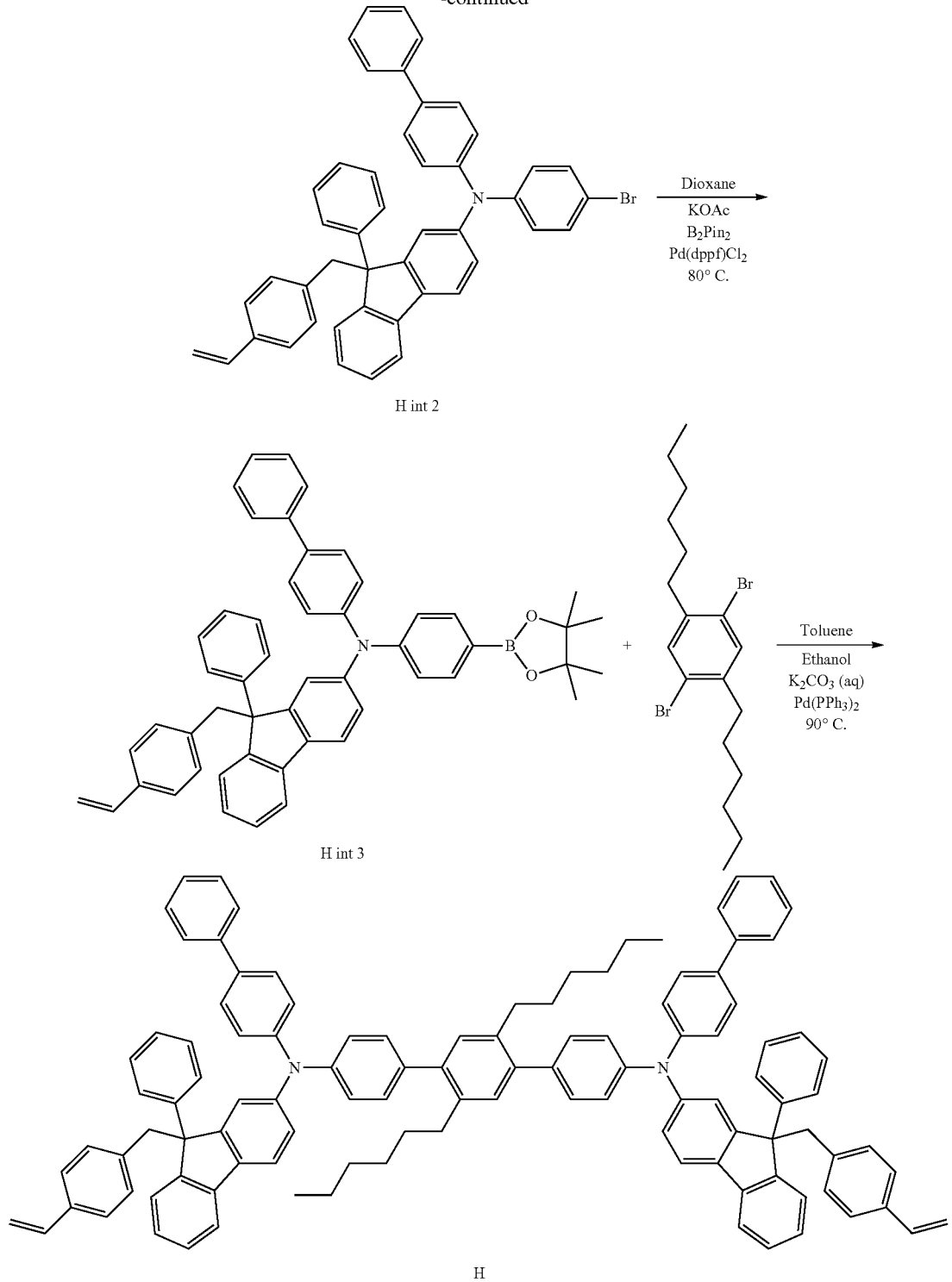

Synthesis of H int 1: Toluene was put into a flask containing F7P (5 g, 11.4 mmol), N-phenyl-[1,1'-biphenyl]-4-amine (2.8 g, 11.4 mmol), and sodium tert-butoxide (2.2 g, 23 mmol). The flask containing the reactants was dipped into an oil bath at 90° C., and then Pd(PtBu$_3$)$_2$ (175 mg, 0.34 mmol) was added thereto, and the flask was rotated for 1 hour. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 5.9 g (yield 86%) of H int 1.

Synthesis of H int 3: A reaction flask containing H int 1 (5.8 g, 9.64 mmol) dissolved in 30 ml of dimethylformamide [DMF] was dipped into an ice bath. N-bromosuccinimide [NBS] (1.66 g, 9.3 mmol) was put into the reaction flask, and the resulting mixture was stirred overnight. The reactant was dropped to 500 ml of water and the resulting mixture was filtered to obtain crude H int 2. 30 ml of anhydrous dioxane was put into a flask containing obtained H int 2, 4,4,4',4',5,5,5',5'-octamethyl-2,2'-bi(1,3,2-dioxaborolane) (4.9 g, 19.3 mmol), and potassium acetate (2.84 g, 29 mmol). The reaction flask was dipped into an oil bath at 80° C., Pd(dppf)Cl$_2$.CM (380 mg, 0.47 mmol) was added thereto, and the resulting mixture was stirred overnight. Dioxane was maximally evaporated by decreasing pressure in vacuum, and the product was extracted using water and dichloromethane (DCM). The collected organic layer was dried over MgSO$_4$ and column purified to obtain 4.5 g (yield 67%) of H int 3.

Synthesis of Compound H: A toluene/EtOH/2 N K$_2$CO$_3$ (aq) (2v:1v:1v) solvent was put into a reaction flask containing H int 3 (2.4 g, 3.3 mmol) and 1,4-dibromo-2,5-dihexylbenzene (0.6 g, 1.5 mmol). The reaction flask was degassed using a vacuum pump. Pd(PPh$_3$)$_4$ (347 mg, 0.3 mmol) was put into the reaction flask, and the resulting mixture was stirred overnight. EtOH was removed using a vacuum pressure reduction concentrator, and the organic material was extracted with dichloromethane (DCM). The organic layer was dried over MgSO$_4$, and then filtered and column purified to obtain 1.57 g (yield 72%, purity 99.1%) of Compound H. The NMR measurement value of Compound H is shown as follows.

$^1$H NMR (H): δ 7.77 (s, 2H), 7.51-7.46 (m, 6H), 7.44 (d, 2H), 7.40-7.37 (m, 4H), 7.32-7.18 (m, 22H), 7.15-7.08 (m, 14H), 7.06-7.01 (m, 6H), 6.57-6.49 (m, 2H), 6.49 (d, 4H), 5.58 (dd, 2H), 5.10 (dt, 2H), 3.85 (d, 2H), 3.63 (d, 2H), 2.80-2.77 (m, 4H), 1.54-1.46 (m, 4H), 1.39-1.27 (m, 12H), 0.90-0.87 (m, 6H).

Preparation Example 20. Synthesis of Compound I

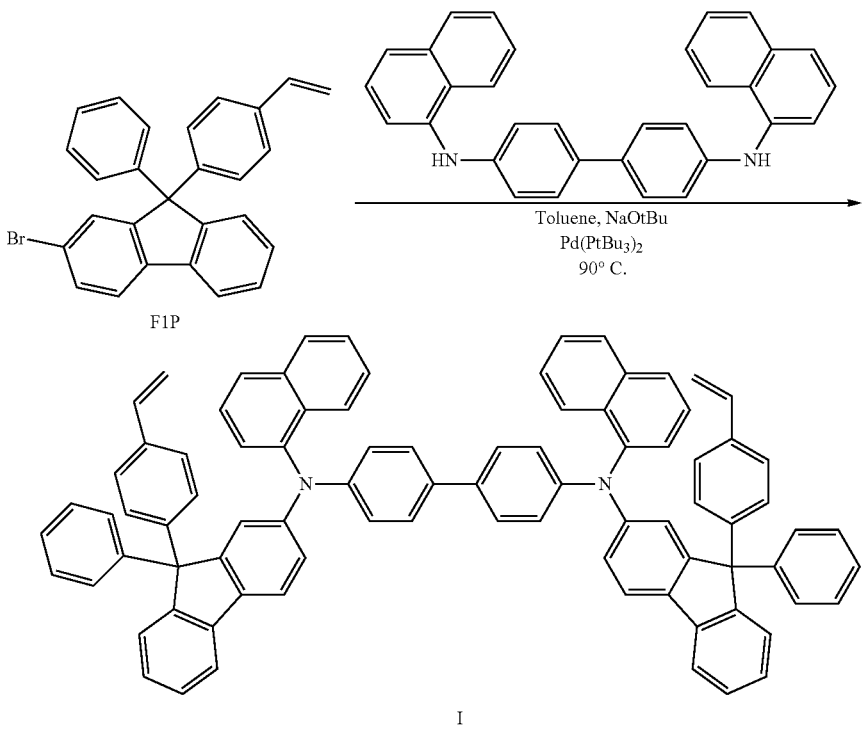

Synthesis of Compound I: Toluene was put into a flask containing F1P (1.78 g, 4.2 mmol), N4,N4'-di(naphthalen-1-yl)-[1,1'-biphenyl]-4,4'-diamine (873 mg, 2.0 mmol), and sodium tert-butoxide (769 mg, 8.0 mmol), and the flask was bubbled with nitrogen. The flask containing the reactants was dipped into an oil bath at 90° C., and then Pd(PtBu$_3$)$_2$ (82 mg, 0.16 mmol) was added thereto, and the flask was rotated for 1 hour. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 1.1 g (yield 49%, HPLC purity 99.0%) of Compound I. The NMR measurement value of Compound I is shown as follows.

$^1$H NMR: δ 7.91-7.89 (m, 2H), 7.86 (dd, 2H), 7.80-7.77 (m, 2H), 7.66 (dt, 2H), 7.58 (dd, 2H), 7.50-7.44 (m, 4H), 7.36-7.29 (m, 12H), 7.22-7.11 (m, 14H), 7.09-7.04 (m, 4H), 7.03-6.96 (m, 10H), 6.65 (dd, 2H), 5.68 (dd, 2H), 5.19 (dd, 2H).

Preparation Example 21. Synthesis of Compound J

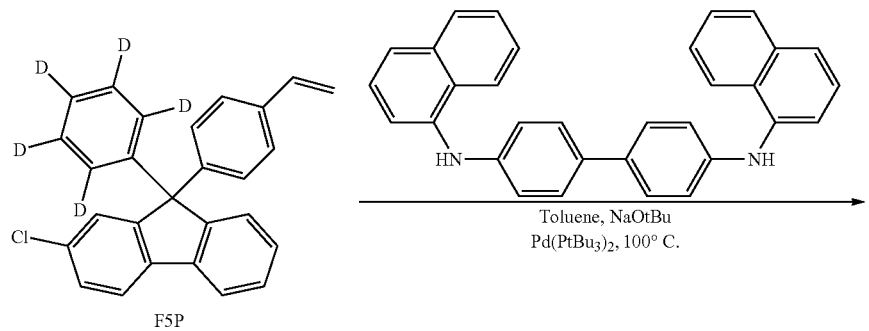

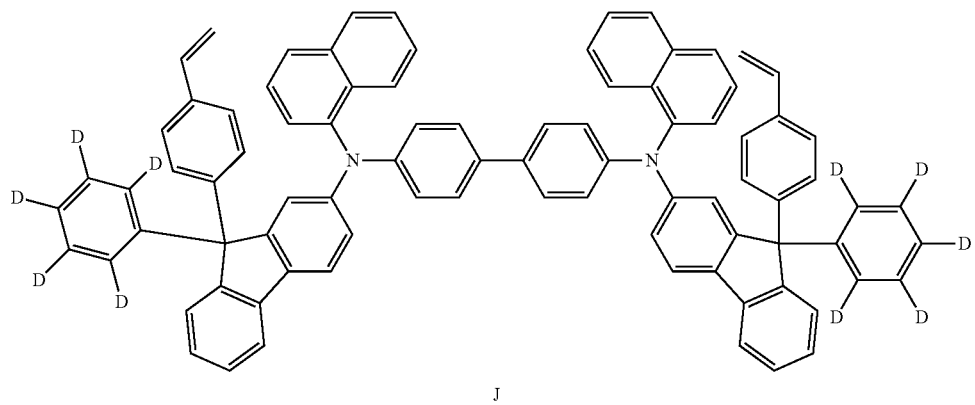

J

Synthesis of Compound J: Toluene was put into a flask containing F5P (1.6 g, 4.2 mmol), N4,N4'-di(naphthalen-1-yl)-[1,1'-biphenyl]-4,4'-diamine (873 mg, 2.0 mmol), and sodium tert-butoxide (769 mg, 8.0 mmol), and the flask was bubbled with nitrogen. The flask containing the reactants was dipped into an oil bath at 100° C., and then Pd(PtBu$_3$)$_2$ (82 mg, 0.16 mmol) was added thereto, and the flask was rotated for 12 hours. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 1.2 g (yield 53%, HPLC purity 99.1%) of Compound J. The NMR measurement value of Compound J is shown as follows.

$^1$H NMR: δ 7.90-7.88 (m, 2H), 7.87 (dd, 2H), 7.79-7.75 (m, 2H), 7.64 (dt, 2H), 7.59 (dd, 2H), 7.49-7.41 (m, 4H), 7.37-7.30 (m, 12H), 7.22-7.11 (m, 8H), 7.09-7.03 (m, 4H), 7.02-6.96 (m, 6H), 6.64 (dd, 2H), 5.67 (dd, 2H), 5.18 (dd, 2H).

Preparation Example 22. Synthesis of Compound K

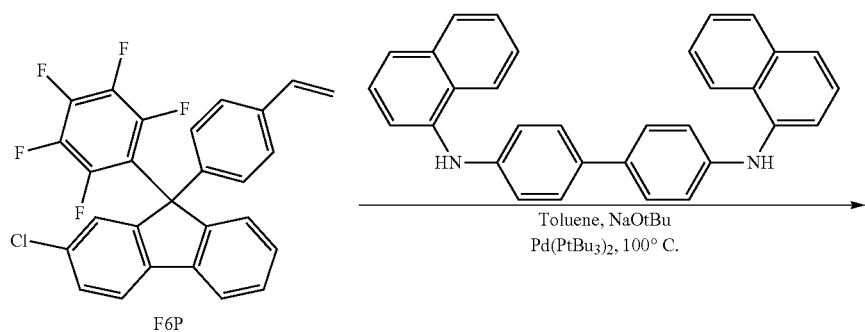

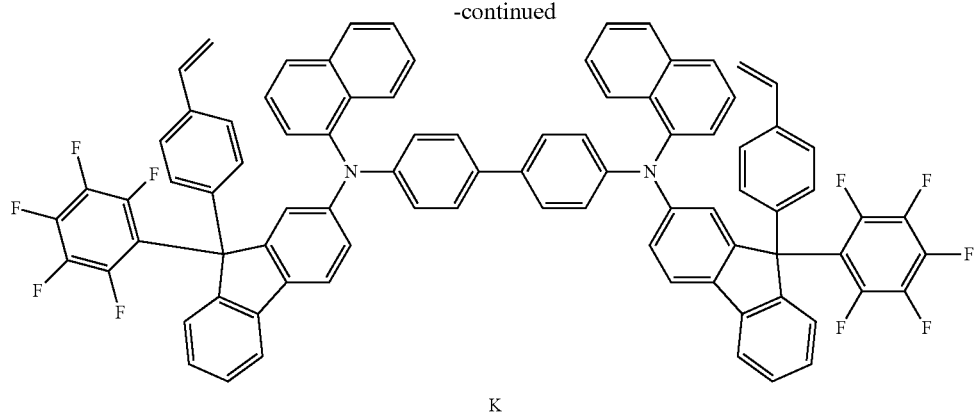

K

Synthesis of Compound K: Toluene was put into a flask containing F6P (2.0 g, 4.2 mmol), N4,N4'-di(naphthalen-1-yl)-[1,1'-biphenyl]-4,4'-diamine (873 mg, 2.0 mmol), and sodium tert-butoxide (769 mg, 8.0 mmol), and the flask was bubbled with nitrogen. The flask containing the reactants was dipped into an oil bath at 100° C., and then $Pd(PtBu_3)_2$ (82 mg, 0.16 mmol) was added thereto, and the flask was rotated for 12 hours. The reaction was stopped by adding water thereto, the product was extracted with dichloromethane (DCM), and then the organic layer was dried over $MgSO_4$. After the organic solvent was removed using a vacuum rotary evaporator, the residue was column purified to obtain 1.1 g (yield 43%, HPLC purity 98.8%) of K. The NMR measurement value of Compound K is shown as follows.

$^1$H NMR: δ 7.92-7.90 (m, 2H), 7.89 (dd, 2H), 7.80-7.77 (m, 2H), 7.64 (dt, 2H), 7.59 (dd, 2H), 7.49-7.41 (m, 4H), 7.37-7.30 (m, 12H), 7.22-7.12 (m, 8H), 7.09-7.03 (m, 4H), 7.03-6.98 (m, 6H), 6.65 (dd, 2H), 5.67 (dd, 2H), 5.18 (dd, 2H).

Preparation Example 23. Synthesis of Compound L

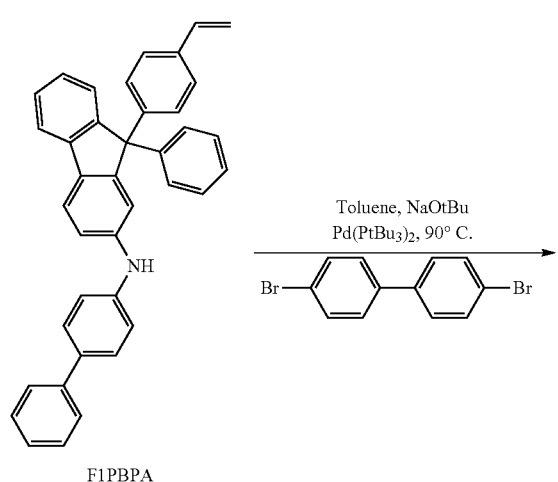

F1PBPA

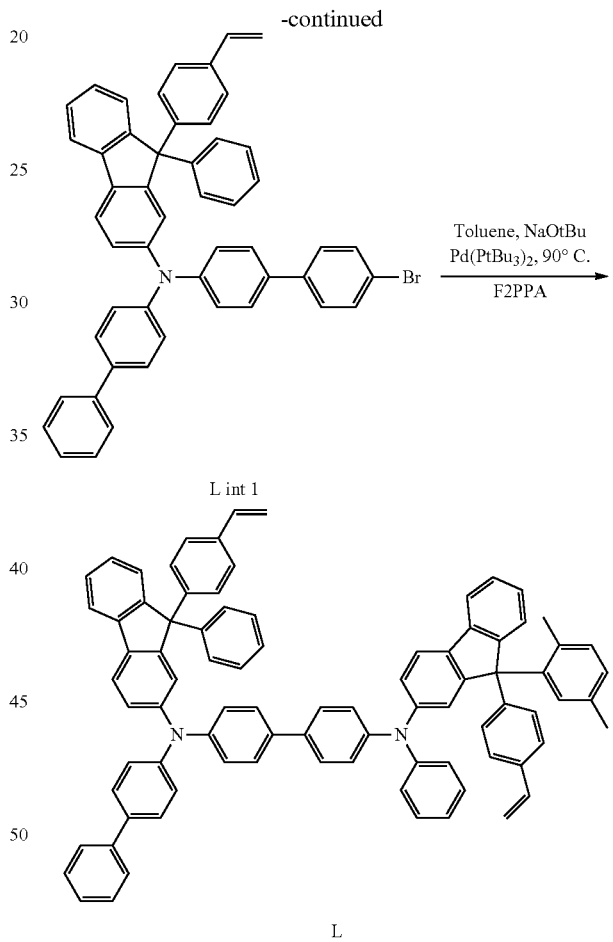

L

Synthesis of L int 1: Toluene was put into a flask containing F1PBPA (3.58 g, 7.0 mmol), 4.4'-dibromo-1.1'-biphenyl (2.18 g, 7.0 mmol), and sodium tert-butoxide (1.34 g, 14.0 mmol), and the flask was bubbled with nitrogen. The flask containing the reactants was dipped into an oil bath at 90° C., and then $Pd(PtBu_3)_2$ (215 mg, 0.42 mmol) was added thereto, and the flask was rotated for 1 hour. The reaction was stopped by adding water thereto, the product was extracted with dichloromethane (DCM), and then the organic layer was dried over $MgSO_4$. After the organic solvent was removed using a vacuum rotary evaporator, the residue was column purified to obtain 3.3 g (yield 63%) of L int 1.

Synthesis of Compound L: Toluene was put into a flask containing L int 1 F2PPA (1.16 g, 2.5 mmol), L int 1 (1.48 g, 2 mmol), and sodium tert-butoxide (384 mg, 4.0 mmol), and the flask was bubbled with nitrogen. The flask containing the reactants was dipped into an oil bath at 90° C., and then Pd(PtBu$_3$)$_2$ (31 mg, 0.06 mmol) was added thereto, and the flask was rotated for 1 hour. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 1.87 g (yield 83%, HPLC purity 99.2%) of Compound L. The NMR measurement value of Compound L is shown as follows.

$^1$H NMR: δ 7.73-7.67 (m, 3H), 7.62 (d, 1H), 7.59 (d, 2H), 7.49-7.21 (m, 26H), 7.19-7.02 (m, 17H), 6.93 (s, 2H), 6.86 (s, 1H), 6.71-6.65 (m, 2H), 5.71-5.66 (m, 2H), 5.21-5.17 (m, 2H), 2.14 (s, 3H), 1.56 (s, 3H)

EXPERIMENTAL EXAMPLE

Experimental Example 1. Measurement of Thin Film Retention Rate

Thin films were formed by spin-coating a 2 wt % toluene coating composition comprising the following Compound A and the following Formula 9-2 at a weight ratio (Compound A:Compound 9-2) of 8:2, and a 2 wt % toluene coating composition comprising the Comparative Compound 1, and the Formula 9-2, respectively, on glass. Each thin film was heat-treated at 220° C. for 30 minutes, and UV absorbance of each thin film was measured. Again, the thin films were dipped in toluene for 10 minutes and dried, and then UV was measured. From the comparison of sizes of the maximum peaks of UV absorbance before and after the dipping, the thin film retention rates could be confirmed.

[Compound A]

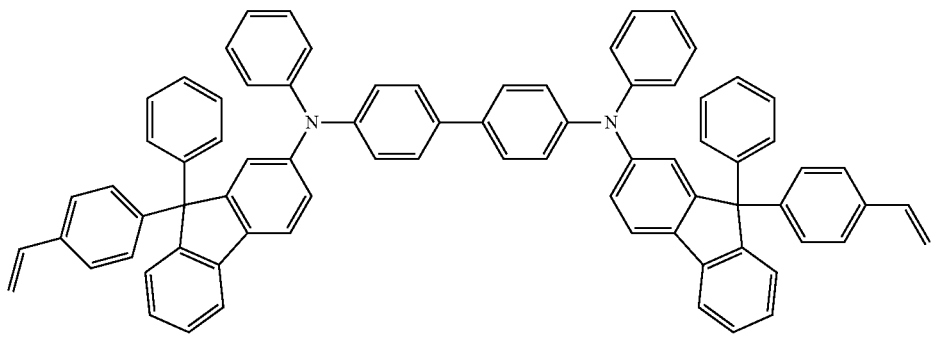

[Formula 9-2]

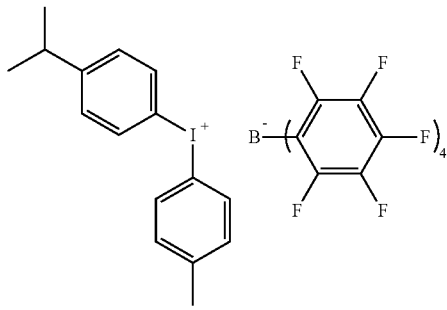

[Comparative Compound 1]

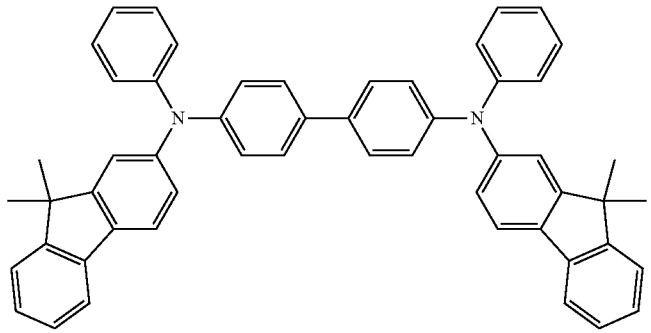

In the case of a thin film formed by using a coating composition comprising Compound A having a curable group directly attached to fluorene or a curable group, the thin film retention rate became 100%. However, in the case of a thin film formed by using a coating composition comprising Comparative Compound 1 having no curable group, it could be confirmed that the thin film was not retained at all.

FIG. 2 is a view illustrating a result of a film retention rate experiment of the thin film formed by using a coating composition comprising Compound A and Formula 9-2 which is a p-doping material.

FIG. 3 is a view illustrating a result of a film retention rate experiment of the thin film formed by using a coating composition comprising Comparative Compound 1 and Formula 9-2 which is a p-doping material. In FIGS. 2 and 3, the horizontal axis means the wavelength, and the vertical axis means the optical density (OD).

Experimental Example 2. Manufacture of Organic Light Emitting Device

Preparation of ITO Substrate

A glass substrate thinly coated with indium tin oxide (ITO) to have a thickness of 1,500 Å was put into distilled water in which a detergent was dissolved, and ultrasonically washed. In this case, a product manufactured by Fischer Co., was used as the detergent, and distilled water, which had been filtered twice with a filter manufactured by Millipore Co., was used as the distilled water. After the ITO was washed for 30 minutes, ultrasonic washing was conducted twice repeatedly using distilled water for 10 minutes.

After the washing with distilled water was completed, the substrate was ultrasonically washed with isopropyl alcohol and acetone solvents, and dried, and then the substrate was cleaned for 5 minutes, and the substrate was transported to a glovebox.

Device Example 1

A 1.5 wt % toluene ink comprising Compound A and Formula 9-2 at a weight ratio (Compound A:Formula 9-2) of 8:2 was spin-coated onto a surface of a transparent ITO electrode, and was subjected to a heat treatment (curing) at 220° C. for 30 minutes, thereby forming a hole injection layer to have a thickness of 30 nm. A 2 wt % toluene ink of α-NPD (N,N-di(1-naphthyl)-N,N-diphenyl-(1,1'-biphenyl)-4,4'-diamine) was spin-coated onto the hole injection layer formed above, thereby forming a hole transport layer to have a thickness of 40 nm. Thereafter, the transparent ITO electrode was transported into a vacuum deposition apparatus, and then ADN and DPAVBi at a weight ratio (ADN:DPAVBi) of 20:1 were vacuum-deposited to have a thickness of 20 nm on the hole transport layer, thereby forming a light emitting layer. BCP was vacuum-deposited to have a thickness of 35 nm on the light emitting layer, thereby forming an electron injection and transport layer. LiF and aluminum were sequentially deposited on the electron injection and transport layer to have a thickness of 1 nm and 100 nm, respectively, thereby forming a cathode.

In the aforementioned procedure, the deposition rate of the organic material was maintained at 0.4 to 0.7 Å/sec, the deposition rates of lithium fluoride and aluminum of the cathode were maintained at 0.3 Å/sec and at 2 Å/sec, respectively, and the degree of vacuum during the deposition was maintained at $2 \times 10^7$ to $5 \times 10^6$ torr.

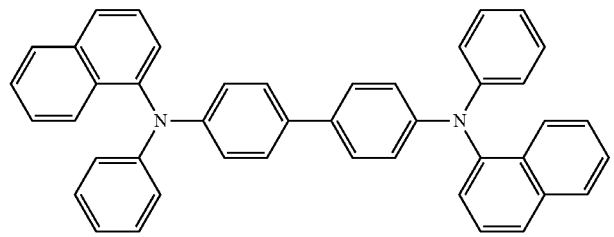

[a-NPD]

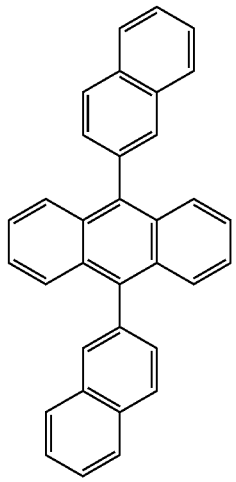

[ADN(9,1-di-2-naphthalenyl-anthracene)]

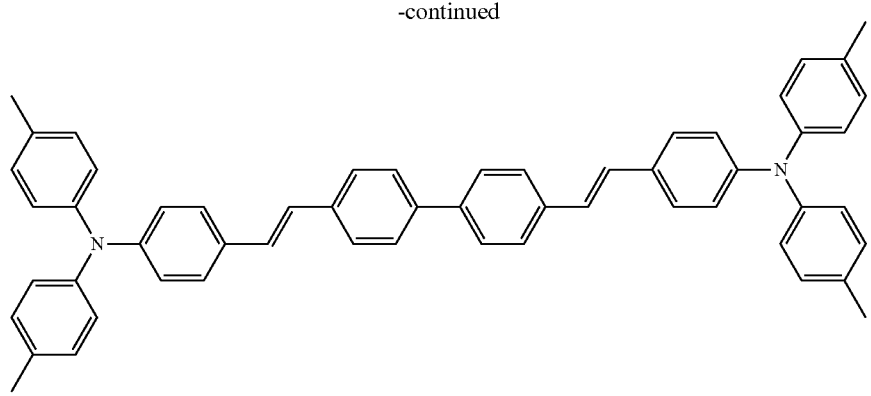

[DPAVBi(4,4′-Bis[4-(di-p-tolylamino)styryl]biphenyl)]

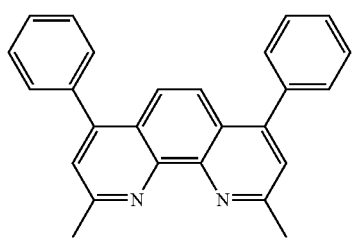

[BCP(2,9-Dimethyl-4,7-diphenyl-1,10-phenanthroline)]

Device Example 2

An organic light emitting device was manufactured in the same manner as in Device Example 1, except that Compound B was used instead of Compound A in Device Example 1.

Device Example 3

An organic light emitting device was manufactured in the same manner as in Device Example 1, except that Compound C was used instead of Compound A in Device Example 1.

Device Example 4

An organic light emitting device was manufactured in the same manner as in Device Example 1, except that Compound D was used instead of Compound A in Device Example 1.

Device Example 5

An organic light emitting device was manufactured in the same manner as in Device Example 1, except that Compound E was used instead of Compound A in Device Example 1.

Device Example 6

An organic light emitting device was manufactured in the same manner as in Device Example 1, except that Compound F was used instead of Compound A in Device Example 1.

Device Example 7

An organic light emitting device was manufactured in the same manner as in Device Example 1, except that Compound G was used instead of Compound A in Device Example 1.

Device Example 8

An organic light emitting device was manufactured in the same manner as in Device Example 1, except that Compound H was used instead of Compound A in Device Example 1.

Device Example 9

An organic light emitting device was manufactured in the same manner as in Device Example 1, except that Compound I was used instead of Compound A in Device Example 1.

Device Example 10

An organic light emitting device was manufactured in the same manner as in Device Example 1, except that Compound J was used instead of Compound A in Device Example 1.

Device Example 11

An organic light emitting device was manufactured in the same manner as in Device Example 1, except that Compound K was used instead of Compound A in Device Example 1.

Device Example 12

An organic light emitting device was manufactured in the same manner as in Device Example 1, except that Compound L was used instead of Compound A in Device Example 1.

Comparative Example 1

An organic light emitting device was manufactured in the same manner as in Device Example 1, except that the following Comparative Compound 2 was used instead of Compound A in Device Example 1.

[Comparative Compound 2]

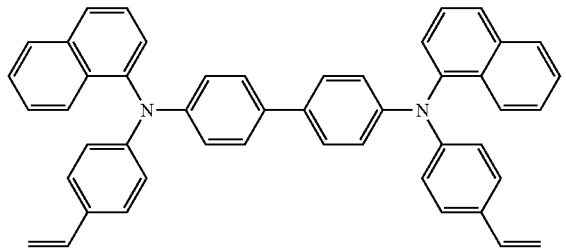

The driving voltage, the current density, the quantum efficiency (QE), and the luminance value at a current density of 10 mA/cm² in each of the devices manufactured by using the materials according to the present invention and the comparative material are shown in the following Table 3. T95 means time taken to be reduced from the initial luminance (500 nit) to 95% of the initial luminance at a current density of 10 mA/cm².

TABLE 3

| HIL | Volt | J (mA/cm²) | Cd/A | lm/W | QE (%) | Cd/m² | CIEx | CIEy | T95 (10 mA/cm²) |
|---|---|---|---|---|---|---|---|---|---|
| Comparative Example 1 | 4.04 | 10.0 | 4.25 | 3.54 | 4.60 | 424.7 | 0.137 | 0.100 | 32.4 |
| Example 1 | 3.81 | 10.0 | 5.05 | 4.38 | 5.52 | 504.7 | 0.137 | 0.099 | 60.8 |
| Example 2 | 3.82 | 10.0 | 5.17 | 4.48 | 5.65 | 516.2 | 0.137 | 0.100 | 60.1 |
| Example 3 | 3.81 | 10.0 | 5.09 | 4.41 | 5.56 | 508.2 | 0.137 | 0.099 | 62.6 |
| Example 4 | 3.86 | 10.0 | 5.01 | 4.51 | 5.66 | 519.4 | 0.137 | 0.099 | 65.7 |
| Example 5 | 3.84 | 10.0 | 5.27 | 4.58 | 5.67 | 526.7 | 0.136 | 0.101 | 59.7 |
| Example 6 | 3.83 | 10.0 | 5.15 | 4.47 | 5.54 | 515.0 | 0.136 | 0.101 | 62.2 |
| Example 7 | 3.83 | 10.0 | 5.28 | 4.58 | 5.75 | 527.6 | 0.137 | 0.100 | 59.9 |
| Example 8 | 3.79 | 10.0 | 5.10 | 4.51 | 5.58 | 518.6 | 0.136 | 0.101 | 58.2 |
| Example 9 | 3.79 | 10.0 | 5.07 | 4.47 | 5.63 | 515.8 | 0.137 | 0.099 | 59.1 |
| Example 10 | 3.80 | 10.0 | 5.12 | 4.51 | 5.61 | 520.8 | 0.136 | 0.101 | 59.4 |
| Example 11 | 3.85 | 10.0 | 5.32 | 4.62 | 5.73 | 532.6 | 0.136 | 0.101 | 55.9 |
| Example 12 | 3.85 | 10.0 | 5.24 | 4.55 | 5.64 | 524.4 | 0.136 | 0.101 | 58.2 |

From Table 3, it can be confirmed that Examples 1 to 12 of the present application have lower driving voltage and better efficiency and service life characteristics than those of Comparative Example 1.

The invention claimed is:

1. A fluorene-based compound represented by the following Formula

[Formula 1]

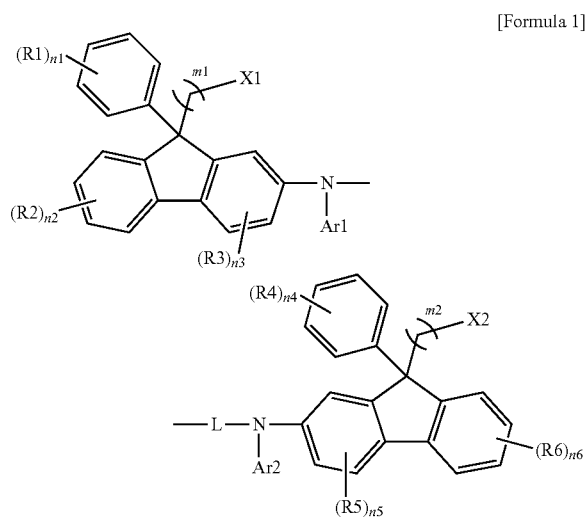

in Formula 1,

L is a substituted or unsubstituted arylene group; or a substituted or unsubstituted heteroarylene group, R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, Ar1 and Ar2 are the same as or different from each other, and are each independently a substituted or unsubstituted aryl group; or a substituted or unsubstituted heteroaryl group, X1 and X2 are the same as or different from each other, and are each independently a photocurable group or a thermosetting group, n1 and n4 are each independently an integer of 0 to 5, n2 and n6 are each independently an integer of 0 to 4, n3 and n5 are each independently an integer of 0 to 3,

173 when n1 to n6 are each 2 or more, R1s to R6s are each independently the same as or different from each other, and m1 and m2 are each 0 or 1, wherein the photocurable group or the thermosetting group in the definitions of X1 and X2 is any one of the following structures:

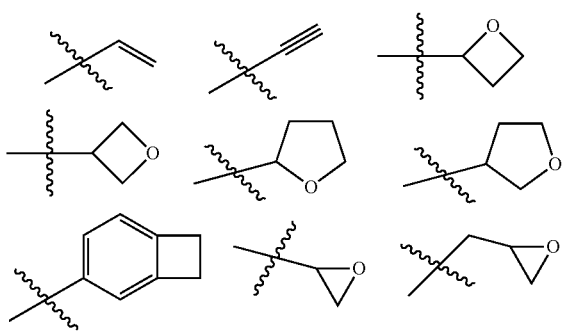

174

-continued

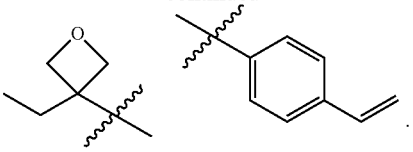

2. The fluorene-based compound of claim 1, wherein L is a substituted or unsubstituted arylene group having 6 to 30 carbon atoms; or a substituted or unsubstituted heteroarylene group having 2 to 30 carbon atoms.

3. The fluorene-based compound of claim 1, wherein Ar1 and Ar2 are the same as or different from each other, and are each independently a substituted or unsubstituted aryl group having 6 to 30 carbon atoms; or a substituted or unsubstituted heteroarylene group having 2 to 30 carbon atoms.

4. The fluorene-based compound of claim 1, wherein Formula 1 is any one of the following compounds:

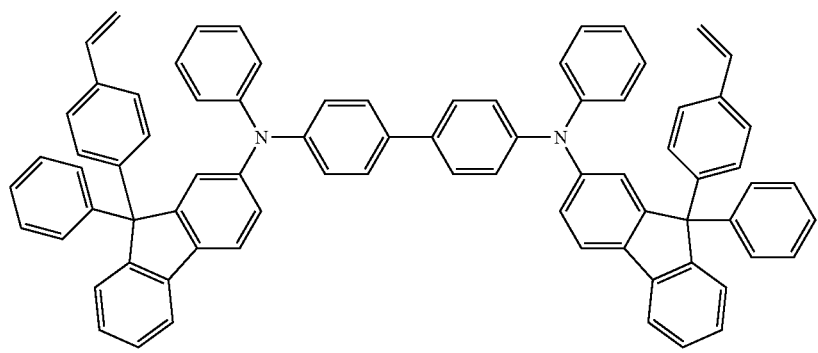

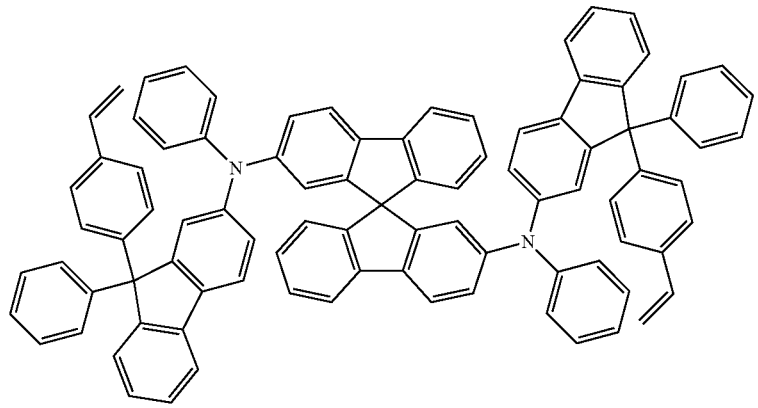

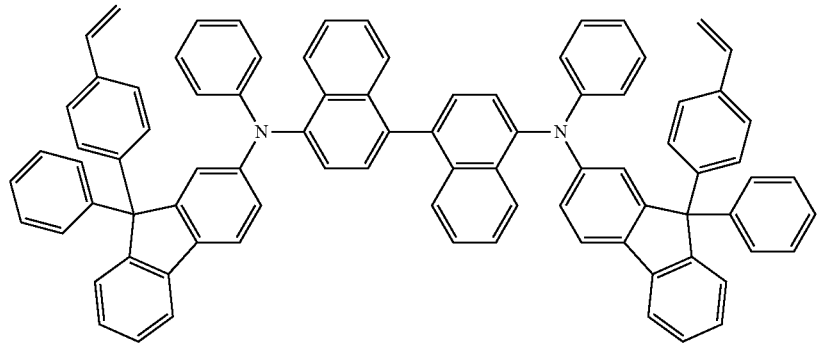

-continued
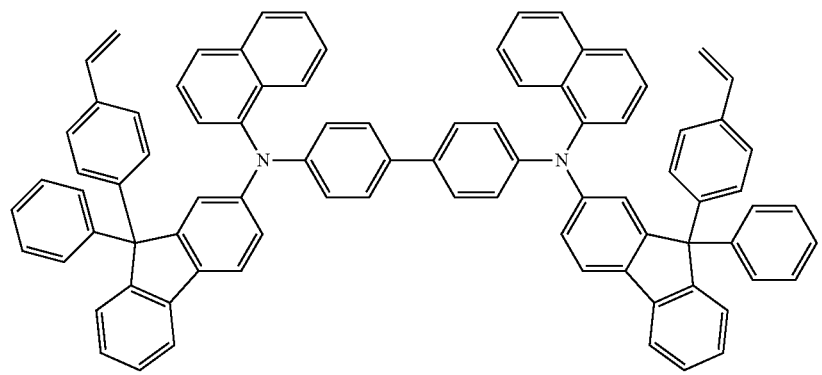
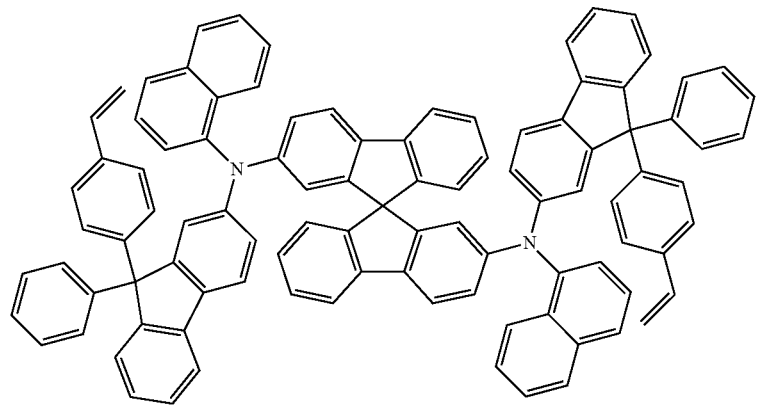
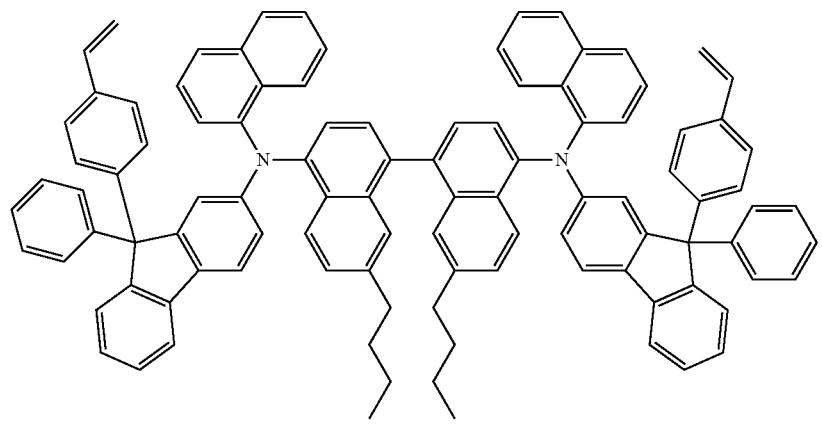
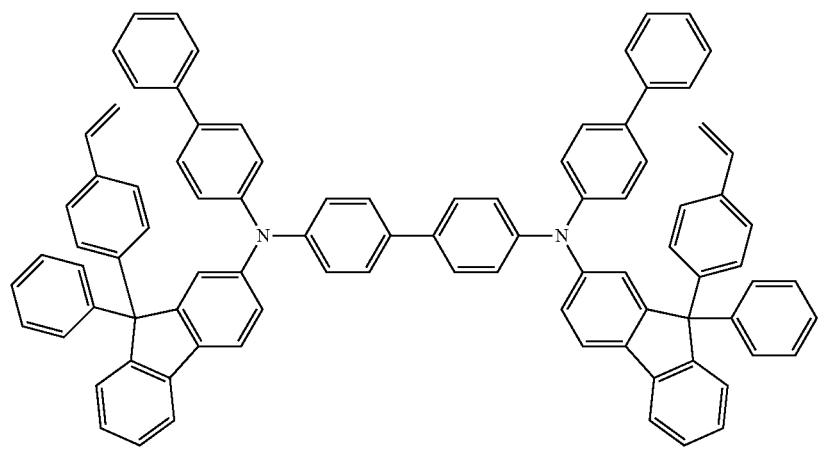

-continued
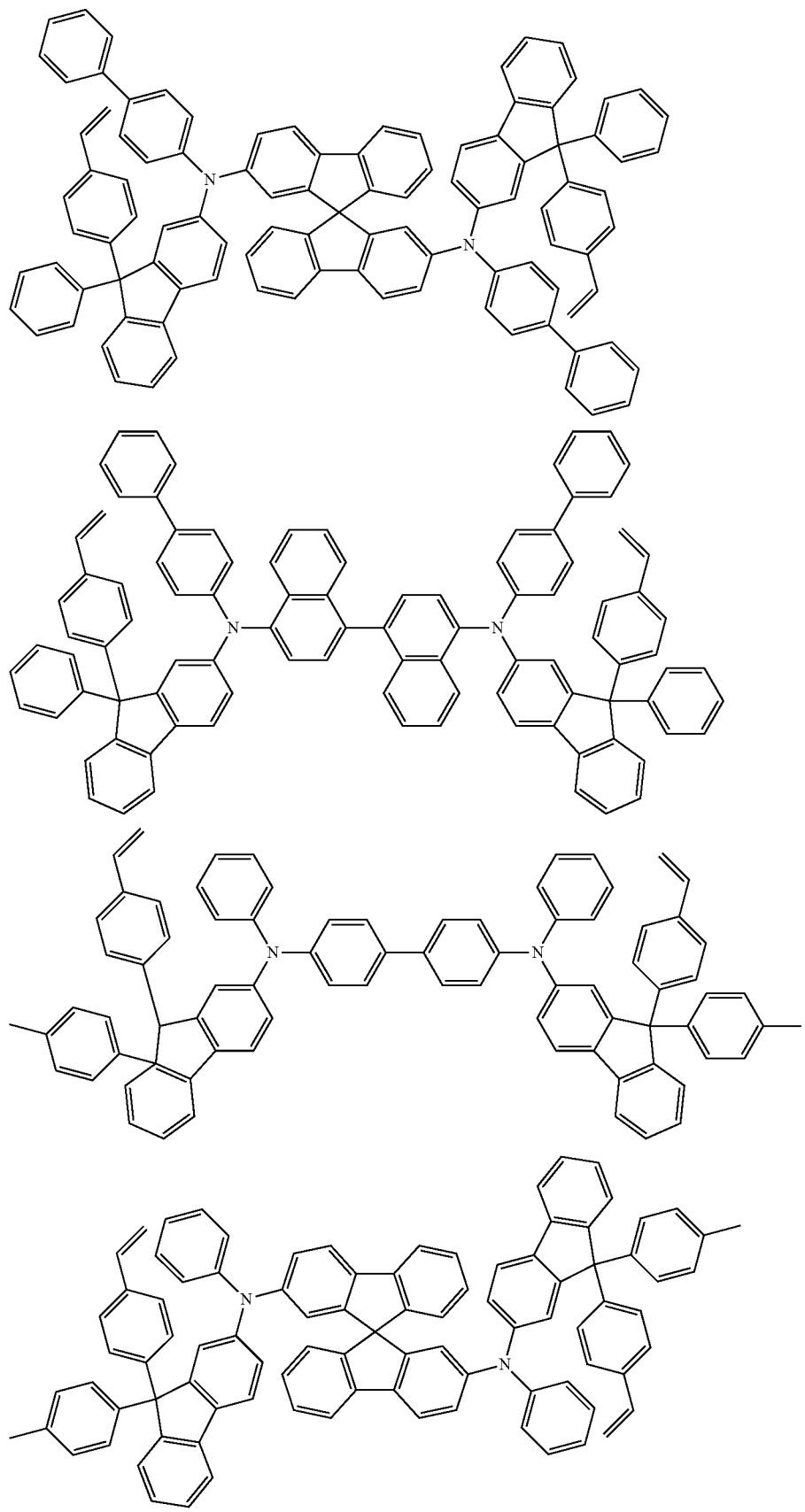

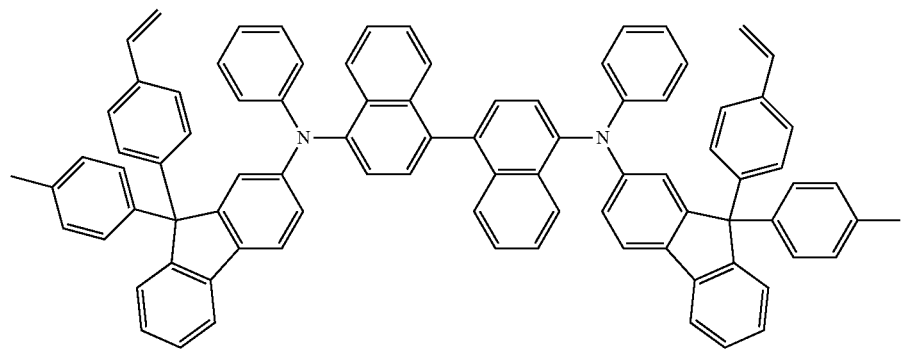
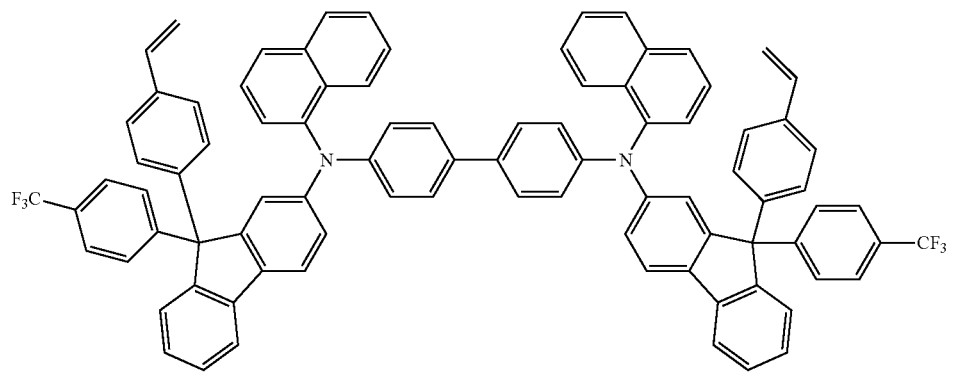
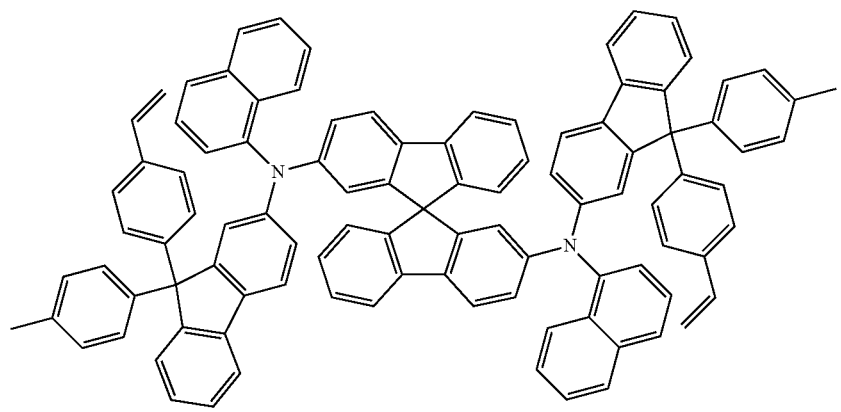
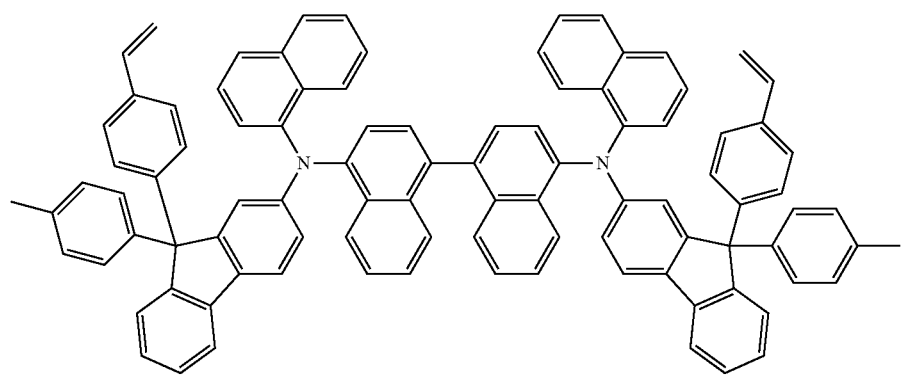

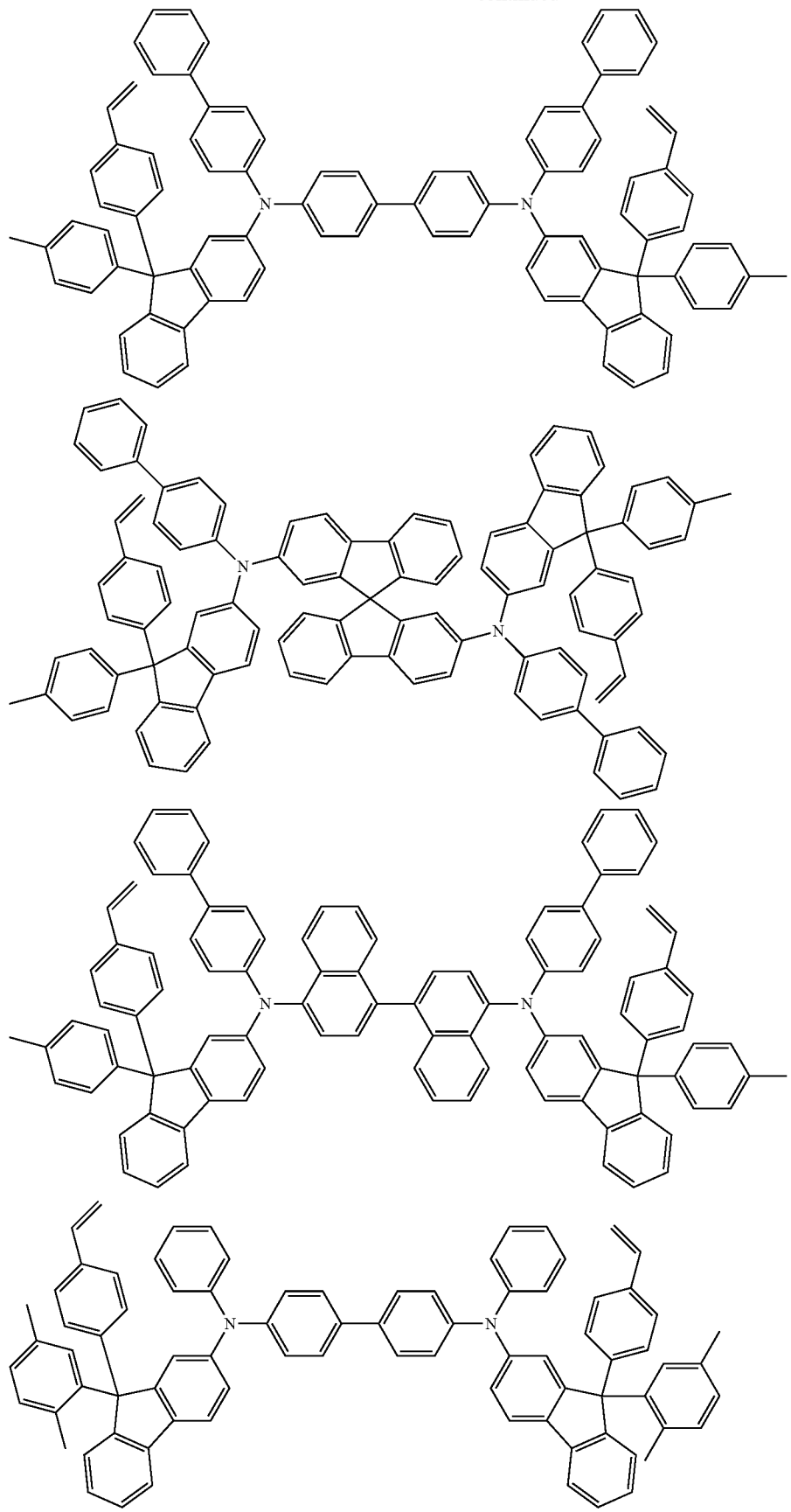

-continued
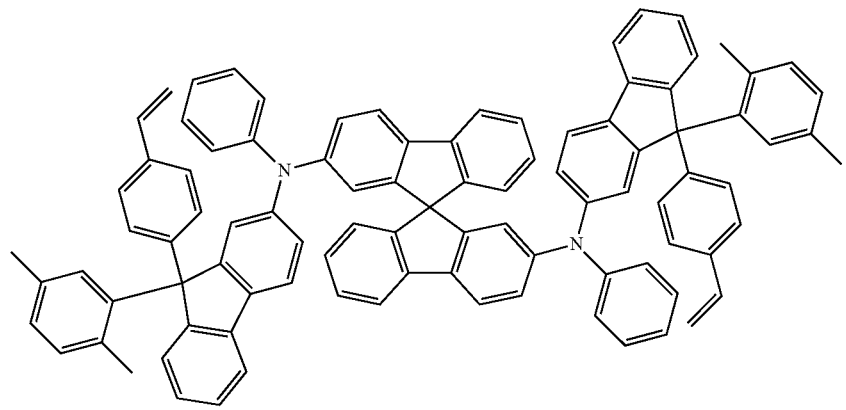
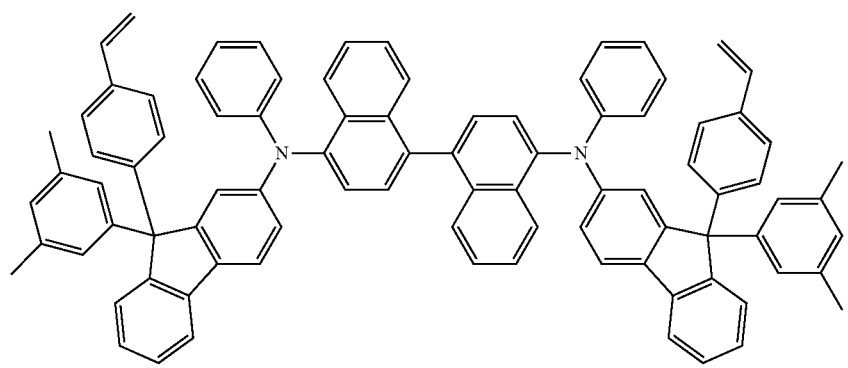
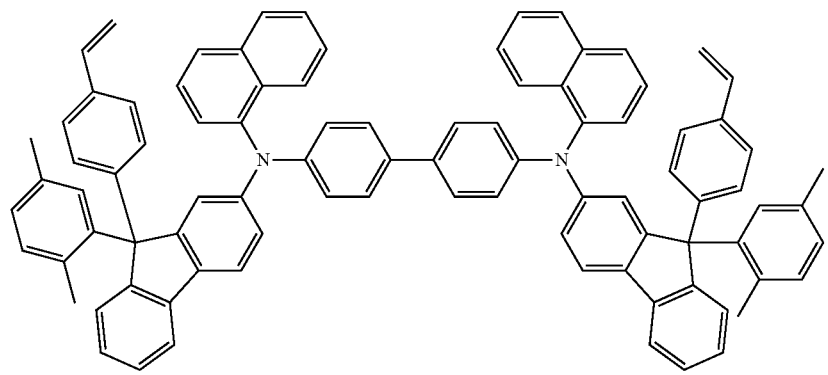
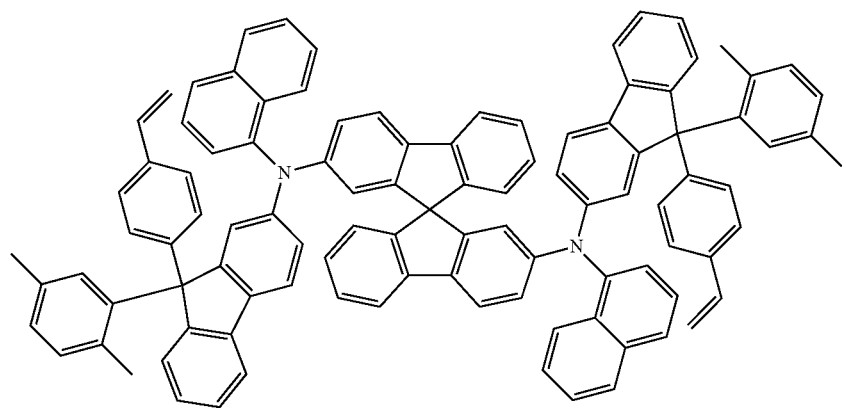

-continued
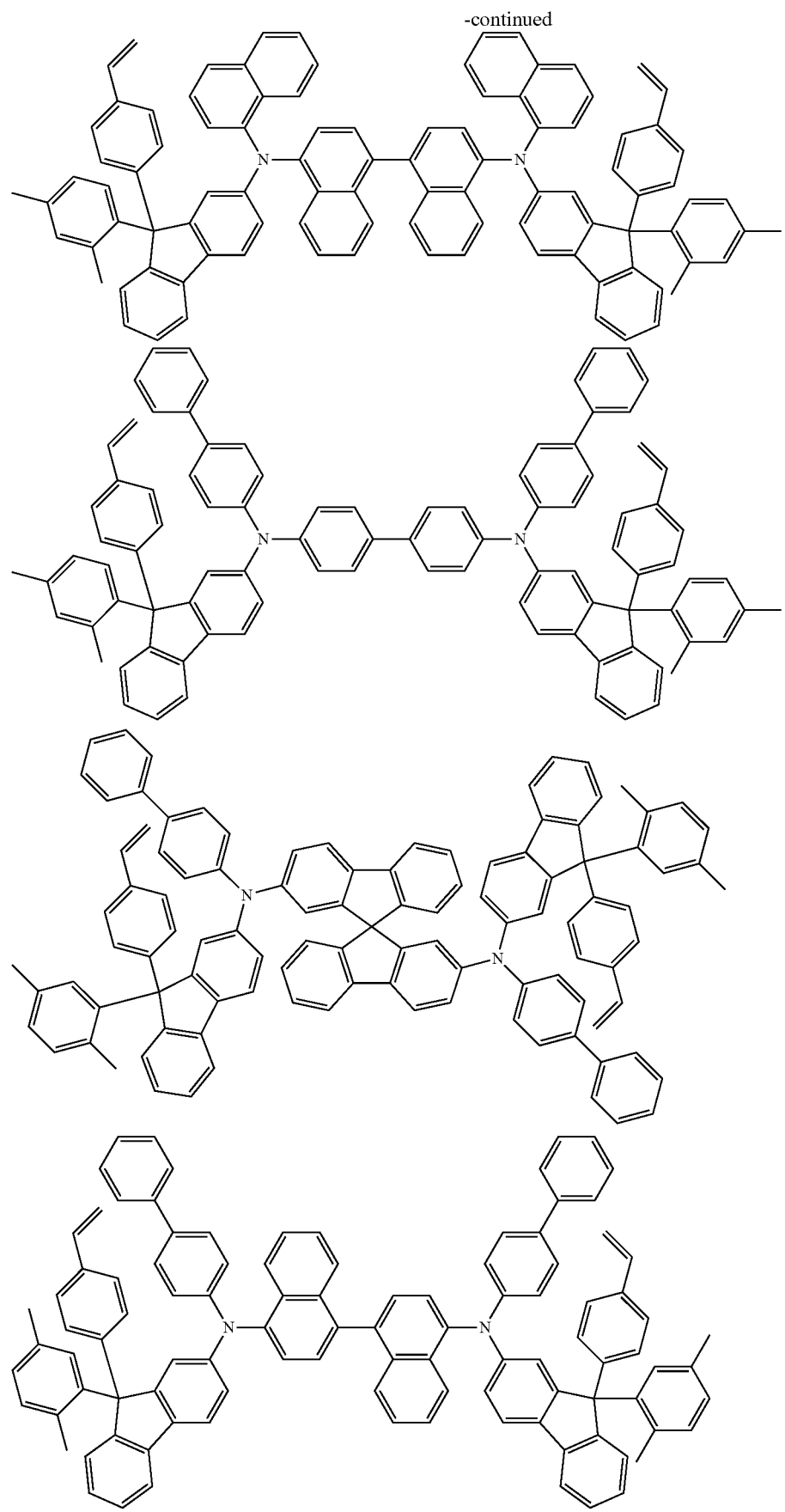

-continued
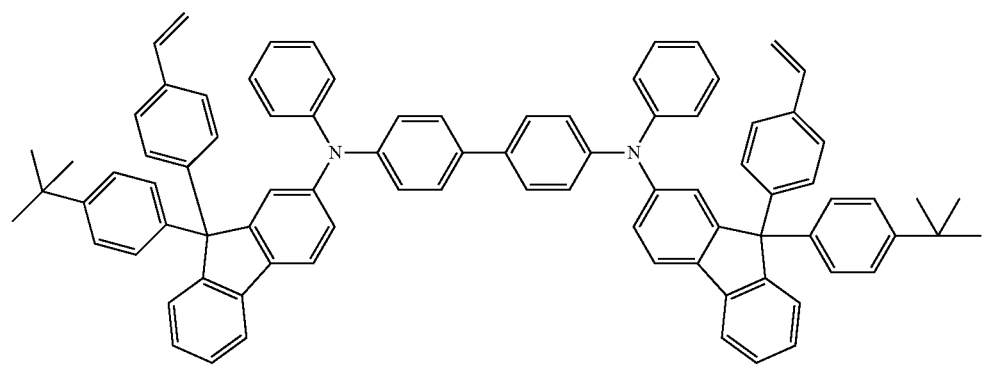
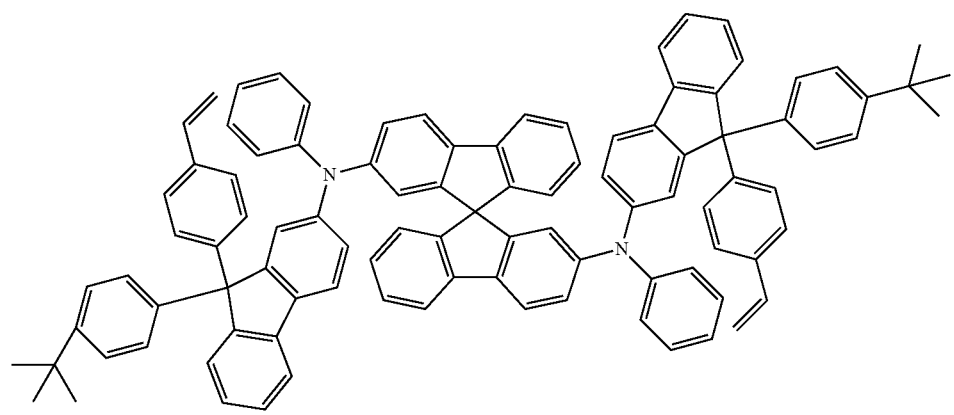
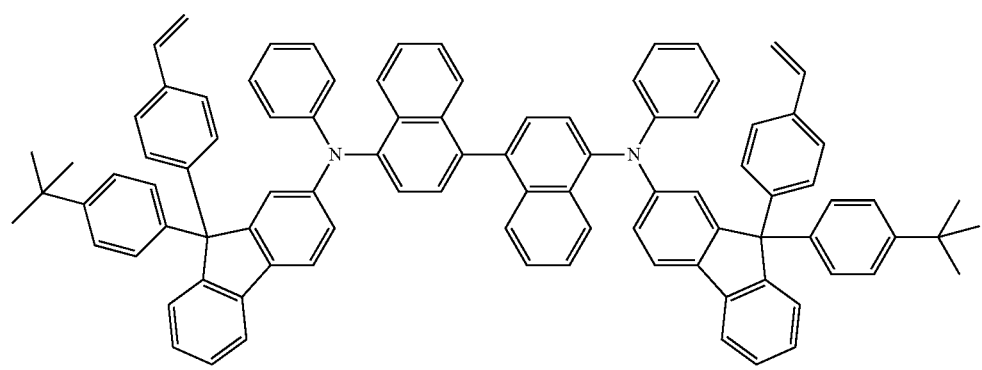
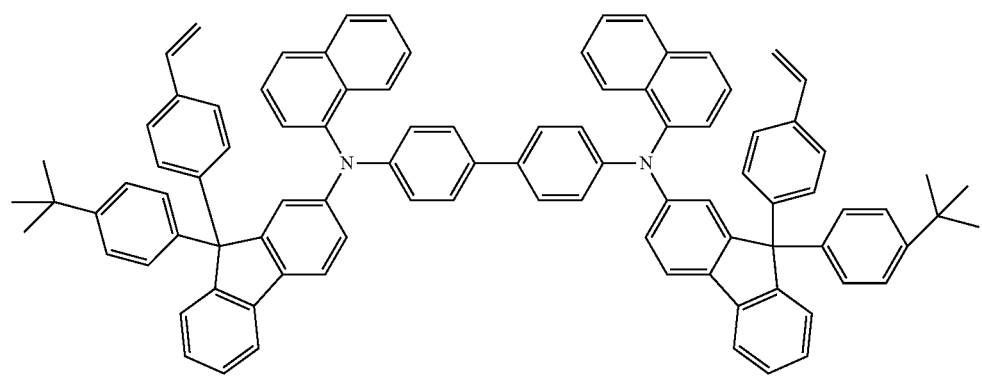

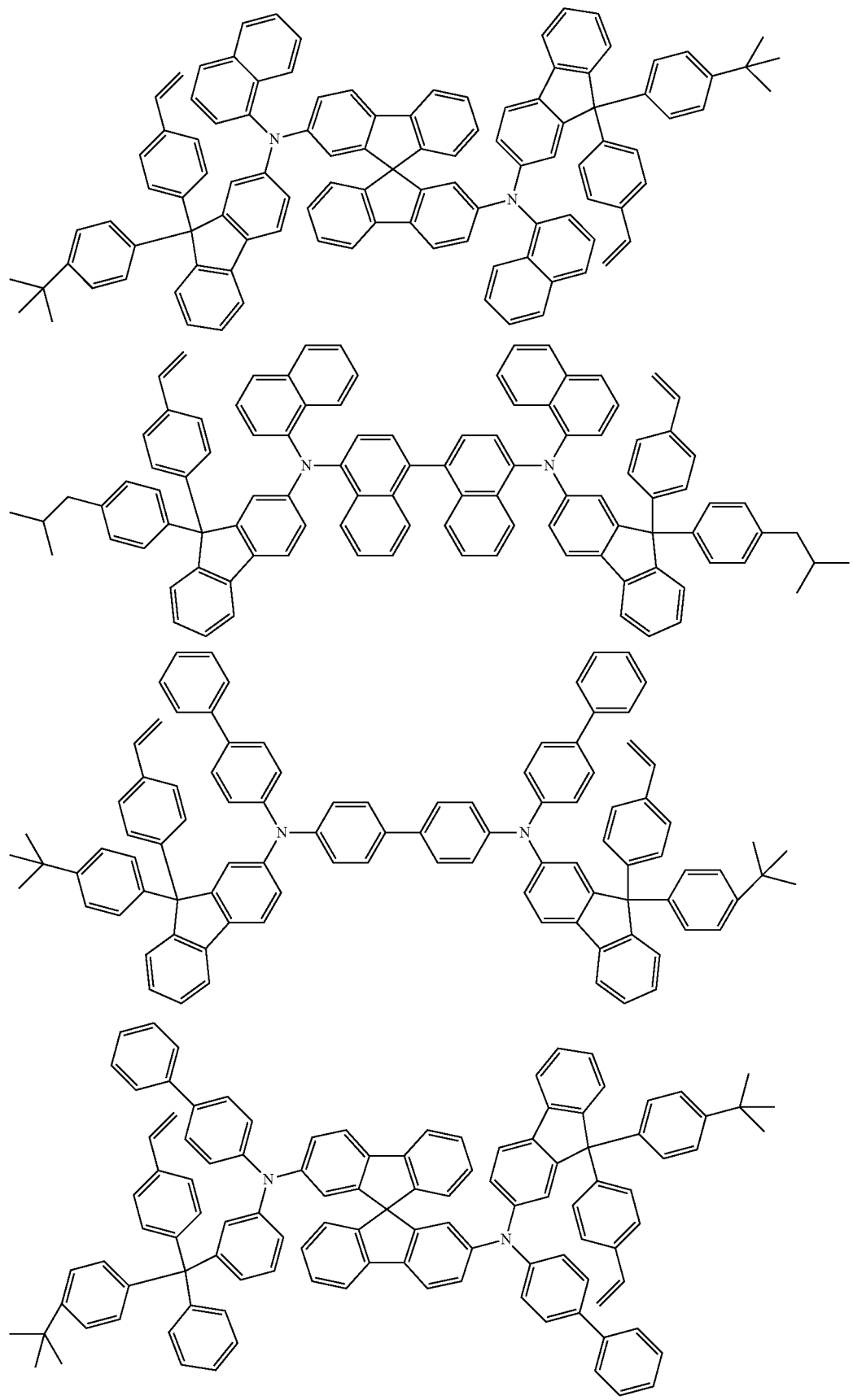

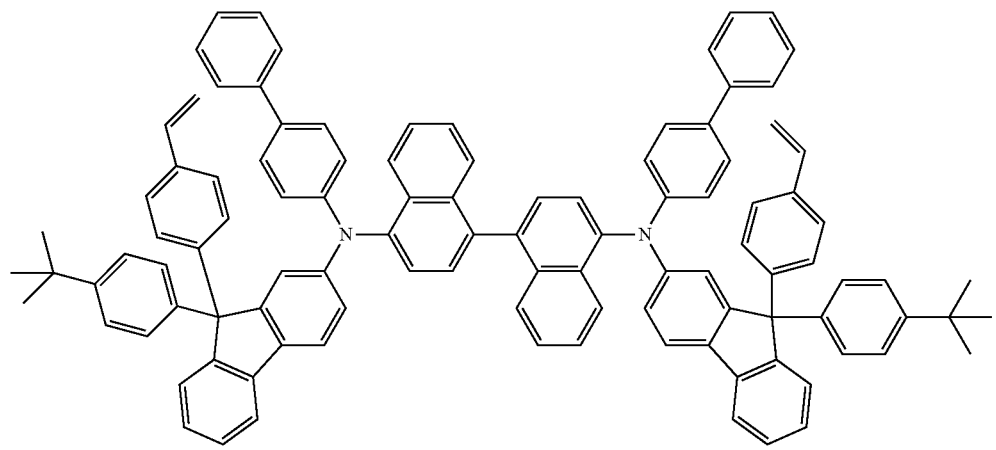
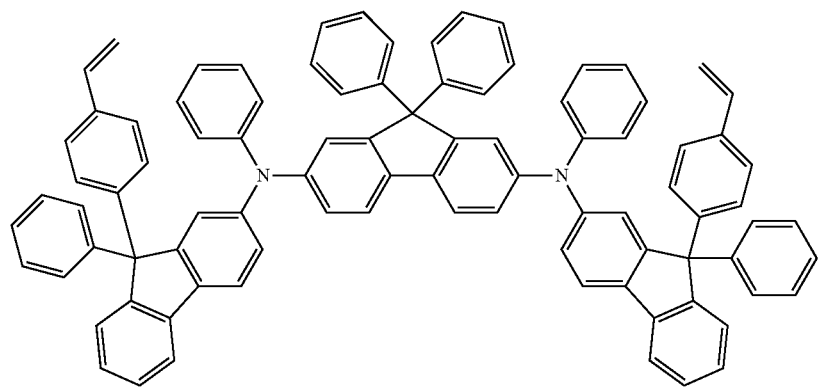
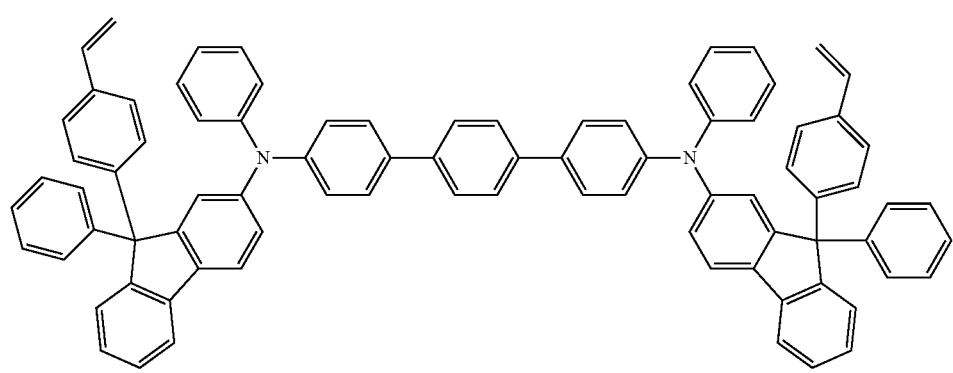
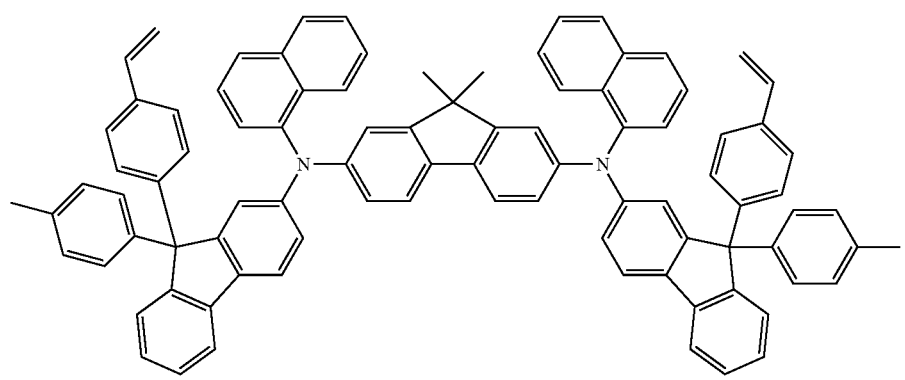

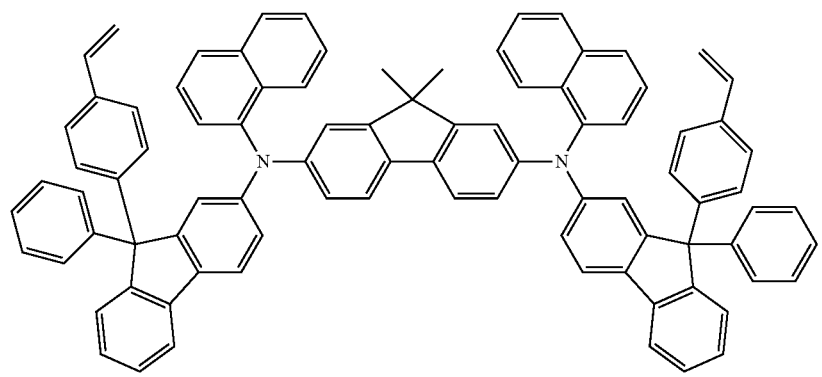
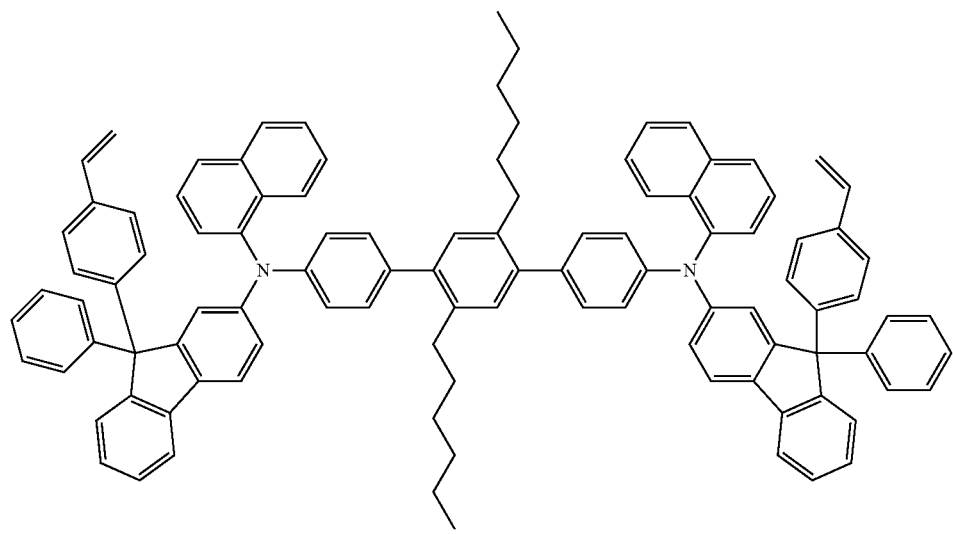
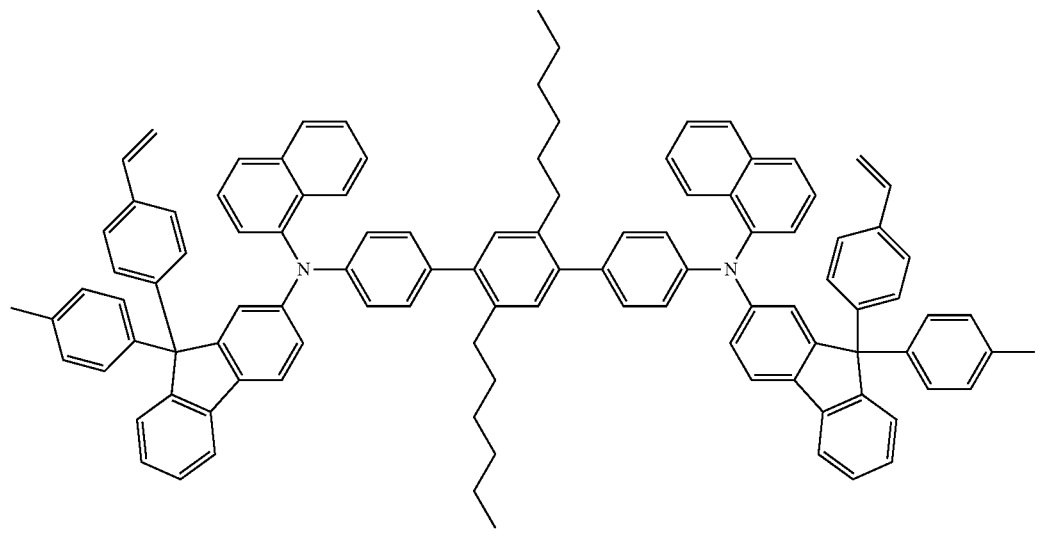

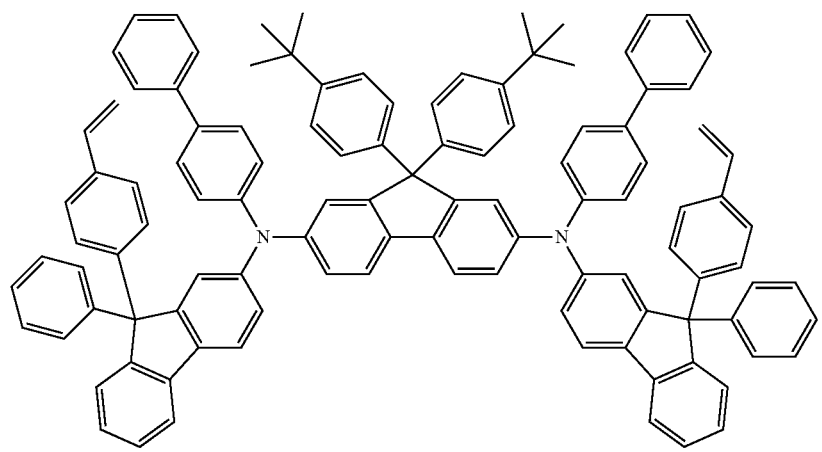
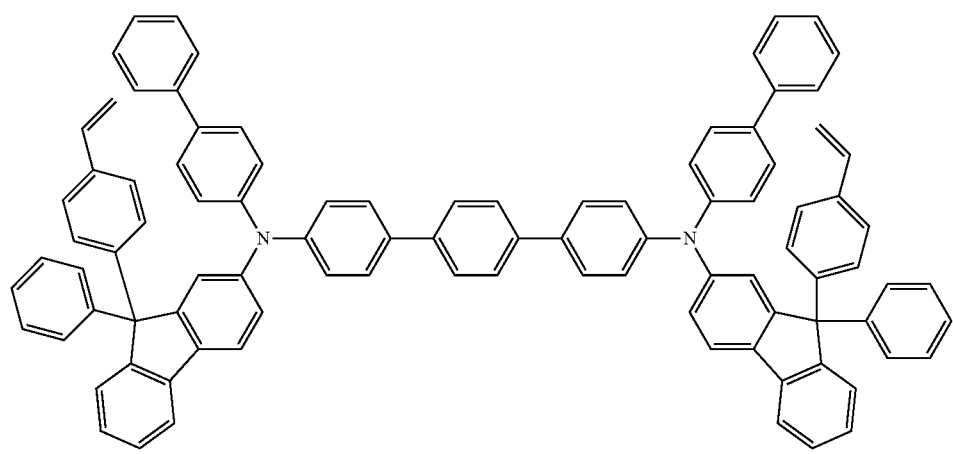
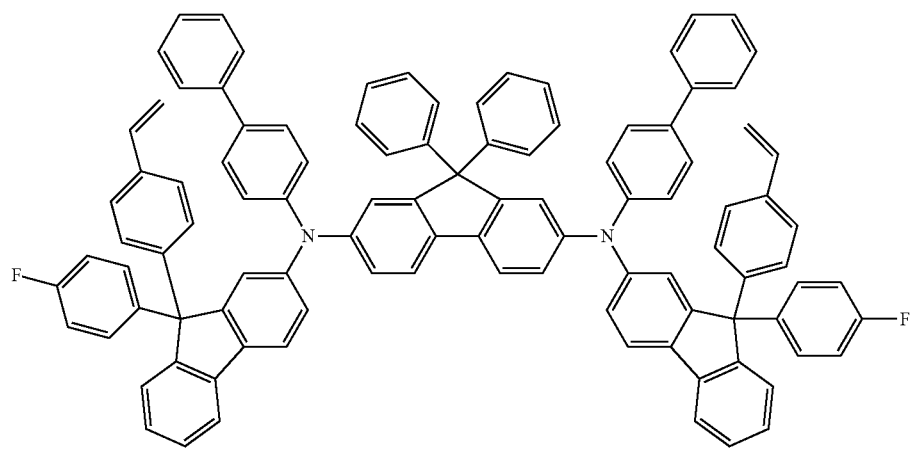

-continued
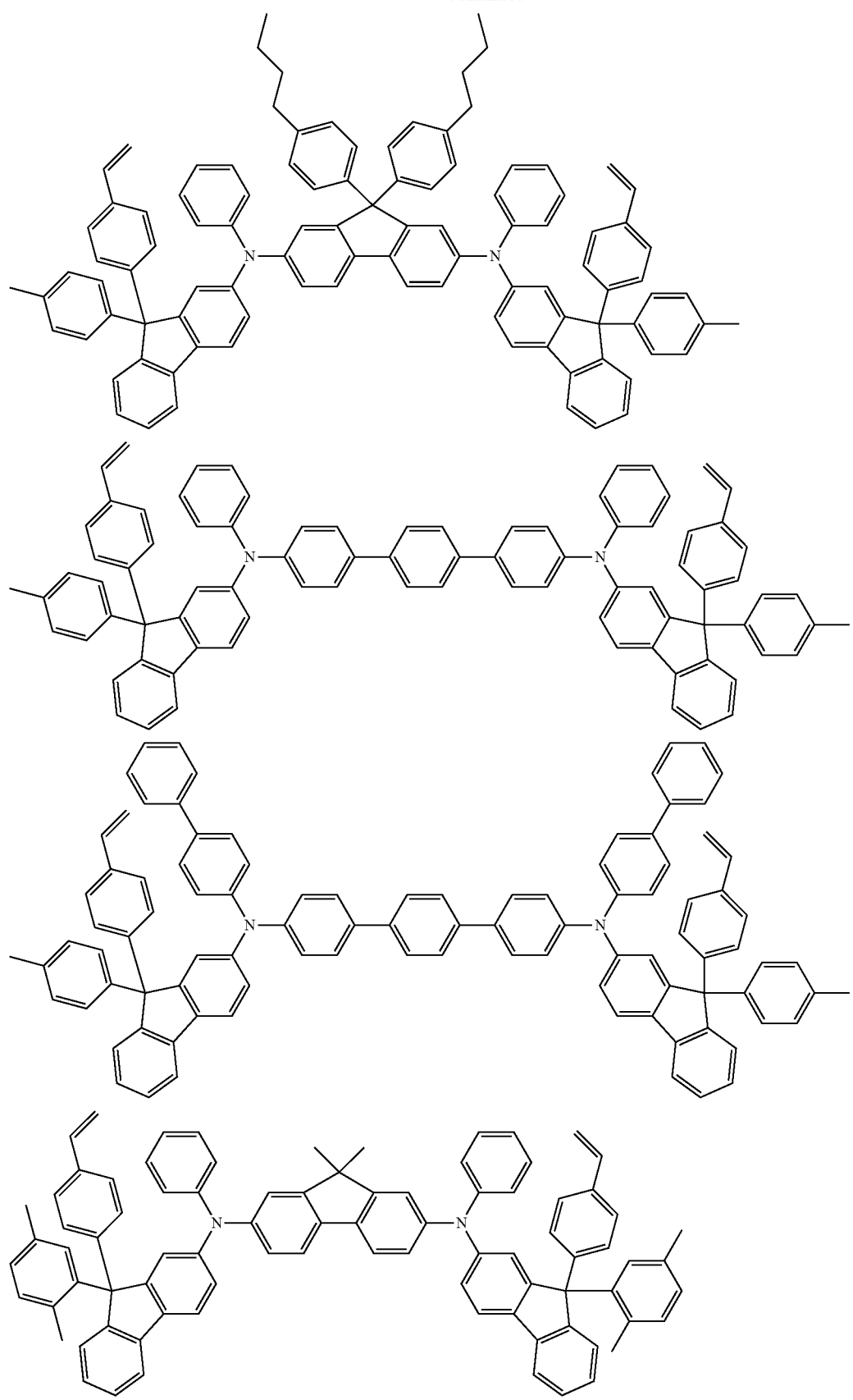

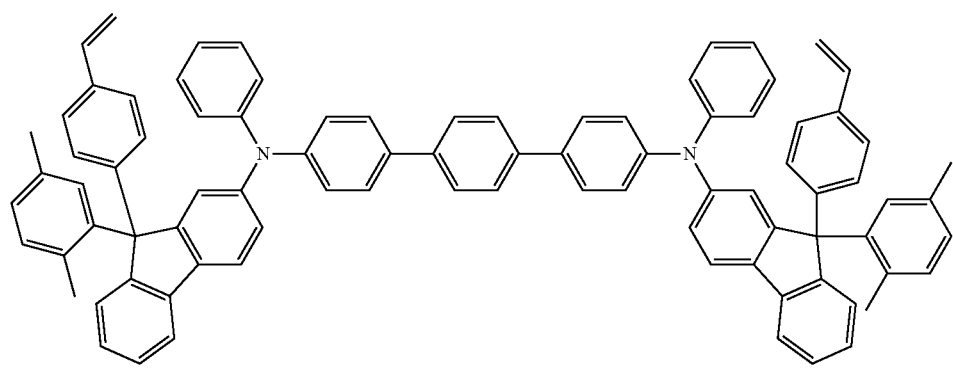
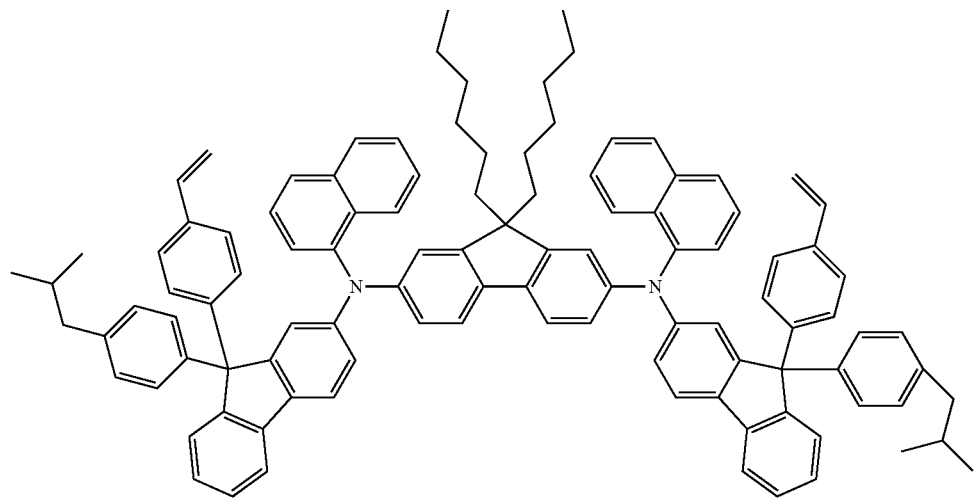
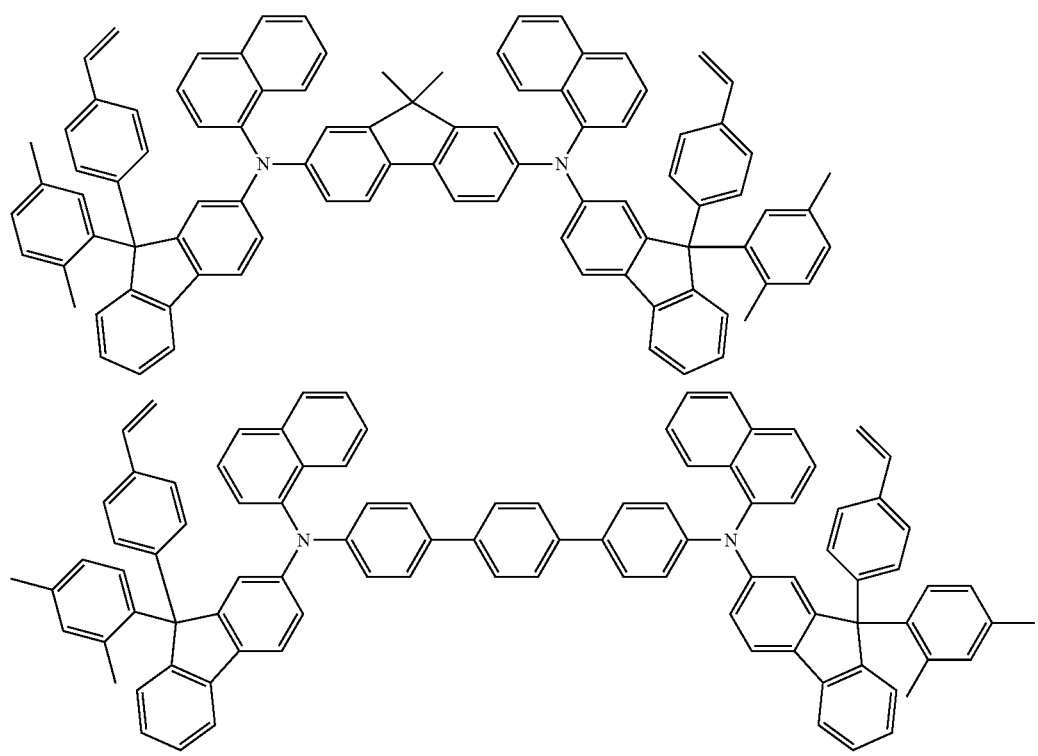

-continued
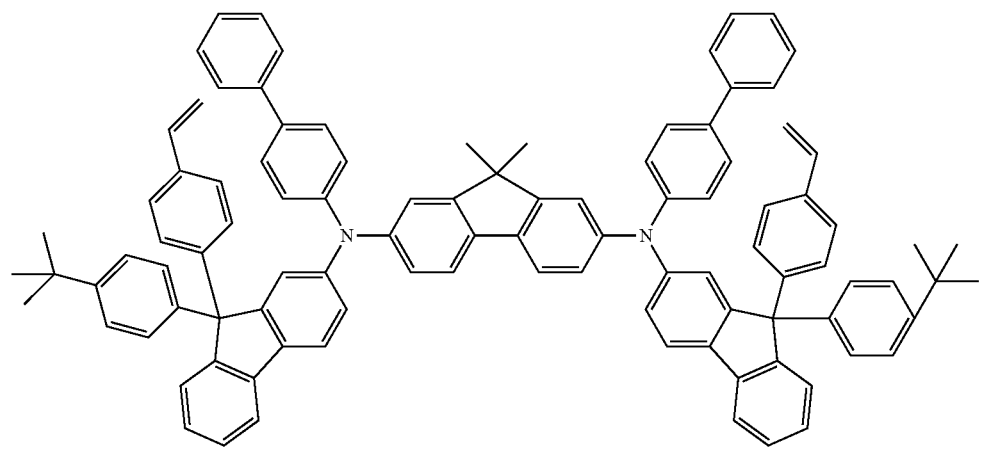
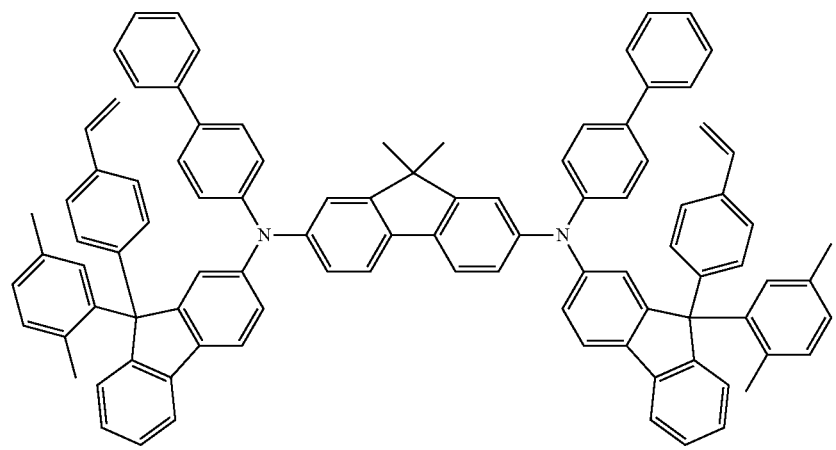
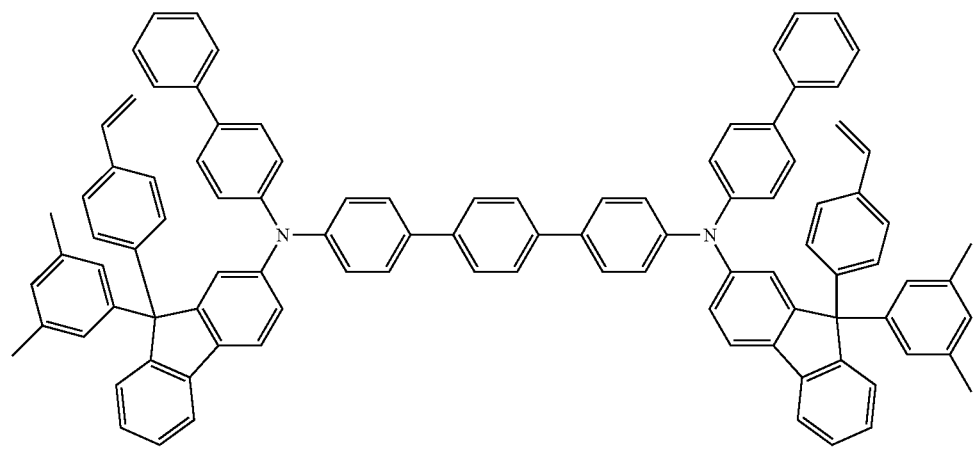
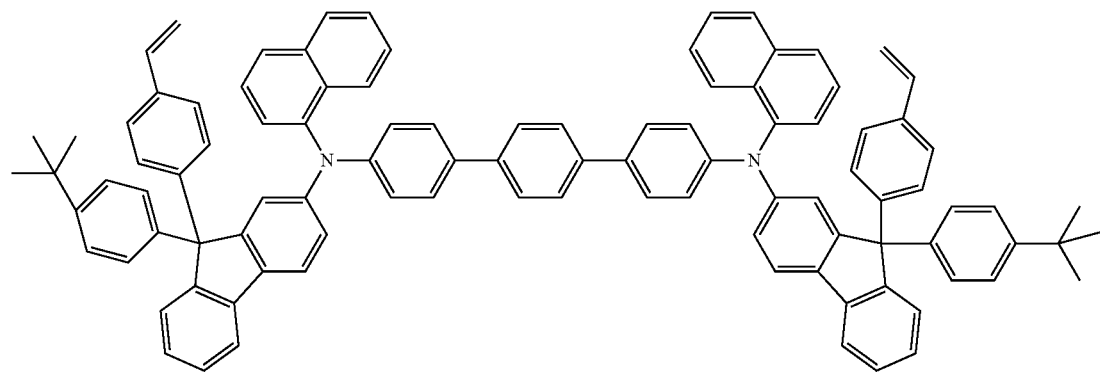

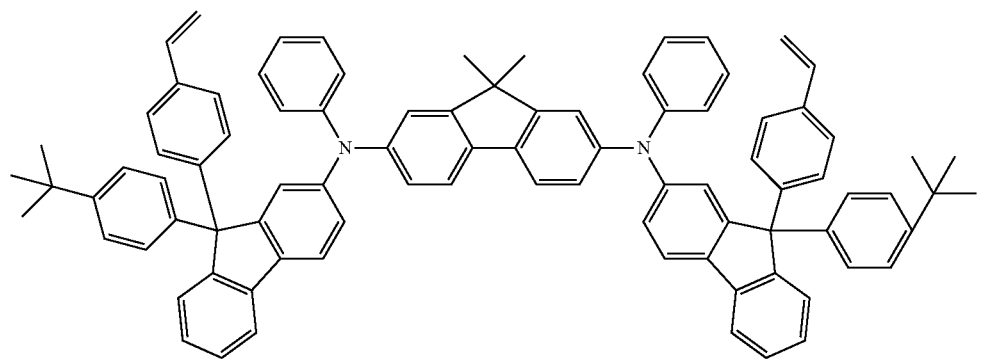
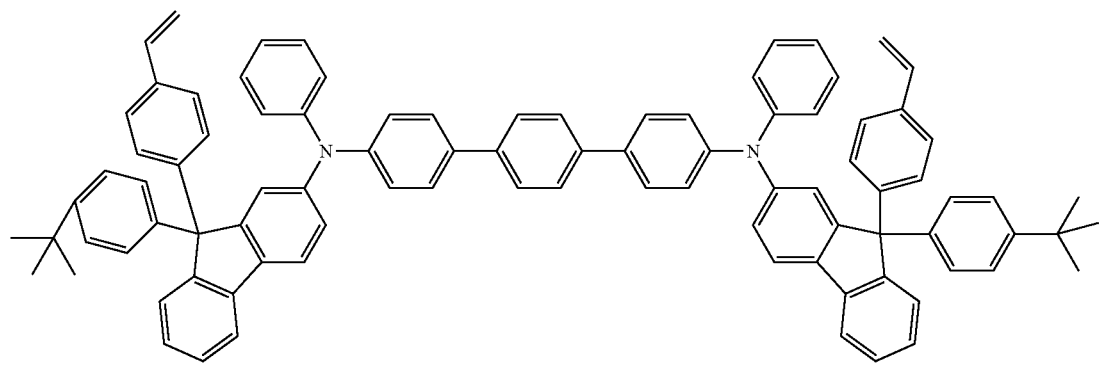
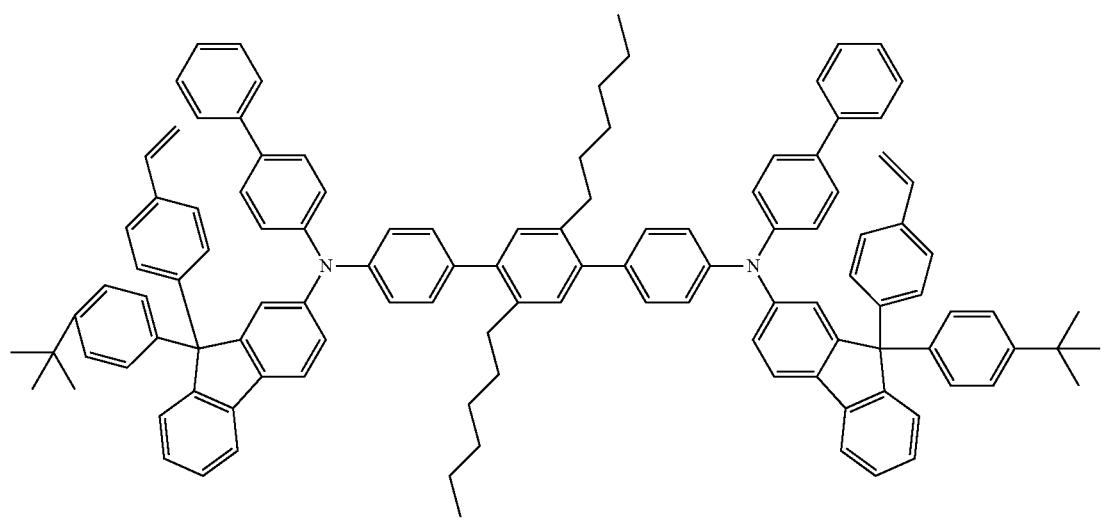
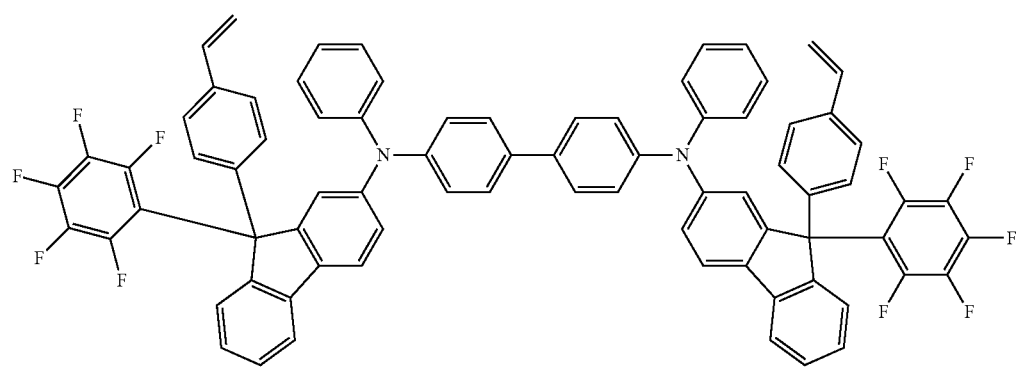

-continued
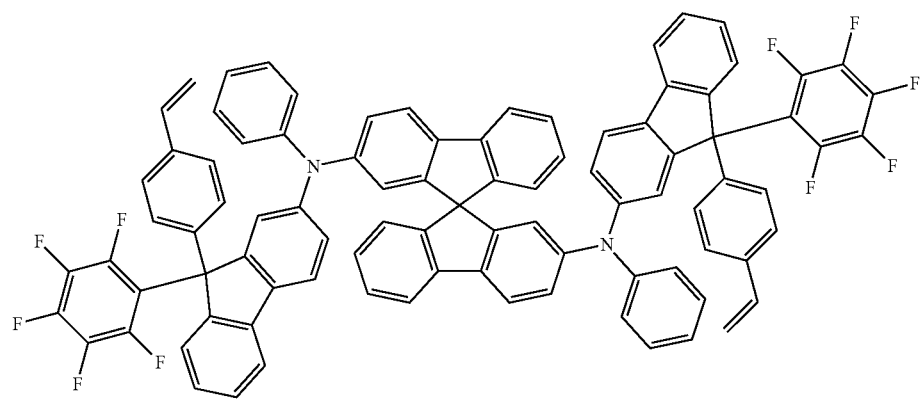
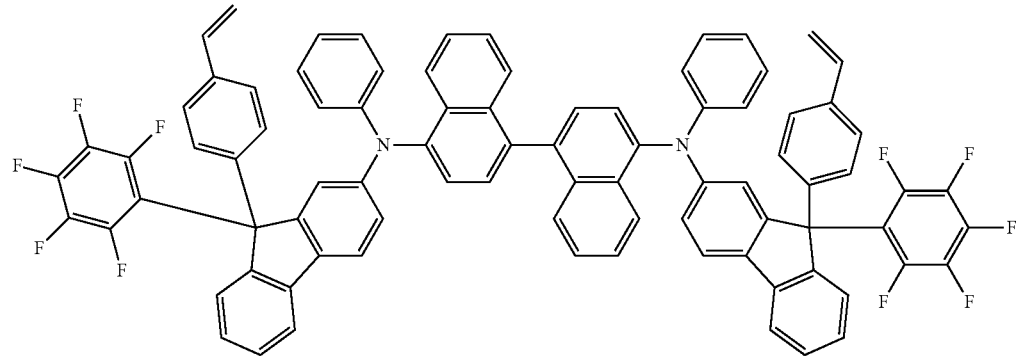
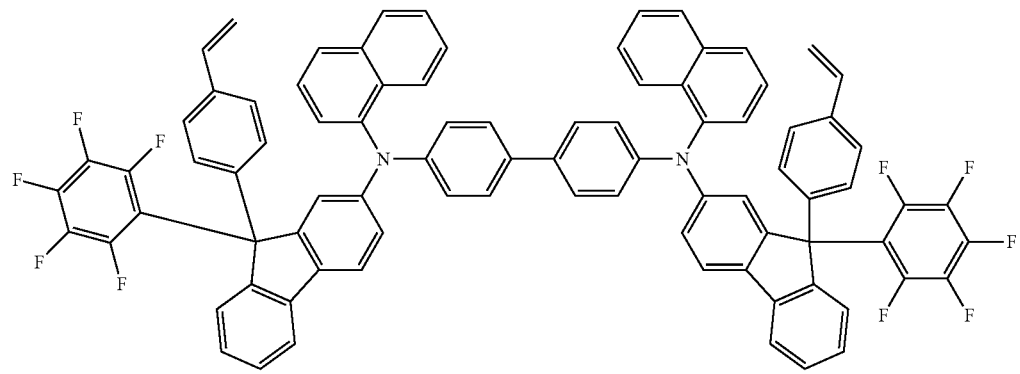
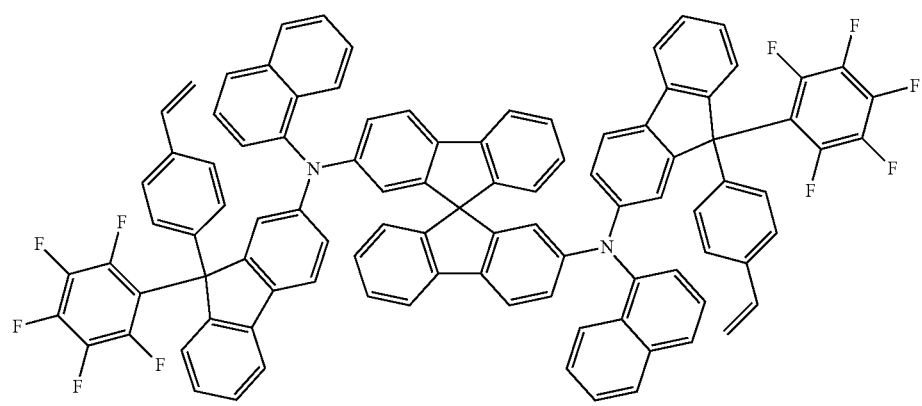

-continued
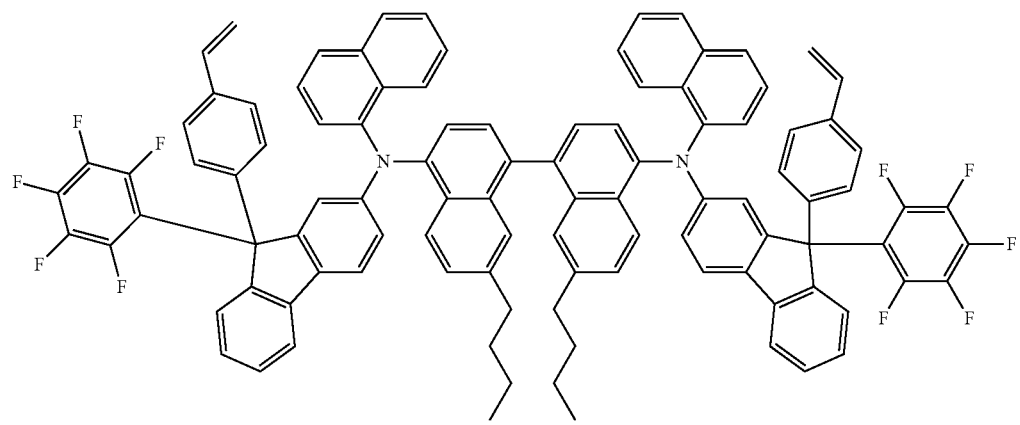
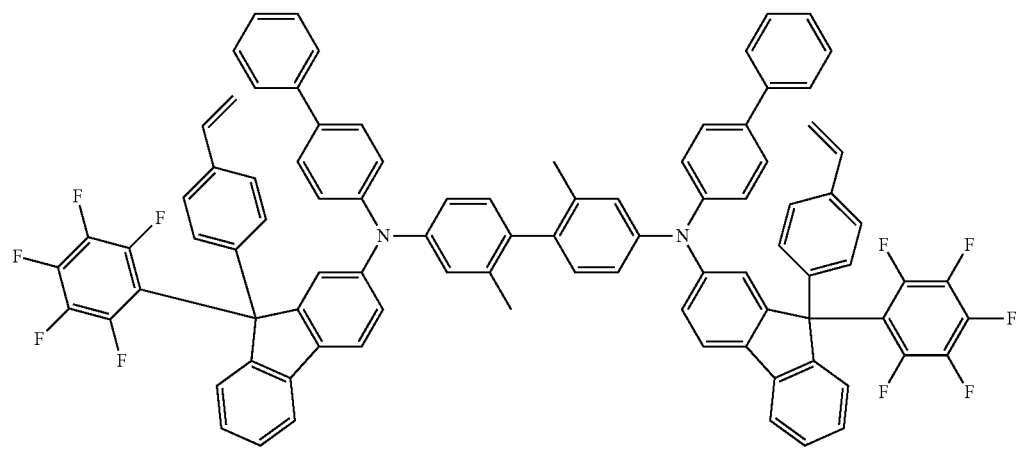
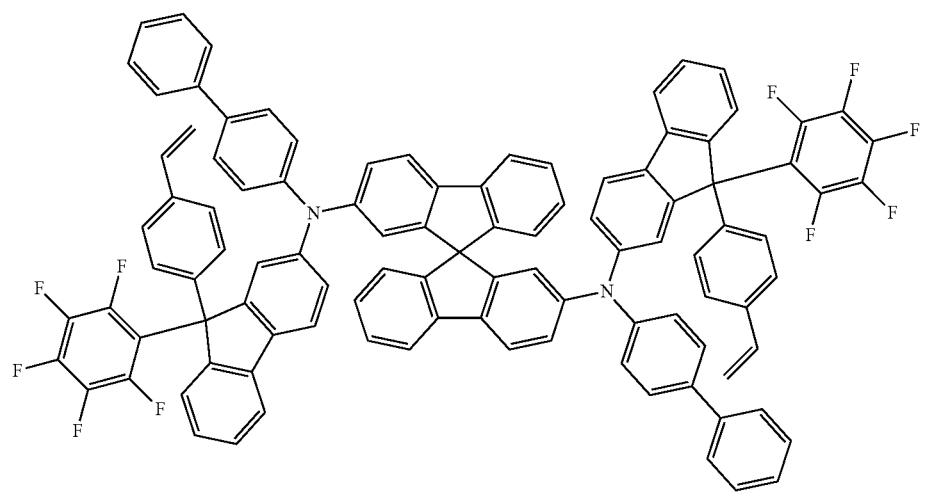

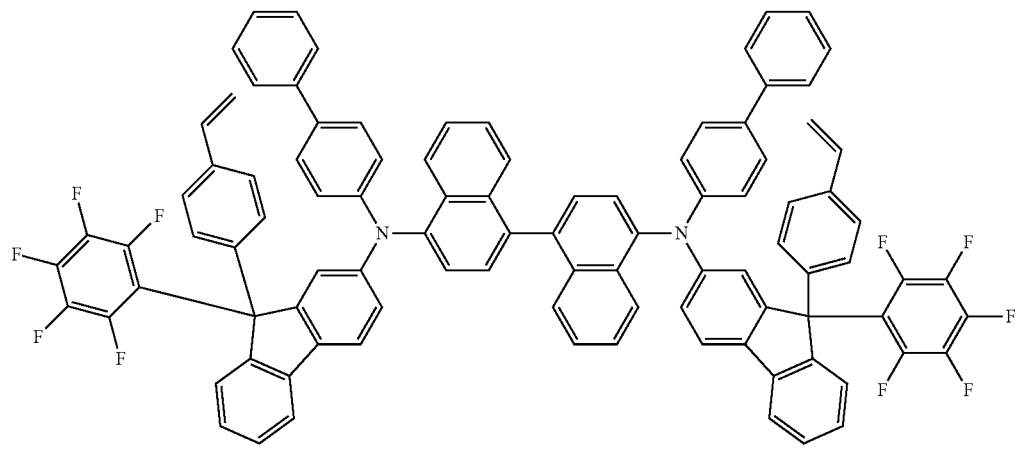
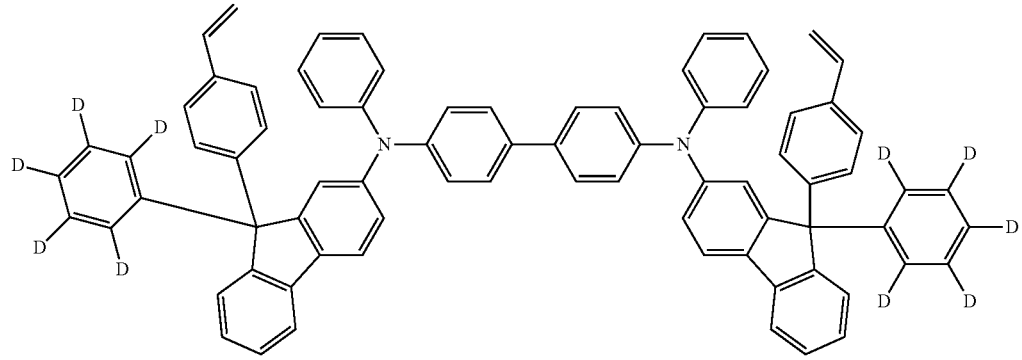
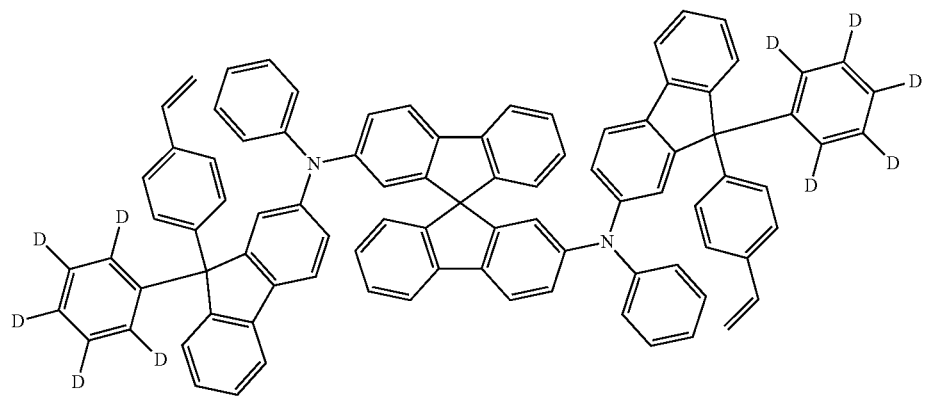
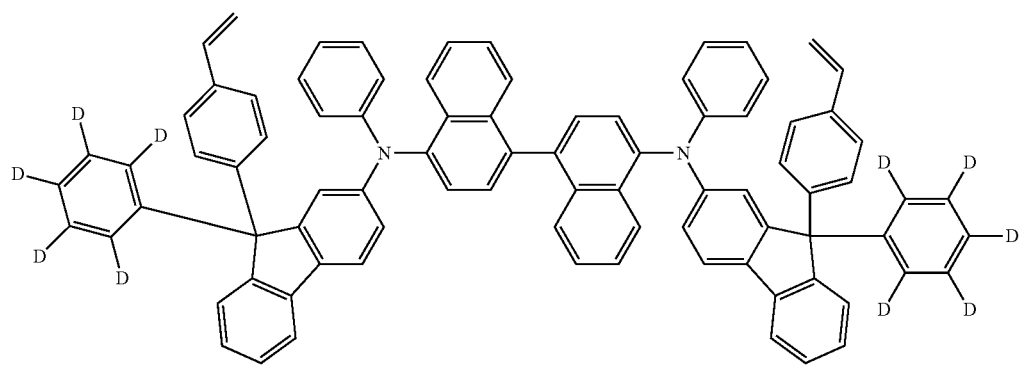

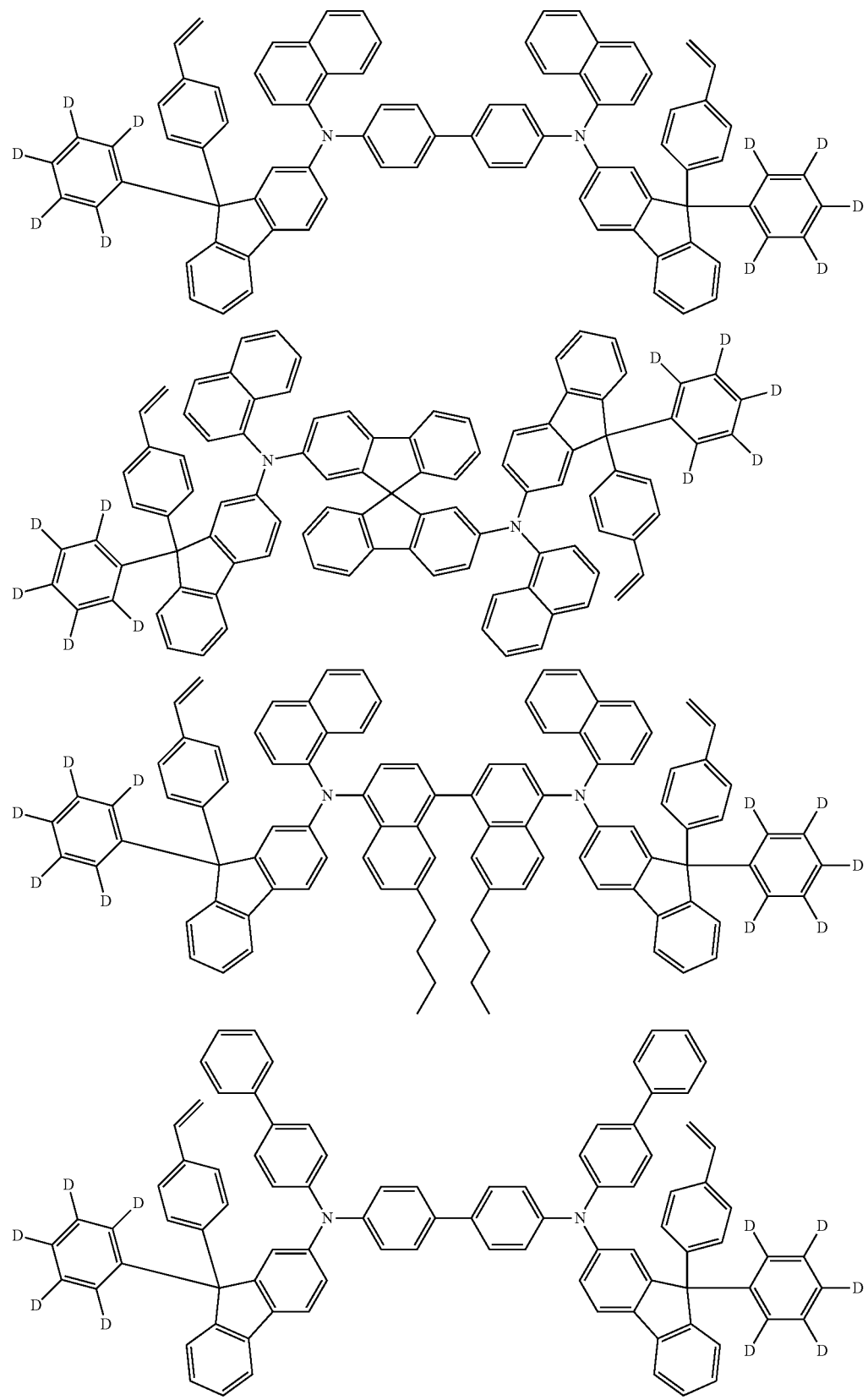

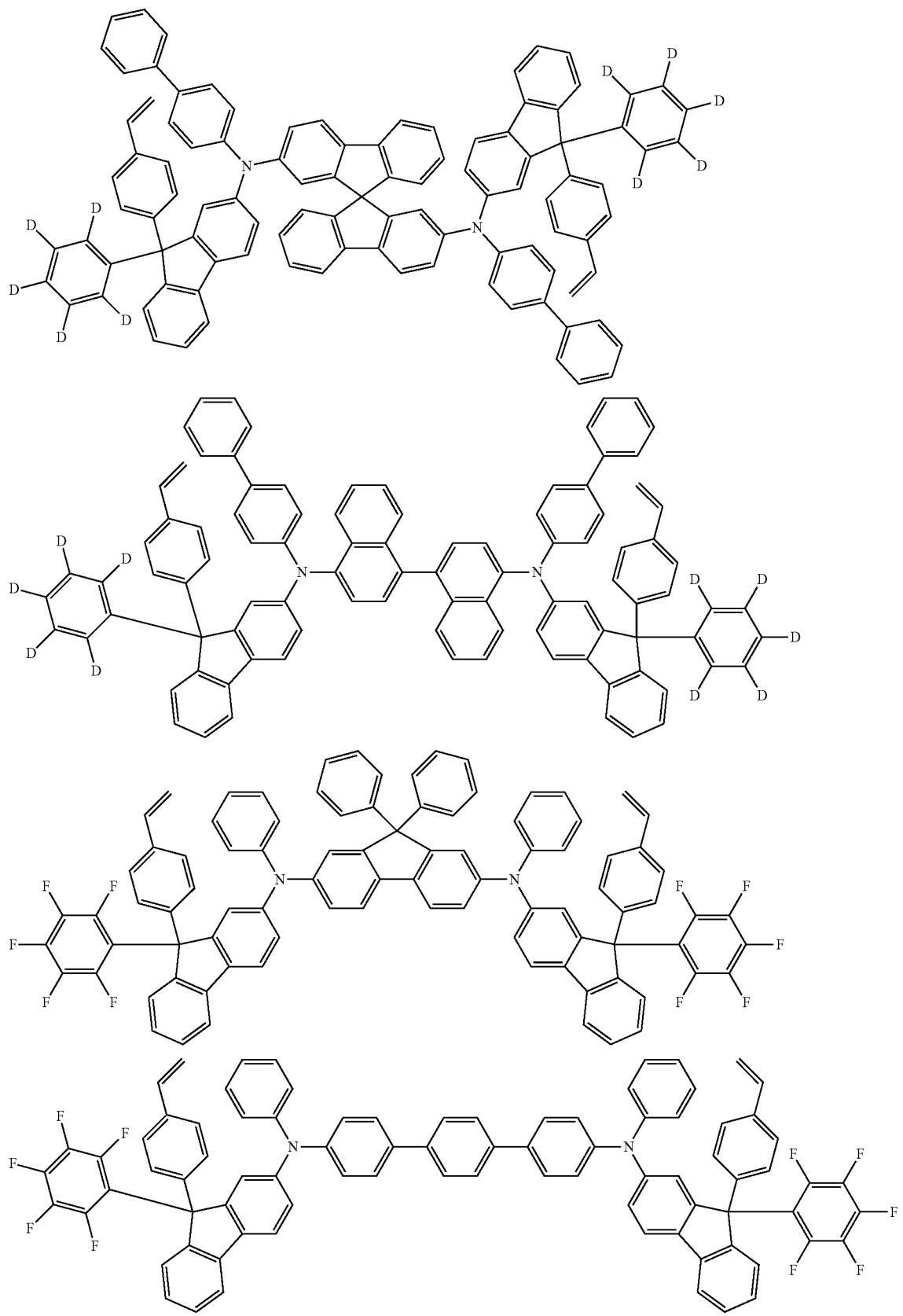

215 216
-continued
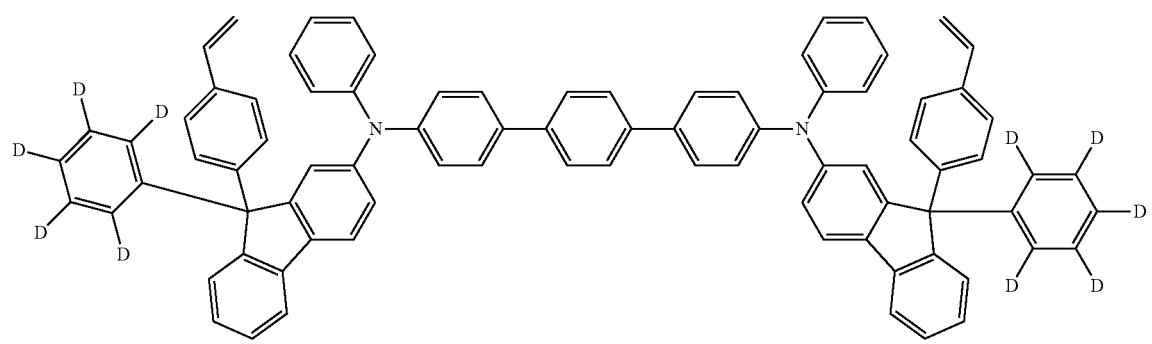
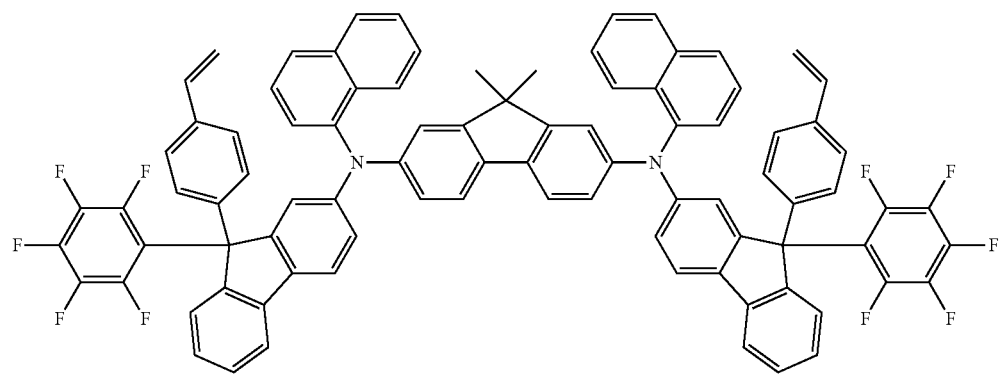
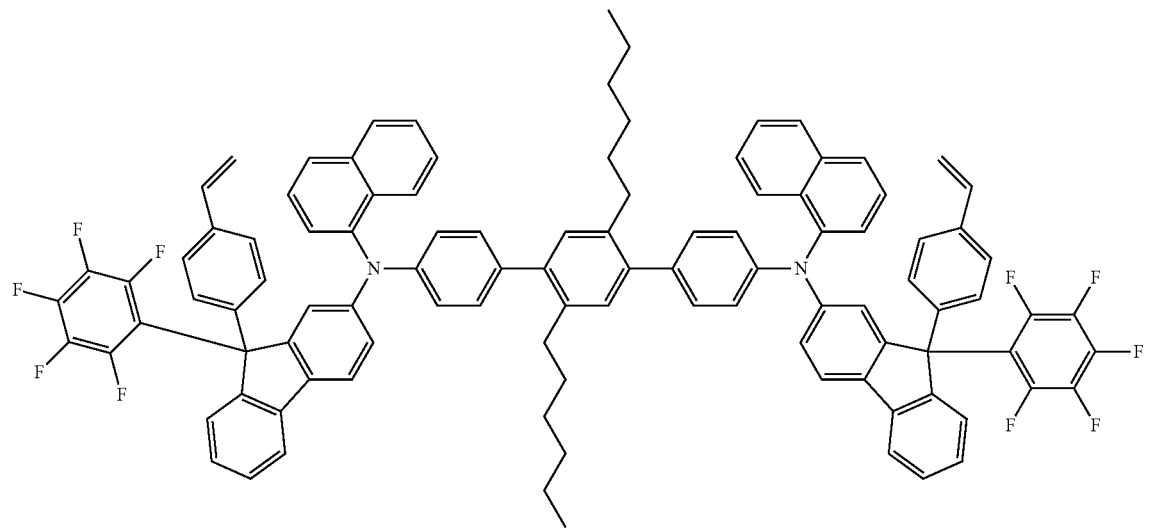
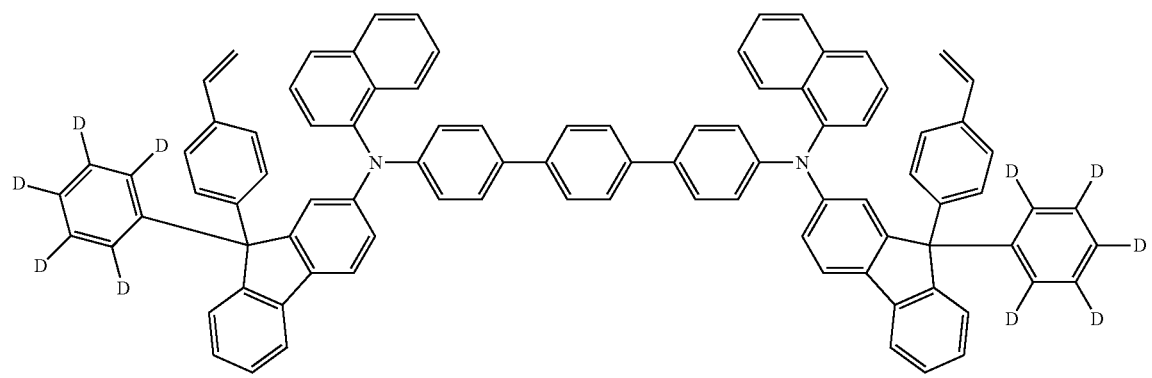

-continued
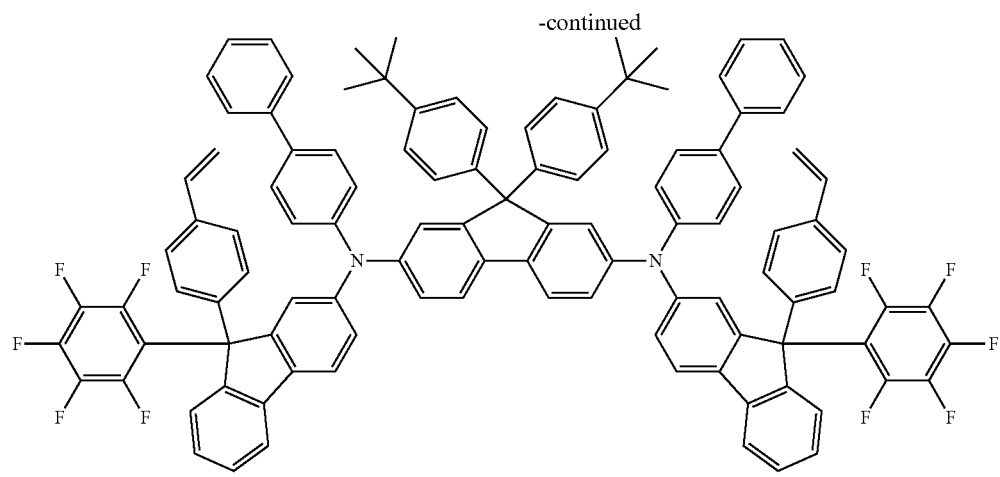
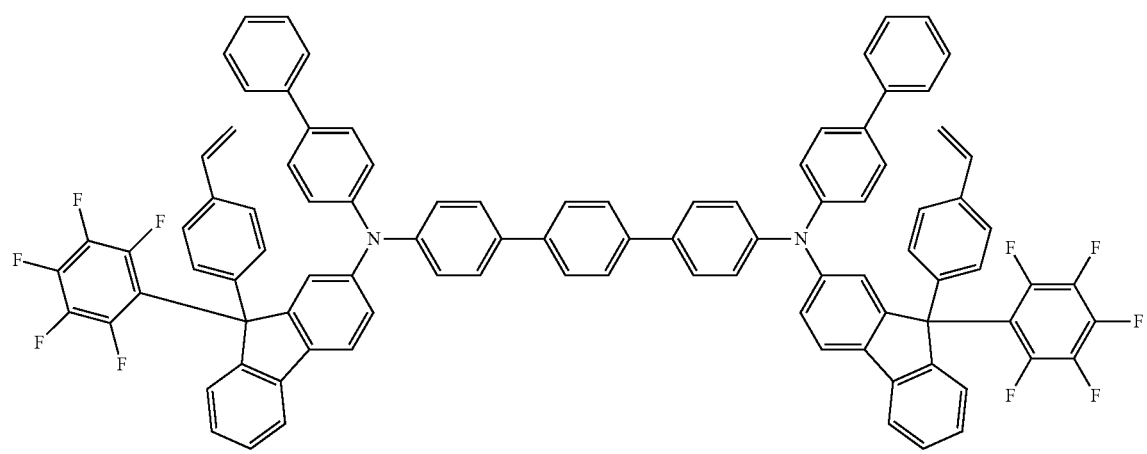
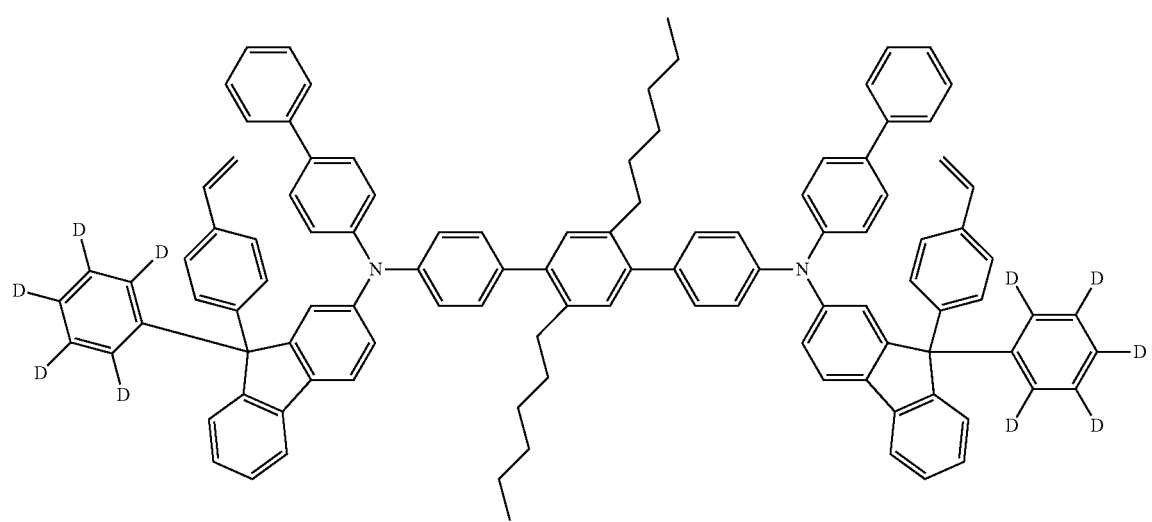

-continued
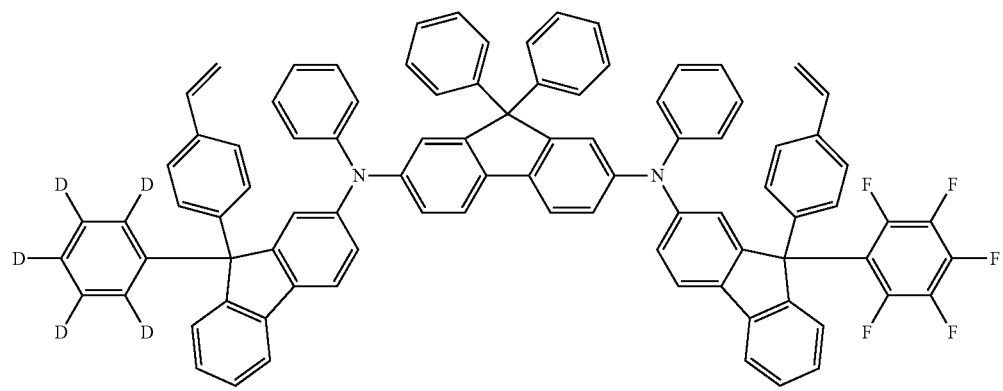
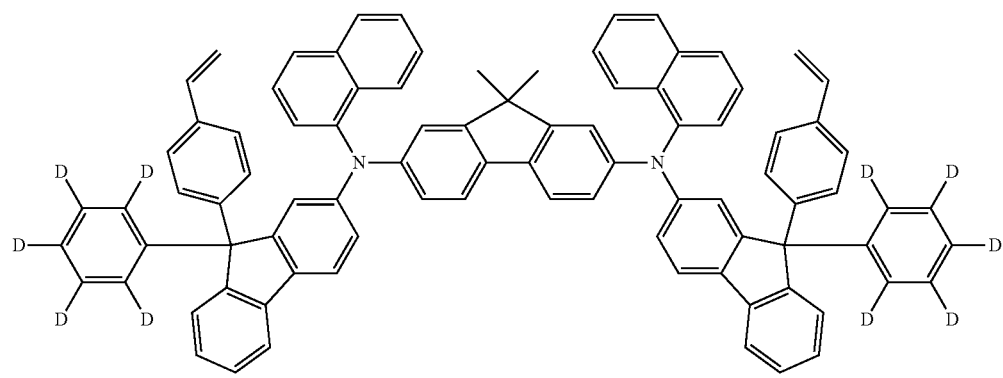
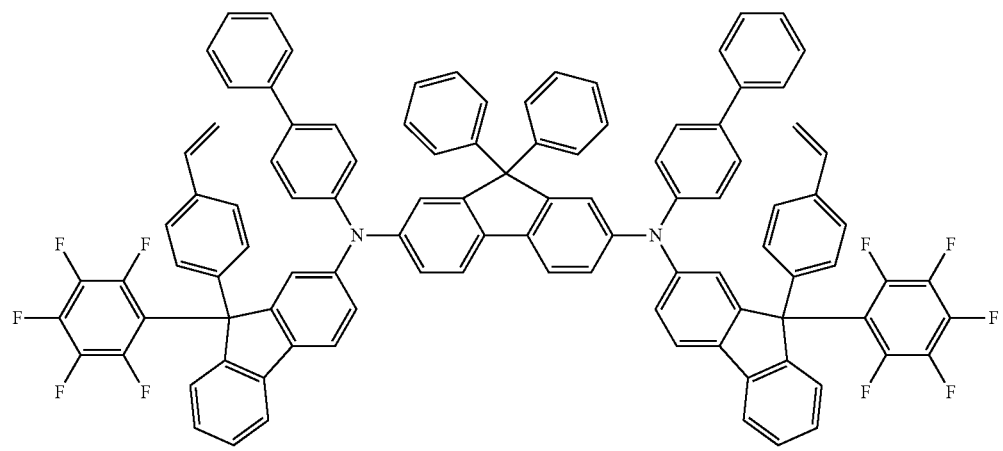
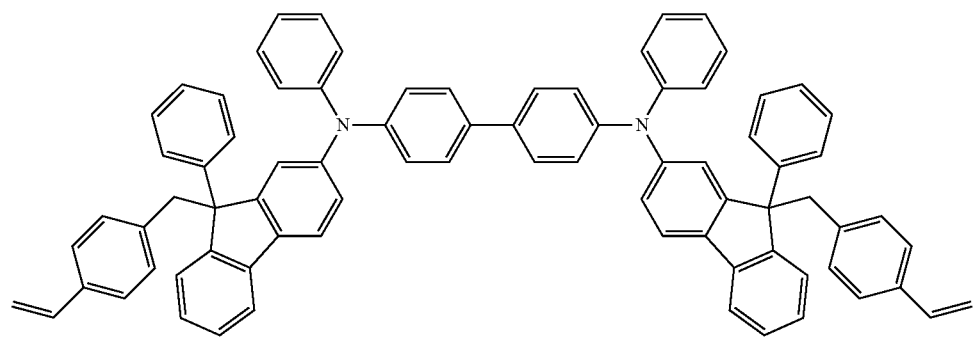

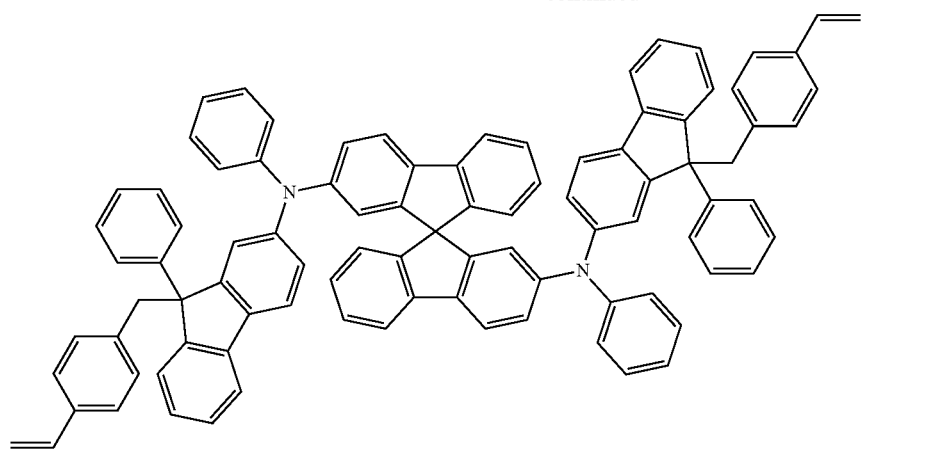
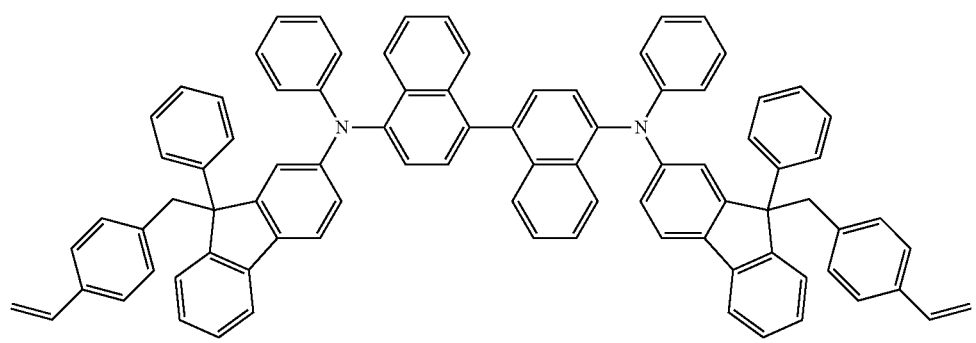
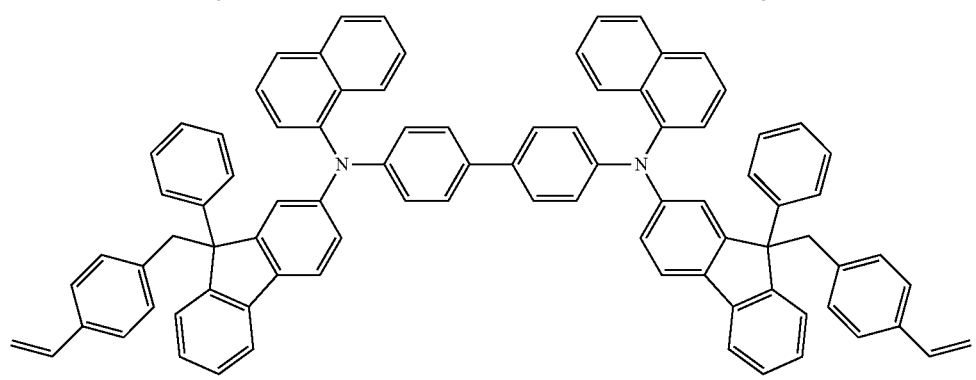
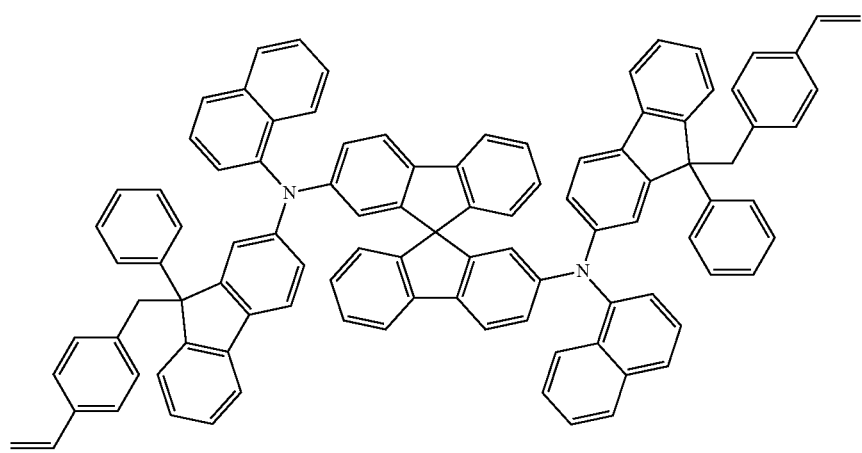

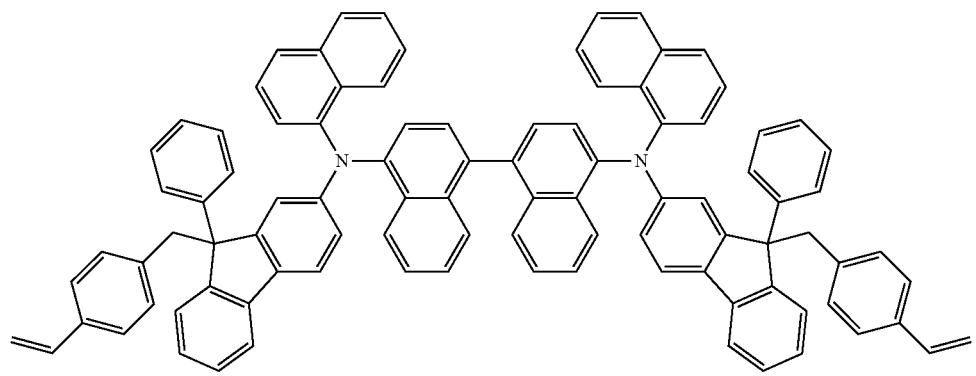
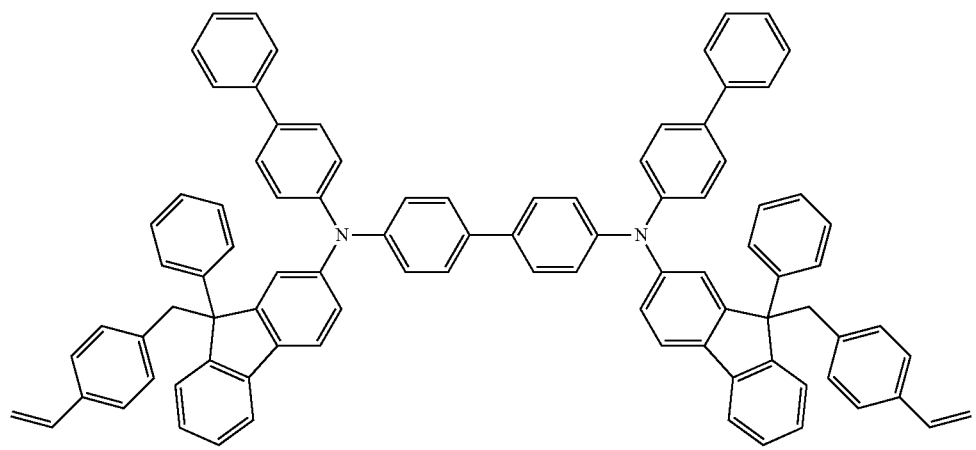
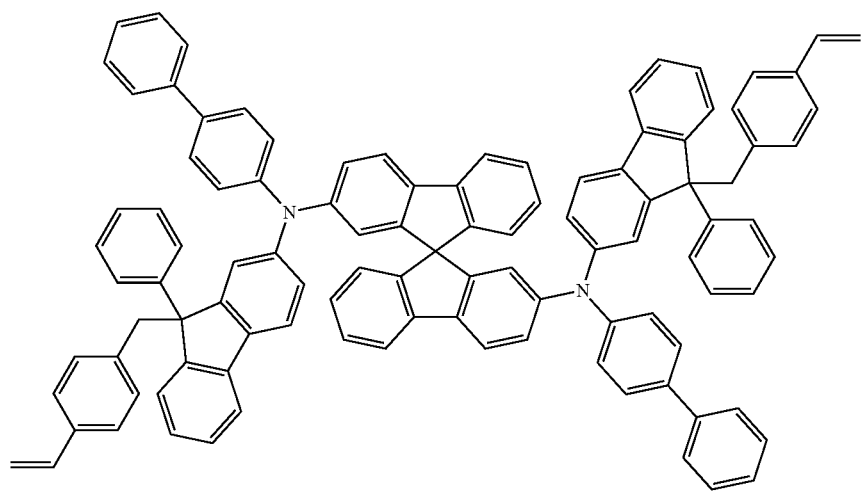

-continued
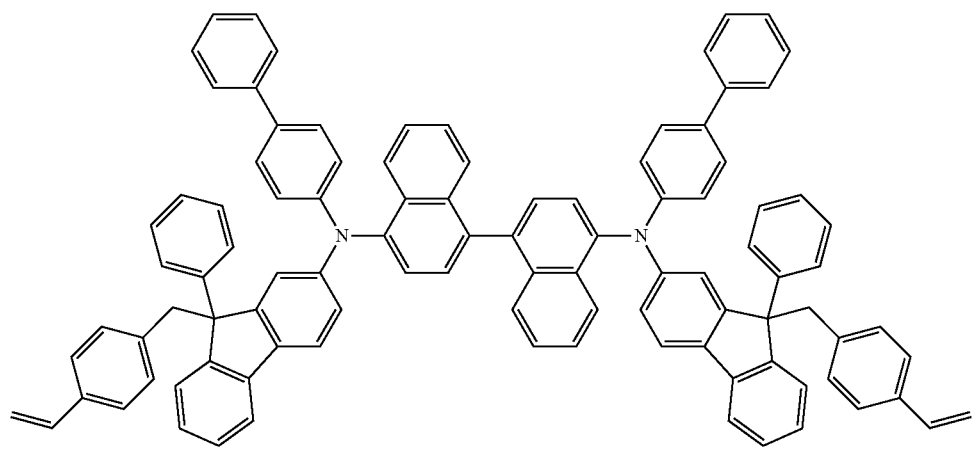
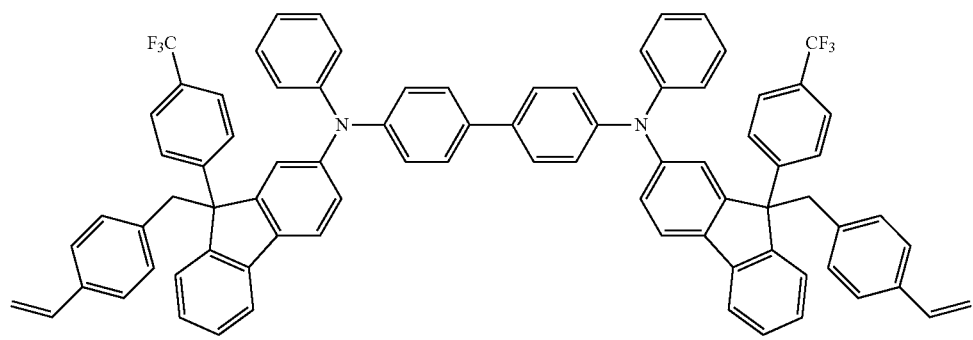
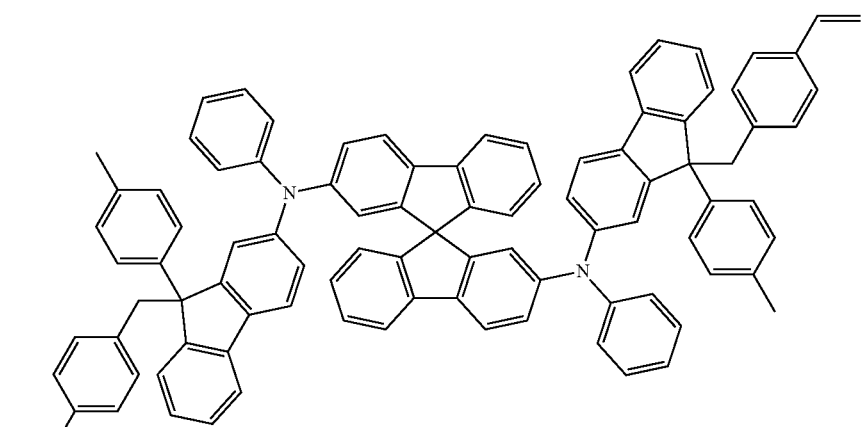
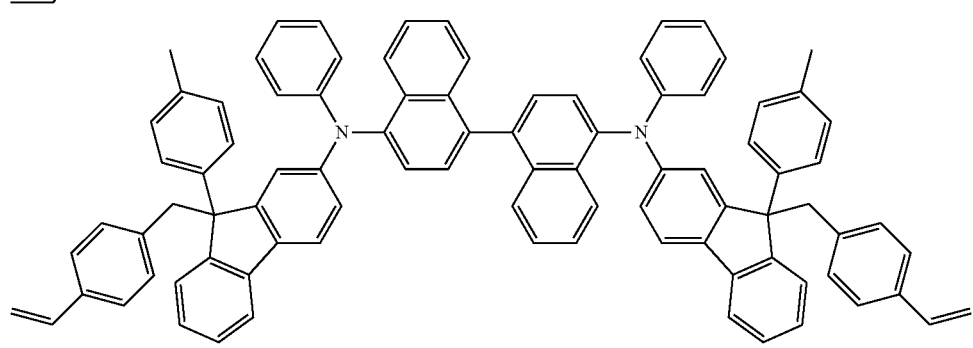

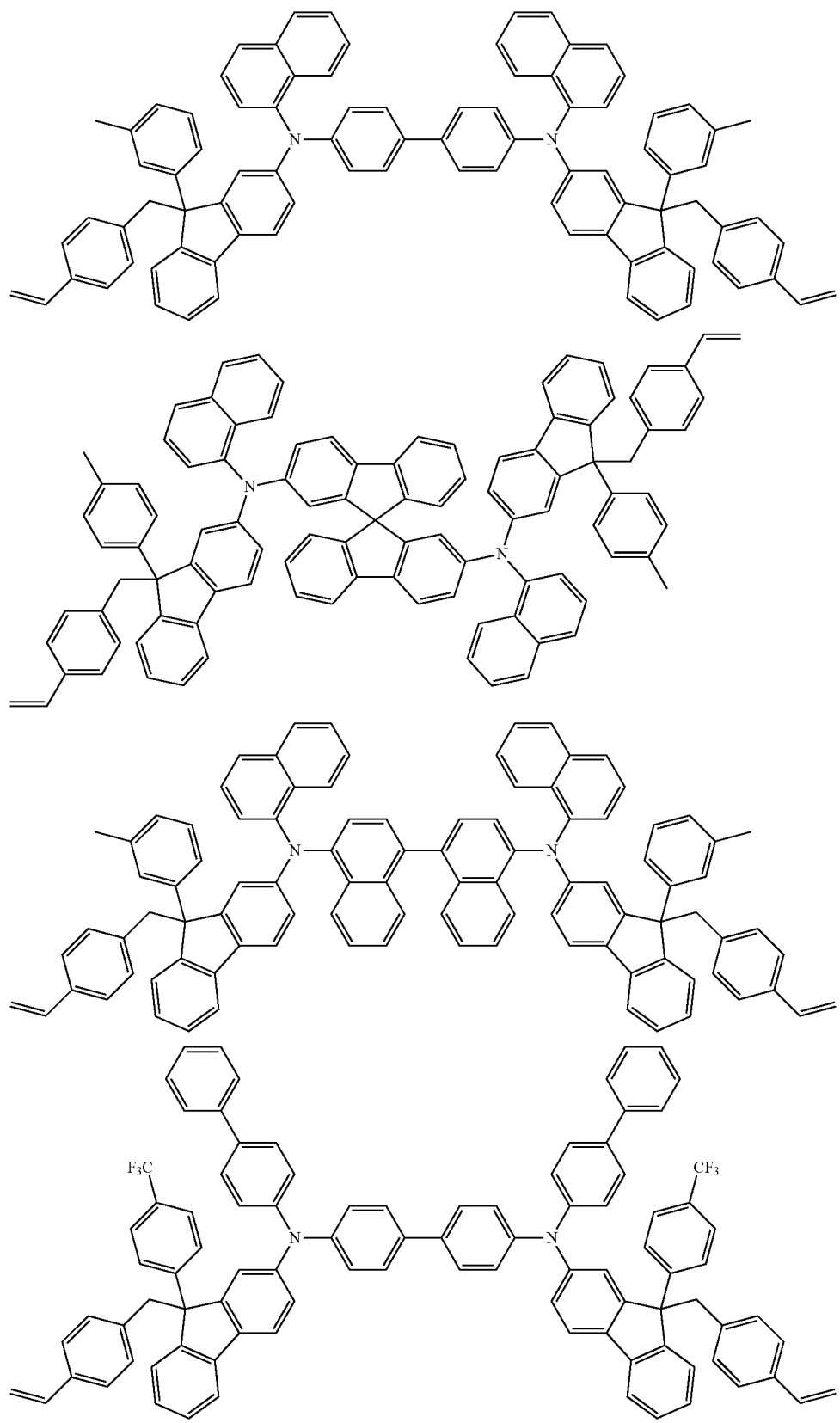

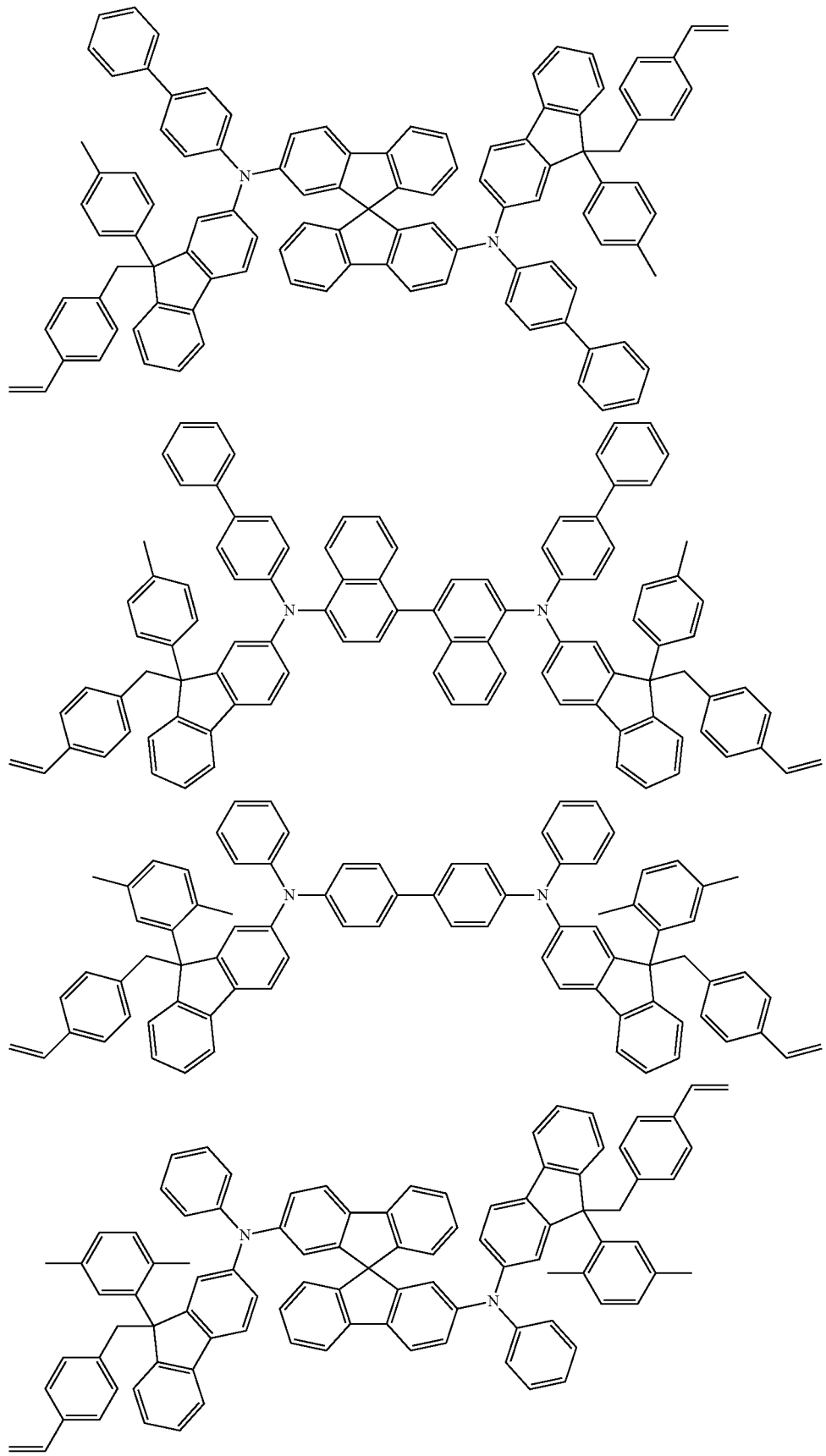

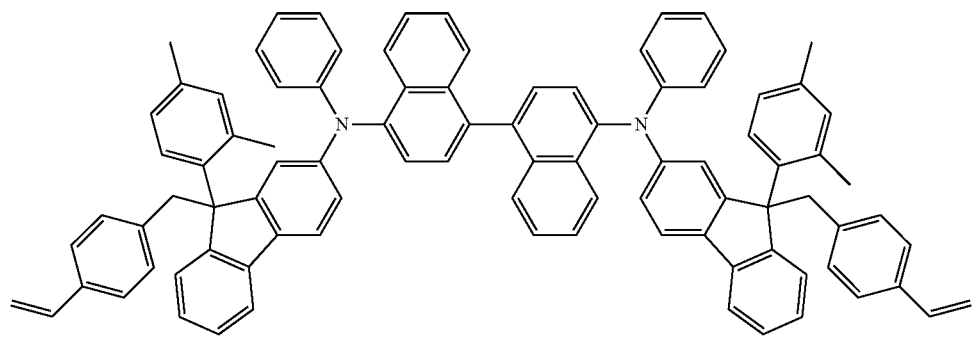
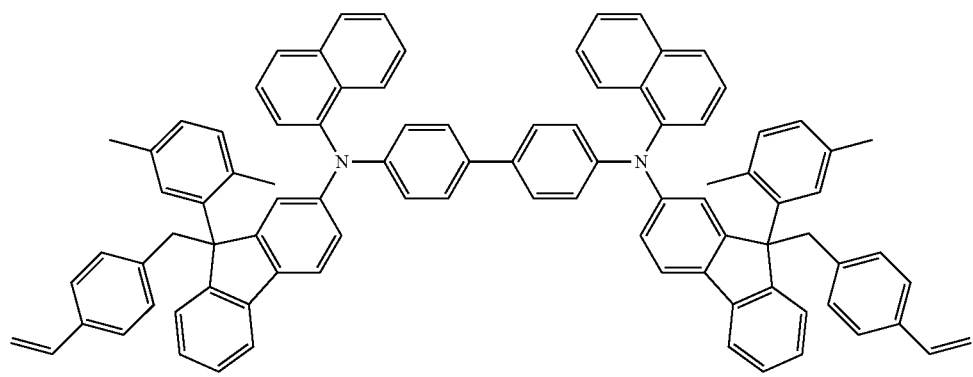
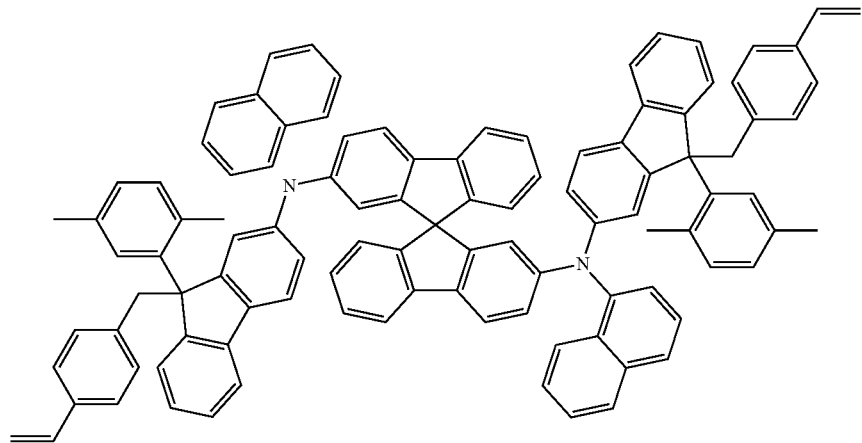
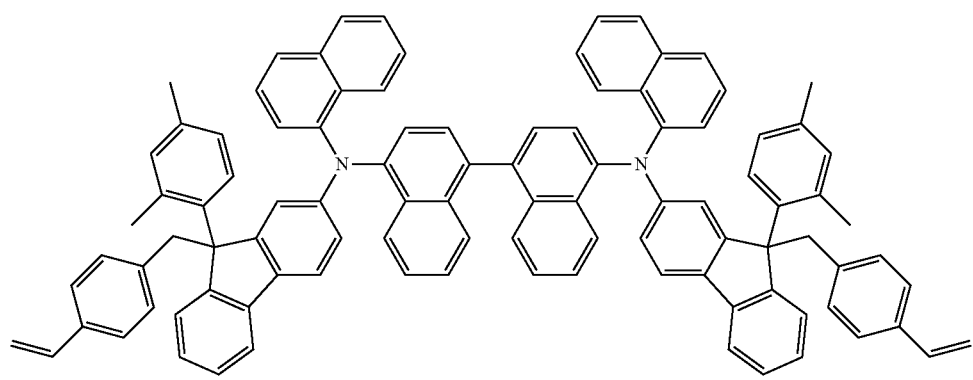

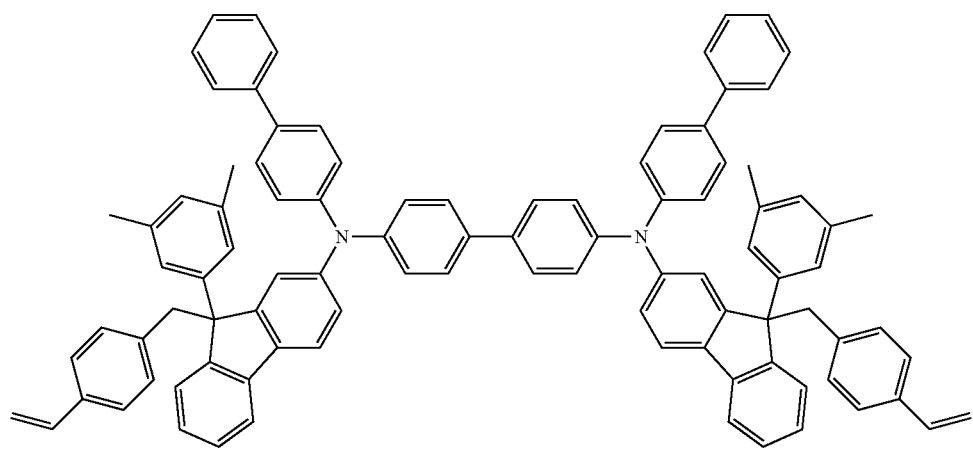
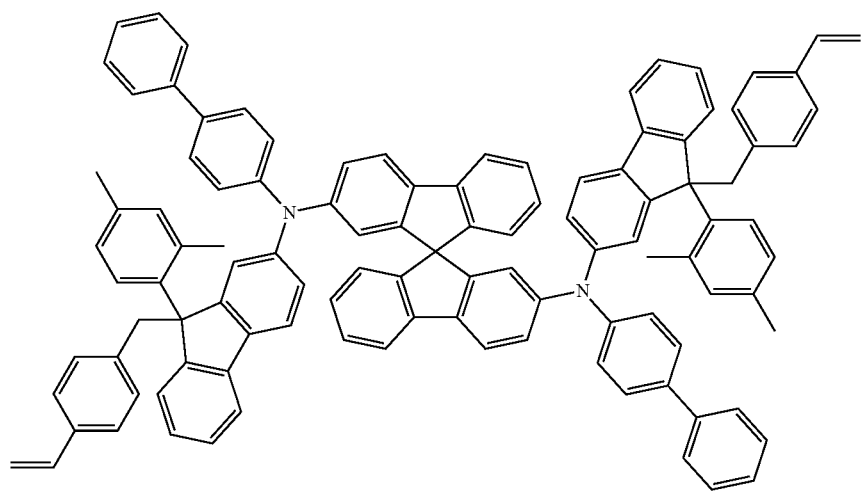
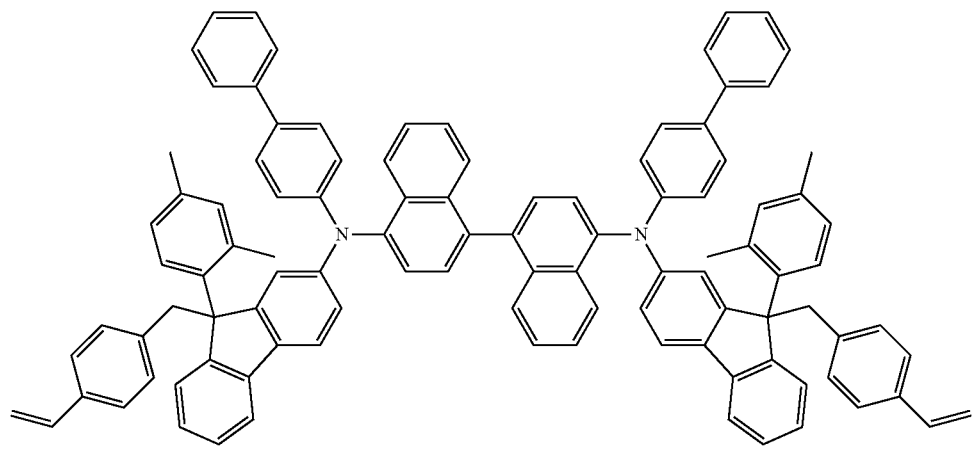

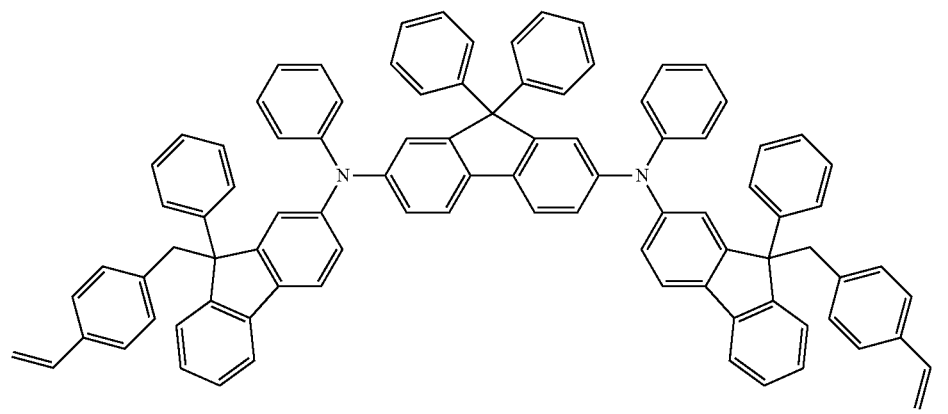
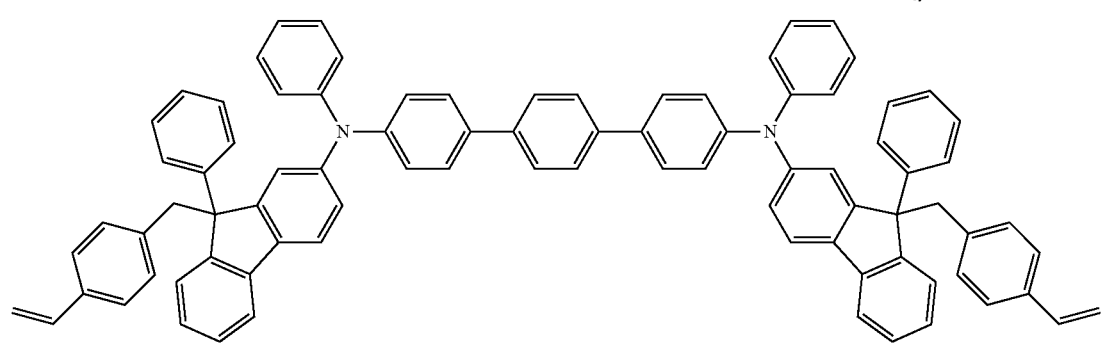
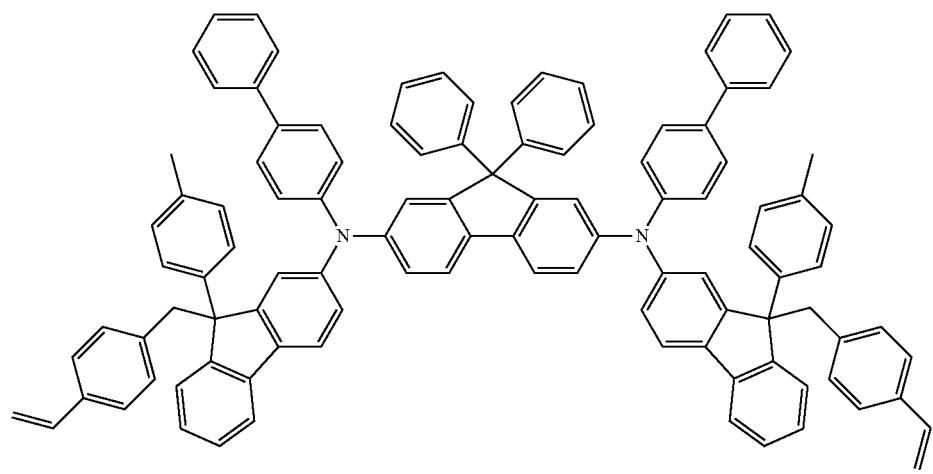
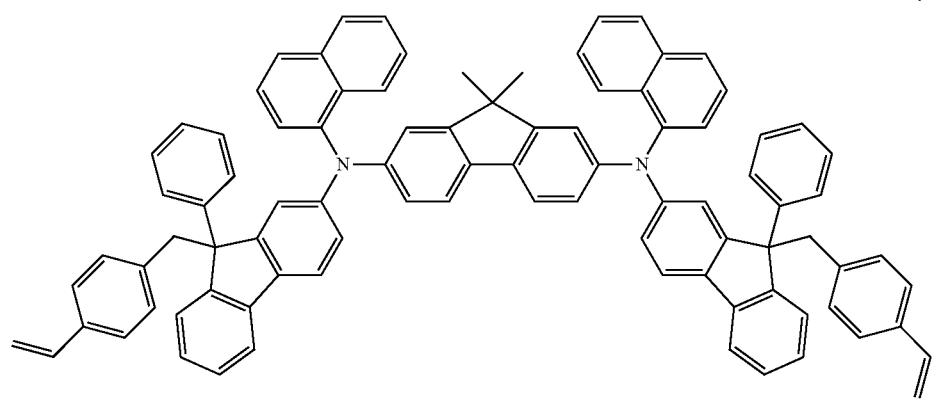

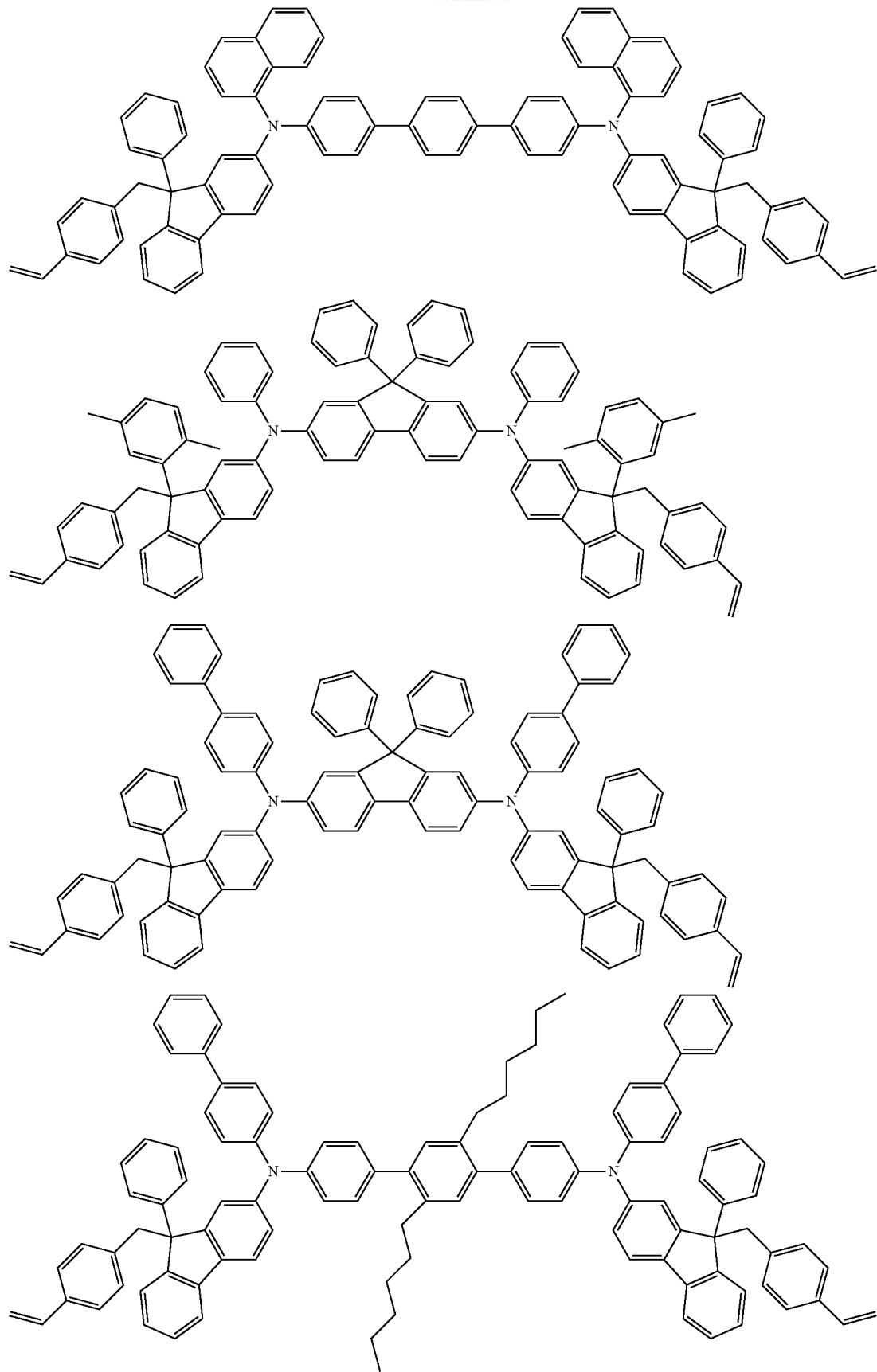

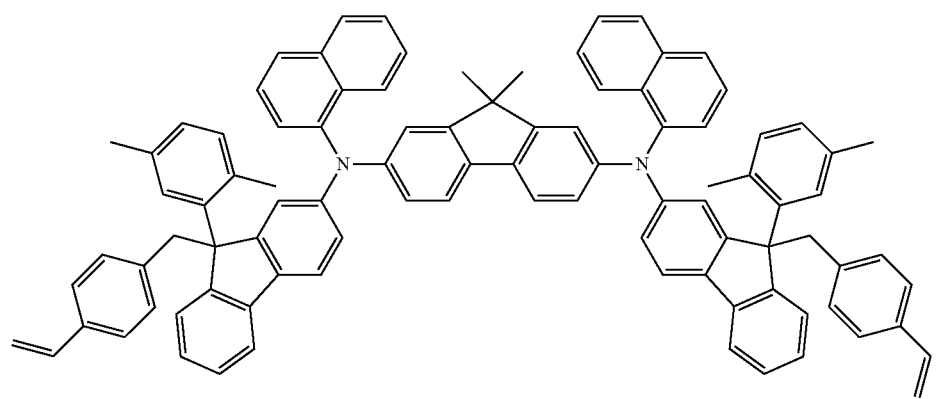
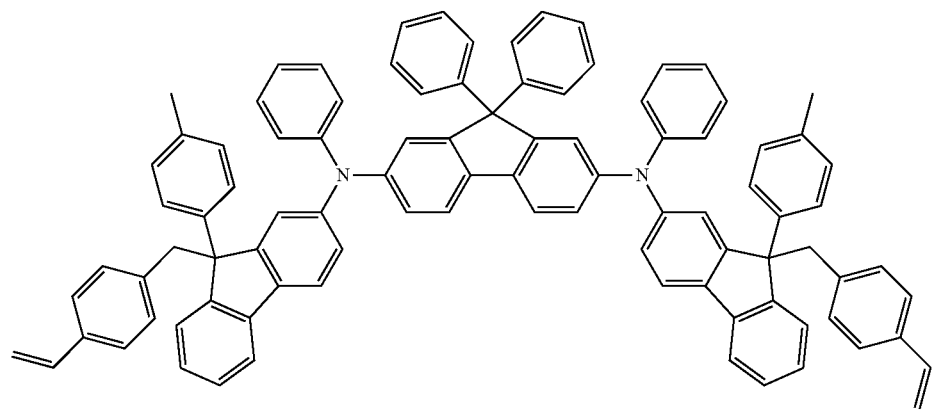
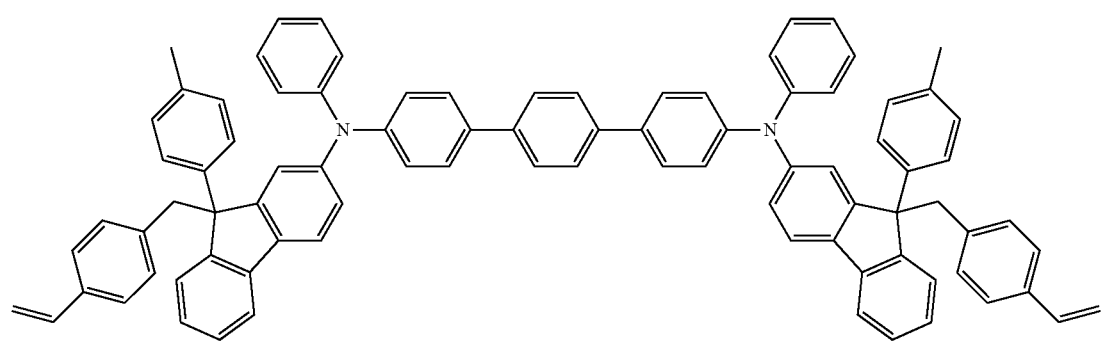
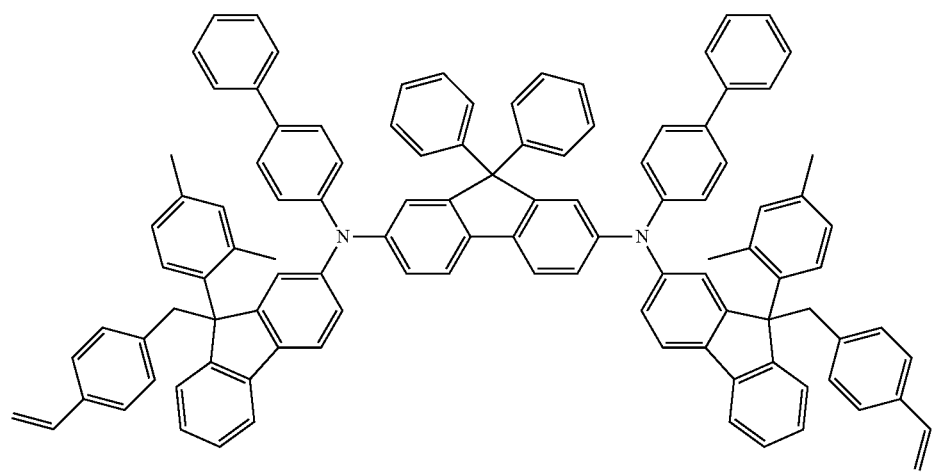

-continued
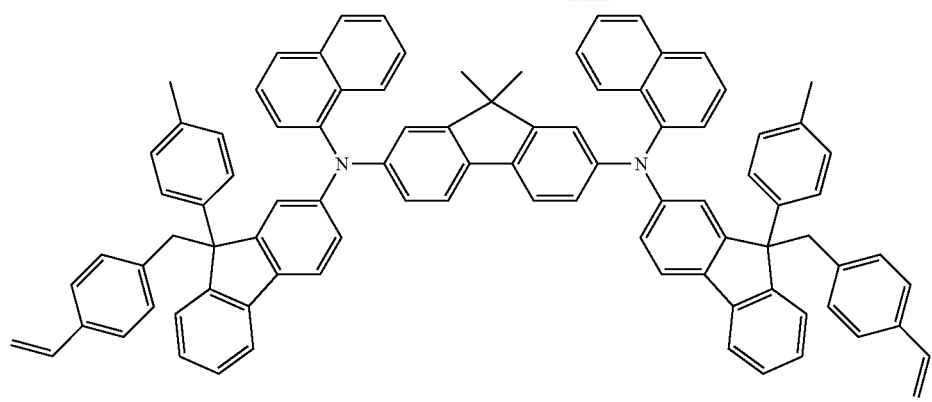
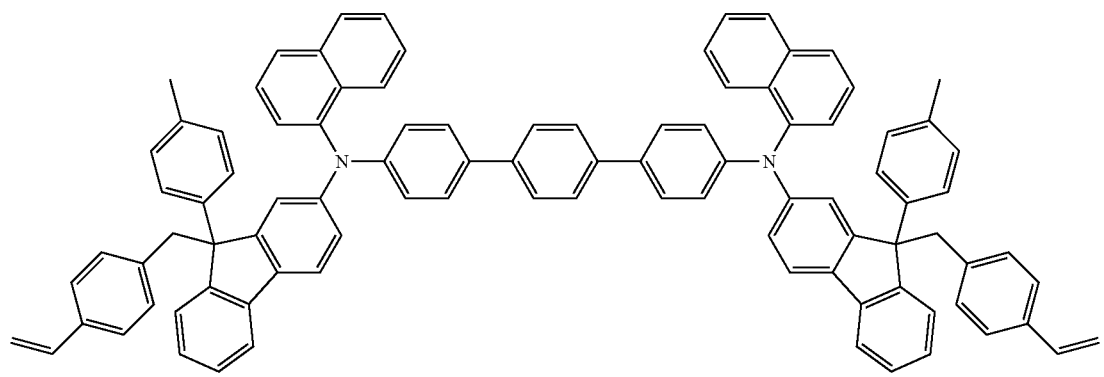
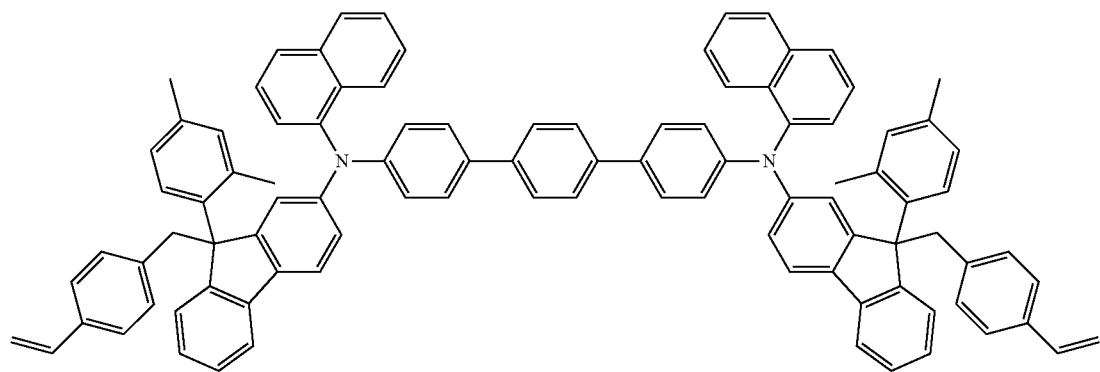
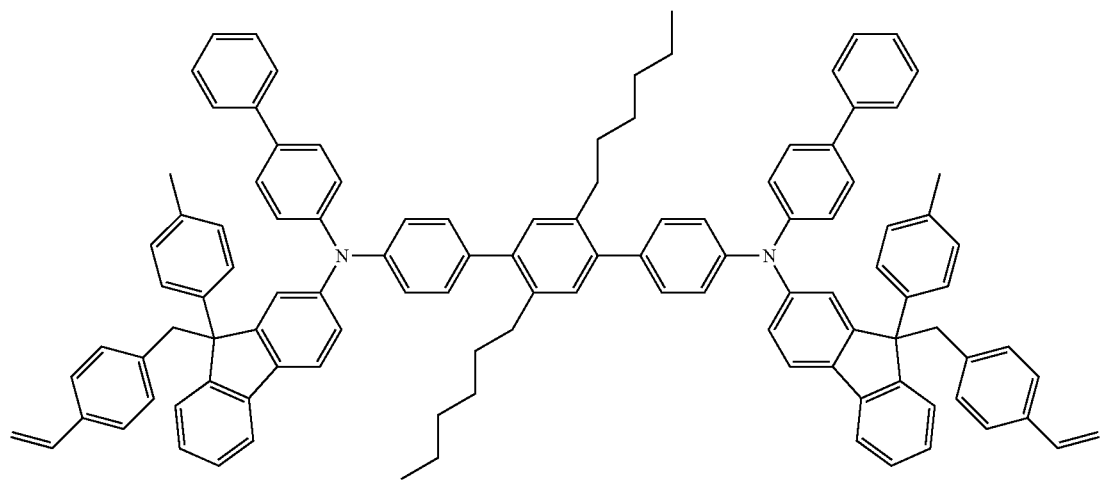

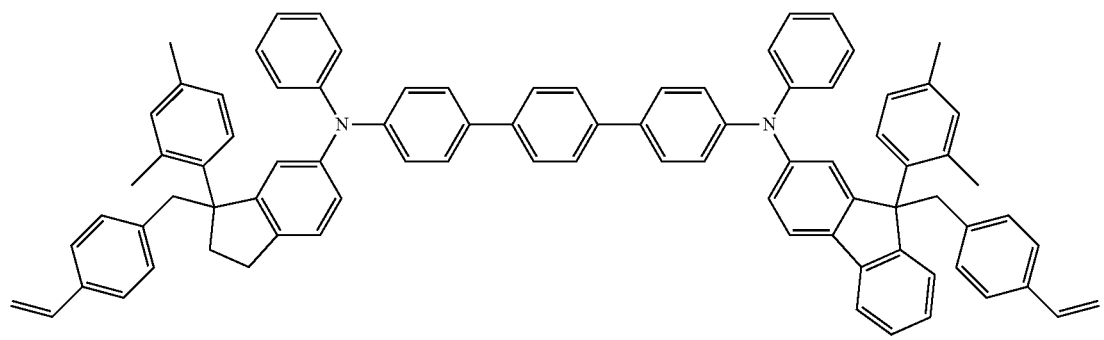
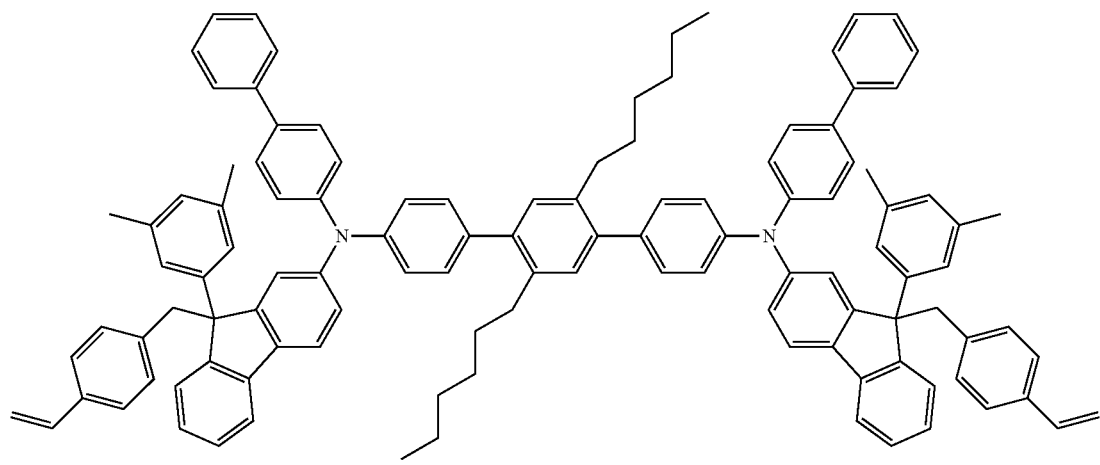
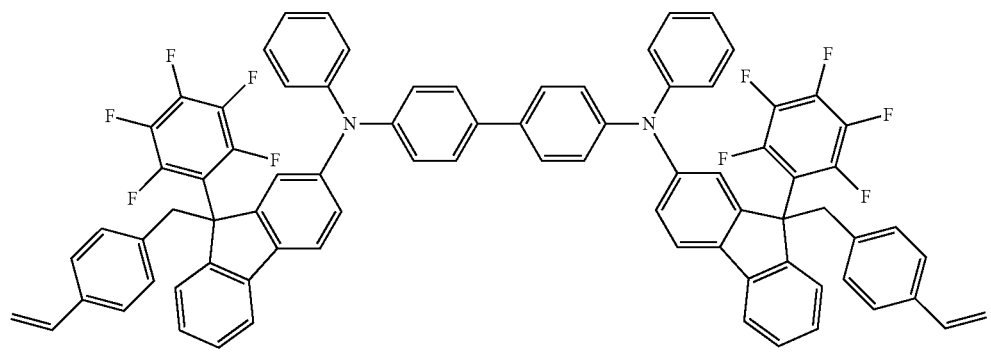
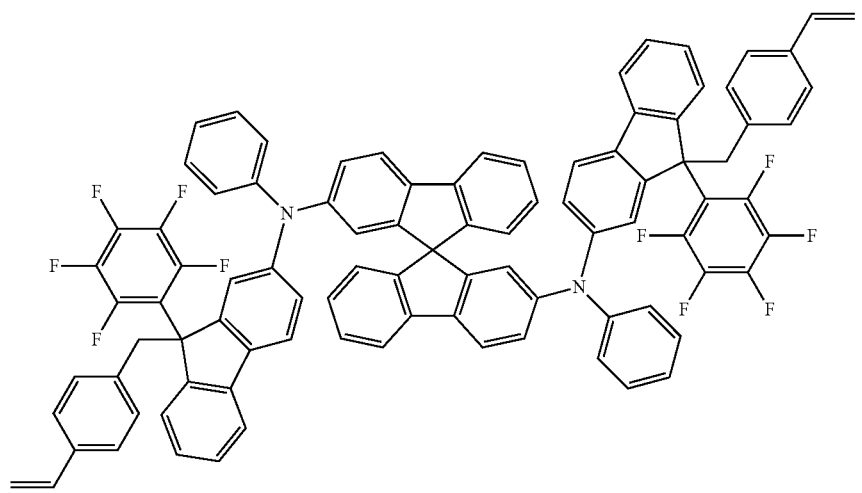

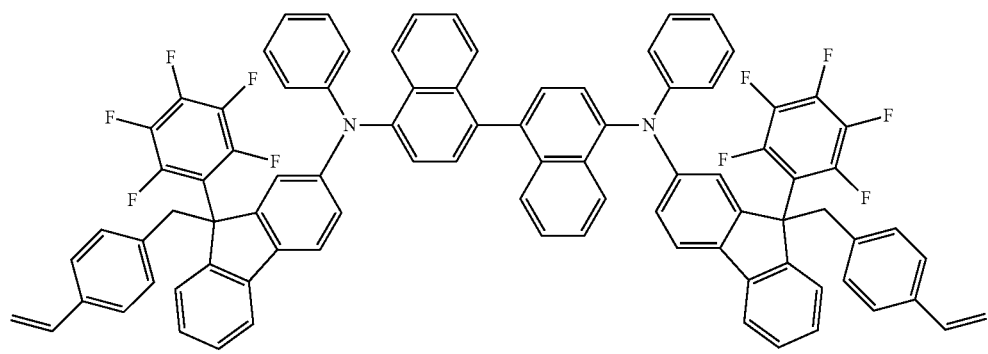
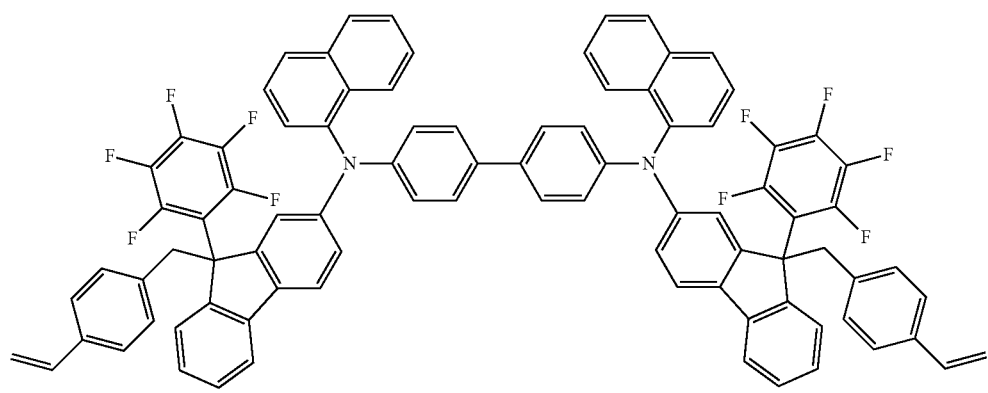
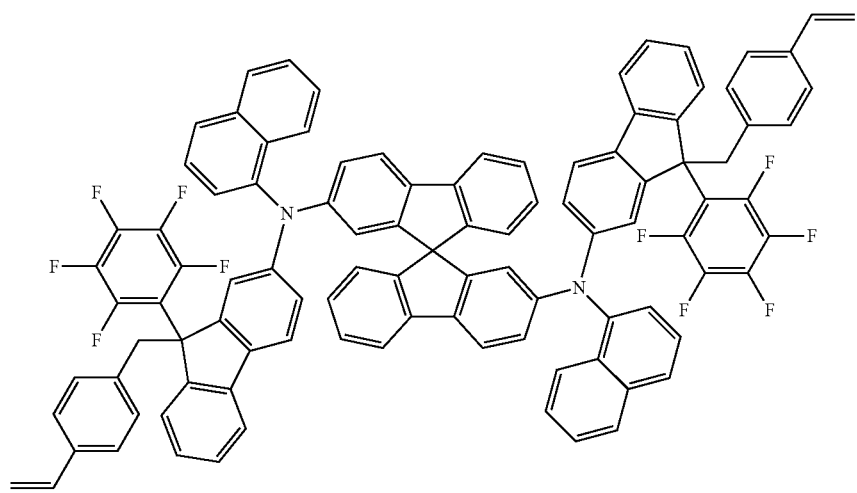
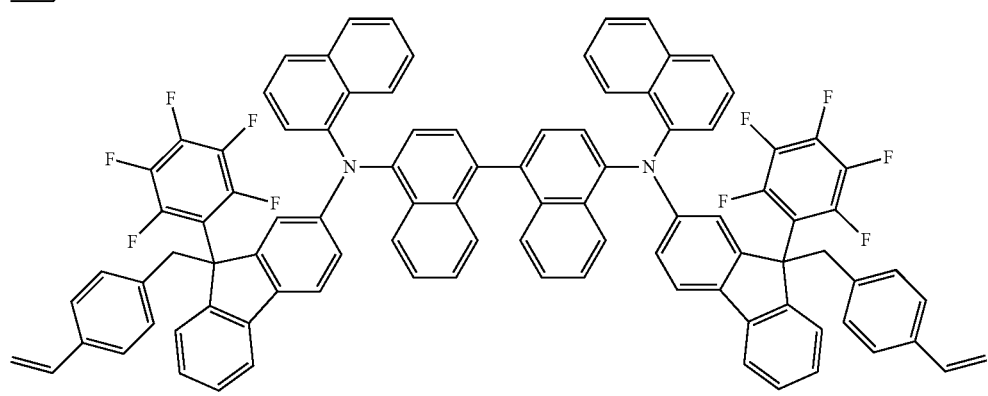

247 248
-continued
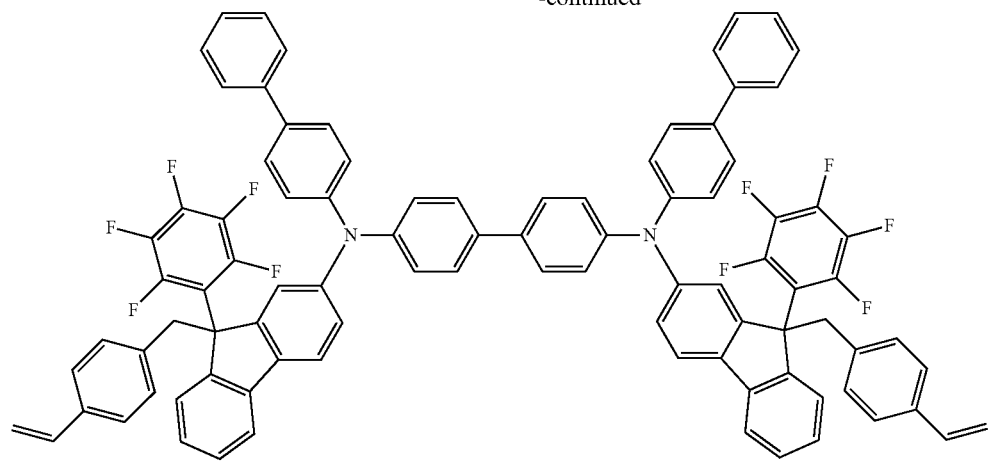
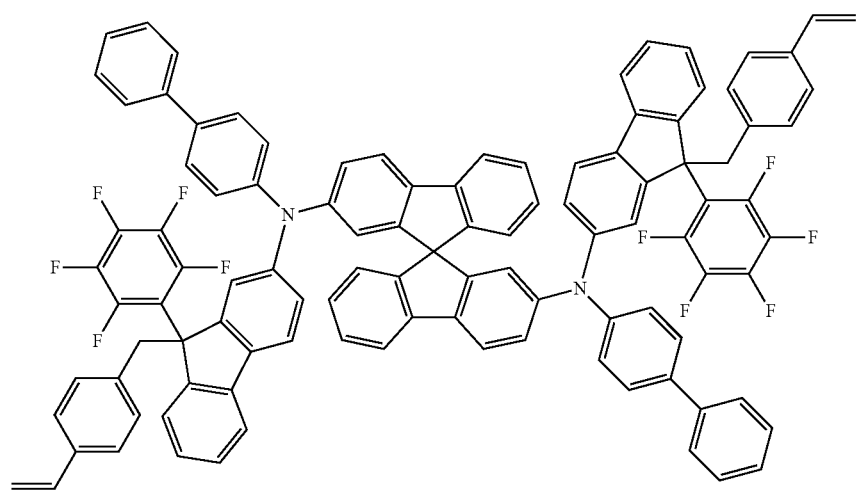
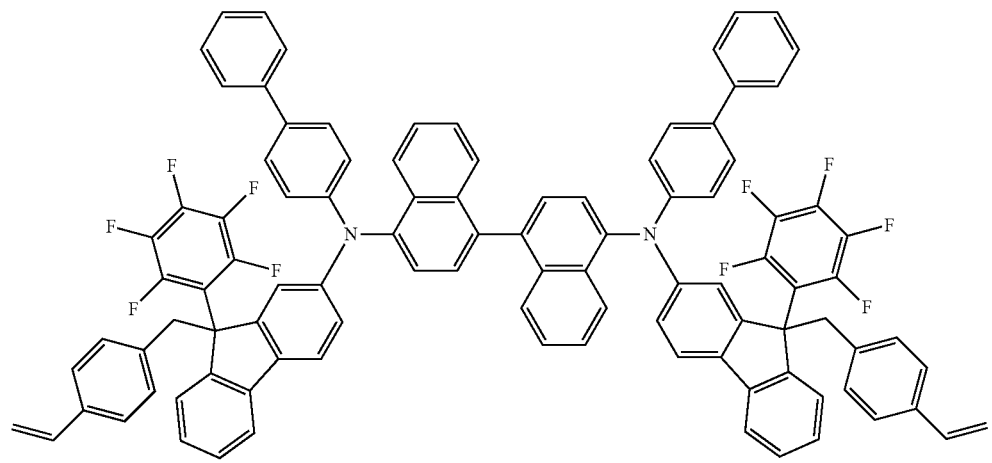

-continued
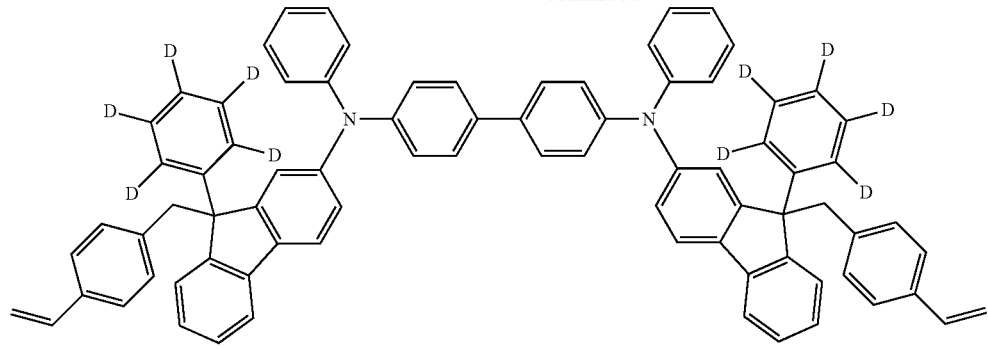
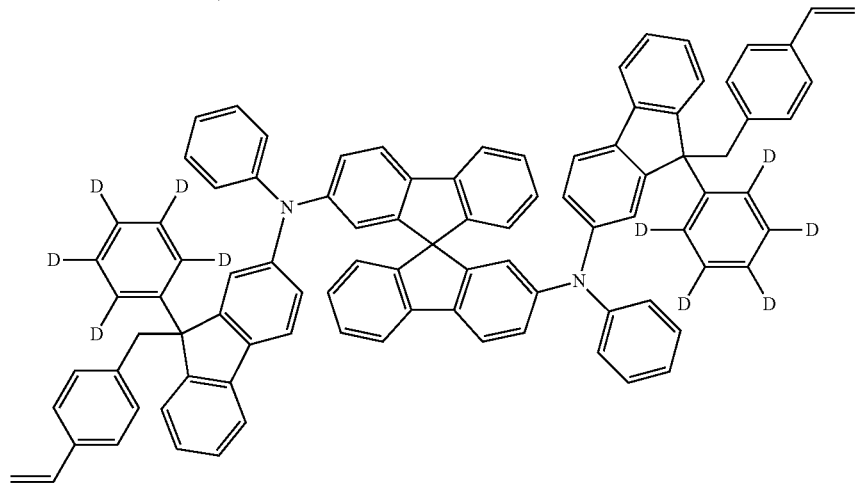
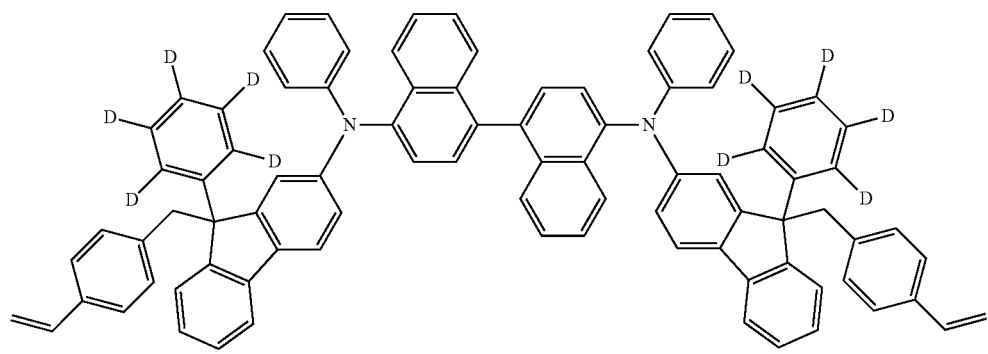
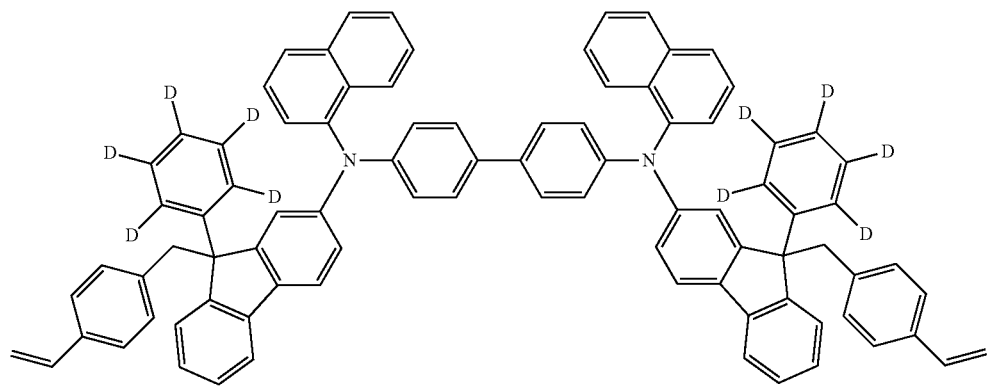

-continued
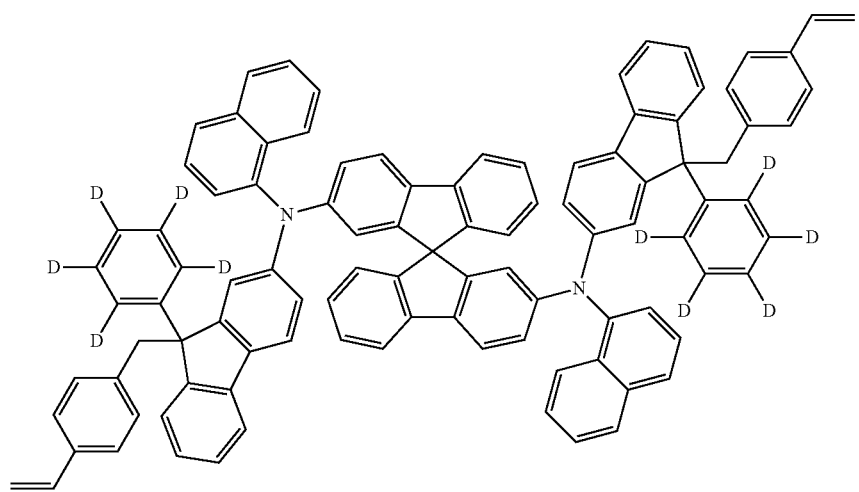

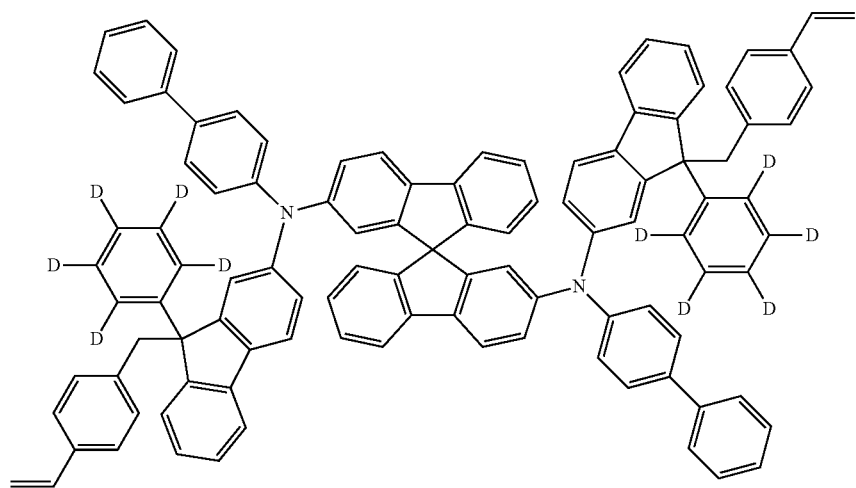
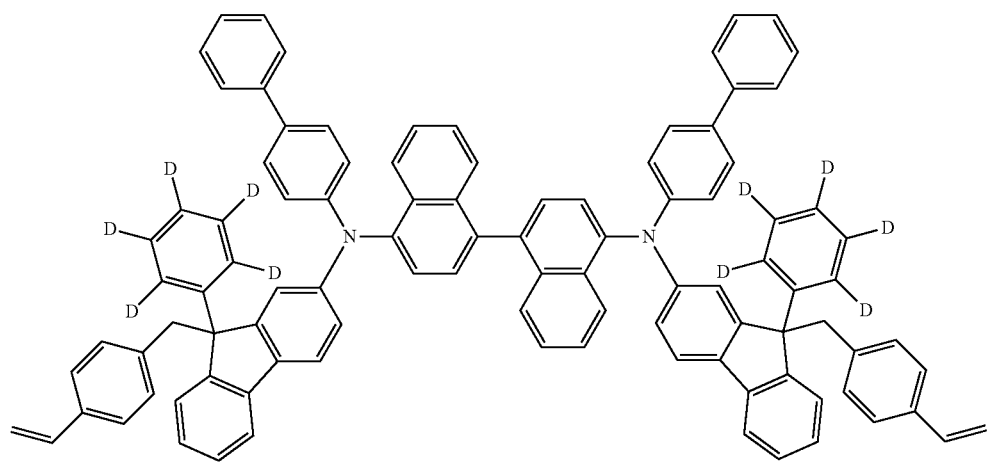
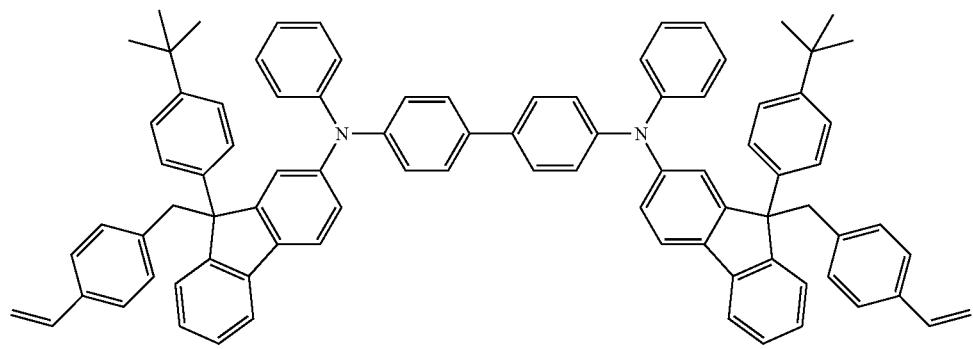

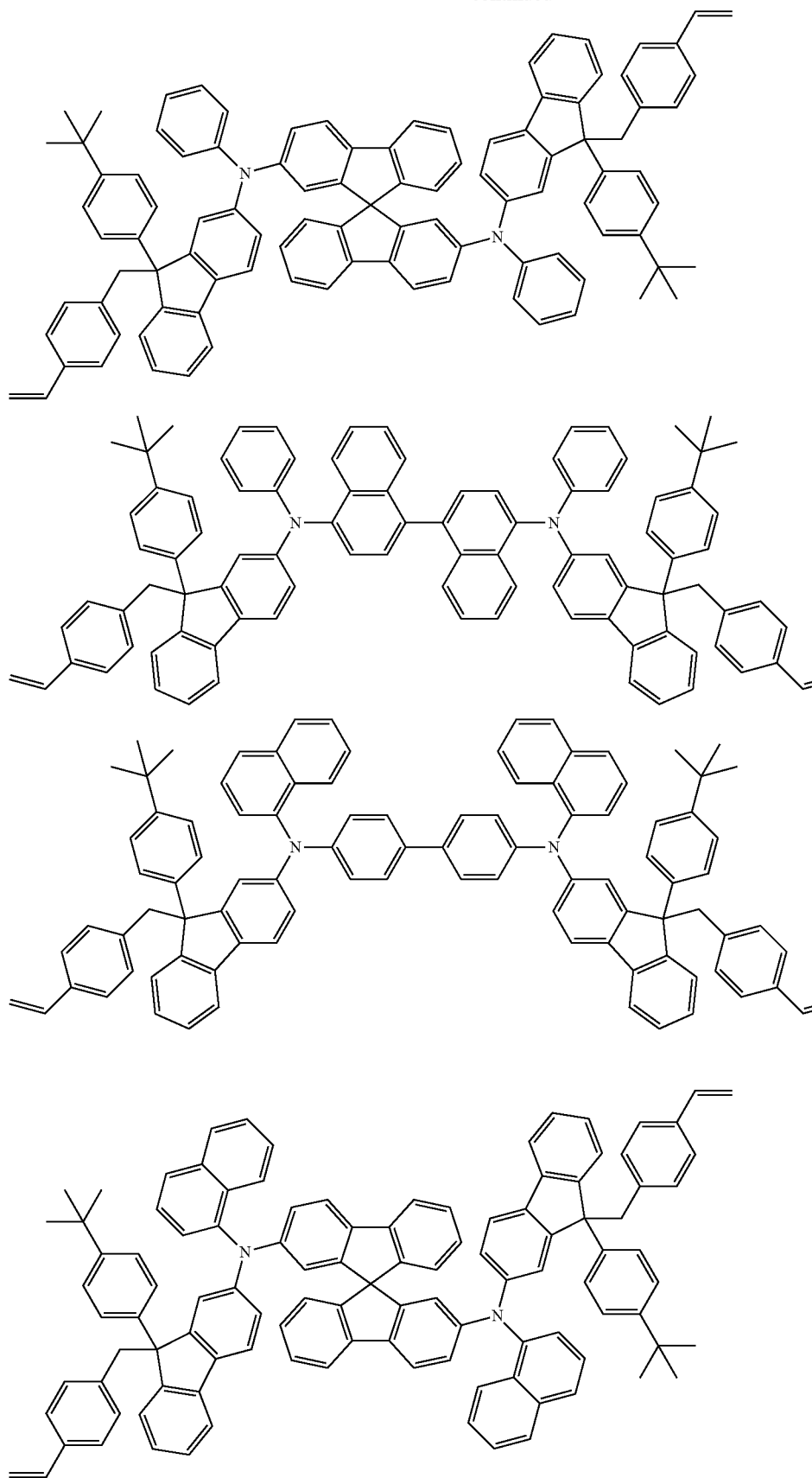

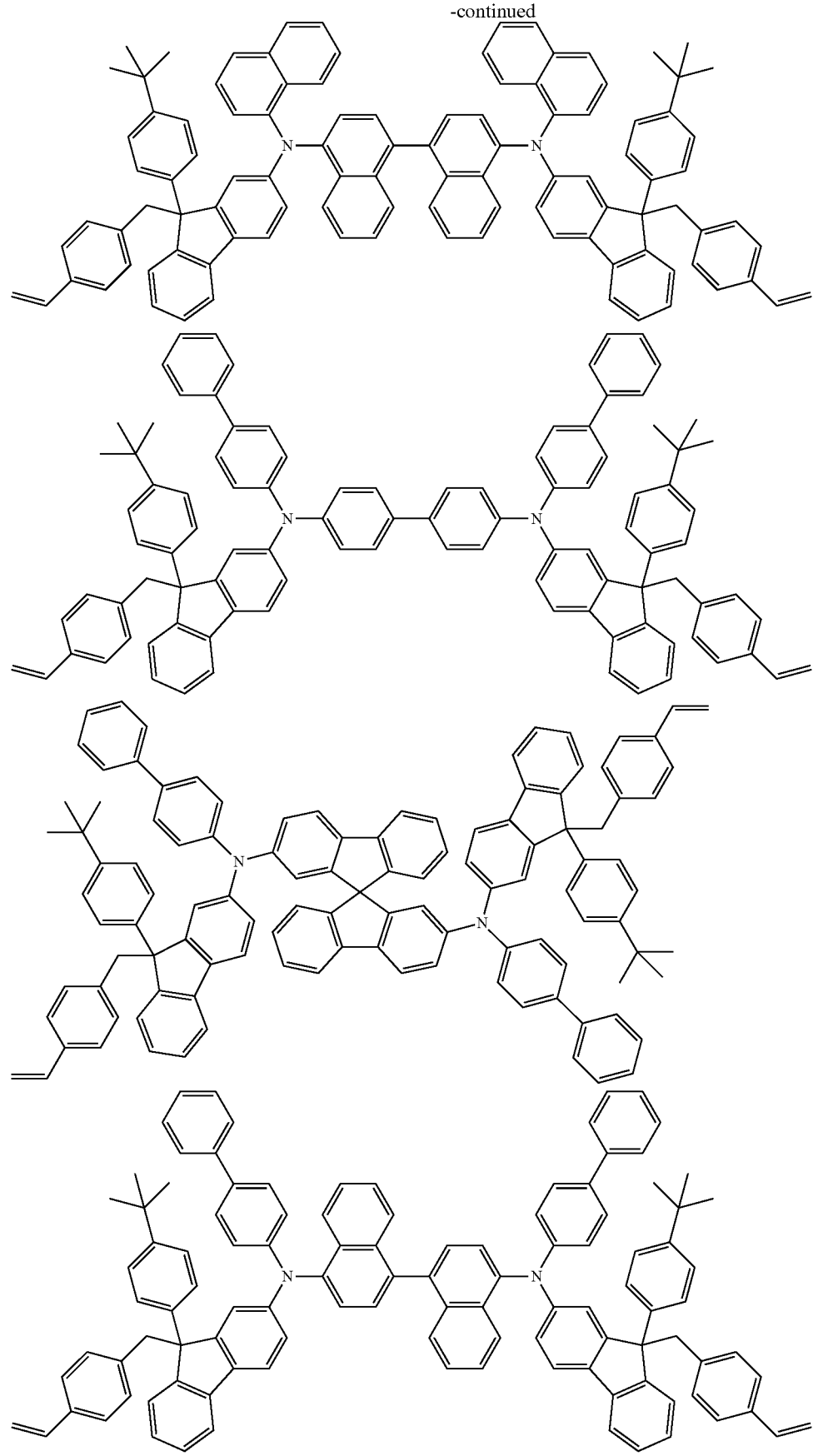

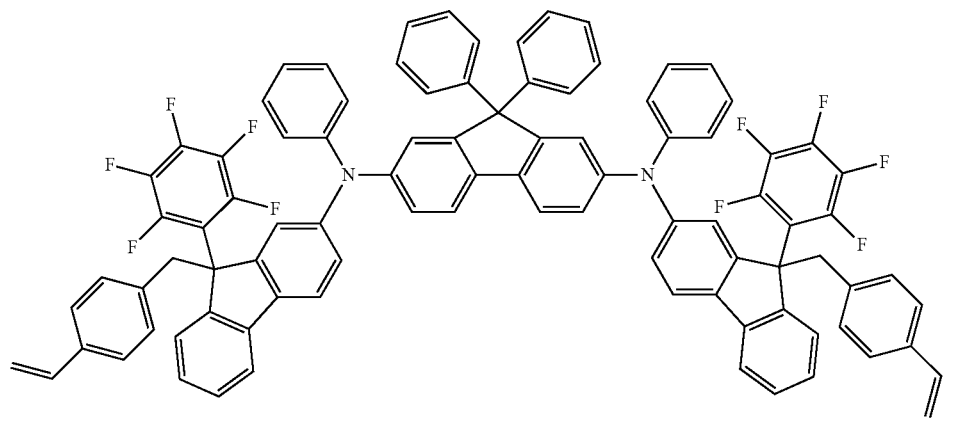
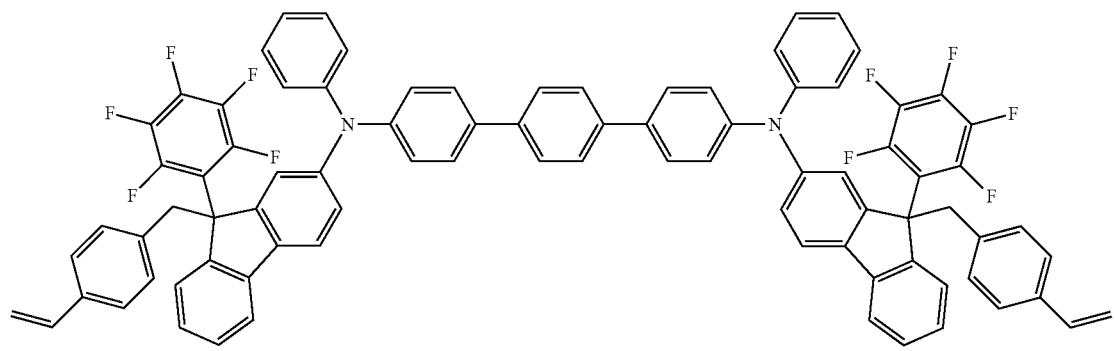
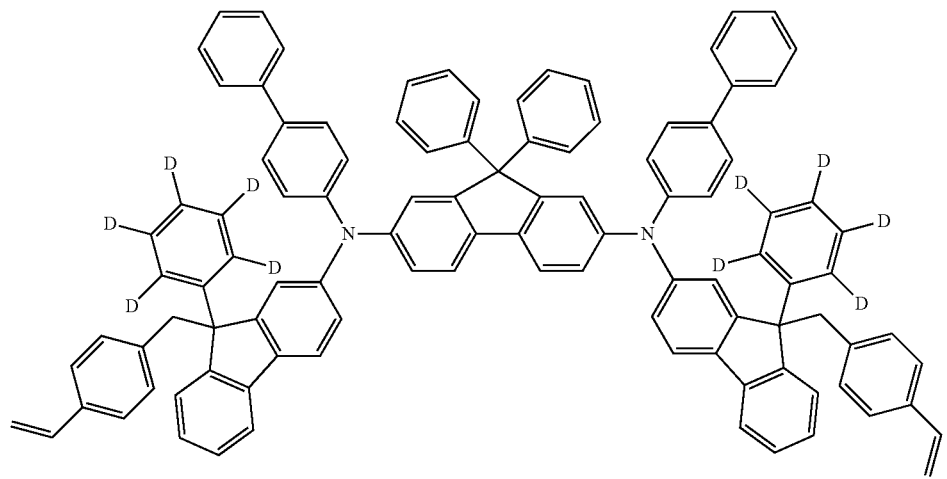
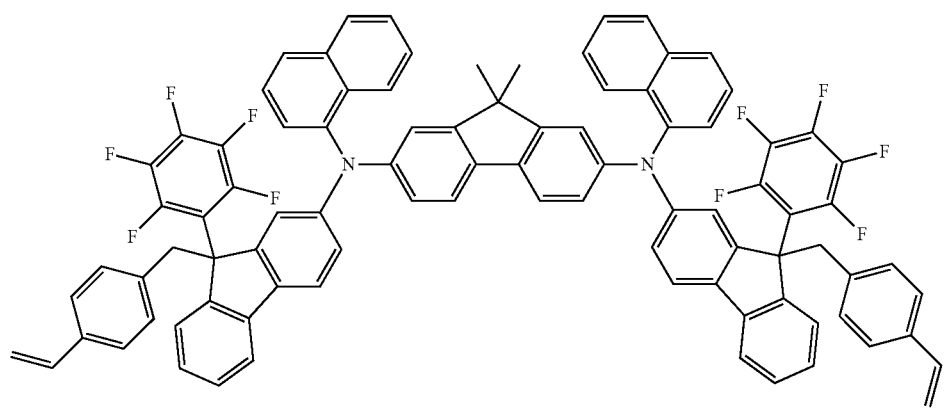

261 262
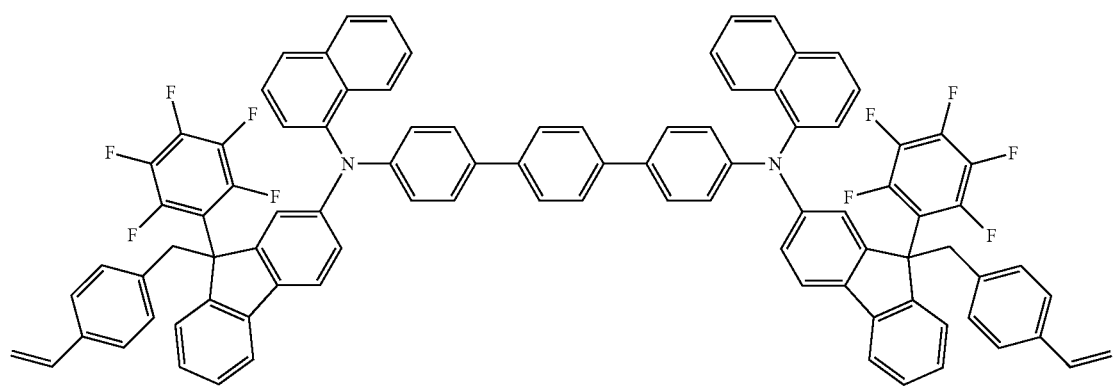
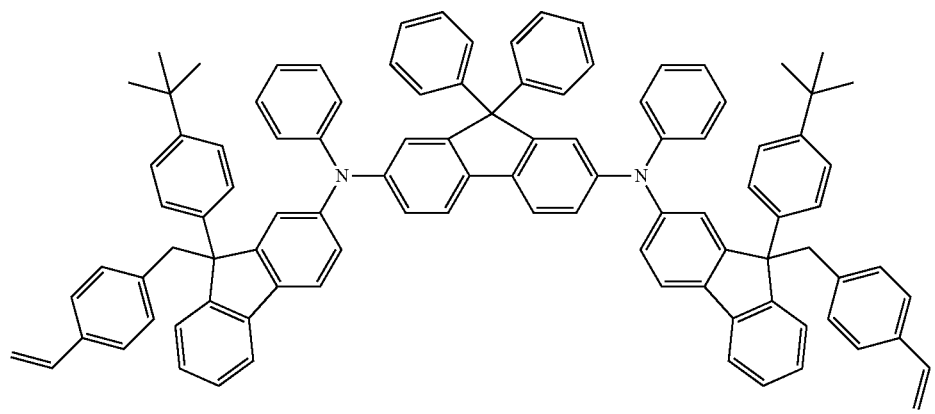
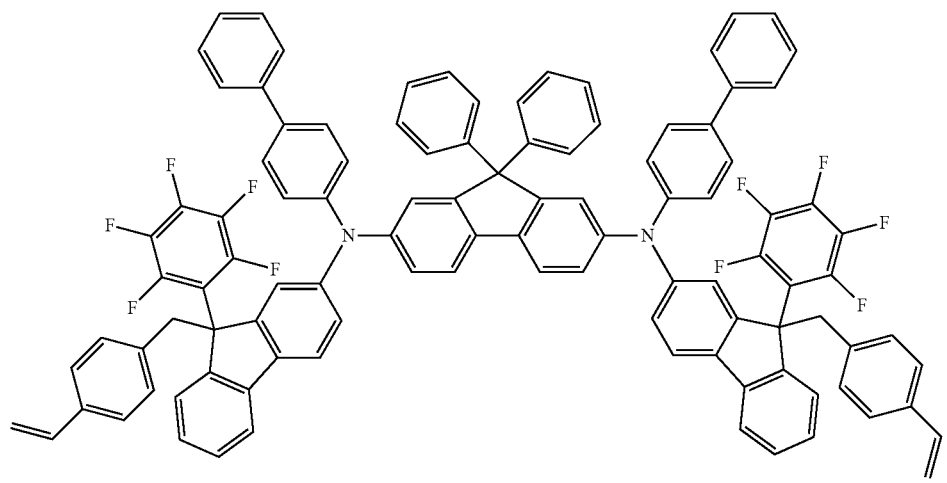

263 264
-continued
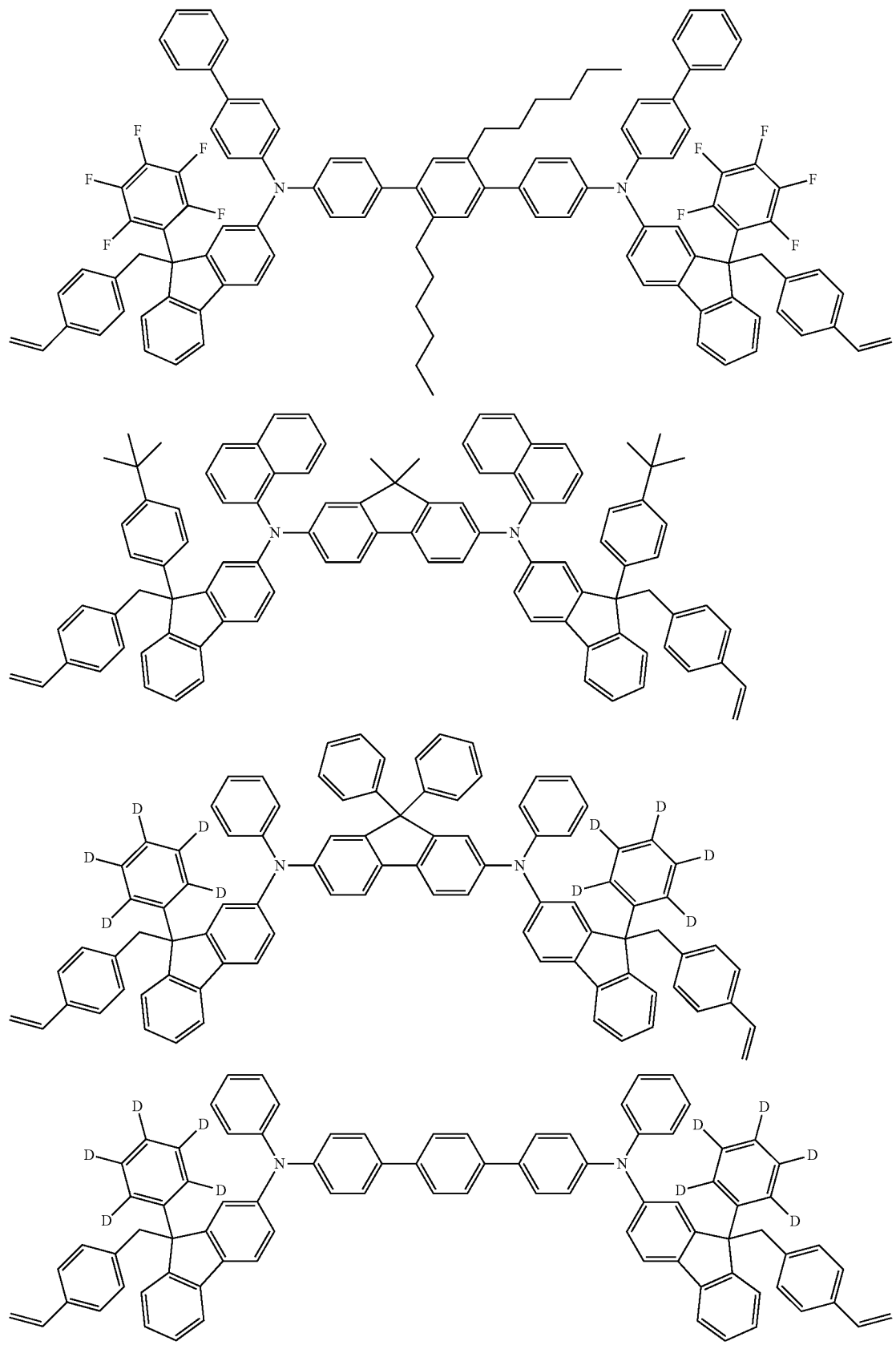

-continued
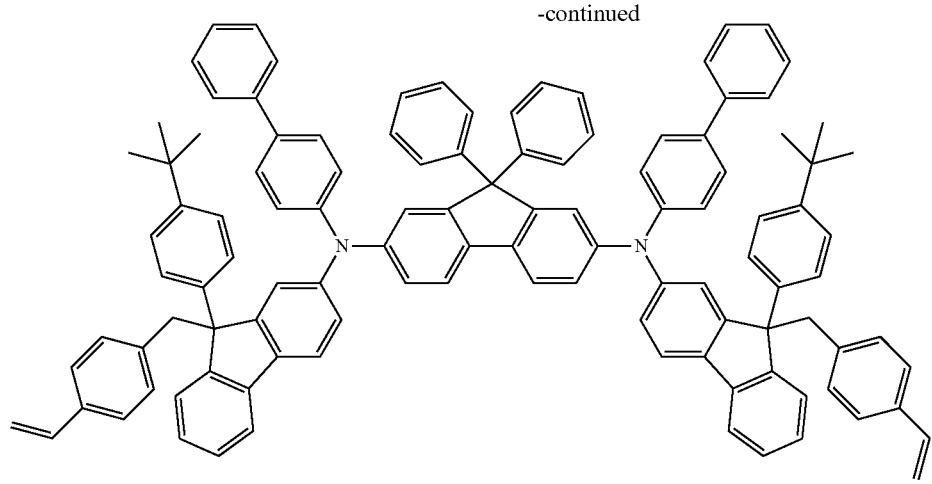
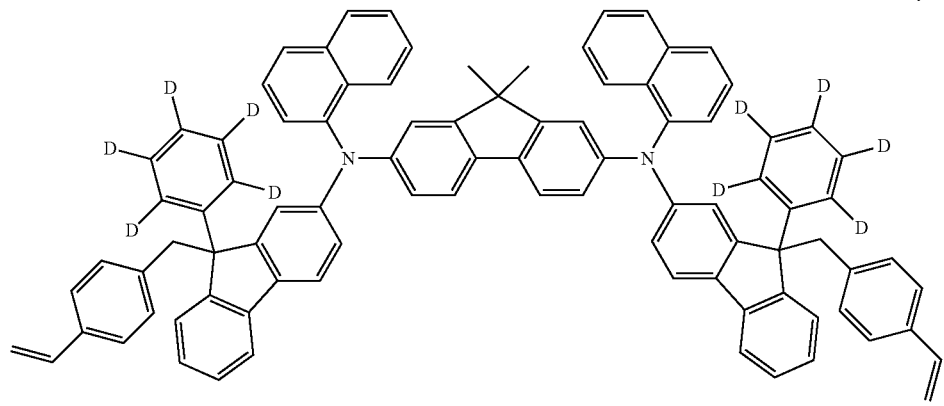
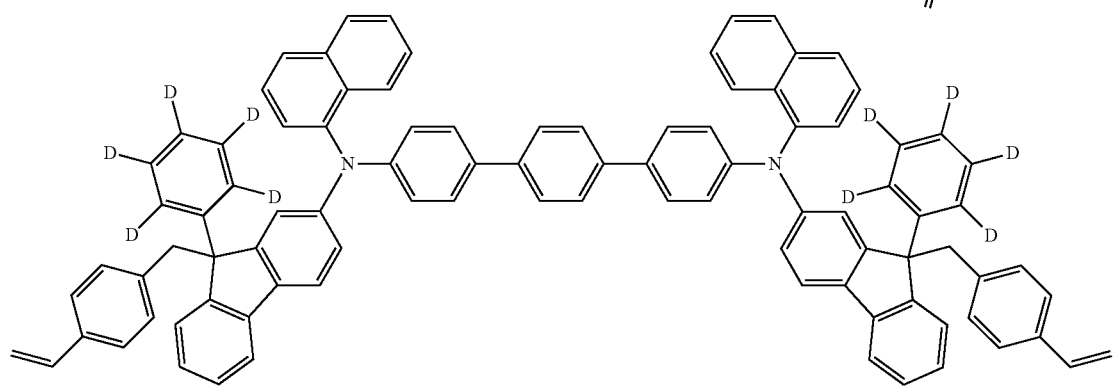
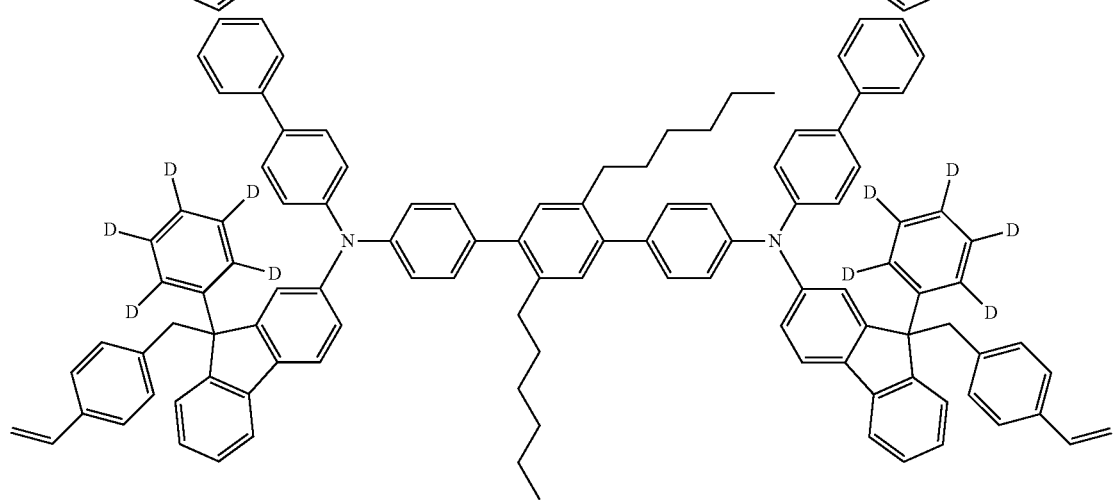

267
268
-continued
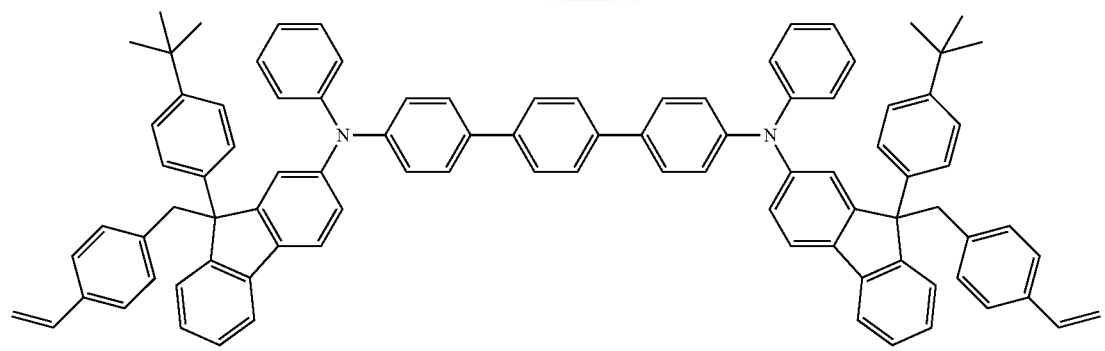
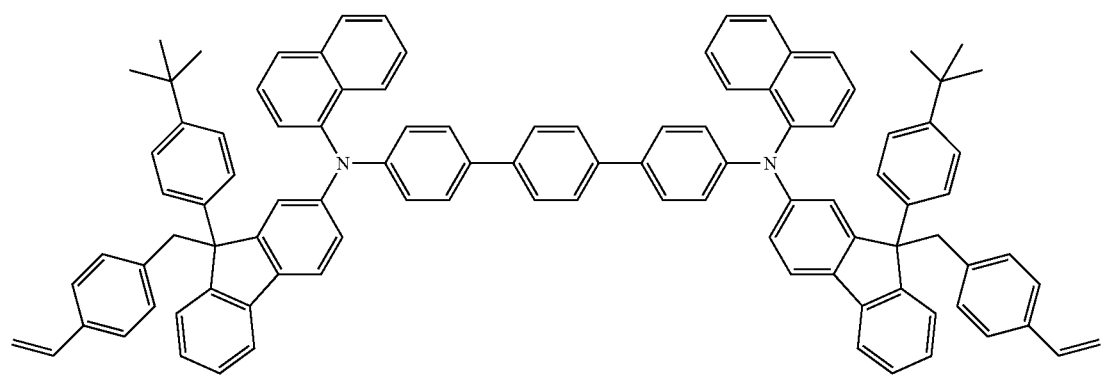
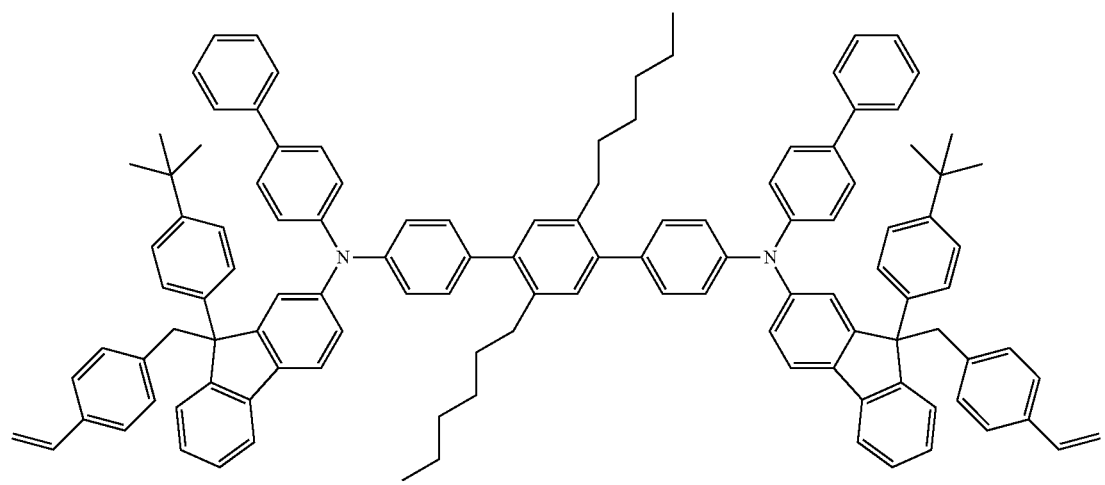
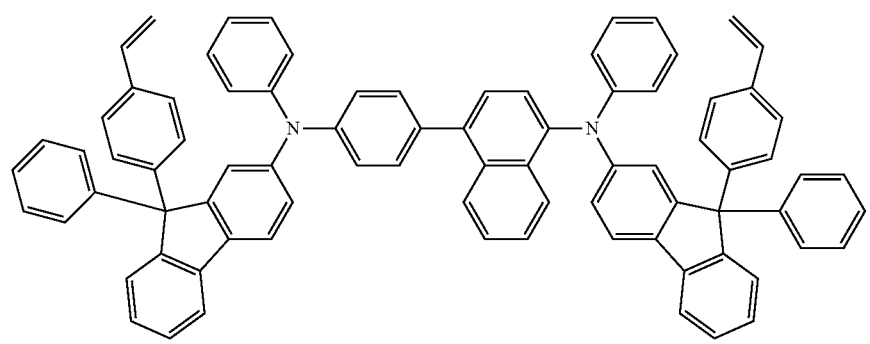

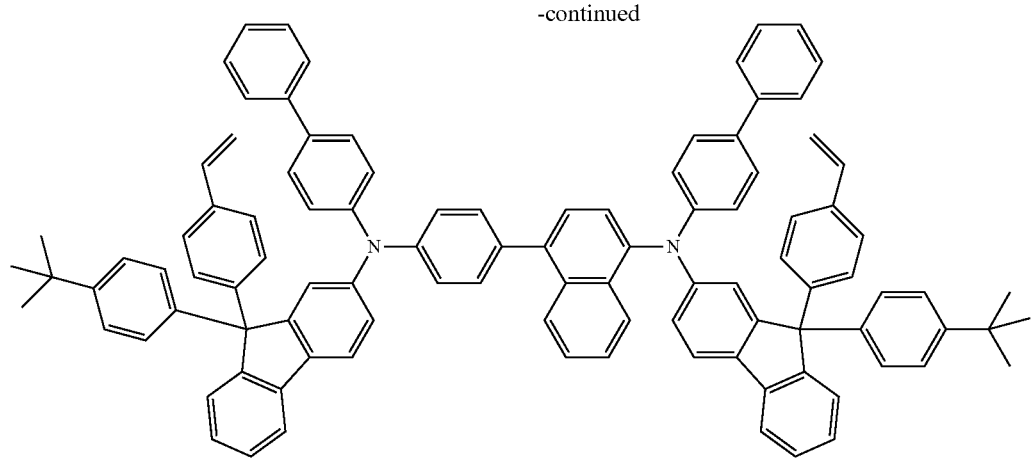
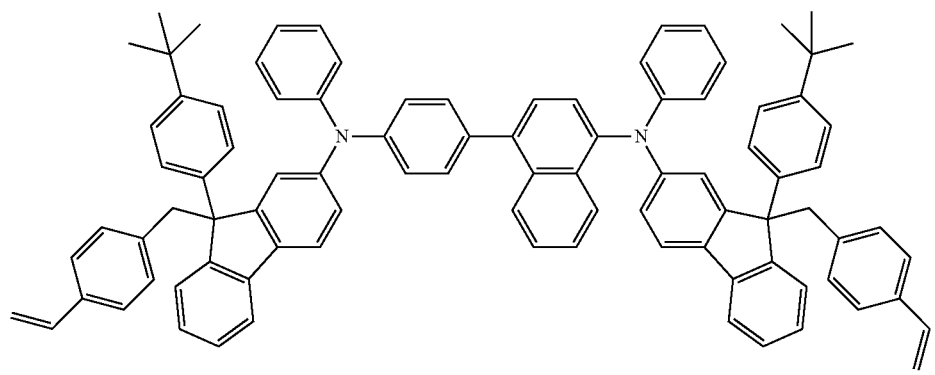
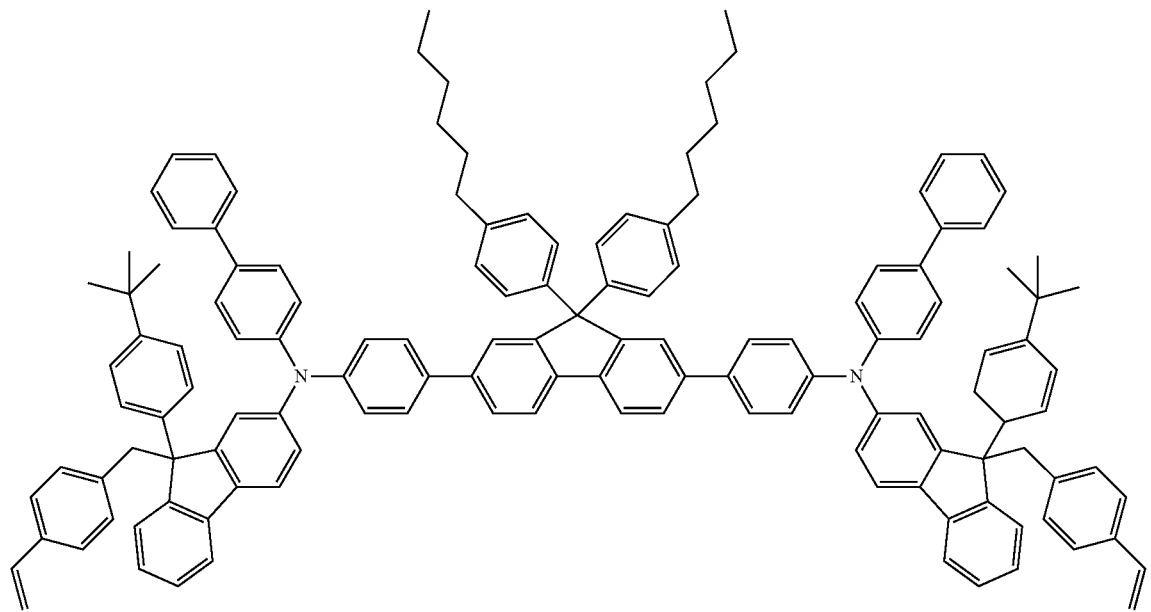

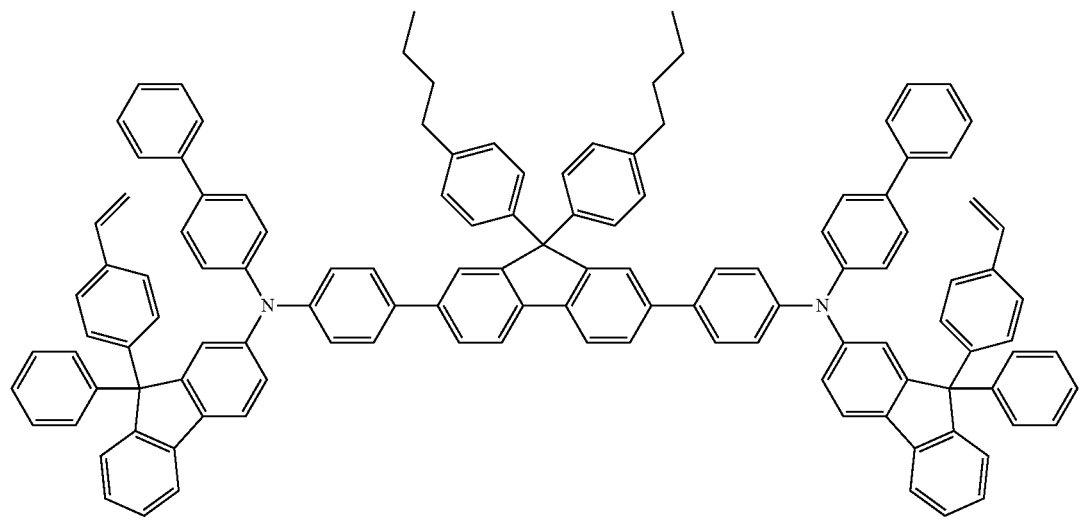
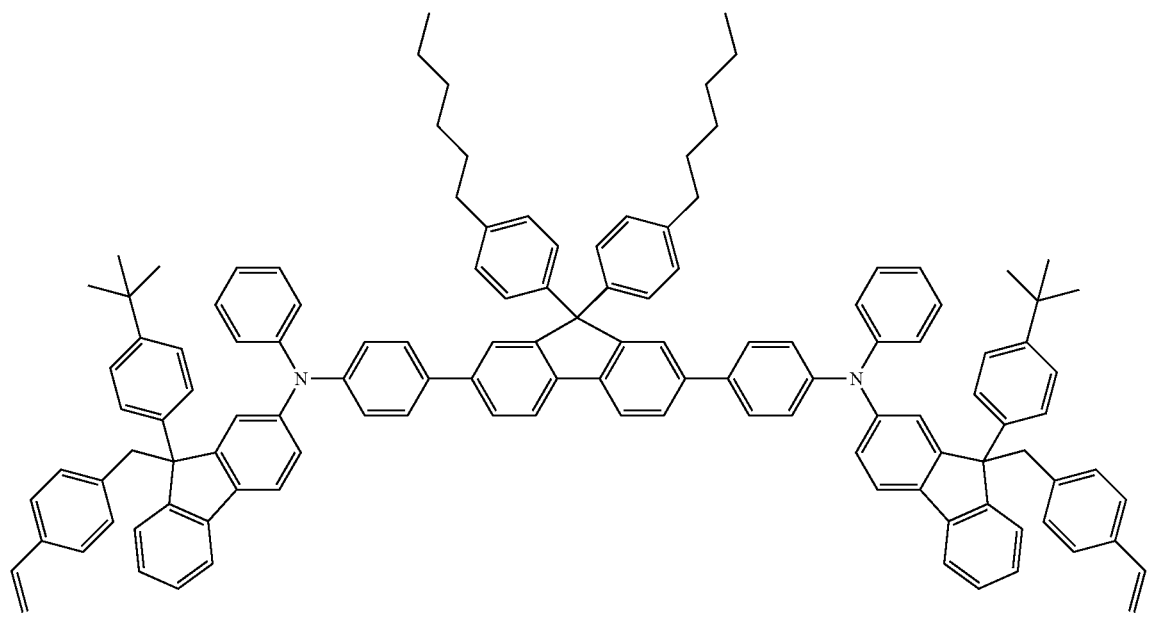
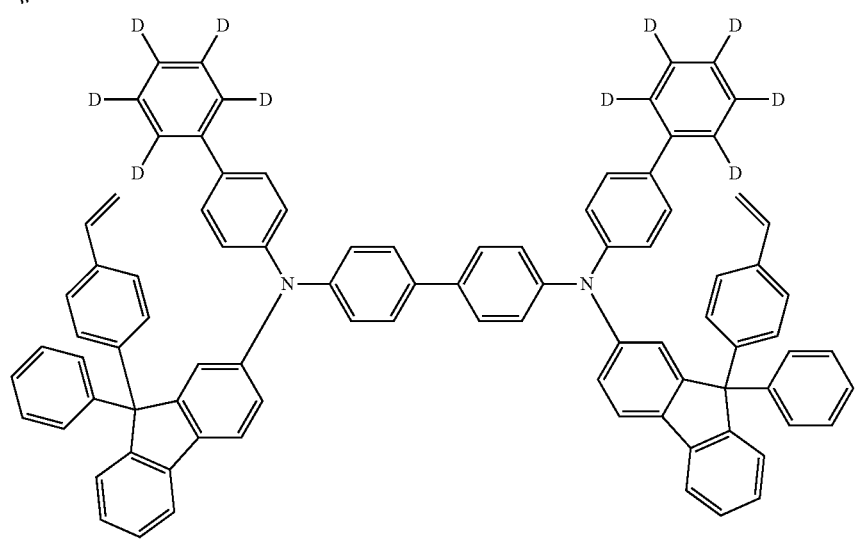

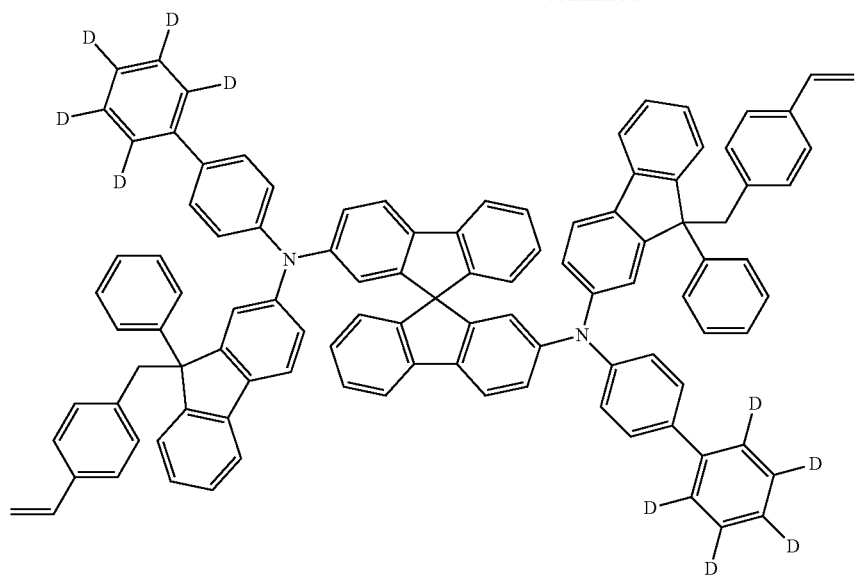
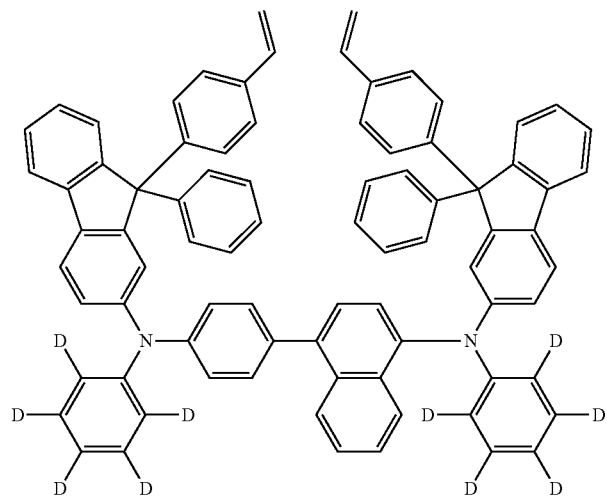
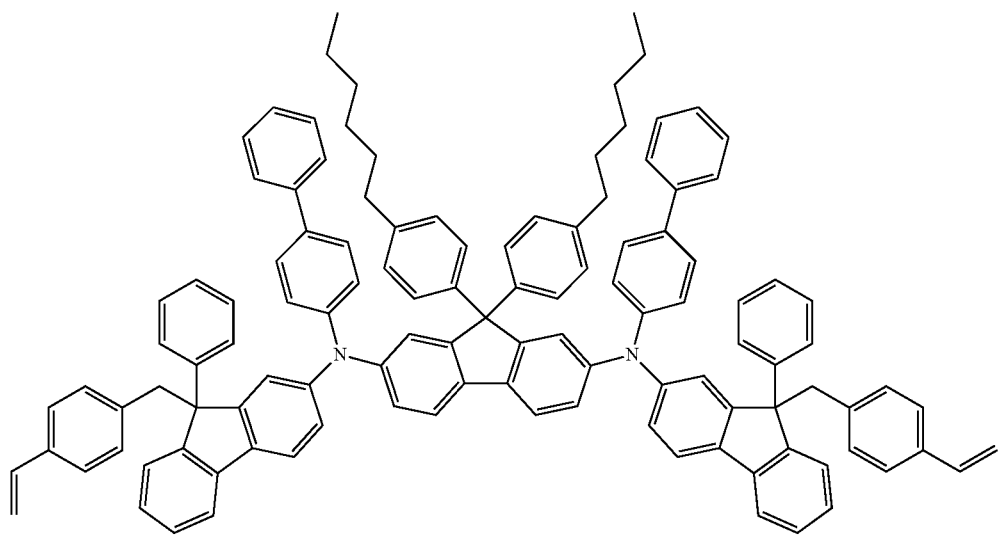

-continued

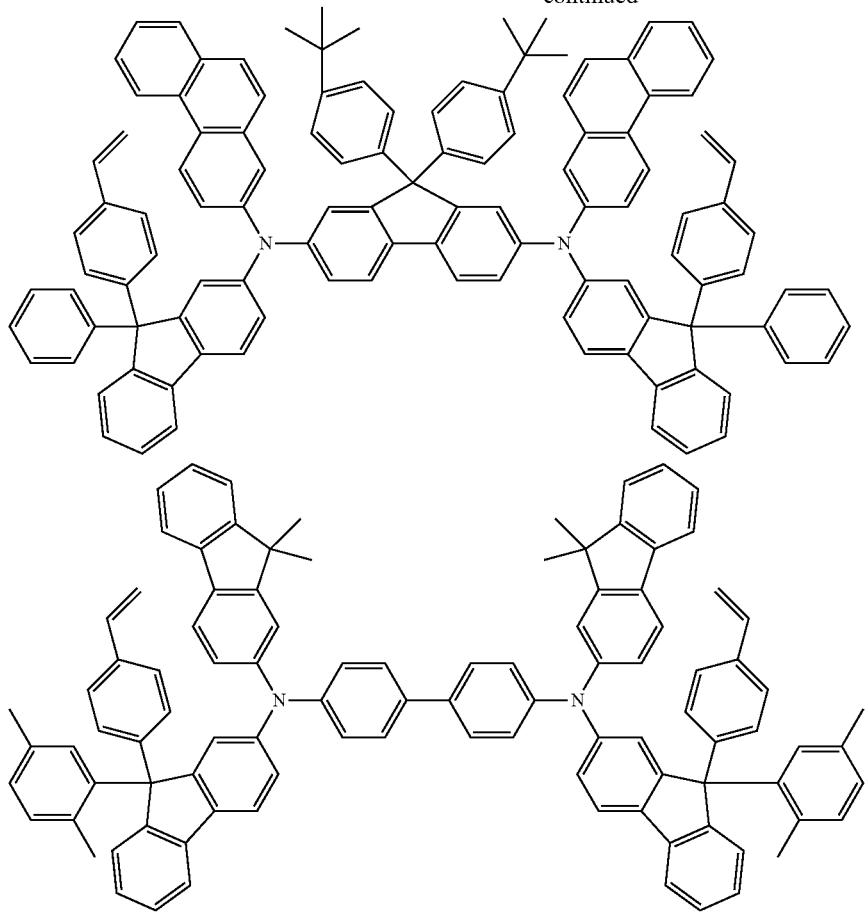

5. A coating composition comprising the fluorene-based compound of claim 1.

6. The coating composition of claim 5, further comprising:
a p-doping material.

7. The coating composition of claim 6, wherein the p-doping material is F4TCNQ; or a compound comprising a boron anion.

8. The coating composition of claim 5, further comprising:
a single molecule comprising a thermosetting group or a photocurable group; or
a single molecule comprising an end group capable of forming a polymer by heat.

9. The coating composition of claim 5 or 6, wherein the coating composition has a thin film retention rate of 95% or more in a thin film retention test, after a heat treatment at 250° C. or less.

10. An organic light emitting device comprising:
a first electrode;
a second electrode; and
an organic material layer having one or more layers provided between the first electrode and the second electrode,
wherein one or more layers of the organic material layer comprise the coating composition of claim 6 or a cured product thereof, and
the cured product of the coating composition is in a state where the coating composition is cured by a heat treatment or a light treatment.

11. The organic light emitting device of claim 10, wherein the organic material layer comprising the coating composition or the cured product thereof is a hole transport layer, a hole injection layer, or a layer which simultaneously transports and injects holes.

12. A method for manufacturing an organic light emitting device, the method comprising:
preparing a substrate;
forming a first electrode on the substrate;
forming an organic material layer having one or more layers on the first electrode; and
forming a second electrode on the organic material layer,
wherein the forming of the organic material layer comprises forming an organic material layer having one or more layers by using the coating composition of claim 5.

13. The method of claim 12, wherein the forming of the organic material layer formed by using the coating composition comprises:
coating the coating composition onto the first electrode; and
subjecting the coated coating composition to a heat treatment or a light treatment.

14. The fluorene-based compound of claim 1, wherein L is any one of the following structures:

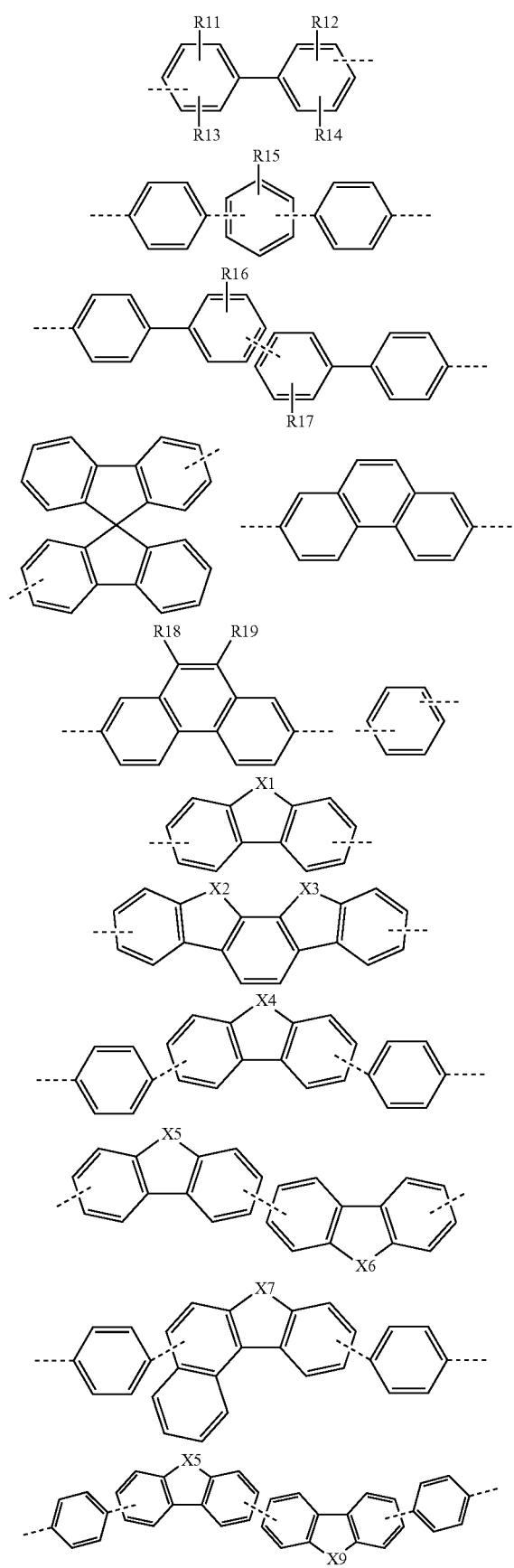
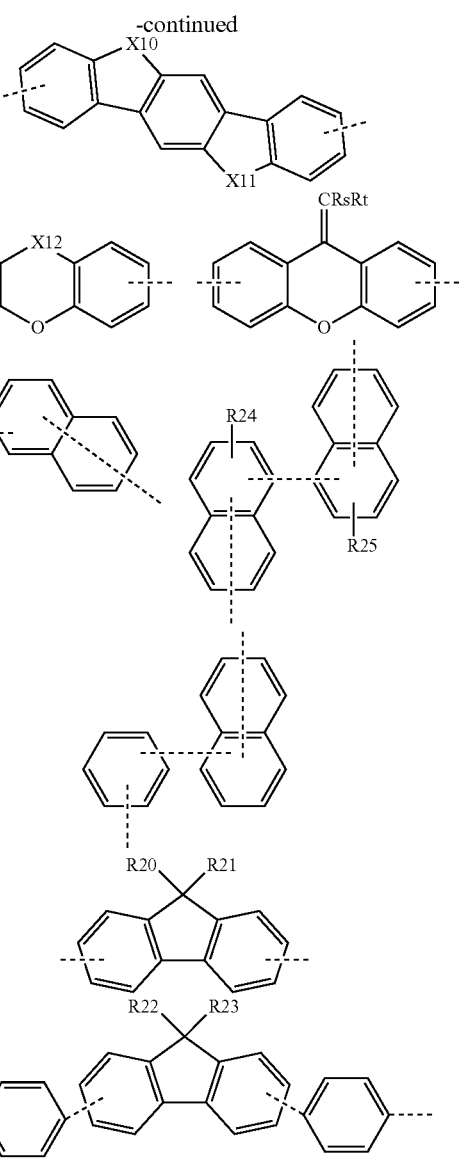

in the structures,

X12 is S, SO, CRuRv, SiRwRx or NRy,

X1 to X11 are the same as or different from each other, and are each independently O, S, SiR'R'' or NR, and R11 to R25, Rs, Rt, Ru, Rv, Rw, Rx, Ry, R, R', and R'' are the same as or different from each other, and are each independently hydrogen; deuterium; a halogen group; a substituted or unsubstituted alkyl group; or a substituted or unsubstituted aryl group.

15. The fluorene-based compound of claim 1, wherein Ar1 and Ar2 are the same as or different from each other, and are each independently one of the following structures:

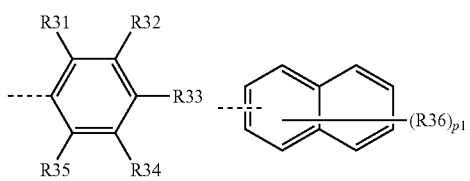

-continued

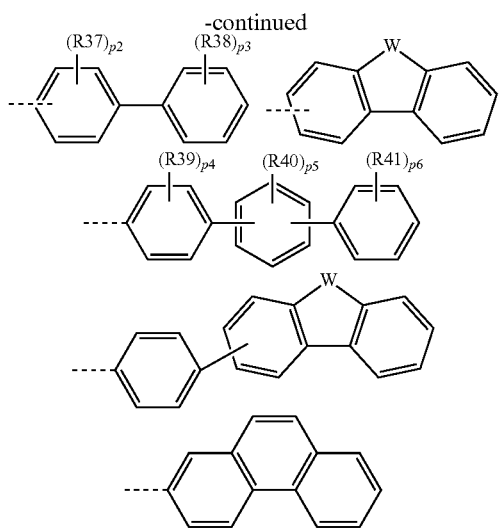

in the structures,

W is O, S, NRa, CRbRc or SiRdRe,

R31 to R41, Ra, Rb, Rc, Rd, and Re are the same as or different from each other, and are each independently hydrogen; deuterium; a halogen group; a substituted or unsubstituted alkyl group; or a substituted or unsubstituted aryl group, p1 is an integer of 0 to 7, p2, p4, and p5 are each an integer of 0 to 4, p3 and p6 are each an integer of 0 to 5, and when p1 to p6 are each 2 or more, R36s to R41s are each independently the same as or different from each other.

16. The coating composition of claim 5, further comprising a solvent.

17. The coating composition of claim 16, wherein the solvent is a chlorine-based solvent; an ether-based solvent; an aromatic hydrocarbon-based solvent; an aliphatic hydrocarbon-based solvent; a ketone-based solvent; an ester-based solvent; a polyhydric alcohol; an alcohol-based solvent; a sulfoxide-based solvent; an amide-based solvent; tetralin; or a mixture thereof.

18. The coating composition of claim 7, wherein the compound comprising a boron anion is any one of the following Formulae 9-2 to 9-3:

[Formula 9-2]

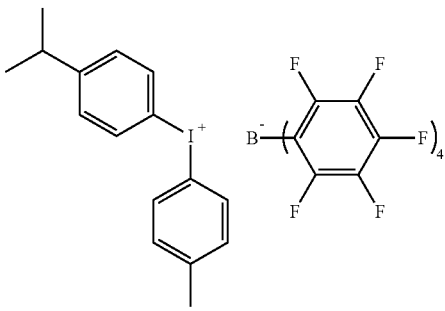

[Formula 9-3]

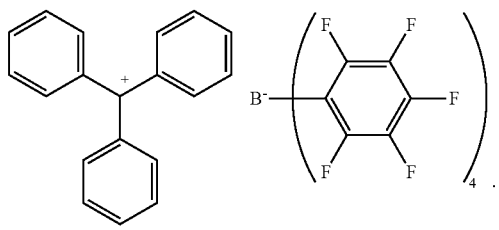

19. The coating composition of claim 6, wherein the p-doping material is present at 1 to 30 wt % based on the total content of the coating composition.

* * * * *